US012565502B2

(12) United States Patent
Strum

(10) Patent No.: US 12,565,502 B2
(45) **Date of Patent: *Mar. 3, 2026**

(54) SUBSTITUTED 1',2'-DIHYDRO-3'H-SPIRO[CYCLOHEXANE-1,4'-PYRIMIDO[5',4':4,5]PYRROLO[2,1-C][1,2,4]TRIAZIN]-3'-ONES AS CYCLIN-DEPENDENT KINASE INHIBITORS

(71) Applicant: Pharmacosmos Holding A/S, Denmark (DK)

(72) Inventor: Jay Copeland Strum, Hillsborough, NC (US)

(73) Assignee: Pharmacosmos Holding A/S, Holbaek (KR)

( * ) Notice: Subject to any disclaimer, the term of this patent is extended or adjusted under 35 U.S.C. 154(b) by 0 days.

This patent is subject to a terminal disclaimer.

(21) Appl. No.: 19/205,807

(22) Filed: May 12, 2025

(65) Prior Publication Data

US 2025/0270226 A1 Aug. 28, 2025

Related U.S. Application Data

(63) Continuation of application No. 18/137,286, filed on Apr. 20, 2023, now Pat. No. 12,312,360, which is a continuation of application No. 17/742,315, filed on May 11, 2022, now Pat. No. 11,643,416, which is a continuation of application No. PCT/US2021/032976, filed on May 18, 2021.

(60) Provisional application No. 63/085,672, filed on Sep. 30, 2020, provisional application No. 63/027,113, filed on May 19, 2020.

(51) Int. Cl.

| | |
|---|---|
| ***A61K 31/519*** | (2006.01) |
| ***C07D 487/04*** | (2006.01) |
| ***C07D 487/20*** | (2006.01) |

(52) U.S. Cl.

CPC ......... *C07D 487/20* (2013.01); *C07D 487/04* (2013.01)

(58) Field of Classification Search

CPC ............................ A61K 31/519; C07D 487/04

USPC .......................................... 514/257; 544/247

See application file for complete search history.

(56) References Cited

U.S. PATENT DOCUMENTS

| | | | |
|---|---|---|---|
| 5,359,073 | A | 10/1994 | Weier et al. |
| 2002/0009494 | A1 | 1/2002 | Curatolo et al. |
| 2004/0236084 | A1 | 11/2004 | Biwersi et al. |
| 2011/0152244 | A1 | 6/2011 | Besong et al. |
| 2014/0142299 | A1 | 5/2014 | Tavares et al. |
| 2014/0271466 | A1 | 9/2014 | Sharpless et al. |
| 2014/0315888 | A1 | 10/2014 | Ho et al. |
| 2015/0111896 | A1 | 4/2015 | Sharpless et al. |
| 2017/0202826 | A1 | 7/2017 | Nause |
| 2019/0135811 | A1 | 5/2019 | Strum et al. |
| 2020/0102315 | A1 | 4/2020 | Buesking et al. |
| 2021/0122755 | A1 | 4/2021 | Smith et al. |
| 2022/0054488 | A1 | 2/2022 | Jin et al. |

FOREIGN PATENT DOCUMENTS

| | | | |
|---|---|---|---|
| CN | 111377924 | A | 7/2020 |
| CN | 111377935 | A | 7/2020 |
| WO | WO 2001/068648 | A1 | 9/2001 |
| WO | WO 2003/062236 | A1 | 7/2003 |
| WO | WO 2004/065378 | A1 | 8/2004 |
| WO | WO 2009/151589 | | 12/2009 |
| WO | WO 2010/020675 | | 2/2010 |
| WO | WO 2011/101409 | | 8/2011 |
| WO | WO 2012/078859 | | 6/2012 |
| WO | WO 2012/082997 | | 6/2012 |
| WO | WO 2013/048214 | | 4/2013 |
| WO | WO 2015/180642 | | 12/2015 |
| WO | WO 2018/106870 | | 6/2018 |
| WO | WO 2019/222521 | | 11/2019 |
| WO | WO 2022/165162 | | 8/2022 |

OTHER PUBLICATIONS

Dorwald, F. Zaragoza, "Side reactions in organic synthesis: A guide to successful synthesis design," Weinheim: Wiley-VCH Verlag GmbH & Co. KGaA, 2005.

International Search Report and Written Opinion for PCT/US21/32976, 10 pages, mailed on Oct. 4, 2021.

(Continued)

*Primary Examiner* — Douglas M Willis

(74) *Attorney, Agent, or Firm* — Knowles Intellectual Property Strategies, LLC

(57) ABSTRACT

This invention is in the area of cell cycle inhibiting compounds for the treatment of disorders involving abnormal cellular proliferation, and include selective CDK2 inhibitors for medical therapy and their pharmaceutically acceptable salts and compositions. The inhibitors are pyrimidine-based N-heterocyclic compounds of formula:

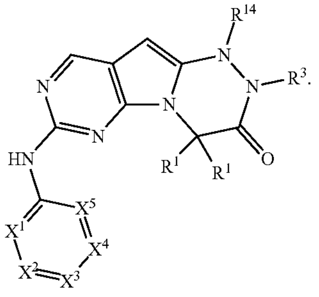

27 Claims, No Drawings

(56) References Cited

OTHER PUBLICATIONS

Johnson et al., "Mitigation of hematological radiation toxicity in mice through pharmacological quiescence induced by CDK4/6 inhibition." J. Clin. Invest., 120(7); 2528-2536, Jun. 23, 2010.
Jordan, V. C., "Tamoxifen: A most unlike pioneering medicine" Nature Reviews, Drug Discovery, 2:205, 2003.
Vanderwel et al., "Pyrido[2,3-d]pyrimidin-7-ones as specific inhibitors of cyclin-dependent kinase 4" J. Med. Chem., 48, 2371-2387, Mar. 2, 2005.
Xin-Jie Chu et al., "Discovery of [4-Amino-2-(1-methanesulfonylpiperidin-4-ylamino)pyrimidin-5-y1](2,3-difluoro-6-methoxyphenyl)methanone (R547), A potent and selective cyclin-dependent kinase inhibitor with significant in vivo antitumor activity" J. Med. Chem., 49, 6549-6560, Sep. 30, 2006.
US, U.S. Pat. No. 8,598,186, B2, U.S. Appl. No. 13/869,520, Tavares et al., Dec. 3, 2013.
US, U.S. Pat. No. 8,598,197, B2, U.S. Appl. No. 13/869,576, Tavares et al., Dec. 3, 2013.
US, U.S. Pat. No. 8,691,830, B2, U.S. Appl. No. 13/869,594, Tavares et al., Apr. 8, 2014.
US, U.S. Pat. No. 8,822,683, B2, U.S. Appl. No. 14/162,637, Tavares et al., Sep. 2, 2014.
US, U.S. Pat. No. 8,829,012, B2, U.S. Appl. No. 14/162,649, Tavares et al., Sep. 9, 2014.
US, U.S. Pat. No. 9,102,682, B2, U.S. Appl. No. 14/452,296, Tavares et al., Aug. 11, 2015.
US, U.S. Pat. No. 9,260,442, B2, U.S. Appl. No. 14/498,796, Tavares, Jan. 27, 2016.
US, U.S. Pat. No. 9,464,092, B2, U.S. Appl. No. 14/212,911, Strum et al., Oct. 11, 2016.
US, U.S. Pat. No. 9,481,691, B2, U.S. Appl. No. 14/712,630, Tavares et al., Nov. 1, 2016.
US, U.S. Pat. No. 9,487,530, B2, U.S. Appl. No. 14/212,430, Strum et al., Nov. 8, 2016.
US, U.S. Pat. No. 9,499,564, B2, U.S. Appl. No. 14/712,582, Tavares et al., Nov. 22, 2016.
US, U.S. Pat. No. 9,527,857, B2, U.S. Appl. No. 14/214,048, Strum et al., Dec. 27, 2016.
US, U.S. Pat. No. 9,717,735, B2, U.S. Appl. No. 14/690,180, Strum et al., Aug. 1, 2017.
US, U.S. Pat. No. 9,745,316, B2, U.S. Appl. No. 14/982,443, Tavares, Aug. 29, 2017.
US, U.S. Pat. No. 9,856,268, B2, U.S. Appl. No. 15/348,862, Tavares, Jan. 2, 2018.
US, U.S. Pat. No. 9,931,345, B2, U.S. Appl. No. 15/288,878, Strum et al., Apr. 3, 2018.
US, U.S. Pat. No. 9,957,276, B2, U.S. Appl. No. 15/348,770, Tavares et al., May 1, 2018.
US, U.S. Pat. No. 10,076,523, B2, U.S. Appl. No. 15/387,083, Strum et al., Sep. 18, 2018.
US, U.S. Pat. No. 10,085,992, B2, U.S. Appl. No. 15/342,990, Strum et al., Oct. 2, 2018.
US, U.S. Pat. No. 10,189,849, B2, U.S. Appl. No. 15/918,834, Tavares et al., Jan. 29, 2019.
US, U.S. Pat. No. 10,189,850, B2, U.S. Appl. No. 15/918,852, Tavares et al., Jan. 29, 2019.
US, U.S. Pat. No. 10,189,851, B2, U.S. Appl. No. 15/918,877, Tavares et al., Jan. 29, 2019.
US, U.S. Pat. No. 10,231,969, B2, U.S. Appl. No. 15/457,699, Strum et al., Mar. 19, 2019.
US, U.S. Pat. No. 10,376,519, B2, U.S. Appl. No. 15/665,071, Strum et al., Aug. 13, 2019.
US, U.S. Pat. No. 10,413,547, B2, U.S. Appl. No. 16/142,574, Strum et al., Sep. 17, 2019.
US, U.S. Pat. No. 10,434,104, B2, U.S. Appl. No. 16/112,362, Strum et al., Oct. 8, 2019.
US, U.S. Pat. No. 10,464,940, B2, U.S. Appl. No. 15/860,483, Tavares et al., Nov. 5, 2019.
US, U.S. Pat. No. 10,618,905, B2, U.S. Appl. No. 16/230,412, Strum et al., Apr. 14, 2020.
US, U.S. Pat. No. 10,660,896, B2, U.S. Appl. No. 15/943,278, Strum et al., May 26, 2020.
US, U.S. Pat. No. 10,654,831, B2, U.S. Appl. No. 16/230,388, Strum et al., May 19, 2020.
US, U.S. Pat. No. 10,696,682, B2, U.S. Appl. No. 16/226,430, Tavares et al., Jun. 30, 2020.
US, U.S. Pat. No. 10,709,711, B2, U.S. Appl. No. 16/228,308, Strum et al., Jul. 14, 2020.
US, U.S. Pat. No. 10,829,490, B2, U.S. Appl. No. 16/230,396, Strum et al., Nov. 10, 2020.
US, U.S. Pat. No. 10,865,210, B2, U.S. Appl. No. 16/230,381, Smith et al., Dec. 15, 2020.
US, U.S. Pat. No. 10,925,878, B2, U.S. Appl. No. 16/178,419, Strum et al., Feb. 23, 2021.
US, U.S. Pat. No. 10,927,120, B2, U.S. Appl. No. 15/931,330, Tavares et al., Feb. 23, 2021.
US, U.S. Pat. No. 10,966,984, B2, U.S. Appl. No. 16/112,360, Strum et al., Apr. 6, 2021.
US, U.S. Pat. No. 10,988,479, B2, U.S. Appl. No. 17/097,854, Schneider, Apr. 27, 2021.
US, U.S. Pat. No. 11,040,042 B2, U.S. Appl. No. 16/886,309, Strum et al., Jun. 22, 2021.
US, U.S. Pat. No. 11,090,306, B2, U.S. Appl. No. 16/572,418, Strum et al., Aug. 17, 2021.
US, U.S. Pat. No. 11,261,193, B2, U.S. Appl. No. 16/721,631, Smith et al., Mar. 1, 2022.
US, U.S. Pat. No. 11,357,779, B2, U.S. Appl. No. 16/924,033, Beelen et al., Jun. 14, 2022.
US, U.S. Pat. No. 11,364,222, B2, U.S. Appl. No. 16/460,502, Strum et al., Jun. 21, 2022.
US, U.S. Pat. No. 11,395,821, B2, U.S. Appl. No. 16/547,342, Sorrentino et al., Jul. 26, 2022.
US, U.S. Pat. No. 11,446,295, B2, U.S. Appl. No. 16/254,364, Strum et al., Sep. 20, 2022.
US, U.S. Pat. No. 11,529,352, B2, U.S. Appl. No. 16/432,244, Sorrentino et al., Dec. 20, 2022.
US, U.S. Pat. No. 11,629,150, B2, U.S. Appl. No. 17/121,392, Smith et al., Apr. 18, 2023.
US, U.S. Pat. No. 11,643,416, B2, U.S. Appl. No. 17/742,315, Strum et al., May 9, 2023.
US, U.S. Pat. No. 11,654,148, B2, U.S. Appl. No. 17/181,638, Strum et al., May 23, 2023.
US, U.S. Pat. No. 11,708,337, B2, U.S. Appl. No. 17/184,354, Schneider et al., Jul. 25, 2023.
US, U.S. Pat. No. 11,717,523, B2, U.S. Appl. No. 17/222,873, Strum et al., Aug. 8, 2023.
US, U.S. Pat. No. 12,139,494, B2, U.S. Appl. No. 17/683,146, Smith et al., Nov. 12, 2024.
US, U.S. Pat. No. 12,168,666, B2, U.S. Appl. No. 17/236,687, Schneider et al., Dec. 17, 2024.
US, U.S. Pat. No. 12,264,135, B2, U.S. Appl. No. 18/225,537, Schneider et al., Apr. 1, 2025.
US, U.S. Pat. No. 12,285,431, B2, U.S. Appl. No. 17/403,577, Strum et al., Apr. 29, 2025.
US, U.S. Pat. No. 12,312,360, B2, U.S. Appl. No. 18/137,286, Strum et al., May 27, 2025.
US, 2022/0175787, A1, U.S. Appl. No. 17/554,940, Roberts et al., Jun. 9, 2022.
US, 2022/0241275, A1, U.S. Appl. No. 17/718,052, Strum et al., Aug. 4, 2022.
US, 2023/0146638, A1, U.S. Appl. No. 17/854,755, Sorrentino et al., May 11, 2023.
US, 2023/0149406, A1, U.S. Appl. No. 17/839,215, Beelen et al., May 18, 2023.
US, 2023/0248733, A1, U.S. Appl. No. 17/890,130, Strum et al., Aug. 10, 2023.
US, 2023/0302001, A1, U.S. Appl. No. 18/072,963, Sorrentino et al., Sep. 28, 2023.
US, 2023/0364098, A1, U.S. Appl. No. 18/117,983, Strum et al., Nov. 16, 2023

(56) References Cited

OTHER PUBLICATIONS

US, 2023/0381189, A1, U.S. Appl. No. 18/231,091, Strum et al., Nov. 30, 2023.
US, 2024/0109906, A1, U.S. Appl. No. 18/120,806, Tavares et al., Apr. 4, 2024.
US 2024/0139196, A1, U.S. Appl. No. 18/394,512, Beelen et al., May 2, 2024.
US, 2025/0101030, A1, U.S. Appl. No. 18/973,646, Schneider et al., Mar. 27, 2025.
US, U.S. Appl. No. 18/943,701, Smith et al., filed Nov. 11, 2024.
US, U.S. Appl. No. 18/957,373, Tavares et al., filed Nov. 22, 2024,
US, U.S. Appl. No. 18/990,892, Strum et al., filed Dec. 20, 2024.
US, U.S. Appl. No. 19/096,395, Schneider et al., filed Mar. 31, 2025.
US, U.S. Appl. No. 19/182,966, Schneider et al., filed Apr. 18, 2025.
US, U.S. Appl. No. 19/182,977, Schneider et al., filed Apr. 18, 2025.
US, U.S. Appl. No. 19/182,985, Schneider et al., filed Apr. 18, 2025.
US, U.S. Appl. No. 19/192,045, Strum et al., filed Apr. 28, 2025.
U.S. Pat. No. 12,364,697-B2, Jul. 22, 2025, Beelen et al., U.S. Appl. No. 17/839,215.
US-2025/0199015-A1, Jun. 19, 2025, Strum et al., U.S. Appl. No. 18/990,892.
US-2025/0243212-A1, Jul. 31, 2025, Schneider et al., U.S. Appl. No. 19/182,966.
US-2025/0243213-A1, Jul. 31, 2025, Schneider et al., U.S. Appl. No. 19/182,977.
US-2025/0243214-A1, Jul. 31, 2025, Schneider et al., U.S. Appl. No. 19/182,985.
U.S. Appl. No. 19/232,623, Sorrentino et al., filed Jun. 9, 2025.
U.S. Appl. No. 19/272,690, Beelen et al., filed Jul. 17, 2025.

SUBSTITUTED 1',2'-DIHYDRO-3'H-SPIRO[CYCLOHEXANE-1,4'-PYRIMIDO[5',4':4,5]PYRROLO[2,1-C][1,2,4]TRIAZIN]-3'-ONES AS CYCLIN-DEPENDENT KINASE INHIBITORS

CROSS-REFERENCE TO RELATED APPLICATIONS

This application is a continuation of U.S. patent application Ser. No. 18/137,286, filed Apr. 20, 2023, which is a continuation of U.S. patent application Ser. No. 17/742,315, filed May 11, 2022, which is a continuation of International Patent Application No. PCT/US2021/032976, filed in the U.S. Receiving Office on May 18, 2021, which claims the benefit of U.S. Provisional Application 63/027,113 filed on May 19, 2020, and U.S. Provisional Application 63/085,672 filed on Sep. 30, 2020. The entirety of each of these applications is hereby incorporated by reference for all purposes.

FIELD OF THE INVENTION

This invention is in the area of pyrimidine-based compounds for the treatment of disorders involving abnormal cellular proliferation, including but not limited to the treatment of cancers and tumors.

BACKGROUND

In normal tissue, cellular proliferation is generally restricted to cells that are required to replenish the tissue. Once cells have terminally differentiated, they have a specialized function and no longer divide. Most tissues are made of non-dividing cells. Thus, normal cell proliferation is tightly controlled to ensure that only the necessary cells divide. There is also a careful balance between cell division and programmed cell death (apoptosis).

Cell division, sometimes referred to as the cell cycle, has four phases: $G_1$ phase (synthesis of various enzymes required for DNA replication), S phase (DNA replication producing two identical sets of chromosomes), $G_2$ (significant protein synthesis, including production of microtubules) and M phase (nuclear division, cytoplasmic division and formation of new cell membrane). Cell division also includes a complex system of cell signaling networks that allow cells to interpret information from numerous extracellular signals, including through receptor proteins, inflammatory factors and pro-apoptotic and anti-apoptotic signals. Dysfunctional signals include those from genetic mutation, infection, exposure to environmental factors including toxins, system stress, autoimmune disorders, and inflammation.

A range of disorders can occur when the process of cell proliferation becomes dysfunctional, including benign growths, neoplasms, tumorigenesis, cancerogenesis, autoimmune disorders, inflammatory disorders graft-versus-host rejection, and fibrotic disorders.

A number of broad-spectrum anti-neoplastic agents have been developed. Cytoskeletal drugs like paclitaxel target tubulin to arrest mitotic cell division and are used to treat a variety of cancers including ovarian, breast, lung, pancreatic, and testicular tumors (See e.g., Jordan, Wilson, Nature Reviews Cancer (2004) 4: 253-265). Organometallic-based drugs such as cisplatin have been used to treat lymphomas, sarcomas, germ cell tumors, and some carcinomas including bladder, small cell lung cancer, and ovarian cancer. Cisplatin has the ability to bind nitrogenous bases and cause extensive DNA cross-linking that ultimately leads to apoptosis (See e.g., Siddick, Oncogene (2003) 22: 7265-7279). Intercalating and alkylating agents have also been extensively used in the clinic for the treatment of various neoplasms, however, the global toxicity associated with these drugs presents a critical concern for patients requiring long-term therapy.

Palbociclib (PD-033299; Ibrance) is sold by Pfizer for the treatment of estrogen-positive, HER2-negative breast cancer in combination with letrozole. The compound inhibits CDK4 and CDK6. The structure of palbociclib is:

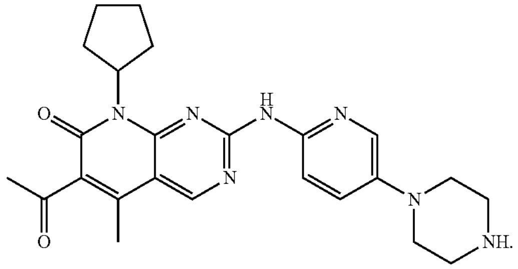 [SMILES: CC(=O)c1c(C)c2cnc(Nc3ccc(N4CCNCC4)cn3)nc2n(C2CCCC2)c1=O]

Abemaciclib (LY2835219) is a CDK 4/6 inhibitor currently in human clinical trials for the treatment of various types of cancers. It is in a phase III trial for stage IV non-small cell lung carcinoma; in combination with Fulvestrant for women with breast cancer; and with either anastrozole or letrozole for first line treatment of breast cancer. The structure of abemaciclib is:

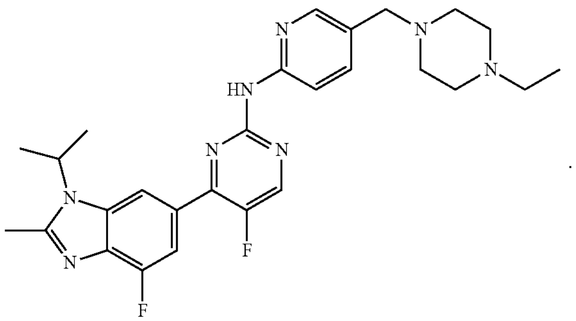 [SMILES: CCN1CCN(Cc2ccc(Nc3ncc(F)c(-c4cc(F)c5nc(C)n(C(C)C)c5c4)n3)nc2)CC1]

Ribociclib (Lee011; Kisqali), is a CDK 4/6 inhibitor approved for use in combination with an aromatase inhibitor to treat some metastatic breast cancers, and is in clinical trials for the treatment of certain other tumors. The structure of ribociclib is:

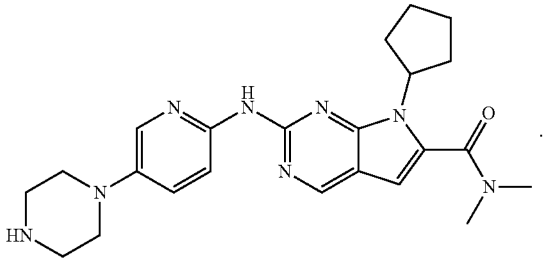 [SMILES: CN(C)C(=O)c1cc2cnc(Nc3ccc(N4CCNCC4)cn3)nc2n1C1CCCC1]

Lerociclib is an oral, selective CDK4/6 inhibitor in clinical development by G1 Therapeutics for use in combination with other targeted therapies in multiple oncology indications. Lerociclib is currently being evaluated in two Phase 1/2 clinical trials: a trial in combination with fulvestrant (Faslodex®) for patients with estrogen receptor-positive, HER2-negative (ER+, HER2-) breast cancer (NCT02983071) and a trial in combination with osmirtinib (Tagrisso®) in EGFRm non-small cell lung cancer. Lerociclib has the structure:

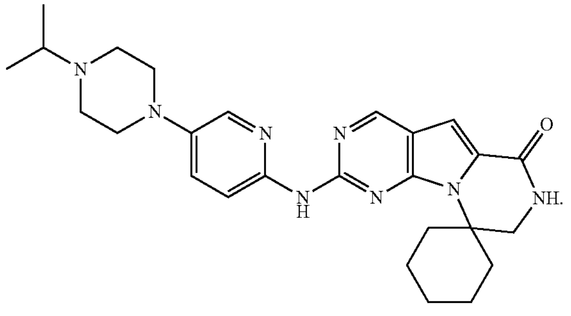 [SMILES: CC(C)N1CCN(c2ccc(Nc3ncc4cc5n(c4n3)C3(CCCCC3)CNC5=O)nc2)CC1]

Trilaciclib is a selective CDK4/6 inhibitor in clinical development by G1 Therapeutics for use as a first-in-class myelopreservation therapy designed to improve outcomes of patients who receive chemotherapy by preserving hematopoietic stem and progenitor cell (HSPC) and immune system function. Trilaciclib is a short-acting intravenous CDK4/6 inhibitor administered prior to chemotherapy and is currently being evaluated in four randomized Phase 2 clinical trials, including in first-line SCLC trials in combination with a chemotherapy regimen of etoposide and carboplatin (NCT02499770); and in first-line SCLC trial in combination with the same chemotherapy regimen and the checkpoint inhibitor Tecentriq® (atezolizumab). Trilaciclib has the structure:

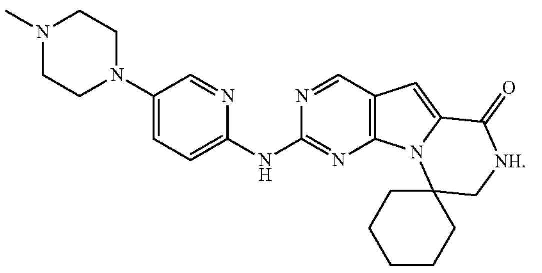 [SMILES: CN1CCN(c2ccc(Nc3ncc4cc5n(c4n3)C3(CCCCC3)CNC5=O)nc2)CC1]

Various other pyrimidine-based agents have been developed for the treatment of hyperproliferative diseases. U.S. Pat. Nos. 8,822,683; 8,598,197; 8,598,186; 8,691,830; 8,829,102; 8,822,683; 9,102,682; 9,260,442; 9,481,691; 9,499,564; 9,957,276; 10,189,849; 10,189,850; and 10,189,851; filed by Tavares and Strum and assigned to G1 Therapeutics describe a class of N-(heteroaryl)-pyrrolo[3,2-d]pyrimidin-2-amine cyclin dependent kinase inhibitors including those of the formula (with variables as defined therein):

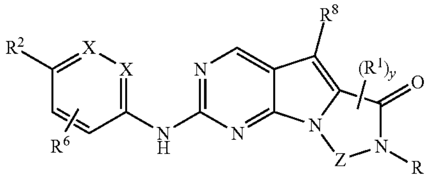

-continued

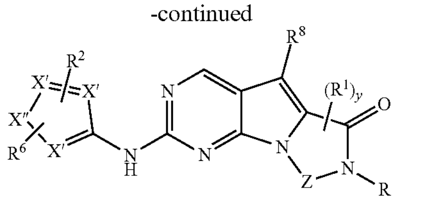

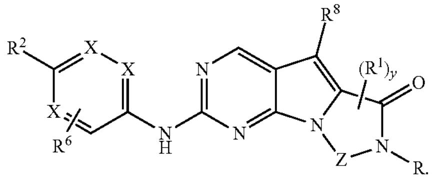

U.S. Pat. Nos. 9,464,092; 9,487,530; 9,527,857; 10,076,523; 10,085,992; and 10,434,104 which are also assigned to G1 Therapeutics describe the use of the above pyrimidine-based agents in the treatment of cancer.

WO 2013/148748 (U.S. Ser. No. 61/617,657) titled "Lactam Kinase Inhibitors", WO 2013/163239 (U.S. Ser. No. 61/638,491) titled "Synthesis of Lactams" and WO 2015/061407 filed by Tavares and also assigned to G1 Therapeutics describes the synthesis of N-(heteroaryl)-pyrrolo[3,2-d]pyrimidin-2-amines and their use as lactam kinase inhibitors.

Other patent publications include the following. WO 2014/144326 filed by Strum et al. and assigned to G1 Therapeutics describes compounds and methods for protection of normal cells during chemotherapy using pyrimidine-based CDK4/6 inhibitors. WO 2014/144596 filed by Strum et al. and assigned to G1 Therapeutics describes compounds and methods for protection of hematopoietic stem and progenitor cells against ionizing radiation using pyrimidine-based CDK4/6 inhibitors. WO 2014/144847 filed by Strum et al. and assigned to G1 Therapeutics describes HSPC-sparing treatments of abnormal cellular proliferation using pyrimidine-based CDK4/6 inhibitors. WO 2014/144740 filed by Strum et al. and assigned to G1 Therapeutics describes highly active anti-neoplastic and anti-proliferative pyrimidine-based CDK 4/6 inhibitors. WO 2015/161285 filed by Strum et al. and assigned to G1 Therapeutics describes tricyclic pyrimidine-based CDK inhibitors for use in radioprotection. WO 2015/161287 filed by Strum et al. and assigned to G1 Therapeutics describes tricyclic pyrimidine-based CDK inhibitors for the protection of cells during chemotherapy. WO 2015/161283 filed by Strum et al. and assigned to G1 Therapeutics describes tricyclic pyrimidine-based CDK inhibitors for use in HSPC-sparing treatments of RB-positive abnormal cellular proliferation. WO 2015/161288 filed by Strum et al. and assigned to G1 Therapeutics describes tricyclic pyrimidine-based CDK inhibitors for use as anti-neoplastic and anti-proliferative agents. WO 2016/040858 filed by Strum et al. and assigned to G1 Therapeutics describes the use of combinations of pyrimidine-based CDK4/6 inhibitors with other anti-neoplastic agents. WO 2016/040848 filed by Strum et al. and assigned to G1 Therapeutics describes compounds and methods for treating certain Rb-negative cancers with CDK4/6 inhibitors and topoisomerase inhibitors. WO 2018/005860, WO 2018/005533, and WO 2018/005863 filed by Strum and assigned to G1 Therapeutics describes various CDK inhibitors. WO 2018/106739 filed by Sorrentino et al., and assigned to G1 Therapeutics describes the use of CDK4/6 inhibitors with specific dosage regimens. WO 2018/156812 filed by Strum et al., and assigned to G1 Therapeutics describes the use of CDK4/6 inhibitors to treat EGFR-driven cancer. WO 2019/199883 filed by Strum et al. and assigned to G1 Therapeutics describes compounds and methods for treating chemotherapy resistant cancer. WO 2019/136451 filed by Beelen et al. and assigned to G1 Therapeutics describes dosage regimes for the administration of G1T38. WO 2019/136244 filed by Strum et al. and assigned to G1 Therapeutics describes additional compounds for inhibiting CDKs. WO 2019/222521 filed by Strum and assigned to G1 Therapeutics describes additional compounds for inhibiting CDKs. WO 2020/041770 filed by Schneider et al. and assigned to G1 Therapeutics describes synthetic methods for preparing CDK inhibiting compounds. WO 2020/097625 filed by Sorrentino et al. and assigned to G1 Therapeutics describes the use of CDK4/6 inhibitors in combination with eribulin. WO 2020/206034 filed by Strum and assigned to G1 Therapeutics describes additional compounds for inhibiting CDKs. WO 2020/206035 filed by Jung et al. and assigned to G1 Therapeutics describes additional compounds for inhibiting CDKs. WO 2020/257536 filed by Roberts et al. and assigned to G1 Therapeutics describes patient selection for the enhancement of tumor treatment with CDK4/6 inhibitors. WO 2021/072319 filed by Strum et al. and assigned to G1 Therapeutics describes the use of CDK4/6 inhibitors to treat fibroblast growth factor mediated cancer.

Despite research in the area of cell cycle inhibiting compounds to treat abnormal cellular proliferation in a host, for example, a human, given the seriousness of these diseases, there remains a need to identify new compounds that can meet this medical need.

Therefore, it is an object of the present invention to provide new compounds, methods, compositions and processes of manufacture to inhibit undesired cell cycling in a host, for example, a human, wherein the compounds can be used to treat abnormal cellular proliferation. It is yet another aspect of the invention to provide compounds, methods and compositions that can be used to treat cell cycle disorders in cells that are naturally or have become resistant to other therapies.

SUMMARY

The invention provides a therapeutically active compound of Formula I, Formula II, Formula III, Formula IV, Formula V, Formula VI, Formula VII, Formula VIII, Formula IX, or Formula X, or a pharmaceutically acceptable salt or composition thereof. In certain embodiments, the active compound or its salt, composition, or isotopic analog thereof is used in an effective amount to treat a medical disorder involving abnormal cellular proliferation, including a tumor or cancer, in a host, typically a human, in need thereof.

In certain embodiments, the compounds of the present invention are active against various cyclin dependent kinases, including for example, having preferential activity against CDK2. In certain embodiments, the compound of the present invention is selective for the inhibition of CDK2 over CDK1, CDK3, CDK4, CDK5, CDK6, CDK7, and/or CDK9. Based on this discovery, compounds and methods are presented for the treatment of a patient with a proliferative disorder including a tumor or cancer that includes administering an effective amount of one or a combination of the compounds described herein, or a pharmaceutically acceptable salt thereof to a patient in need thereof, optionally in a pharmaceutically acceptable carrier. In certain embodiments, the antiproliferative disorder is selected from a cancer, tumor, neoplasm, benign growth, autoimmune disorder, inflammatory disorder, graft-versus-host rejection and a fibrotic disorder. In a typical embodiment, the patient is a human.

In certain embodiments, a compound of the present invention has high oral bioavailability, for example an oral bioavailability of more than about 50%, 60%, 70%, 80%, 90%, or 95% F (fraction of drug that reaches systemic circulation as the intact drug). In certain embodiments, a compound of the present invention has high metabolic stability, for example a compound of the present invention may exhibit stability in human microsomes of greater than about 30 minutes, 45 minutes, an hour, 1.5 hours, or 2 hours.

The present invention also provides advantageous methods to treat a patient with a selective CDK4/6 inhibitor resistant proliferative disorder, for example a tumor or cancer, which includes administering an effective amount of a compound Formula I, Formula II, Formula III, Formula IV, Formula V, Formula VI, Formula VII, Formula VIII, Formula IX, or Formula X, or a pharmaceutically acceptable composition, salt, or isotopic analog thereof. Despite the development of selective CDK4/6 inhibitors, MYC-driven tumor types with retinoblastoma (Rb) protein loss or high expression levels of cyclin E, such as triple negative breast cancer (TNBC) and small cell lung cancer (SCLC) are difficult to treat due to an intrinsic or primary resistance to existing selective CDK4/6 inhibitors. In addition, certain cancers, despite being Rb-positive, are intrinsically resistant to the effects of selective CDK4/6 inhibitors. In addition, certain cancers that have an intact Rb-pathway may otherwise be intrinsically resistant to a selective CDK4/6 inhibitor due to the presence of other genetic or phenotypical abnormalities. For example, it is estimated that 40% of uterine, 20% of ovarian, 15% of bladder, 20% or prostate, and 15% of breast cancers may be intrinsically resistant to selective CDK4/6 inhibition due to the upregulation of Cyclin E, despite intact Rb. See, e.g., Knudsen et al., The Strange Case of CDK4/6 Inhibitors: Mechanisms, Resistance, and Combination Strategies. Trends Cancer. 2017 January; 3(1): 39-55. Furthermore, certain cancers, for example ER+ breast cancers, are capable of acquiring resistance to selective CDK4/6 inhibitors during the course of selective CDK4/6 inhibitor therapy, for example by upregulation of cyclin E, which allows G1 to S cell cycle progression through CDK2. In certain embodiments, a compound described herein effectively inhibits cell-cycle progression in cancer cells that are intrinsically resistant to, susceptible to acquiring resistance to, or have become resistant to selective CDK4/6 inhibitors.

The active compounds described herein act as inhibitors of a cyclin-dependent kinase (CDK), for example through inhibition of CDK2 and/or CDK4 and/or CDK6, or a combination thereof providing for cell-cycle inhibition in a replicating cell. Unlike selective CDK4/6 inhibitors, however, certain of the active compounds herein are capable of inhibiting cells that are or have become selective CDK4/6 inhibitor resistant by the active compounds ability to preferentially inhibit another CDK for example CDK2, thus providing additional cell-cycle inhibition mechanism. In one embodiment, this invention provides a selective CDK2 inhibitor. This characteristic is especially useful in inhibiting the cell-cycle progression of cancers or other proliferative disorders that are or have become Rb-negative, thus escaping CDK4/6 cell-cycle control.

In certain aspects of the present invention a compound of Formula I, Formula II, Formula III, Formula IV, or Formula V:

(I)

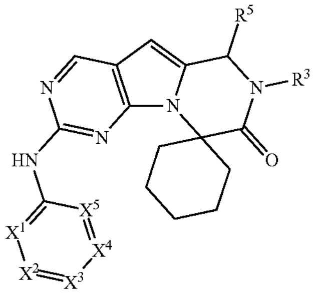

(II)

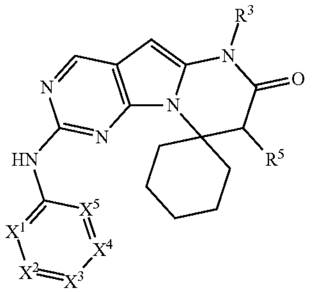

(III)

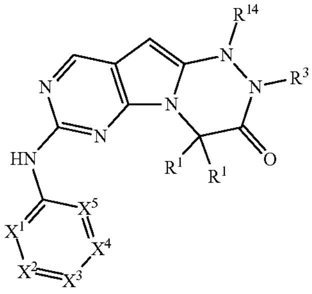

(IV)

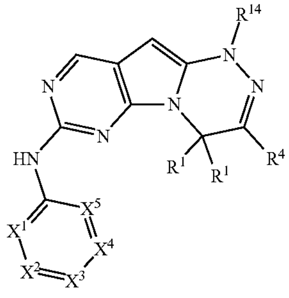

(V)

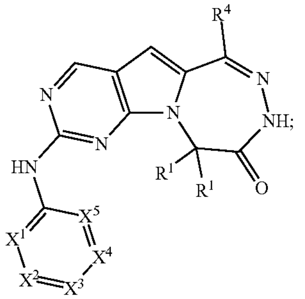

or a pharmaceutically acceptable salt, N-oxide, isotopic analog, and/or a pharmaceutically acceptable composition thereof;

wherein:

$X^1$, $X^2$, $X^3$, $X^4$, and $X^5$ are independently selected from N, CH, $CR^2$, and $CR^4$; wherein at least one of $X^1$, $X^2$, $X^3$, $X^4$, and $X^5$ is $CR^2$; and wherein no more than 2 of $X^1$, $X^2$, $X^3$, $X^4$, and $X^5$ are selected to be N;

each $R^1$ is independently selected from the group consisting of hydrogen, halogen, —$OR^{14}$, $NR^{14}R^{15}$, alkyl, aryl, cycloalkyl, haloalkyl, heteroaryl, alkylhydroxyl, and heterocycle, wherein two $R^1$s may come together with the ring atom to which they are attached to optionally constitute a 3, 4, 5, 6, 7, or 8-membered cycloalkyl or 4, 5, 6, 7, or 8-membered heterocycle that has 1, 2, or 3 heteroatoms selected from N, O, and S; wherein the cycloalkyl or heterocycle formed by combining two $R^1$s with the atom to which they are attached can be optionally substituted with 1 or 2 substituents independently selected from $R^{50}$;

each $R^2$ is independently selected from the group consisting of —NR $^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, and —$S(O)_2R^6$;

or each $R^2$ is independently selected from the group consisting of —$NR^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, —$S({=}NR^{14})_2R^6$, —$S({=}NR^{14})(O)R^6$ and —$S(O)_2R^6$;

$R^3$ is selected from the group consisting of hydrogen, —$OR^{14}$, —$NR^{14}R^{15}$, alkyl, alkenyl, alkynyl, —$C(O)R^6$, —C(O)alkyl, —C(S)alkyl, aryl, —$SO_2$alkyl, heteroaryl, heterocycle, -alkyl-aryl, and -alkyl-heteroaryl;

each $R^4$ is independently selected from the group consisting of hydrogen, alkyl, aryl, cycloalkyl, haloalkyl, heteroaryl, heterocycle, halogen, cyano, —$OR^{14}$, —$NR^{14}R^{15}$, —$NR^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, and —$S(O)_2R^6$;

$R^5$ is hydrogen, alkyl, haloalkyl, halogen, cyano, —$OR^{14}$, or —$NR^{14}R^{15}$; each $R^6$ is independently selected from the group consisting of hydrogen, alkyl, alkenyl, alkynyl, cycloalkyl, heterocycle, aryl, heteroaryl, $NR^7R^7$, and $OR^7$; each of which $R^6$ except hydrogen, $NR^7R^7$, and $OR^7$ is optionally substituted with 1, 2, 3, or 4 $R^8$ groups;

each $R^7$ is independently selected from the group consisting of hydrogen, alkyl, alkenyl, alkynyl, cycloalkyl, heterocycle, aryl, alkyl-aryl, alkyl-heteroaryl, and heteroaryl; each of which $R^7$ except hydrogen is optionally substituted with 1, 2, 3, or 4 $R^8$ groups;

each $R^8$ is independently selected from the group consisting of hydrogen, halogen, haloalkyl, alkyl, alkenyl, alkynyl, cycloalkyl, heterocycle, aryl, heteroaryl, —$S(O)_2$alkyl, $NR^{12}R^{13}$, alkyl-heteroaryl, alkyl-aryl, and $OR^{12}$;

each $R^{12}$ and $R^{13}$ is independently selected from the group consisting of hydrogen, alkyl, alkenyl, alkynyl, —C(O)alkyl, —C(S)alkyl, aryl, —$SO_2$alkyl, —S(O)alkyl, heteroaryl, alkyl-aryl, cycloalkyl, heterocycle, and alkyl-heteroaryl;

each $R^{14}$ and $R^{15}$ is independently selected from the group consisting of hydrogen, alkyl, alkenyl, alkynyl, —$C(O)R^6$, —C(O)alkyl, —C(S)alkyl, aryl, —$SO_2$alkyl, heteroaryl, heterocycle, -alkyl-aryl, and -alkyl-heteroaryl; and each $R^{50}$ is independently selected from the group consisting of hydrogen, —$NR^{14}R^{15}$, $OR^{14}$, and $R^4$.

In an alternative embodiment Formula I is:

(I)

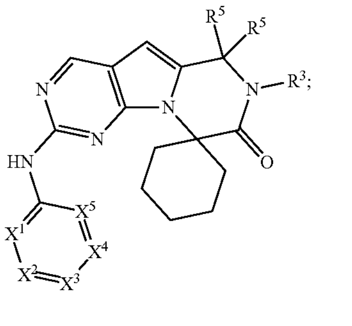

or a pharmaceutically acceptable salt, N-oxide, isotopic analog, and/or a pharmaceutically acceptable composition thereof;

wherein each $R^5$ is independently selected from hydrogen, alkyl, haloalkyl, halogen, cyano, —$OR^{14}$, and —$NR^{14}R^{15}$ and all other variables are as defined herein.

In certain aspects of the present invention a compound of Formula VI, Formula VII, Formula VIII, Formula IX, or Formula X is provided:

(VI)

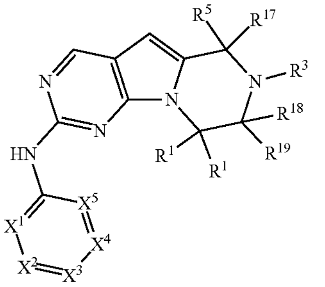

(VII)

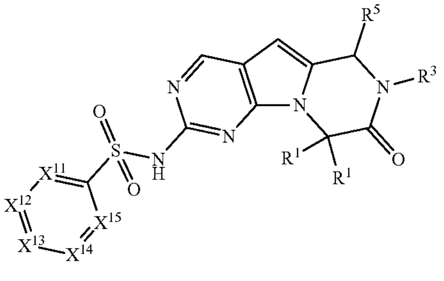

(VIII)

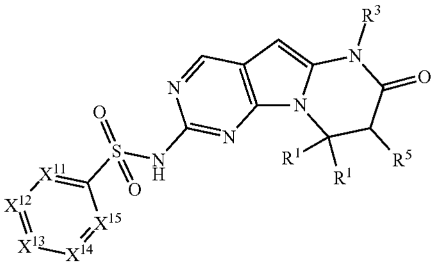

-continued (IX)

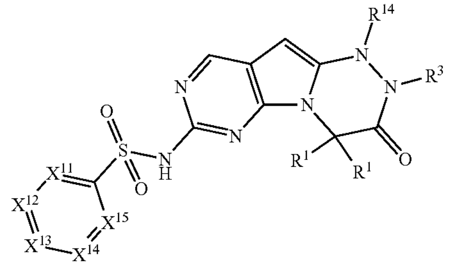

(X)

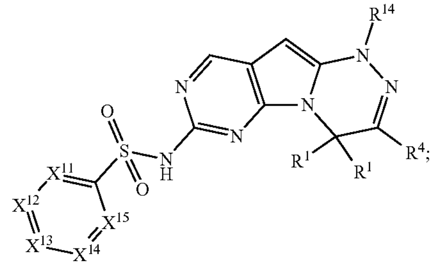

or a pharmaceutically acceptable salt, N-oxide, isotopic analog, and/or a pharmaceutically acceptable composition thereof;

wherein:

$X^{11}$, $X^{12}$, $X^{13}$, $X^1$, and $X^{15}$ are independently selected from N, CH, and $CR^4$; wherein no more than 2 of $X^{11}$, $X^{12}$, $X^{13}$, $X^{14}$, and $X^{15}$ are selected to be N;

$R^{17}$ and $R^{18}$ are independently selected from the group consisting of hydrogen, alkyl, alkenyl, alkynyl, cycloalkyl, heterocycle, aryl, alkyl-aryl, alkyl-heteroaryl, and heteroaryl each of which except hydrogen is optionally substituted with 1, 2, 3, or 4 $R^8$ groups; and $R^{19}$ is hydrogen, alkyl, haloalkyl, halogen, cyano, —$OR^{14}$, or —$NR^{14}R^{15}$.

In certain embodiments, a compound of the present invention has a preference for CDK2 or CDK9 inhibition over CDK4 and/or CDK6 inhibition. In certain embodiments, the compound of the present invention is a CDK inhibitor with increased activity against CDK2.

These compounds can be used to treat conditions of abnormal cellular proliferation in a host in need thereof, typically a human.

In another embodiment, a method for the treatment of a fibrotic disorder in a host is provided that includes the administration of an effective amount of a compound of the present invention or a pharmaceutically acceptable salt thereof, optionally in a pharmaceutically acceptable carrier.

In another embodiment, a method for the treatment of rheumatoid arthritis or psoriasis in a host is provided that includes the administration of an effective amount of a compound of the present invention or a pharmaceutically acceptable salt thereof, optionally in a pharmaceutically acceptable carrier.

In yet another embodiment, a method for the treatment of an autoimmune disorder in a host is provided that includes the administration of an effective amount of a compound of the present invention or a pharmaceutically acceptable salt thereof, optionally in a pharmaceutically acceptable carrier.

In certain embodiments, a method for the treatment of a tumor or cancer in a host is provided that includes the administration of an effective amount of a compound of the present invention or a pharmaceutically acceptable salt thereof, optionally in a pharmaceutically acceptable carrier. In an aspect of this embodiment, the cancer is an Rb-positive tumor or cancer.

In another aspect of this embodiment, the cancer is an Rb-negative tumor or cancer. In certain aspects, the cancer is selected from breast cancer, prostate cancer (including androgen-resistant prostate cancer), colon, including metastatic colon, another cancer of the reproductive system such as endometrial, ovarian or testicular cancer, small cell lung carcinoma, glioblastoma and head and/or neck cancer.

In yet another embodiment, a method for the treatment of a disorder of abnormal cellular proliferation in a host such as a human is provided that includes administering an effective amount of a combination of one or more of the active compounds described herein in combination or alternation with another active compound. In certain aspects of the invention, the second compound is a chemotherapeutic agent. In another aspect of this embodiment, the second active compound is an immune modulator, including but not limited to a checkpoint inhibitor such as an anti-PD1, Ant-PD-L1, anti-CTLA, anti-LAG-3, anti-Tim, etc. antibody, small molecule, peptide, nucleotide or other inhibitor, including but not limited to ipilimumab (Yervoy), pembrolizumab (Keytruda) nivolumab (Opdivo), cemiplimab (Libtayo), atezolizumab (Tecentriq), avelumab (Bavencio), and durvalumab (Imfinzi).

In yet another embodiment, one of the active compounds described herein is administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist.

In another embodiment, one of the active compounds described herein is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In certain embodiments, the prostate or testicular cancer is androgen-resistant.

In certain embodiments, the compounds described herein inhibit cyclin dependent kinase ("CDK"). For example, a compound described in the present invention provides a dose-dependent G1-arresting effect on a subject's CDK replication dependent healthy cells, for example HSPCs or renal epithelial cells. The methods provided for herein are sufficient to afford chemoprotection to targeted CDK replication dependent healthy cells during chemotherapeutic agent exposure, for example, during the time period that a DNA-damaging chemotherapeutic agent is capable of DNA-damaging effects on CDK replication dependent healthy cells in the subject.

In certain embodiments, the administration of a compound using a method described herein is combined with the use of a hematopoietic growth factor including, but not limited to, granulocyte colony stimulating factor (G-CSF), granulocyte-macrophage colony stimulating factor (GM-CSF), thrombopoietin, interleukin (IL)-12, steel factor, and erythropoietin (EPO), or their derivatives. In certain embodiments, the compound is administered prior to administration of the hematopoietic growth factor. In certain embodiments, the hematopoietic growth factor administration is timed so that the compound's effect on HSPCs has dissipated.

In certain embodiments, a compound described herein is administered in combination with a BTK inhibitor. In another embodiment, a compound described herein is administered in combination with an EGFR inhibitor.

The present invention also provides advantageous methods to treat a patient with a selective CDK4/6 inhibitor resistant cancer, which includes administering an effective amount of a compound of Formula I, Formula II, Formula III, Formula IV, Formula V, Formula VI, Formula VII, Formula VIII, Formula IX, or Formula X or a pharmaceutically acceptable composition, salt, or isotopic analog thereof. In certain aspects, a compound of the present invention, is used to treat a patient with a cancer intrinsically resistant to selective CDK4/6 inhibition. In certain aspects, a compound of the present invention, is used to treat a patient with a cancer that has acquired resistance to one or more selective CDK4/6 inhibitors. In certain aspects, a compound of the present invention, is administered in combination with a selective CDK4/6 inhibitor to a patient with a CDK4/6 inhibition responsive cancer in order to extend the therapeutic effectiveness of cell-cycle inhibition in the cancer.

Likewise, cancers initially susceptible to selective CDK4/6 inhibitor inhibition, such as ER+ breast cancer, may acquire resistance to selective CDK4/6 inhibition by upregulation of cyclin E which allows G1 to S cell cycle progression through CDK2. Thus, a compound of the present invention can be used in an effective amount to treat patients with a cancer that has developed selective CDK4/6 inhibitor resistance over time, either due to prior exposure to a CDK 4/6 inhibitor or through a natural progression of the tumor. Accordingly, the invention includes methods of administering an effective amount of a compound of the present invention to treat a patient with a cancer initially responsive to selective CDK4/6 inhibition or susceptible to selective CDK4/6 inhibition that extend the efficacy of the selective CDK4/6 inhibitor treatment against a CDK4/6 responsive cancer by delaying acquired resistance to the inhibitory effects of the selective CDK4/6 inhibitor.

In a particular aspect, the present invention provides methods for treating a patient with cancer that has developed acquired resistance to a selective CDK4/6 inhibitor by administering to the patient an effective amount of a compound of the present invention. In some embodiments, the selective CDK4/6 inhibitor to which the cancer has developed resistance is selected from palbociclib, abemaciclib, lerociclib, trilaciclib, SH6390, and ribociclib.

In certain aspects the invention is a method of treating a patient with cancer by administering a therapeutically effective amount of a compound of the present invention, in combination with a selective CDK 4/6 inhibitor, wherein the patient is selective CDK4/6 inhibitor treatment naïve. By administering a compound of the present invention, in combination with a selective CDK 4/6 inhibitor, a delay in the onset of selective CDK4/6 inhibitor acquired resistance may be realized. In some embodiments, the selective CDK4/6 inhibitor administered in combination with a compound of the present invention, is selected from palbociclib, abemaciclib, ribociclib, trilaciclib, SHR6390, and lerociclib.

In certain aspects of the invention, a method of treating a patient with cancer is provided that includes administering a therapeutically effective amount of a compound of the present invention, wherein the patient has previously received a selective CDK4/6 inhibitor, and the cancer has become selective CDK4/6 inhibitor resistant. By administering a compound of the present invention, following the development of selective CDK 4/6 inhibitor resistance, the current methods allow continued use of cell-cycle inhibition to treat the cancer. In some embodiments, the selective CDK4/6 inhibitor to which the cancer has developed resistance is selected from palbociclib, abemaciclib, ribociclib, trilaciclib, SHR6390, and lerociclib.

In one alternative aspect, the invention is a method of treating a patient with an Rb-positive cancer which includes:

a) administering to the patient a selective CDK4/6 inhibitor;
b) monitoring the patient's cyclin E levels in the cancer; and,
c) administering to the patient a compound of Formula I, Formula II, Formula III, Formula IV, Formula V, Formula VI, Formula VII, Formula VIII, Formula IX, or Formula X upon the detection of an increase in cyclin E levels that confers resistance upon the cancer to the inhibitory effects of the selective CDK4/6 inhibitor. In some embodiments, the selective CDK4/6 inhibitor administered is selected from palbociclib, abemaciclib, ribociclib, trilaciclib, SHR6390, and lerociclib.

In one alternative aspect, the invention is a method of treating a patient with cancer which includes:

a) determining the cancer's Rb-status;
b) if the Rb-status is positive, administering to the patient a selective CDK4/6 inhibitor in combination with a compound of Formula I, Formula II, Formula III, Formula IV, Formula V, Formula VI, Formula VII, Formula VIII, Formula IX, or Formula X;
c) if the Rb-status is negative, administering to the patient a compound of Formula I, Formula II, Formula III, Formula IV, Formula V, Formula VI, Formula VII, Formula VIII, Formula IX, or Formula X, without a selective CDK 4/6 inhibitor.

In some embodiments, the selective CDK4/6 inhibitor administered in combination with a compound of Formula I, Formula II, Formula III, Formula IV, Formula V, Formula VI, Formula VII, Formula VIII, Formula IX, or Formula X, is selected from palbociclib, abemaciclib, ribociclib, trilaciclib, SHR6390, and lerociclib.

In one alternative aspect, the invention is a method of treating a patient with an abnormal cellular proliferations such as cancer which includes:

a) administering to the patient a selective CDK4/6 inhibitor;
b) monitoring the patient's cancer's response to the selective CDK4/6 inhibitor;
c) administering to the patient a compound of Formula I, Formula II, Formula III, Formula IV, Formula V, Formula VI, Formula VII, Formula VIII, Formula IX, or Formula X, upon the detection of the patient's cancer becoming non-responsive to the selective CDK4/6 inhibitor.

In some embodiments, the CDK4/6 inhibitor administered in combination with a compound of Formula I, Formula II, Formula III, Formula IV, Formula V, Formula VI, Formula VII, Formula VIII, Formula IX, or Formula X, is selected from palbociclib, abemaciclib, ribociclib, trilaciclib, SHR6390, and lerociclib. In some embodiments, the non-responsiveness is disease progression.

In another alternative aspect, the invention is a method of treating a patient with an abnormal cellular proliferation, for example cancer, which includes:

a) administering to the patient a selective CDK4/6 inhibitor;
b) monitoring one or more cellular signals indicating the development of selective CDK4/6 inhibitor resistance in the cancer;
c) administering to the patient a compound of Formula I, Formula II, Formula III, Formula IV, Formula V, Formula VI, Formula VII, Formula VIII, Formula IX, or Formula X, if one or more cellular signals indicate the development of selective CDK4/6 inhibitor resistance in the cancer. In some embodiments, the selective CDK4/6 inhibitor administered is selected from palbociclib, abemaciclib, ribociclib, trilaciclib, SHR6390, and lerociclib.

In some embodiments, one or more cellular signals indicating the development of selective CDK4/6 inhibitor resistance in the cancer is selected from an increase in cyclin E expression, CCNE1/2 amplification, E2F amplification, CDK2 amplification, amplification of CDK6, amplification of CDK4, p16 amplification, WEE1 overexpression, DM2 overexpression, CDK7 overexpression, loss of FZR1, HDAC activation, activation of the FGFR pathway, activation of the PI3K/AKT/mTOR pathway, loss of ER or PR expression, higher transcriptional activity of AP-1, epithelial-mesenchymal transition, Smad 3 suppression, autophagy activation, Rbl-loss, and inactivating RB1 mutations.

In another alternative aspect, the invention is a pharmaceutically acceptable composition comprising a compound of Formula I, Formula II, Formula III, Formula IV, Formula V, Formula VI, Formula VII, Formula VIII, Formula IX, or Formula X, and a selective CDK4/6 inhibitor, for example but not limited to one selected from palbociclib, abemaciclib, ribociclib, trilaciclib, SHR6390, and lerociclib.

In yet another embodiment, a method for the treatment of a disorder of abnormal cellular proliferation in a host such as a human is provided that includes administering an effective amount of a combination a compound of Formula I, Formula II, Formula III, Formula IV, Formula V, Formula VI, Formula VII, Formula VIII, Formula IX, or Formula X, and a selective CDK4/6 inhibitor in combination or alternation with an additional active compound. In certain aspects of the invention, the additional active compound is a chemotherapeutic agent. In another aspect of this embodiment, the additional active compound is an immune modulator, including but not limited to a checkpoint inhibitor such as an anti-PD1, anti-PD-L1, anti-CTLA, anti-LAG-3, anti-Tim, etc. antibody, small molecule, peptide, nucleotide or other inhibitor including but not limited to ipilimumab (Yervoy), pembrolizumab (Keytruda) nivolumab (Opdivo), cemiplimab (Libtayo), atezolizumab (Tecentriq), avelumab (Bavencio), and durvalumab (Imfinzi).

In yet another embodiment, a compound of the present invention, in combination with a selective CDK4/6 inhibitor, is administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist.

In another embodiment, a compound of the present invention, in combination with a selective CDK4/6 inhibitor, is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In some embodiments, the prostate or testicular cancer is androgen-resistant.

In some embodiments, a compound of the present invention, in combination with a CDK4/6 inhibitor, is administered in an effective amount in combination with a BTK inhibitor. In another embodiment, a compound of the present invention, in combination with a CDK4/6 inhibitor, is administered in an effective amount in combination with an EGFR inhibitor.

In certain embodiments the compound of the present invention inhibits CDK2, CDK4, CDK6, and/or CDK9. In certain embodiments the compound is a CDK2 inhibitor. In certain embodiments the compound is a CDK4 inhibitor. In certain embodiments the compound is a CDK6 inhibitor. In certain embodiments the compound is a CDK9 inhibitor.

The present invention thus includes at least the following features:

(a) a compound of the present invention as described herein, or a pharmaceutically acceptable salt thereof;

(b) a compound of the present invention as described herein, or a pharmaceutically acceptable salt thereof that is useful in an effective amount to treat a disorder of abnormal cellular proliferation, including a tumor or cancer;

(c) a compound of the present invention as described herein, or a pharmaceutically acceptable salt thereof that is useful in the treatment of cancer that is resistant to treatment with a compound that is a CDK4/6 inhibitor for example treatment with palbociclib, abemaciclib, or ribociclib;

(d) use of a compound of the present invention, or a pharmaceutically acceptable salt thereof in the manufacture of a medicament for the treatment of a disorder of abnormal cellular proliferation, such as a tumor or cancer;

(e) use of a compound of the present invention, or a pharmaceutically acceptable salt thereof in the manufacture of a medicament for the treatment of a cancer that is resistant to treatment with a compound that is a CDK4/6 inhibitor for example treatment with palbociclib, abemaciclib, or ribociclib;

(f) a method for manufacturing a medicament intended for the therapeutic use of treating a disorder of abnormal cellular proliferation including a tumor or cancer, characterized in that a compound of the present invention as described herein is used in the manufacture;

(q) a pharmaceutical formulation comprising an effective host-treating amount of the compound of the present invention or a pharmaceutically acceptable salt thereof together with a pharmaceutically acceptable carrier or diluent;

(r) a compound of the present invention as described herein as a mixture of enantiomers or diastereomers (as relevant), including as a racemate;

(s) a compound of the present invention as described herein in enantiomerically or diastereomerically (as relevant) enriched form, including as an isolated enantiomer or disastereomer (i.e., greater than 85, 90, 95, 97 or 99% pure);

(t) a process for the preparation of therapeutic products that contain an effective amount of a compound of the present invention, as described herein.

(u) a solid dosage form of a compound of the present invention or its pharmaceutically acceptable salt in a pharmaceutically acceptable carrier for oral delivery;

(v); a parenteral dosage form of a compound of the present invention or its pharmaceutically acceptable salt in a pharmaceutically acceptable carrier for systemic delivery, including via intravenous delivery; and (w) a method for manufacturing a medicament intended for anti-neoplastic therapy, characterized in that a compound of the present invention as described herein is used in the manufacture.

DETAILED DESCRIPTION

I. COMPOUNDS

In certain embodiments, the compound of the present invention is of formula:

(I-1)

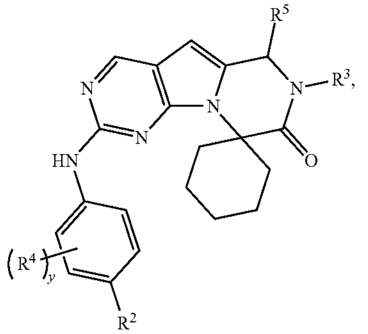

(II-1)

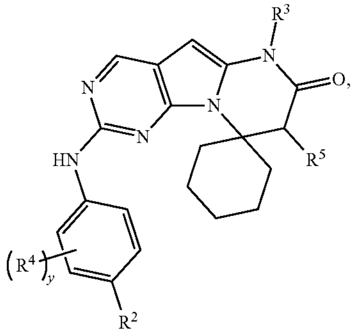

(III-1)

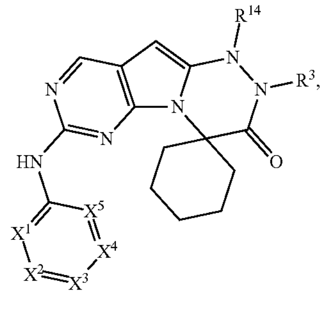

-continued (IV-1)

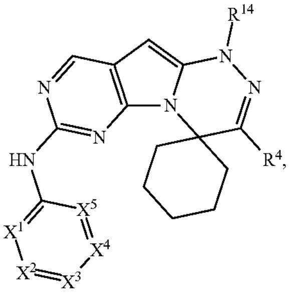

or (V-1)

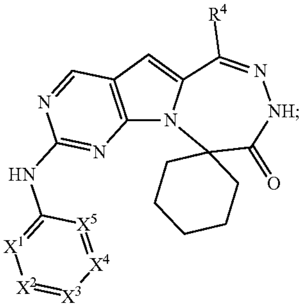

or a pharmaceutically acceptable salt, N-oxide, isotopic analog, and/or a pharmaceutically acceptable composition thereof; wherein y is 0, 1, 2, 3, or 4 and the remaining variables are as defined herein.

In certain embodiments, the compound of the present invention is of formula:

(I-2)

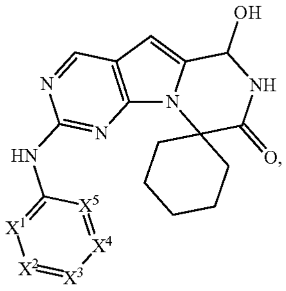

(II-2)

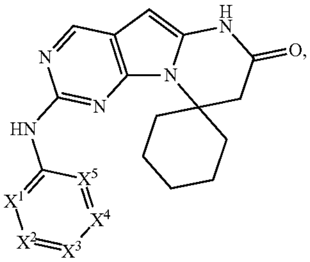

-continued (III-2)

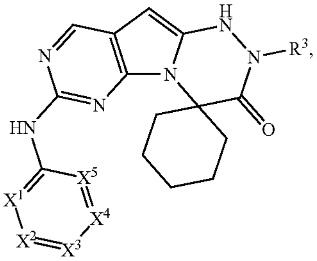

(IV-2)

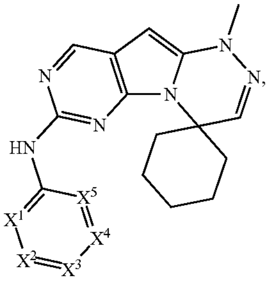

or (V-2)

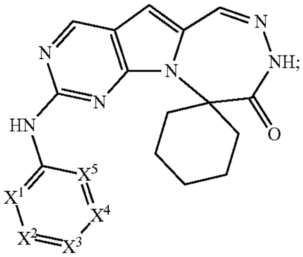

or a pharmaceutically acceptable salt, N-oxide, isotopic analog, and/or a pharmaceutically acceptable composition thereof; wherein the variables are as defined herein.

In certain embodiments, the compound of the present invention is of formula:

(I-3)

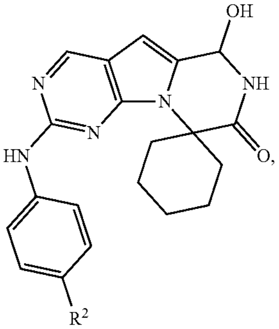

-continued
(II-3)
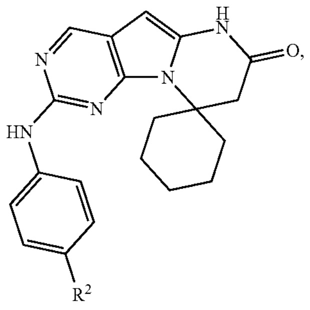
(III-3)
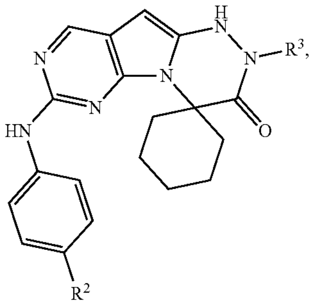
(IV-3)
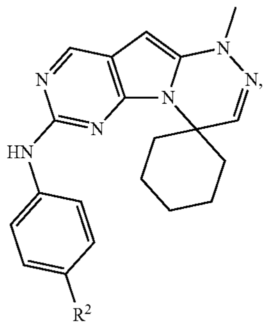
or
(V-3)
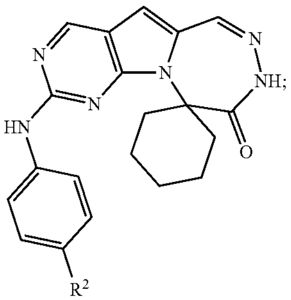
or a pharmaceutically acceptable salt, N-oxide, isotopic analog, and/or a pharmaceutically acceptable composition thereof; wherein the variables are as defined herein.
In certain embodiments, the compound of the present invention is of formula:
(I-4)
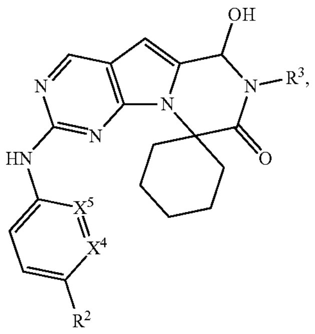
(II-4)
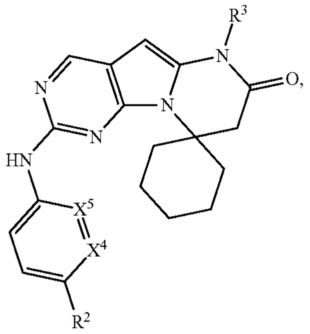
(III-4)
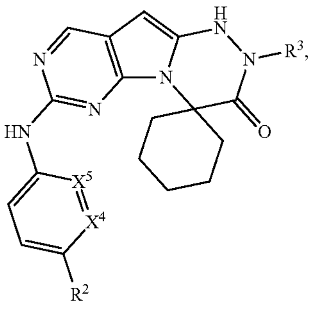
(IV-4)
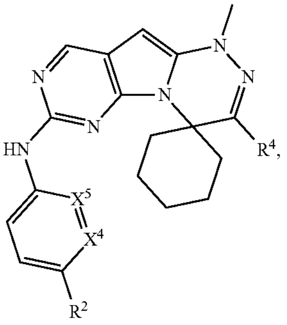
or
(V-4)
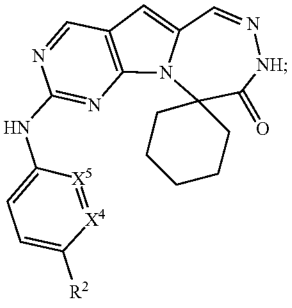

or a pharmaceutically acceptable salt, N-oxide, isotopic analog, and/or a pharmaceutically acceptable composition thereof; wherein the variables are as defined herein.

In certain embodiments, the compound of the present invention is of formula:

(I-5)

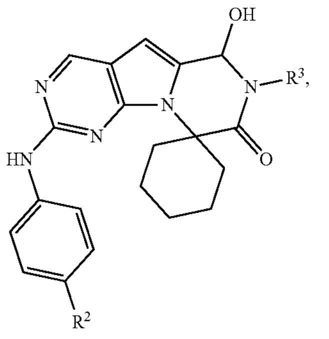

(II-5)

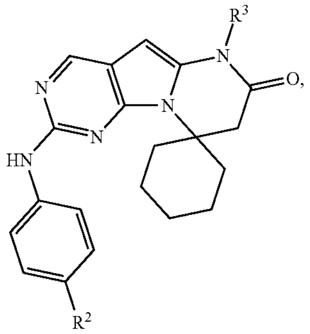

(III-5)

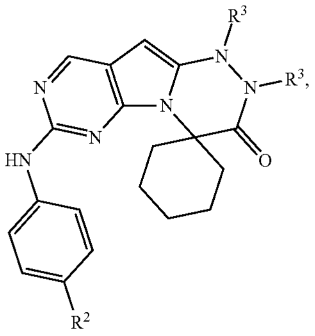

(IV-5)

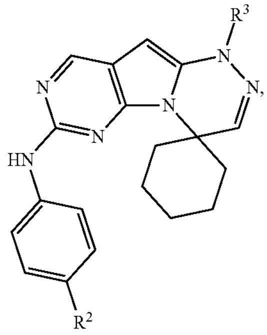

or

-continued (V-5)

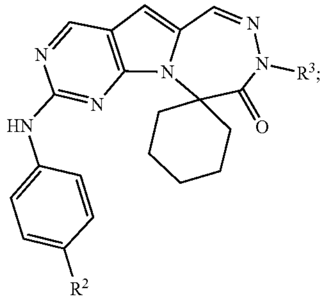

or a pharmaceutically acceptable salt, N-oxide, isotopic analog, and/or a pharmaceutically acceptable composition thereof; wherein the variables are as defined herein.

In certain embodiments, the compound of the present invention is of formula:

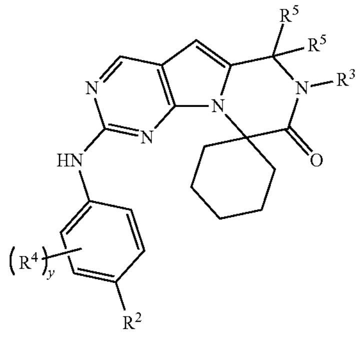

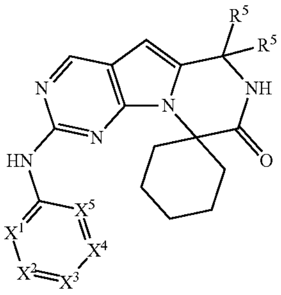

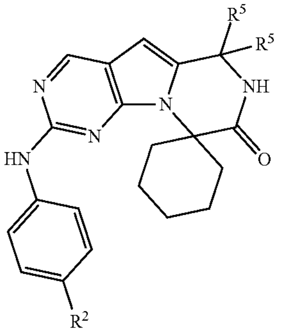

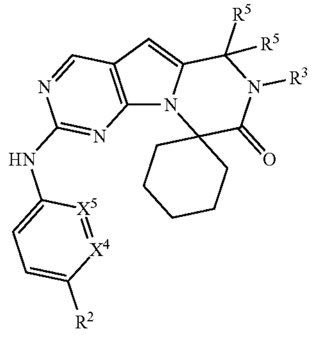

-continued

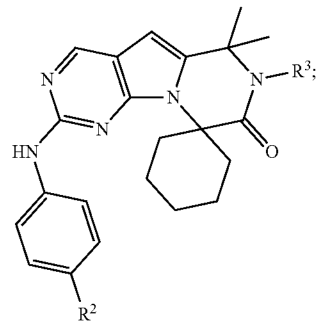

or a pharmaceutically acceptable salt, N-oxide, isotopic analog, and/or a pharmaceutically acceptable composition thereof; wherein the variables are as defined herein.

In certain embodiments, the compound of the present invention is selected from:

(VI-1)

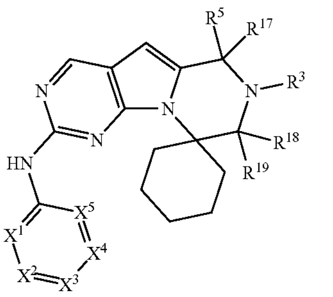

(VII-1)

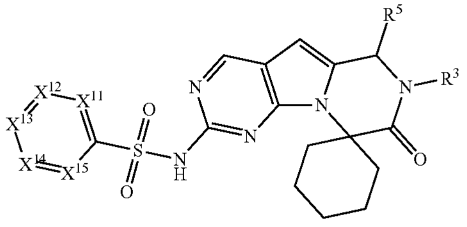

(VIII-1)

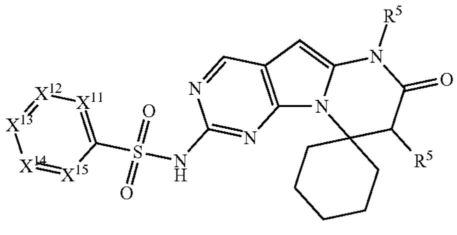

(IX-1)

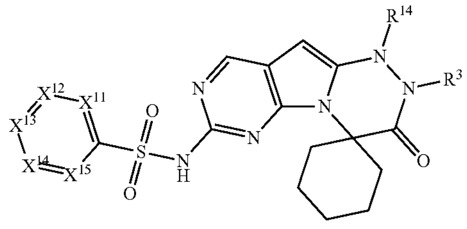

-continued (X-1)

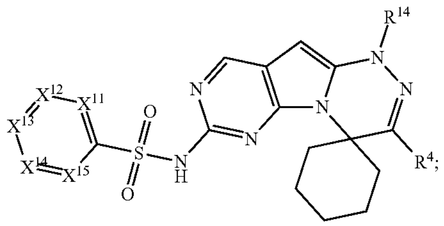

or a pharmaceutically acceptable salt thereof.

In certain embodiments, the compound of the present invention is selected from:

(VI-2)

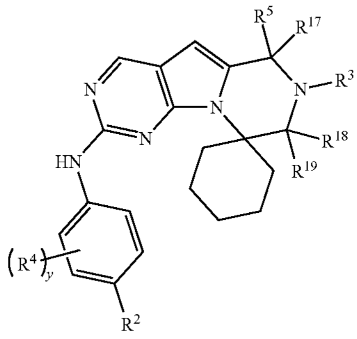

(VII-2)

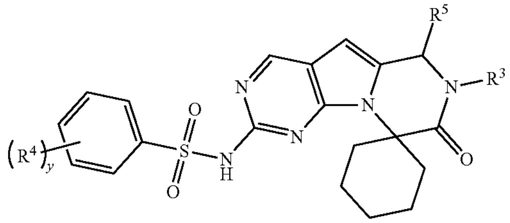

(VIII-2)

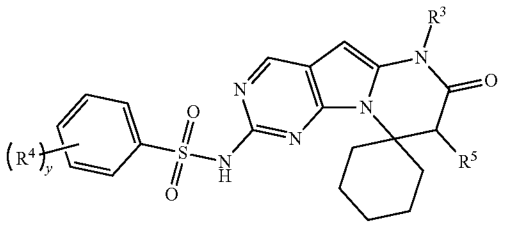

(IX-2)

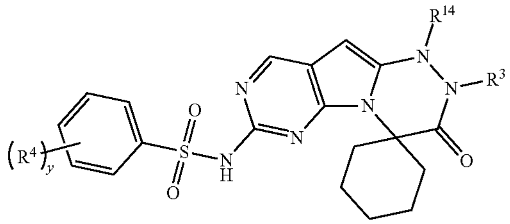

-continued (X-2)

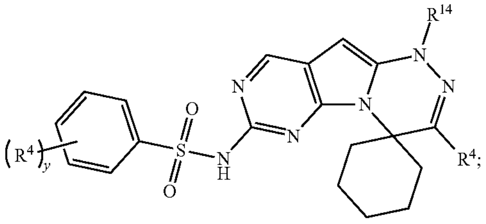

or a pharmaceutically acceptable salt thereof.

In certain embodiments, the compound of the present invention is selected from:

(VI-3)

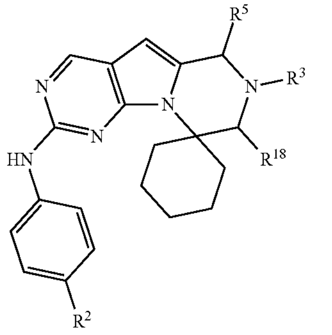

(VII-3)

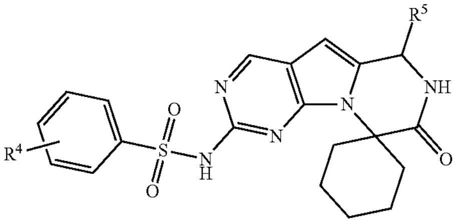

(VIII-3)

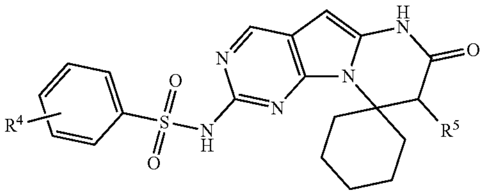

(IX-3)

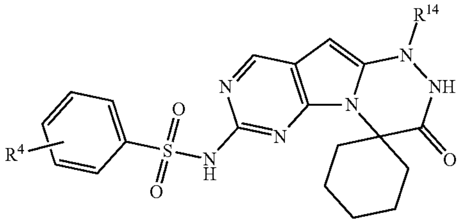

(X-3)

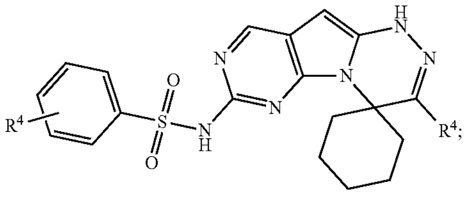

or a pharmaceutically acceptable salt thereof.

Embodiments of "Alkyl"

In certain embodiments, "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In certain embodiments, "alkyl" has one carbon.

In certain embodiments, "alkyl" has two carbons.

In certain embodiments, "alkyl" has three carbons.

In certain embodiments, "alkyl" has four carbons.

In certain embodiments, "alkyl" has five carbons.

In certain embodiments, "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In certain embodiments, "alkyl" is "substituted alkyl."

In certain embodiments, "alkenyl" is "substituted alkenyl."

In certain embodiments, "alkynyl" is "substituted alkynyl."

Embodiments of "Haloalkyl"

In certain embodiments "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In certain embodiments, "haloalkyl" has one carbon.

In certain embodiments, "haloalkyl" has one carbon and one halogen.

In certain embodiments, "haloalkyl" has one carbon and two halogens.

In certain embodiments, "haloalkyl" has one carbon and three halogens.

In certain embodiments, "haloalkyl" has two carbons.

In certain embodiments, "haloalkyl" has three carbons.

In certain embodiments, "haloalkyl" has four carbons.

In certain embodiments, "haloalkyl" has five carbons.

In certain embodiments, "haloalkyl" has six carbons.

Non-limiting examples of "haloalkyl" include:

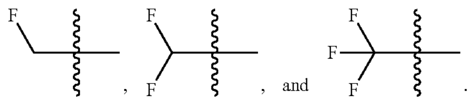

Additional non-limiting examples of "haloalkyl" include:

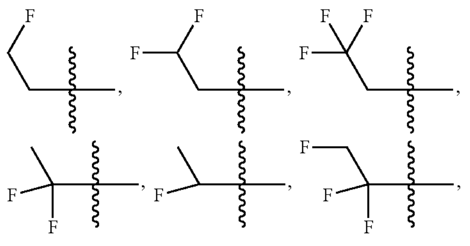

-continued

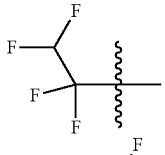, 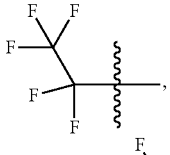, 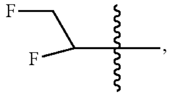, 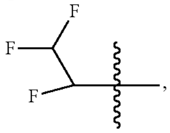, and 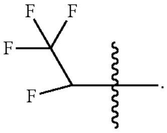.

Additional non-limiting examples of "haloalkyl" include:

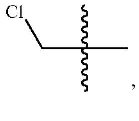, 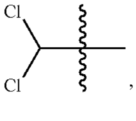, and 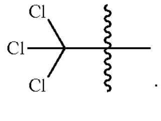.

Additional non-limiting examples of "haloalkyl" include:

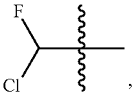, 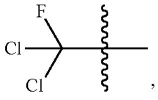, and 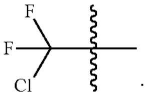.

Embodiments of "Aryl"

In certain embodiments, "aryl" is a 6 carbon aromatic group (phenyl).

In certain embodiments, "aryl" is a 10 carbon aromatic group (napthyl).

In certain embodiments, "aryl" is a 6 carbon aromatic group fused to a heterocycle; wherein the point of attachment is the aryl ring. Non-limiting examples of "aryl" include indoline, tetrahydroquinoline, tetrahydroisoquinoline, and dihydrobenzofuran; and wherein the point of attachment for each group is on the aromatic ring.

For example,

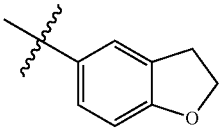 [SMILES: *c1ccc2c(c1)CCO2]

is an "aryl" group.

However,

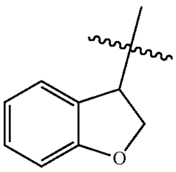 [SMILES: *C1COc2ccccc21]

is a "heterocycle" group.

In certain embodiments, "aryl" is a 6 carbon aromatic group fused to a cycloalkyl wherein the point of attachment is the aryl ring. Non-limiting examples of "aryl" include dihydro-indene and tetrahydronaphthalene wherein the point of attachment for each group is on the aromatic ring.

For example,

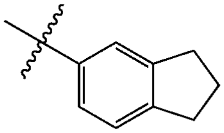 [SMILES: *c1ccc2c(c1)CCC2]

is an "aryl" group.

However,

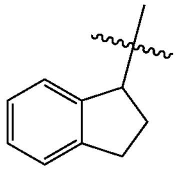 [SMILES: *C1CCc2ccccc21]

is a "cycloalkyl" group.

In certain embodiments, "aryl" is "substituted aryl".

Embodiments of "Heteroaryl"

In certain embodiments, "heteroaryl" is a 5 membered aromatic group containing 1, 2, 3, or 4 nitrogen atoms.

In certain embodiments, "heteroaryl" is a 5 membered aromatic group containing 1, 2, 3, or 4 atoms independently selected from nitrogen and oxygen.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

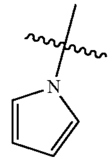, 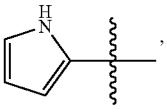, 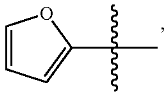, 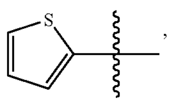, 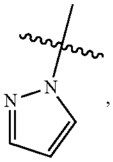, 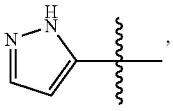, 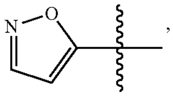, 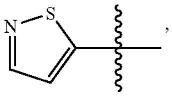, 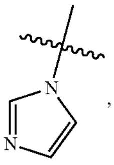, 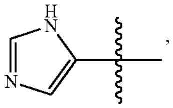, 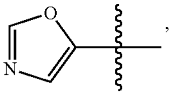, 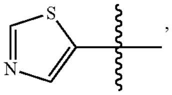, -continued

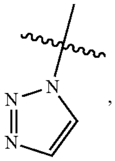, 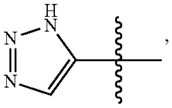, 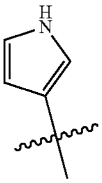, 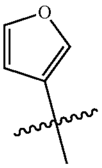,

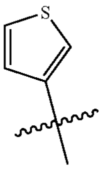, 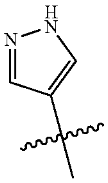, 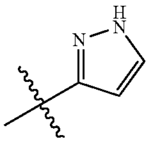, 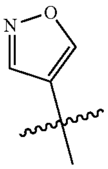,

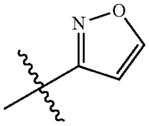, 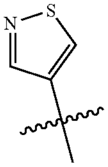, 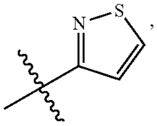,

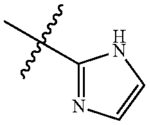, 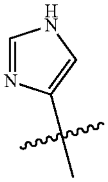, 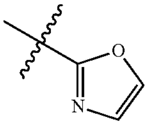, 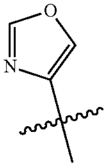,

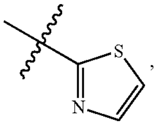, 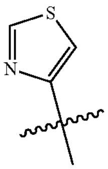, and 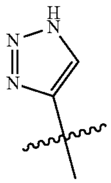.

In certain embodiments, “heteroaryl” is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered “heteroaryl” groups with 1 or 2 nitrogen atoms include:

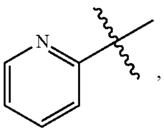, 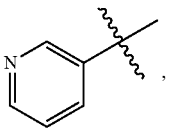, 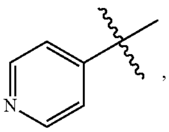,

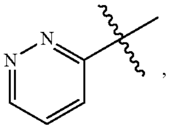, 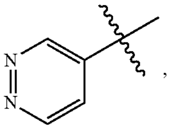, 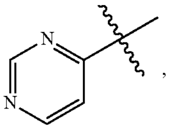,

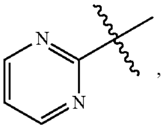, 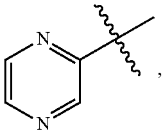, 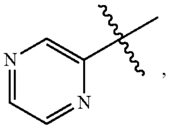, and

-continued

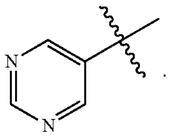.

In certain embodiments, “heteroaryl” is a 9 membered bicyclic aromatic group containing 1 or 2 atoms selected from nitrogen, oxygen, and sulfur.

Non-limiting examples of “heteroaryl” groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of “heteroaryl” groups that are bicyclic include:

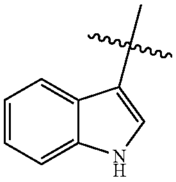, 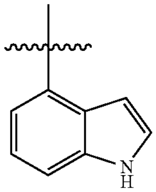,

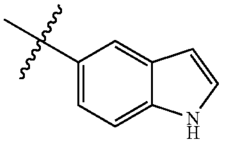, 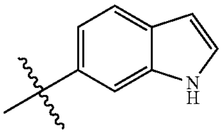,

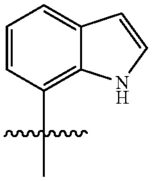, 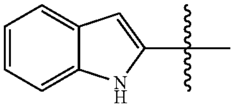, and

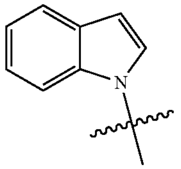.

Additional non-limiting examples of “heteroaryl” groups that are bicyclic include:

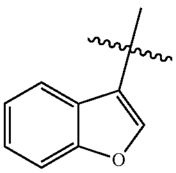, 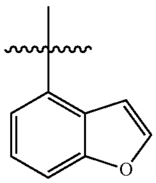,

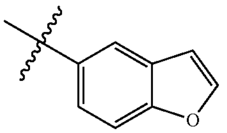, 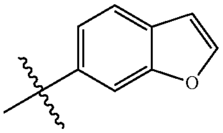,

-continued

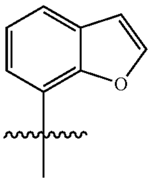, and 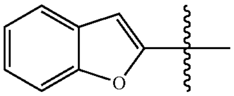.

Additional non-limiting examples of "heteroaryl" groups that are bicyclic include:

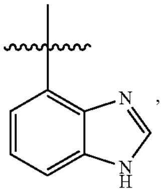, 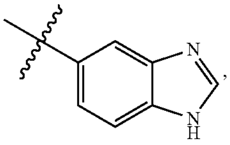, 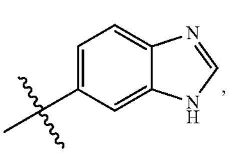, 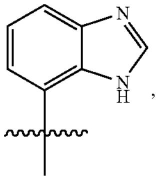, 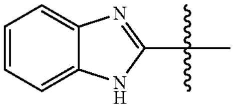, and 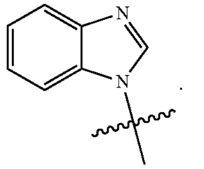.

In certain embodiments, "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

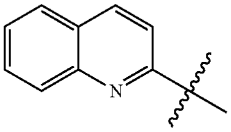, 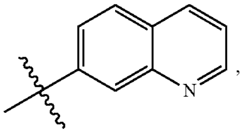, 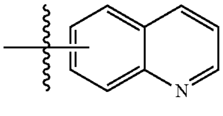, 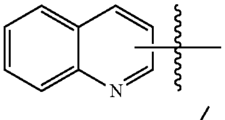, 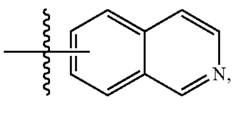, and 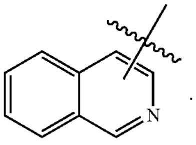.

In certain embodiments, "heteroaryl" is "substituted heteroaryl".

Embodiments of "Cycloalkyl"

In certain embodiments, "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In certain embodiments, "cycloalkyl" has three carbons.

In certain embodiments, "cycloalkyl" has four carbons.

In certain embodiments, "cycloalkyl" has five carbons.

In certain embodiments, "cycloalkyl" has six carbons.

In certain embodiments, "cycloalkyl" has seven carbons.

In certain embodiments, "cycloalkyl" has eight carbons.

In certain embodiments, "cycloalkyl" has nine carbons.

In certain embodiments, "cycloalkyl" has ten carbons.

Non-limiting examples of "cycloalkyl" include: cyclopropyl, cyclobutyl, cyclopentyl, cyclohexyl, cycloheptyl, cyclooctyl, cyclononyl, and cyclodecyl.

Additional non-limiting examples of "cycloalkyl" include dihydro-indene and tetrahydronaphthalene wherein the point of attachment for each group is on the cycloalkyl ring.

For example,

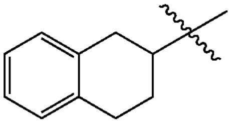 [SMILES: *C1CCc2ccccc2C1]

is an "cycloalkyl" group.

However,

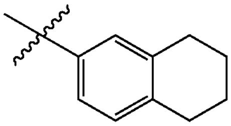 [SMILES: *c1ccc2c(c1)CCCC2]

is an "aryl" group.

In certain embodiments, "cycloalkyl" is a "substituted cycloalkyl".

Embodiments of "Heterocycle"

In certain embodiments, "heterocycle" refers to a cyclic ring with one nitrogen and 3, 4, 5, 6, 7, or 8 carbon atoms.

In certain embodiments, "heterocycle" refers to a cyclic ring with one nitrogen and one oxygen and 3, 4, 5, 6, 7, or 8 carbon atoms.

In certain embodiments, "heterocycle" refers to a cyclic ring with two nitrogens and 3, 4, 5, 6, 7, or 8 carbon atoms.

In certain embodiments, "heterocycle" refers to a cyclic ring with one oxygen and 3, 4, 5, 6, 7, or 8 carbon atoms.

In certain embodiments, "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

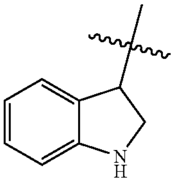 [SMILES: *C1CNc2ccccc21]

is a "heterocycle" group.

However,

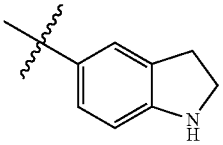 [SMILES: *c1ccc2c(c1)CCN2]

is an "aryl" group.

Non-limiting examples of "heterocycle" also include:

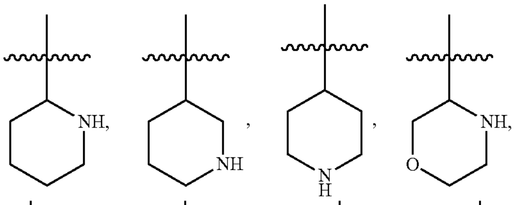

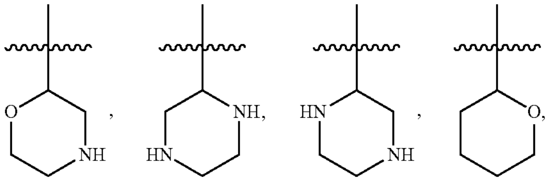

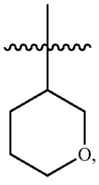 and 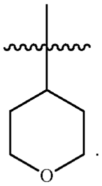

Additional non-limiting examples of "heterocycle" include:

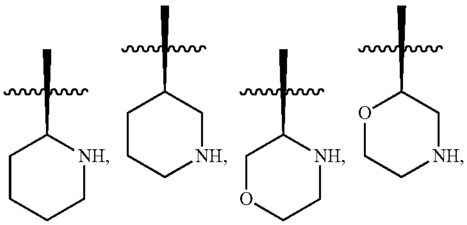

-continued

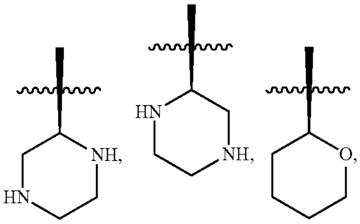 and 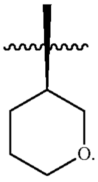

Additional non-limiting examples of "heterocycle" include:

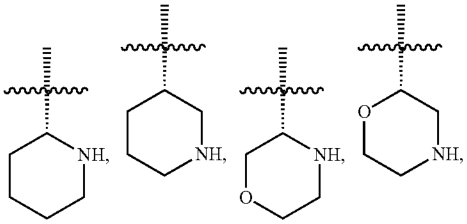

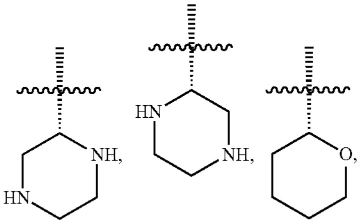 and 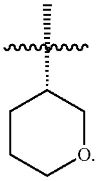

Non-limiting examples of "heterocycle" also include:

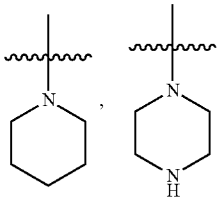 and 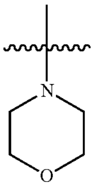

Non-limiting examples of "heterocycle" also include:

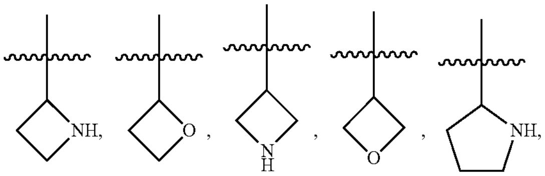

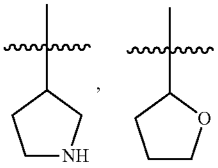 and 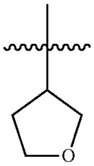

Additional non-limiting examples of "heterocycle" include:

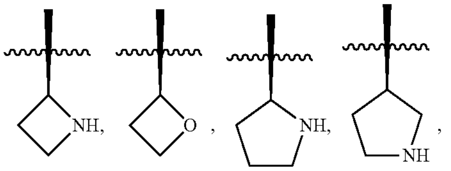

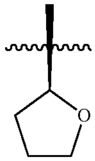

, and

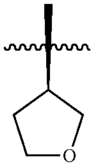

.

Additional non-limiting examples of "heterocycle" include:

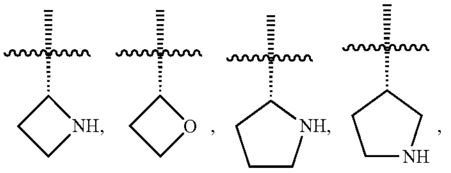

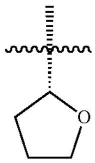

, and

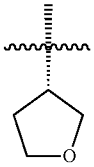

.

In certain embodiments "heterocycle" is "substituted heterocycle".

Embodiments of "-Alkyl-Aryl"

In certain embodiments, the "-alkyl-aryl" refers to a 1 carbon alkyl group substituted with an aryl group.

Non-limiting examples of "-alkyl-aryl" include:

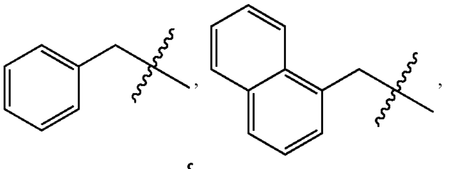

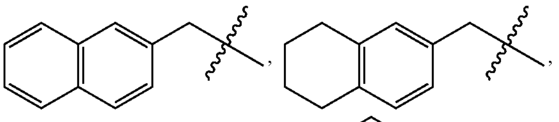

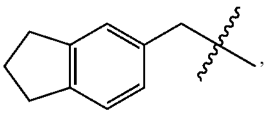

, and

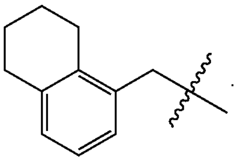

.

In certain embodiments, "-alkyl-aryl" is

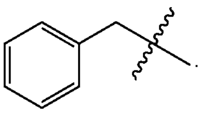 [SMILES: *Cc1ccccc1]

.

In certain embodiments, the "-alkyl-aryl" refers to a 2 carbon alkyl group substituted with an aryl group.

Non-limiting examples of "-alkyl-aryl" include;

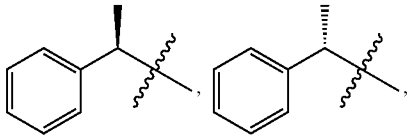

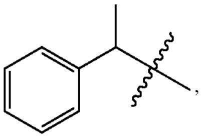

, and

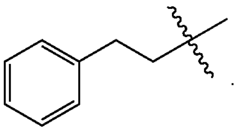

.

In certain embodiments the "alkyl-aryl" refers to a 3 carbon alkyl group substituted with an aryl group.

Optional Substituents

In certain embodiments, a group described herein that can be substituted with 1 or 2 substituents is substituted with one substituent.

In certain embodiments, a group described herein that can be substituted with 1 or 2 substituents is substituted with two substituents.

In certain embodiments, a group described herein that can be substituted with 1, 2, 3, or 4 substituents is substituted with one substituent.

In certain embodiments, a group described herein that can be substituted with 1, 2, 3, or 4 substituents is substituted with two substituents.

In certain embodiments, a group described herein that can be substituted with 1, 2, 3, or 4 substituents is substituted with three substituents.

In certain embodiments, a group described herein that can be substituted with 1, 2, 3, or 4 substituents is substituted with four substituents.

Embodiments of $R^1$

In certain embodiments, one $R^1$ is H and the other $R^1$ is aryl.

In certain embodiments, one $R^1$ is H and the other $R^1$ is phenyl.

In certain embodiments, one $R^1$ is H and the other $R^1$ is alkyl.

In certain embodiments, at least one $R^1$ is hydroxyl.

In certain embodiments, at least one $R^1$ is halogen.

In certain embodiments, at least one $R^1$ is haloalkyl.

In certain embodiments, at least one $R^1$ is fluorine.

In certain embodiments, at least two $R^1$s are fluorine.

In certain embodiments, at least two $R^1$s are alkyl.

In certain embodiments, two $R^1$s combine to form a 5 membered cycloalkyl. In certain embodiments, the cycloalkyl is substituted with one $R^{50}$ substituent. In certain embodiments, the cycloalkyl is substituted with two $R^{50}$ substituents. In certain embodiments, the cycloalkyl is substituted with $NH_2$. In certain embodiments, the cycloalkyl is substituted with $OR^{14}$. In certain embodiments, the cycloalkyl is substituted with OH. In certain embodiments, the cycloalkyl is substituted with alkyl. In certain embodiments, the cycloalkyl is substituted with $CH_3$.

In certain embodiments, two $R^1$s combine to form a 6 membered cycloalkyl. In certain embodiments, the cycloalkyl is substituted with one $R^{50}$ substituent. In certain embodiments, the cycloalkyl is substituted with two $R^{50}$ substituents. In certain embodiments, the cycloalkyl is substituted with $NH_2$. In certain embodiments, the cycloalkyl is substituted with $OR^{14}$. In certain embodiments, the cycloalkyl is substituted with OH. In certain embodiments, the cycloalkyl is substituted with alkyl. In certain embodiments, the cycloalkyl is substituted with $CH_3$.

In certain embodiments, two $R^1$s combine to form a 5 membered heterocycle. In certain embodiments, the heterocycle is substituted with one $R^{50}$ substituent. In certain embodiments, the heterocycle is substituted with two $R^{50}$ substituents. In certain embodiments, the heterocycle is substituted with $NH_2$. In certain embodiments, the heterocycle is substituted with $OR^{14}$. In certain embodiments, the heterocycle is substituted with OH. In certain embodiments, the heterocycle is substituted with alkyl. In certain embodiments, the heterocycle is substituted with $CH_3$.

In certain embodiments, two $R^1$s combine to form a 6 membered heterocycle. In certain embodiments, the heterocycle is substituted with one $R^{50}$ substituent. In certain embodiments, the heterocycle is substituted with two $R^{50}$ substituents. In certain embodiments, the heterocycle is substituted with $NH_2$. In certain embodiments, the heterocycle is substituted with $OR^{14}$. In certain embodiments, the heterocycle is substituted with OH. In certain embodiments, the heterocycle is substituted with alkyl. In certain embodiments, the heterocycle is substituted with $CH_3$.

In certain embodiments, two $R^1$s combine to form a 5-membered spirocycle selected from:

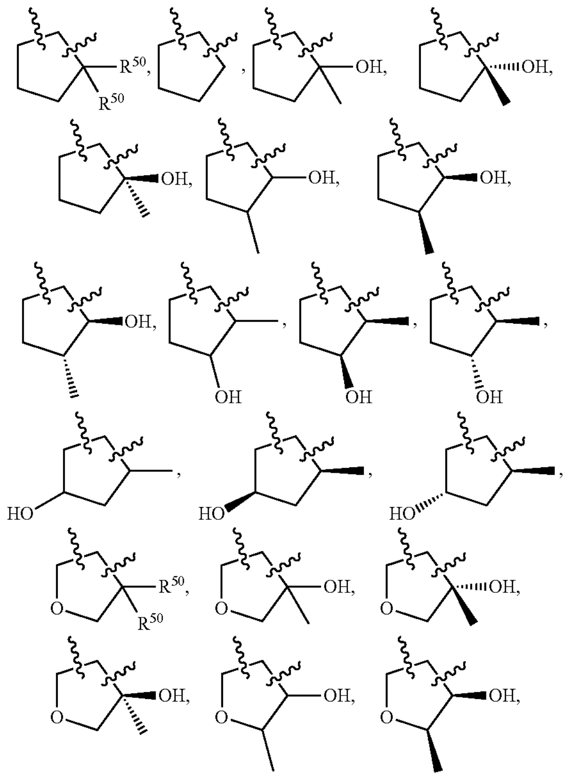

-continued

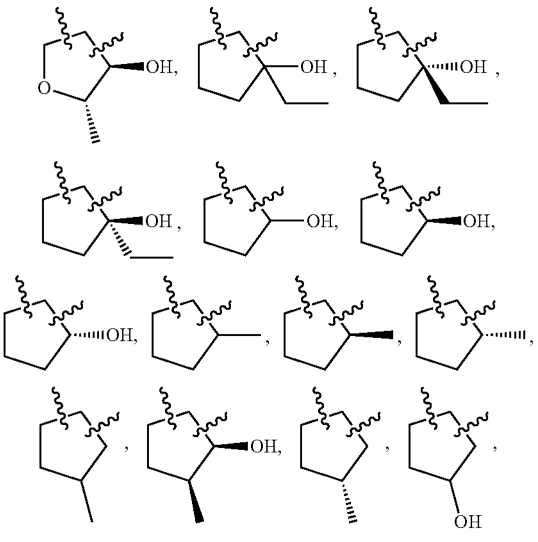

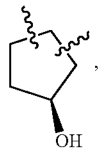

, and

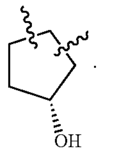

.

In certain embodiments, two $R^1$s combine to form a 6-membered spirocycle selected from:

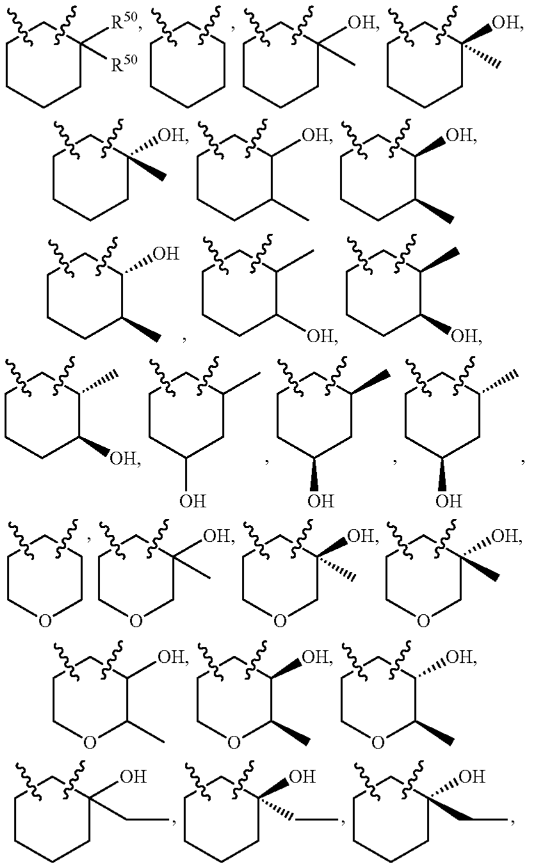

-continued

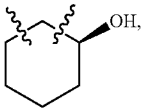 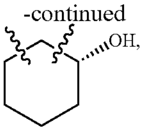 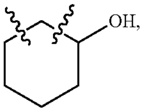

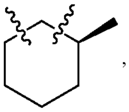, 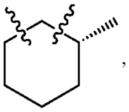, and 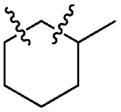.

In certain embodiments, one $R^1$ is hydrogen.

In certain embodiments, one $R^1$ is alkyl.

In certain embodiments, one $R^1$ is $—NR^{12}R^{13}$.

In certain embodiments, one $R^1$ is cycloalkyl.

In certain embodiments, one $R^1$ is heterocycle.

In certain embodiments, one $R^1$ is aryl.

In certain embodiments, one $R^1$ is heteroaryl.

In certain embodiments, $R^1$ is independently hydrogen, halogen, $—OR^{14}$, or $NR^{14}R^{15}$, wherein $R^{14}$ is independently selected from hydrogen, alkyl, $—C(O)R^6$, and —C(O)alkyl; and wherein $R^{15}$ is independently selected from hydrogen and alkyl.

In certain embodiments, $R^1$ is $—OR^{14}$, wherein $R^{14}$ is independently selected from hydrogen, alkyl, and $—C(O)R^6$; wherein $R^6$ is selected independently from hydrogen and alkyl.

In certain embodiments, $R^1$ is $NR^{14}R^{15}$; wherein $R^{14}$ is independently selected from hydrogen, alkyl, $—C(O)R^6$, and —C(O)alkyl; and wherein $R^{15}$ are independently selected from hydrogen and alkyl.

In certain embodiments, two $R^1$s come together with the ring atom to which they are attached to constitute a 3, 4, 5, 6, 7, or 8-membered cycloalkyl or 4, 5, 6, 7, or 8-membered heterocycle that has 1, 2, or 3 heteroatoms selected from N, O, and S.

In certain embodiments, two $R^1$s come together with the ring atom to which they are attached to constitute a 3, 4, 5, 6, 7, or 8-membered cycloalkyl or 4, 5, 6, 7, or 8-membered heterocycle that has 1, 2, or 3 heteroatoms selected from N, O, and S; and wherein the cycloalkyl or heterocycle formed by combining two $R^1$s with the atom to which they are attached can be optionally substituted with 1 or 2 substituents independently selected from $R^{50}$.

Embodiments of $R^2$

In certain embodiments, $R^2$ is $—NR^{14}C(O)R^6$, $—NR^{14}S(O)R^6$, $—NR^{14}S(O)_2R^6$, $—NR^{14}C(S)R^6$, $—OC(O)R^6$, $—OS(O)R^6$, $—OS(O)_2R^6$, $—OC(S)R^6$, $—C(O)R^6$; $—C(S)R^6$, $—S(O)R^6$, or $—S(O)_2R^6$.

In certain embodiments, $R^2$ is $—C(O)R^6$; $—C(S)R^6$, $—S(O)R^6$, or $—S(O)_2R^6$.

In certain embodiments, $R^2$ is $—C(O)R^6$.

In certain embodiments, $R^2$ is $—C(O)NH_2$.

In certain embodiments, $R^2$ is $—C(O)CH_3$.

In certain embodiments, $R^2$ is $—S(O)_2R^6$.

In certain embodiments, $R^2$ is $—S(O)_2NH_2$.

In certain embodiments, $R^2$ is

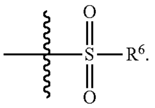

In certain embodiments, $R^2$ is

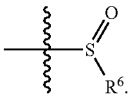

In certain embodiments, $R^2$ is

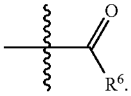

In certain embodiments, $R^2$ is

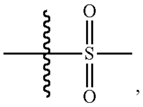, 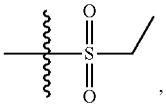, or 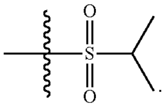.

In certain embodiments, $R^2$ is

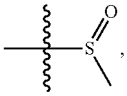, 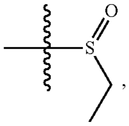, or 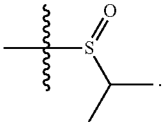.

In certain embodiments, $R^2$ is

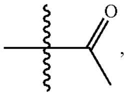, 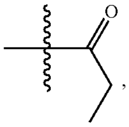, or 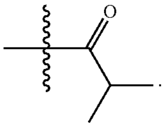.

In certain embodiments, $R^2$ is

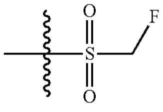 or 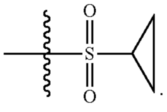.

In certain embodiments, $R^2$ is

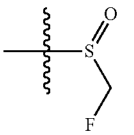 or 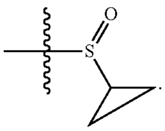.

In certain embodiments, $R^2$ is

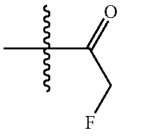

or

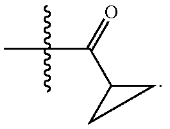

In certain embodiments, $R^2$ is

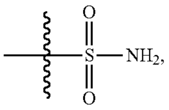

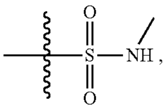

or

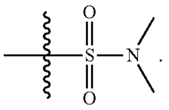

In certain embodiments, $R^2$ is

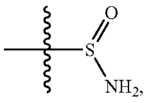

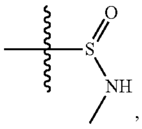

, or

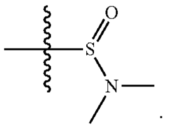

In certain embodiments, $R^2$ is

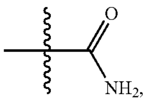

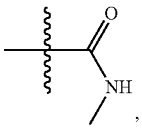

, or

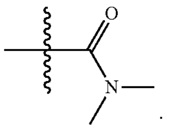

In certain embodiments, $R^2$ is

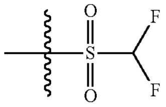

or

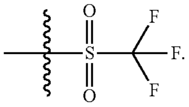

In certain embodiments, $R^2$ is

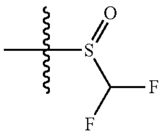

or

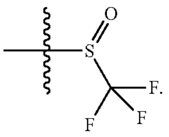

In certain embodiments, $R^2$ is

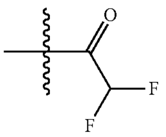

or

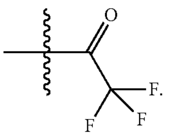

In certain embodiments, $R^2$ is

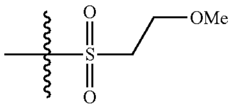

or

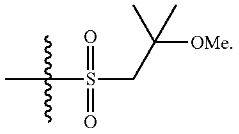

In certain embodiments, $R^2$ is

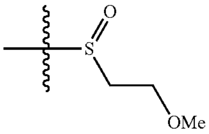

or

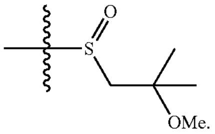

In certain embodiments, $R^2$ is

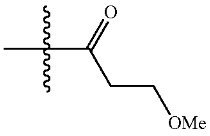

or

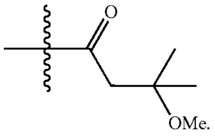

In certain embodiments, $R^2$ is

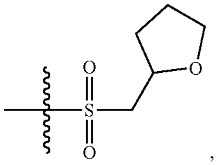

,

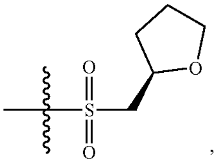

, or

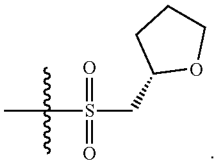

In certain embodiments, $R^2$ is

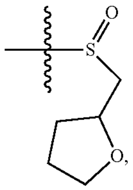

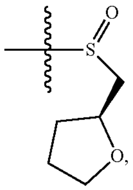

or

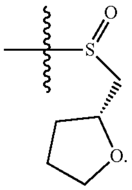

In certain embodiments, $R^2$ is

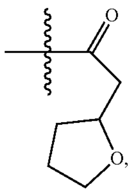

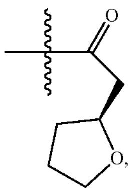

or

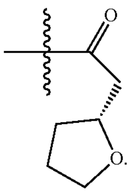

In certain embodiments, $R^2$ is
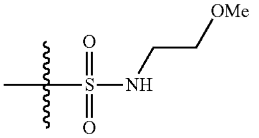
or
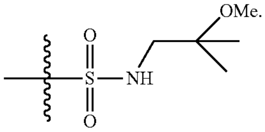
In certain embodiments, $R^2$ is
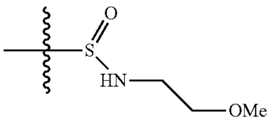
or
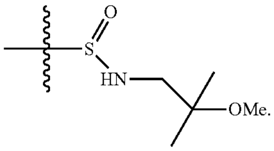
In certain embodiments, $R^2$ is
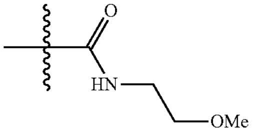
or
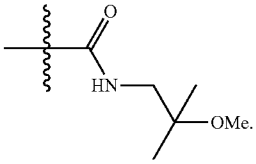
In certain embodiments, $R^2$ is
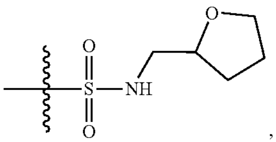
,
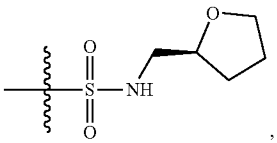
, or
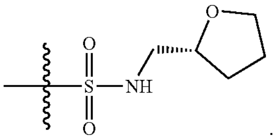
.
In certain embodiments, $R^2$ is
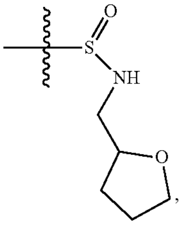
,
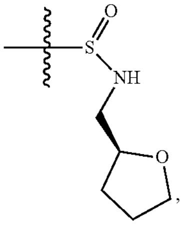
, or
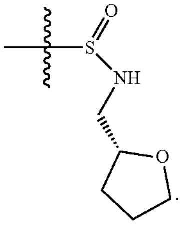
In certain embodiments, $R^2$ is
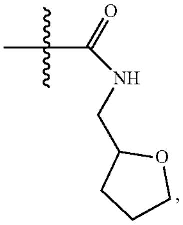
,
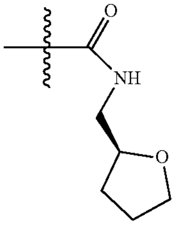
, or
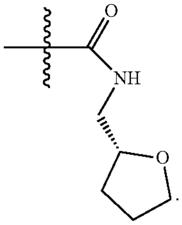
In certain embodiments, $R^2$ is
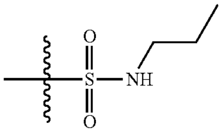
or
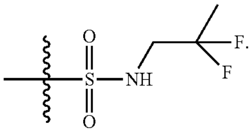
In certain embodiments, $R^2$ is
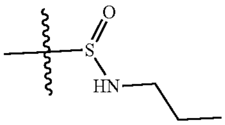
or
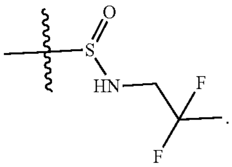

In certain embodiments, $R^2$ is
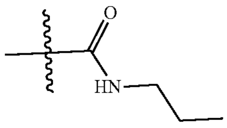 or 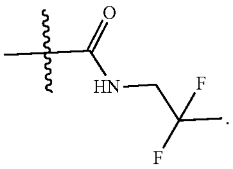
In certain embodiments, $R^2$ is
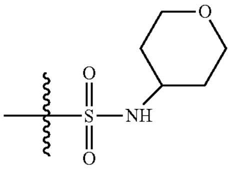 or 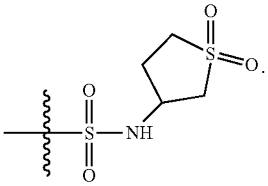
In certain embodiments, $R^2$ is
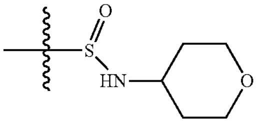 or
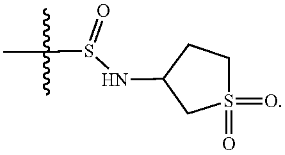
In certain embodiments, $R^2$ is
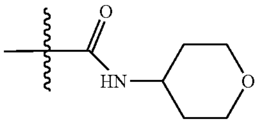 or
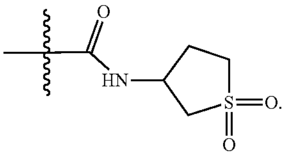
In certain embodiments, $R^2$ is
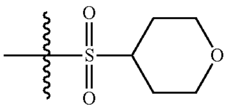 or 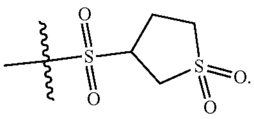
In certain embodiments, $R^2$ is
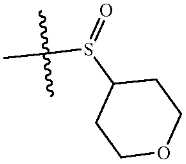 or 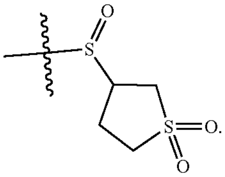
In certain embodiments, $R^2$ is
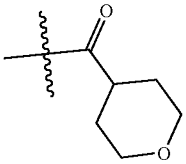 or 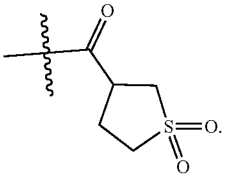
In certain embodiments, $R^2$ is
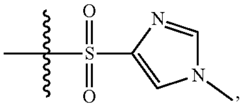, 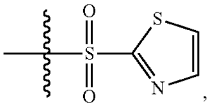, 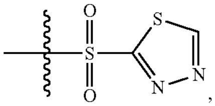, or 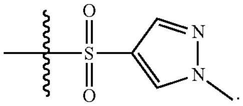
In certain embodiments, $R^2$ is
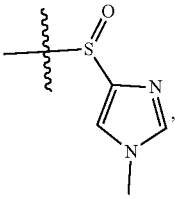, 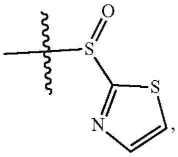, 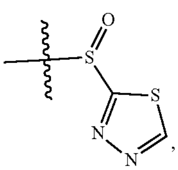, or 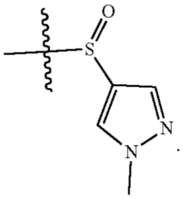
In certain embodiments, $R^2$ is
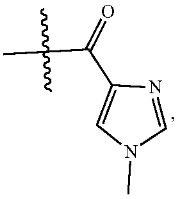, 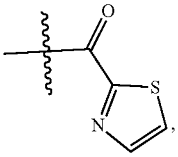, -continued

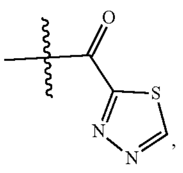

, or

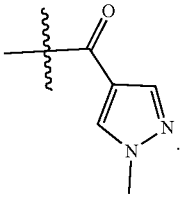

.

Embodiments of $R^3$

In certain embodiments, $R^3$ is hydrogen.

In certain embodiments, $R^3$ is alkyl.

In certain embodiments, $R^3$ is —$NR^{12}R^{13}$.

In certain embodiments, $R^3$ is —S(O)alkyl.

In certain embodiments, $R^3$ is —$SO_2$alkyl.

In certain embodiments, $R^3$ is cycloalkyl.

In certain embodiments, $R^3$ is heterocycle.

In certain embodiments, $R^3$ is aryl.

In certain embodiments, $R^3$ is heteroaryl.

In certain embodiments, $R^3$ is alkyl-aryl.

In certain embodiments, $R^3$ is alkyl-heteroaryl.

Embodiments of $R^4$

In certain embodiments, $R^4$ is hydrogen.

In certain embodiments, $R^4$ is alkyl.

In certain embodiments, $R^4$ is —$NR^{12}R^{13}$.

In certain embodiments, $R^4$ is —S(O)alkyl.

In certain embodiments, $R^4$ is —$SO_2$alkyl.

In certain embodiments, $R^4$ is cycloalkyl.

In certain embodiments, $R^4$ is heterocycle.

In certain embodiments, $R^4$ is aryl.

In certain embodiments, $R^4$ is heteroaryl.

Embodiments of $R^5$

In certain embodiments, $R^5$ is hydrogen.

In certain embodiments, $R^5$ is alkyl.

In certain embodiments, $R^5$ is haloalkyl.

In certain embodiments, $R^5$ is halogen.

In certain embodiments, $R^5$ is cyano.

In certain embodiments, $R^5$ is —$OR^{14}$.

In certain embodiments, $R^5$ is —$NR^{14}R^{15}$.

Embodiments of $R^6$

In certain embodiments, $R^6$ is hydrogen.

In certain embodiments, $R^6$ is alkyl.

In certain embodiments, $R^6$ is alkenyl or alkynyl.

In certain embodiments, $R^6$ is cycloalkyl optionally substituted with 1, 2, 3, or 4 $R^8$ groups.

In certain embodiments, $R^6$ is cycloalkyl.

In certain embodiments, $R^6$ is heterocycle optionally substituted with 1, 2, 3, or 4 $R^8$ groups.

In certain embodiments, $R^6$ is heterocycle.

In certain embodiments, $R^6$ is aryl optionally substituted with 1, 2, 3, or 4 $R^8$ groups.

In certain embodiments, $R^6$ is aryl.

In certain embodiments, $R^6$ is heteroaryl optionally substituted with 1, 2, 3, or 4 $R^8$ groups.

In certain embodiments, $R^6$ is $NR^7R^7$.

In certain embodiments, $R^6$ is $NH_2$.

In certain embodiments, $R^6$ is OH.

In certain embodiments, $R^6$ is $OCH_3$.

Embodiments of $R^7$

In certain embodiments, each $R^7$ is independently selected from hydrogen and alkyl.

In certain embodiments, $R^7$ is hydrogen.

In certain embodiments, $R^7$ is alkyl.

In certain embodiments, $R^7$ is alkenyl or alkynyl.

In certain embodiments, $R^7$ is cycloalkyl optionally substituted with 1, 2, 3, or 4 $R^8$ groups.

In certain embodiments, $R^7$ is cycloalkyl.

In certain embodiments, $R^7$ is heterocycle optionally substituted with 1, 2, 3, or 4 $R^8$ groups.

In certain embodiments, $R^8$ is heterocycle.

In certain embodiments, $R^7$ is aryl optionally substituted with 1, 2, 3, or 4 $R^8$ groups.

In certain embodiments, $R^7$ is aryl.

In certain embodiments, $R^7$ is heteroaryl optionally substituted with 1, 2, 3, or 4 $R^8$ groups.

Embodiments of $R^8$

In certain embodiments, each $R^8$ is independently selected from halogen, haloalkyl, alkyl, $NR^{12}R^{13}$, and $OR^{12}$.

In certain embodiments, each $R^8$ is halogen.

In certain embodiments, each $R^8$ is haloalkyl.

In certain embodiments, each $R^8$ is alkyl.

In certain embodiments, at least one $R^8$ is halogen.

In certain embodiments, at least one $R^8$ is haloalkyl.

In certain embodiments, at least one $R^8$ is alkyl.

In certain embodiments, each $R^8$ is cycloalkyl.

In certain embodiments, at least one $R^8$ is heterocycle.

In certain embodiments, at least one $R^8$ is aryl.

In certain embodiments, at least one $R^8$ is heteroaryl.

In certain embodiments, at least one $R^8$ is —$S(O)_2$alkyl.

In certain embodiments, at least one $R^8$ is $NR^{12}R^{13}$.

In certain embodiments, at least one $R^8$ is alkyl-heteroaryl.

In certain embodiments, at least one $R^8$ is alkyl-aryl.

In certain embodiments, at least one $R^8$ is $OR^{12}$.

In certain embodiments, each $R^8$ is independently selected from hydrogen, halogen, haloalkyl, alkyl, cycloalkyl, heterocycle, aryl, heteroaryl, —$S(O)_2$alkyl, $NR^{12}R^{13}$, alkyl-heteroaryl, alkyl-aryl, and $OR^{12}$.

In certain embodiments, each $R^8$ is independently selected from hydrogen, alkyl, $NR^{12}R^{13}$, alkyl-heteroaryl, alkyl-aryl, and $OR^{12}$.

Embodiments of $R^{12}$ and $R^{13}$

In certain embodiments, each $R^{12}$ and $R^{13}$ are independently selected from hydrogen, and alkyl.

In certain embodiments, both $R^{12}$ and $R^{13}$ are hydrogen.

In certain embodiments, both $R^{12}$ and $R^{13}$ are alkyl.

In certain embodiments, one of $R^{12}$ and $R^{13}$ is hydrogen.

In certain embodiments, one of $R^{12}$ and $R^{13}$ is alkyl.

In certain embodiments, one of $R^{12}$ and $R^{13}$ is —C(O) alkyl.

In certain embodiments, one of $R^{12}$ and $R^{13}$ is —C(S) alkyl.

In certain embodiments, one of $R^{12}$ and $R^{13}$ is aryl.

In certain embodiments, one of $R^{12}$ and $R^{13}$ is —$SO_2$alkyl.

In certain embodiments, one of $R^{12}$ and $R^{13}$ is —S(O) alkyl.

In certain embodiments, one of $R^{12}$ and $R^{13}$ is heteroaryl.

In certain embodiments, one of $R^{12}$ and $R^{13}$ is alkyl-aryl.

In certain embodiments, one of $R^{12}$ and $R^{13}$ is cycloalkyl.

In certain embodiments, one of $R^{12}$ and $R^{13}$ is heterocycle.

In certain embodiments, one of $R^{12}$ and $R^{13}$ is alkyl-heteroaryl.

Embodiments of $R^{14}$ and $R^{15}$

In certain embodiments, each $R^{14}$ and $R^{15}$ are independently selected from hydrogen, and alkyl.

In certain embodiments, both $R^{14}$ and $R^{15}$ are hydrogen.

In certain embodiments, both $R^{14}$ and $R^{15}$ are alkyl.

In certain embodiments, one of $R^{14}$ and $R^{15}$ is hydrogen.

In certain embodiments, one of $R^{14}$ and $R^{15}$ is alkyl.

In certain embodiments, one of $R^{14}$ and $R^{15}$ is —C(O)alkyl.

In certain embodiments, one of $R^{14}$ and $R^{15}$ is —C(S)alkyl.

In certain embodiments, one of $R^{14}$ and $R^{15}$ is aryl.

In certain embodiments, one of $R^{14}$ and $R^{15}$ is —$SO_2$alkyl.

In certain embodiments, one of $R^{14}$ and $R^{15}$ is —S(O)alkyl.

In certain embodiments, one of $R^{14}$ and $R^{15}$ is heteroaryl.

In certain embodiments, one of $R^{14}$ and $R^{15}$ is alkyl-aryl.

In certain embodiments, one of $R^{14}$ and $R^{15}$ is cycloalkyl.

In certain embodiments, one of $R^{14}$ and $R^{15}$ is heterocycle.

In certain embodiments, one of $R^{14}$ and $R^{15}$ is alkyl-heteroaryl.

Embodiments of $R^{17}$ and $R^{18}$

In certain embodiments, each $R^{17}$ is independently selected from hydrogen and alkyl.

In certain embodiments, $R^{17}$ is hydrogen.

In certain embodiments, $R^{17}$ is alkyl.

In certain embodiments, $R^{17}$ is alkenyl or alkynyl.

In certain embodiments, $R^{17}$ is cycloalkyl optionally substituted with 1, 2, 3, or 4 $R^8$ groups.

In certain embodiments, $R^{17}$ is cycloalkyl.

In certain embodiments, $R^{17}$ is heterocycle optionally substituted with 1, 2, 3, or 4 $R^8$ groups.

In certain embodiments, $R^{17}$ is heterocycle.

In certain embodiments, $R^{17}$ is aryl optionally substituted with 1, 2, 3, or 4 $R^8$ groups.

In certain embodiments, $R^{17}$ is aryl.

In certain embodiments, $R^{17}$ is heteroaryl optionally substituted with 1, 2, 3, or 4 $R^8$ groups.

In certain embodiments, each $R^{18}$ is independently selected from hydrogen and alkyl.

In certain embodiments, $R^{18}$ is hydrogen.

In certain embodiments, $R^{18}$ is alkyl.

In certain embodiments, $R^{18}$ is alkenyl or alkynyl.

In certain embodiments, $R^{18}$ is cycloalkyl optionally substituted with 1, 2, 3, or 4 $R^8$ groups.

In certain embodiments, $R^{18}$ is cycloalkyl.

In certain embodiments, $R^{18}$ is heterocycle optionally substituted with 1, 2, 3, or 4 $R^8$ groups.

In certain embodiments, $R^{18}$ is heterocycle.

In certain embodiments, $R^{18}$ is aryl optionally substituted with 1, 2, 3, or 4 $R^8$ groups.

In certain embodiments, $R^{18}$ is aryl.

In certain embodiments, $R^{18}$ is heteroaryl optionally substituted with 1, 2, 3, or 4 $R^8$ groups.

Embodiments of $R^{19}$

In certain embodiments, $R^{19}$ is hydrogen.

In certain embodiments, $R^{19}$ is alkyl.

In certain embodiments, $R^{19}$ is haloalkyl.

In certain embodiments, $R^{19}$ is halogen.

In certain embodiments, $R^{19}$ is cyano.

In certain embodiments, $R^{19}$ is —$OR^{14}$.

In certain embodiments, $R^{19}$ is —$NR^{14}R^{15}$.

Embodiments of $R^{50}$

In certain embodiments, each $R^{50}$ is independently selected from amino, —$NHR^{14}$, —$NR^{14}R^{15}$, hydroxyl, $OR^{14}$, and $R^4$.

In certain embodiments, there is one $R^{50}$ group and it is —$NR^{14}R^{15}$.

In certain embodiments, there is one $R^{50}$ group and it is $OR^{14}$.

In certain embodiments, there is one $R^{50}$ group and it is $R^4$.

Embodiments of $X^1$, $X^2$, $X^3$, $X^4$ and $X^5$

In certain embodiments, each of $X^1$, $X^2$, $X^3$, $X^4$, and $X^5$ is independently CH.

In certain embodiments, at least one of $X^1$, $X^2$, $X^3$, $X^4$, and $X^5$ is N.

In certain embodiments, two of $X^1$, $X^2$, $X^3$, $X^4$, and $X^5$ are N.

In certain embodiments, at least one of $X^1$, $X^2$, $X^3$, $X^4$, and $X^5$ is $CR^4$; wherein $R^4$ is independently hydrogen, alkyl, aryl, cycloalkyl, haloalkyl, heteroaryl, heterocycle, halogen, cyano, —$OR^{14}$, —$NR^{14}R^{15}$, —$NR^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, or —$S(O)_2R^6$.

In certain embodiments, at least one of $X^1$, $X^2$, $X^3$, $X^4$, and $X^5$ is $CR^4$; wherein $R^4$ is $OR^{14}$, —$NR^{14}R^{15}$, —$NR^{14}C(O)R^6$, —$NR^{14}S(O)R^6$, —$NR^{14}S(O)_2R^6$, $S(O)R^6$, or —$S(O)_2R^6$.

In certain embodiments, at least one of $X^1$, $X^2$, $X^3$, $X^4$, and $X^5$ is $CR^4$; wherein $R^4$ is $OR^{14}$, —$NR^{14}R^{15}$, —$NR^{14}S(O)_2R^6$, $S(O)R^6$, or —$S(O)_2R^6$.

In certain embodiments, at least one of $X^1$, $X^2$, $X^3$, $X^4$, and $X^5$ is $CR^4$; wherein $R^4$ is hydrogen, haloalkyl or halogen.

Embodiments of $X^{11}$, $X^{12}$, $X^{13}$, $X^{14}$ and $X^{15}$

In certain embodiments, each of $X^{11}$, $X^{12}$, $X^{13}$, $X^{14}$, and $X^{15}$ is independently CH.

In certain embodiments, at least one of $X^{11}$, $X^{12}$, $X^{13}$, $X^{14}$, and $X^{15}$ is N.

In certain embodiments, two of $X^{11}$, $X^{12}$, $X^{13}$, $X^{14}$, and $X^{15}$ are N.

In certain embodiments, at least one of $X^{11}$, $X^{12}$, $X^{13}$, $X^{14}$, and $X^{15}$ is $CR^4$; wherein $R^4$ is independently hydrogen, alkyl, aryl, cycloalkyl, haloalkyl, heteroaryl, heterocycle, halogen, cyano, —$OR^{14}$, —$NR^{14}R^{15}$, —$NR^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, or —$S(O)_2R^6$.

In certain embodiments, at least one of $X^{11}$, $X^{12}$, $X^{13}$, $X^{14}$, and $X^{15}$ is $CR^4$; wherein $R^4$ is $OR^{14}$, —$NR^{14}R^{15}$, —$NR^{14}C(O)R^6$, —$NR^{14}S(O)R^6$, —$NR^{14}S(O)_2R^6$, $S(O)R^6$, or —$S(O)_2R^6$.

In certain embodiments, at least one of $X^{11}$, $X^{12}$, $X^{13}$, $X^{14}$, and $X^{15}$ is $CR^4$; wherein $R^4$ is $OR^{14}$, $—N^{14}R^1$, $—NR^{14}S(O)_2R^6$, $S(O)R^6$, or $—S(O)_2R^6$.

In certain embodiments, at least one of $X^{11}$, $X^{12}$, $X^{13}$, $X^{14}$, and $X^{15}$ is $CR^4$; wherein $R^4$ is hydrogen, haloalkyl or halogen.

Additional Embodiments

1. In certain embodiments a compound is provided of Formula:

(I)

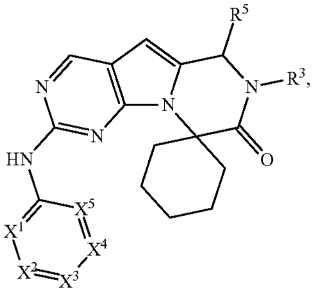

(II)

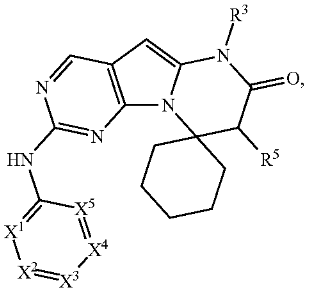

(III)

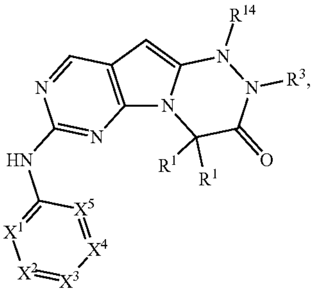

(IV)

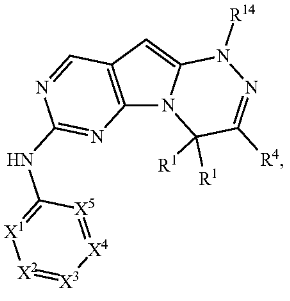

-continued (V)

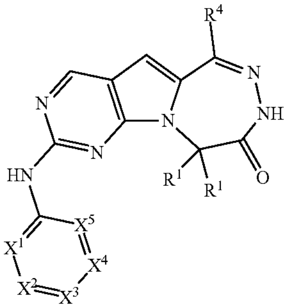

(VI)

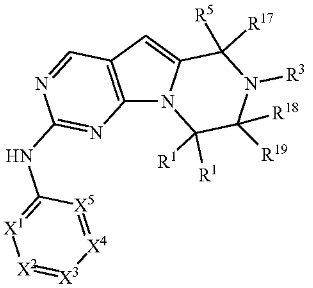

(VII)

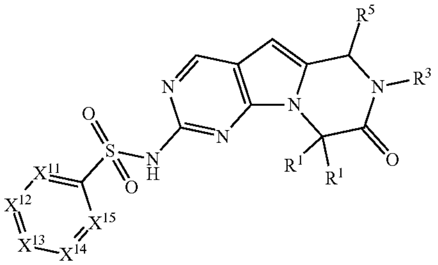

(VIII)

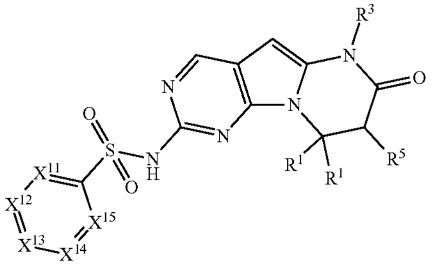

(IX)

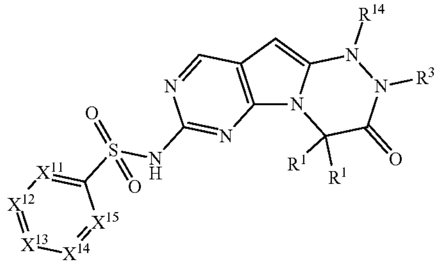

-continued (X)

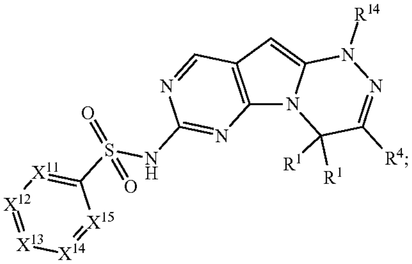

or a pharmaceutically acceptable salt, N-oxide, isotopic analog, and/or a pharmaceutically acceptable composition thereof;

wherein:

$X^1$, $X^2$, $X^3$, $X^4$, and $X^5$ are independently selected from N, CH, $CR^2$, and $CR^4$; wherein at least one of $X^1$, $X^2$, $X^3$, $X^4$, and $X^5$ is $CR^2$; and wherein no more than 2 of $X^1$, $X^2$, $X^3$, $X^4$, and $X^5$ are selected to be N;

$X^{11}$, $X^{12}$, $X^{13}$, $X^{14}$, and $X^{15}$ are independently selected from N, CH, $CR^2$, and $CR^4$; wherein no more than 2 of $X^{11}$, $X^{12}$, $X^{13}$, $X^{14}$, and $X^{15}$ are selected to be N;

each $R^1$ is independently selected from the group consisting of hydrogen, halogen, —$OR^{14}$, $NR^{14}R^{15}$, alkyl, aryl, cycloalkyl, haloalkyl, heteroaryl, alkyl-hydroxyl, and heterocycle, wherein two $R^1$s may come together with the ring atom to which they are attached to optionally constitute a 3, 4, 5, 6, 7, or 8-membered cycloalkyl or 4, 5, 6, 7, or 8-membered heterocycle that has 1, 2, or 3 heteroatoms selected from N, O, and S; wherein the cycloalkyl or heterocycle formed by combining two $R^1$s with the atom to which they are attached can be optionally substituted with 1 or 2 substituents independently selected from $R^{50}$;

each $R^2$ is independently selected from the group consisting of —NR $^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, —$S(=NR^{14})_2R^6$, —$S(=NR^{14})(O)R^6$ and —$S(O)_2R^6$;

$R^3$ is selected from the group consisting of hydrogen, —$OR^{14}$, —$NR^{14}R^{15}$, alkyl, alkenyl, alkynyl, —$C(O)R^6$, —C(O)alkyl, —C(S)alkyl, aryl, —$SO_2$alkyl, heteroaryl, heterocycle, -alkyl-aryl, and -alkyl-heteroaryl;

each $R^4$ is independently selected from the group consisting of hydrogen, alkyl, aryl, cycloalkyl, haloalkyl, heteroaryl, heterocycle, halogen, cyano, —$OR^{14}$, —$NR^{14}R^{15}$, —$NR^{14}C(O)R^6$, —$NR^{14}S(O)R^6$, —$NR^{14}S(O)_2R^6$, —$NR^{14}C(S)R^6$, —$OC(O)R^6$, —$OS(O)R^6$, —$OS(O)_2R^6$, —$OC(S)R^6$, —$C(O)R^6$; —$C(S)R^6$, —$S(O)R^6$, and —$S(O)_2R^6$;

$R^5$ is hydrogen, alkyl, haloalkyl, halogen, cyano, —$OR^{14}$, or —$NR^{14}R^{15}$;

each $R^6$ is selected independently selected from the group consisting of hydrogen, alkyl, alkenyl, alkynyl, cycloalkyl, heterocycle, aryl, heteroaryl, $NR^7R^7$, and $OR^7$ each of which $R^6$ except hydrogen, $NR^7R^7$, and $OR^7$ is optionally substituted with 1, 2, 3, or 4 $R^8$ groups;

each $R^7$ is independently selected from the group consisting of hydrogen, alkyl, alkenyl, alkynyl, cycloalkyl, heterocycle, aryl, alkyl-aryl, alkyl-heteroaryl, and heteroaryl each of which $R^7$ except hydrogen is optionally substituted with 1, 2, 3, or 4 $R^8$ groups;

each $R^8$ is independently selected from the group consisting of hydrogen, halogen, haloalkyl, alkyl, alkenyl, alkynyl, cycloalkyl, heterocycle, aryl, heteroaryl, —$S(O)_2$alkyl, $NR^{12}R^{13}$, alkyl-heteroaryl, alkyl-aryl, and $OR^{12}$;

each $R^{12}$ and $R^{13}$ are independently selected from the group consisting of hydrogen, alkyl, alkenyl, alkynyl, —C(O)alkyl, —C(S)alkyl, aryl, —$SO_2$alkyl, —S(O)alkyl, heteroaryl, alkyl-aryl, cycloalkyl, heterocycle, and alkyl-heteroaryl;

each $R^{14}$ and $R^{15}$ are independently selected from the group consisting of hydrogen, alkyl, alkenyl, alkynyl, —$C(O)R^6$, —C(O)alkyl, —C(S)alkyl, aryl, —$SO_2$alkyl, heteroaryl, heterocycle, -alkyl-aryl, and -alkyl-heteroaryl;

$R^{17}$ and $R^{18}$ are independently selected from the group consisting of hydrogen, alkyl, alkenyl, alkynyl, cycloalkyl, heterocycle, aryl, alkyl-aryl, alkyl-heteroaryl, and heteroaryl each of which except hydrogen is optionally substituted with 1, 2, 3, or 4 $R^8$ groups; and $R^{19}$ is hydrogen, alkyl, haloalkyl, halogen, cyano, —$OR^{14}$, or —$NR^{14}R^{15}$; and each $R^{50}$ is independently selected from the group consisting of hydrogen, —$NR^{14}R^{15}$, $OR^{14}$, and $R^4$.

2. In certain embodiments a compound is provided of Formula:

(I)

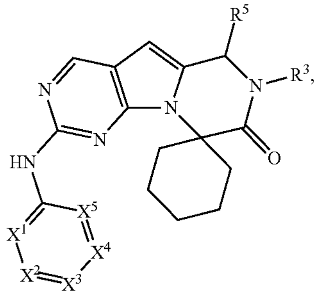

(II)

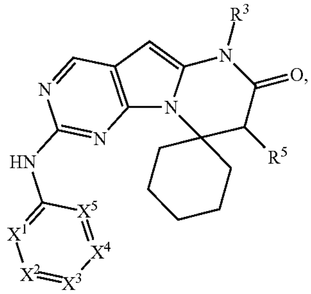

(III)

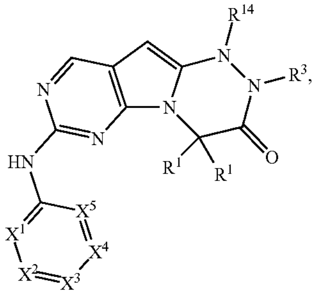

-continued (IV)

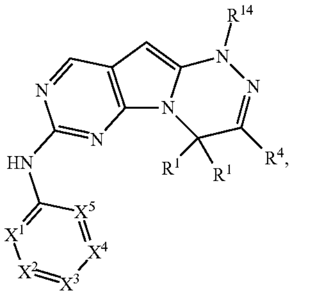

or (V)

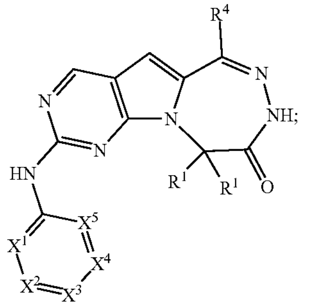

or a pharmaceutically acceptable salt, N-oxide, isotopic analog, and/or a pharmaceutically acceptable composition thereof;

wherein each $R^2$ is independently selected from the group consisting of —NR $^{14}C(O)R^6$, $—NR^{14}S(O)R^6$, $—NR^{14}S(O)_2R^6$, $—NR^{14}C(S)R^6$, $—OC(O)R^6$, —OS(O)$R^6$, $—OS(O)_2R^6$, $—OC(S)R^6$, $—C(O)R^6$; —C(S)$R^6$, $—S(O)R^6$, and $—S(O)_2R^6$.

3. The compound of embodiment 1 of formula:

(I)

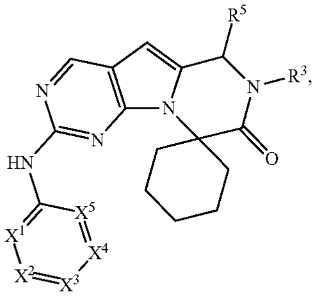

or a pharmaceutically acceptable salt thereof.

4. The compound of embodiment 1, wherein $R^5$ is hydroxyl.

5. The compound of embodiment 1 of formula:

(II)

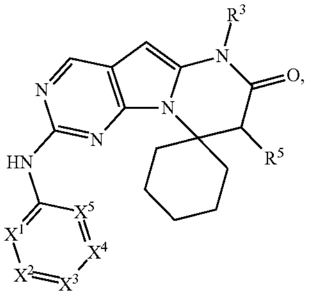

or a pharmaceutically acceptable salt thereof.

6. The compound of embodiment 1, wherein one $R^1$ is hydrogen.

7. The compound of embodiment 1, wherein both $R^1$s are hydrogen.

8. The compound of embodiment 1, wherein neither $R^1$ is hydrogen.

9. The compound of embodiment 1 of formula:

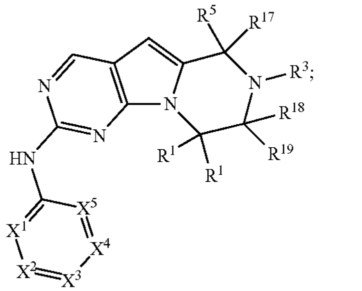

or a pharmaceutically acceptable salt thereof.

10. The compound of embodiment 1 of formula:

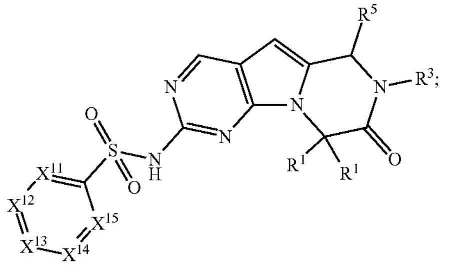

or a pharmaceutically acceptable salt thereof.

11. The compound of embodiment 1 of formula:

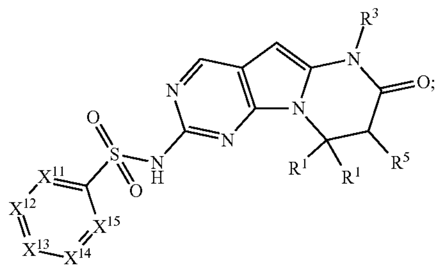

or a pharmaceutically acceptable salt thereof.

12. The compound of embodiment 1 of formula:

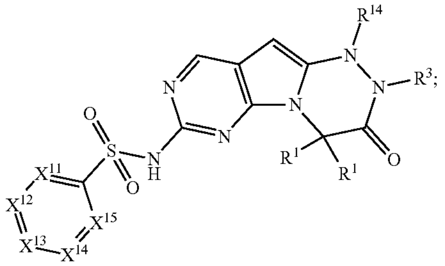

or a pharmaceutically acceptable salt thereof.

13. The compound of any one of embodiments 10-12, wherein $X^{11}$ is CH.

14. The compound of any one of embodiments 10-12, wherein $X^{11}$ is N.

15. The compound of any one of embodiments 10-12, wherein $X^{11}$ is $CR^4$.

16. The compound of any one of embodiments 10-15, wherein $X^{12}$ is CH.

17. The compound of any one of embodiments 10-15, wherein $X^{12}$ is N.

18. The compound of any one of embodiments 10-15, wherein $X^{12}$ is $CR^4$.

19. The compound of any one of embodiments 10-18, wherein $X^{13}$ is CH.

20. The compound of any one of embodiments 10-18, wherein $X^{13}$ is N.

21. The compound of any one of embodiments 10-18, wherein $X^{13}$ is $CR^4$.

22. The compound of any one of embodiments 10-21, wherein $X^{14}$ is CH.

23. The compound of any one of embodiments 10-21, wherein $X^{14}$ is N.

24. The compound of any one of embodiments 10-21, wherein $X^{14}$ is $CR^4$.

25. The compound of any one of embodiments 10-24, wherein $X^{15}$ is CH.

26. The compound of any one of embodiments 10-24, wherein $X^{15}$ is N.

27. The compound of any one of embodiments 10-24, wherein $X^{15}$ is $CR^4$.

28. The compound of embodiment 1 of formula:

(III)

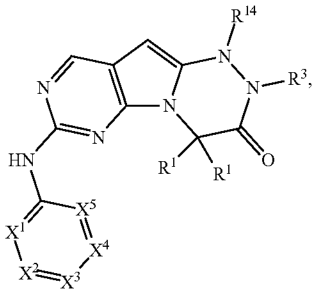

or a pharmaceutically acceptable salt thereof.

29. The compound of any one of embodiments 1-28, wherein $R^3$ is hydrogen.

30. The compound of any one of embodiments 1-28, wherein $R^3$ is alkyl.

31. The compound of any one of embodiments 1-28, wherein $R^3$ is $—NR^{14}R^{15}$.

32. The compound of any one of embodiments 1-28, wherein $R^3$ is $—NH_2$.

33. The compound of embodiment 1 of formula:

(IV)

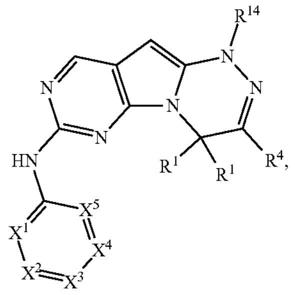

or a pharmaceutically acceptable salt thereof.

34. The compound of embodiment 1 of formula:

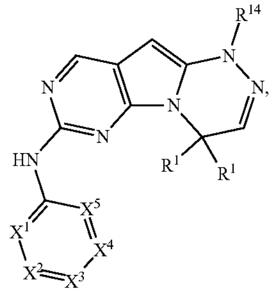

or a pharmaceutically acceptable salt thereof.

35. The compound of embodiment 1 of formula:

(V)

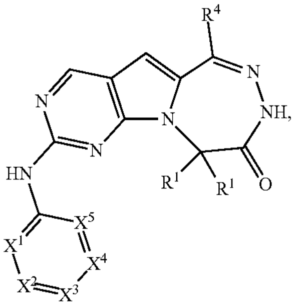

or a pharmaceutically acceptable salt thereof.

36. The compound of embodiment 1 of formula:

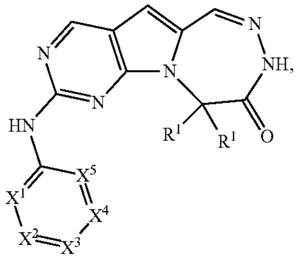

or a pharmaceutically acceptable salt thereof.

37. The compound of embodiment 1 of formula:

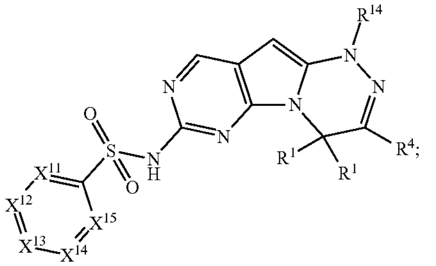

or a pharmaceutically acceptable salt thereof.

38. The compound of embodiment 1 or any one of embodiments 33-37, wherein two $R^1$s together with the carbon to which they are attached form a 3-8 membered cycle. 39. The compound of embodiment 1 or any one of embodiments 33-37, wherein two $R^1$s together with the carbon to which they are attached form a 6-membered carbocycle.

40. The compound of embodiment 1 or any one of embodiments 33-37, wherein one $R^1$ is halogen.

41. The compound of embodiment 1 or any one of embodiments 33-37, wherein one $R^1$ is haloalkyl.

42. The compound of embodiment 1 or any one of embodiments 33-37, wherein one $R^1$ is hydroxyl.

43. The compound of embodiment 1 or any one of embodiments 33-37, wherein $R^1$ is selected from alkyl, aryl, cycloalkyl, and haloalkyl.

44. The compound of any one of embodiments 1-43, wherein $R^2$ is —C(O)$R^6$; —C(S)$R^6$, —S(O)$R^6$, or —$S(O)_2R^6$.

45. The compound of any one of embodiments 1-43, wherein $R^2$ is —C(O)$R^6$.

46. The compound of any one of embodiments 1-43, wherein $R^2$ is —$S(O)_2R^6$.

47. The compound of any one of embodiments 1-46, wherein each $R^6$ is selected independently from hydrogen, alkyl, alkenyl, alkynyl, cycloalkyl, heterocycle, aryl, and heteroaryl.

48. The compound of any one of embodiments 1-46, wherein each $R^6$ is selected independently from $NR^7R^7$ and $OR^7$.

49. The compound of any one of embodiments 1-43, wherein $R^2$ is —$S(O)_2NH_2$.

50. The compound of any one of embodiments 1-49, wherein

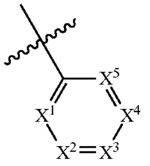 is 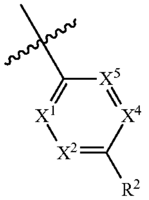 or 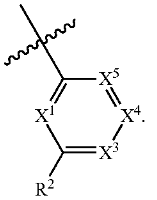

51. The compound of any one of embodiments 1-50, wherein $X^1$ is CH.

52. The compound of any one of embodiments 1-50, wherein $X^1$ is N.

53. The compound of any one of embodiments 1-50, wherein $X^1$ is $CR^2$.

54. The compound of any one of embodiments 1-50, wherein $X^1$ is $CR^4$.

55. The compound of any one of embodiments 1-54, wherein $X^2$ is CH.

56. The compound of any one of embodiments 1-54, wherein $X^2$ is N.

57. The compound of any one of embodiments 1-54, wherein $X^2$ is $CR^2$.

58. The compound of any one of embodiments 1-54, wherein $X^2$ is $CR^4$.

59. The compound of any one of embodiments 1-58, wherein

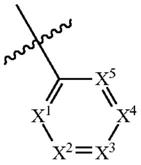

is

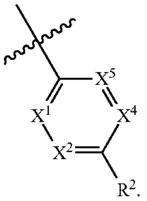

60. The compound of any one of embodiments 1-58, wherein $X^3$ is CH.

61. The compound of any one of embodiments 1-58, wherein $X^3$ is N.

62. The compound of any one of embodiments 1-58, wherein $X^3$ is $CR^2$.

63. The compound of any one of embodiments 1-58, wherein $X^3$ is $CR^4$.

64. The compound of any one of embodiments 60-63, wherein

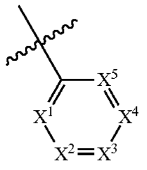

is

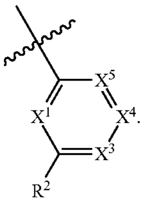

65. The compound of any one of embodiments 1-64, wherein $X^4$ is CH.

66. The compound of any one of embodiments 1-64, wherein $X^4$ is N.

67. The compound of any one of embodiments 1-64, wherein $X^4$ is $CR^2$.

68. The compound of any one of embodiments 1-64, wherein $X^4$ is $CR^4$.

69. The compound of any one of embodiments 1-68, wherein $X^5$ is CH.

70. The compound of any one of embodiments 1-68, wherein $X^5$ is N.

71. The compound of any one of embodiments 1-68, wherein $X^5$ is $CR^2$.

72. The compound of any one of embodiments 1-68, wherein $X^5$ is $CR^4$.

73. The compound of any one of embodiments 1-72, wherein at least one $R^4$ is $OR^{14}$.

74. The compound of any one of embodiments 1-72, wherein at least one $R^4$ is halogen.

75. The compound of any one of embodiments 1-72, wherein at least one $R^4$ is alkyl.

76. The compound of any one of embodiments 1-72, wherein at least one $R^3$ is alkyl.

77. In certain embodiments, the compound is selected from:

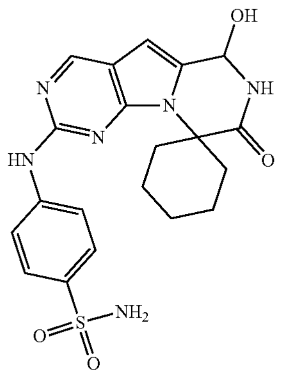

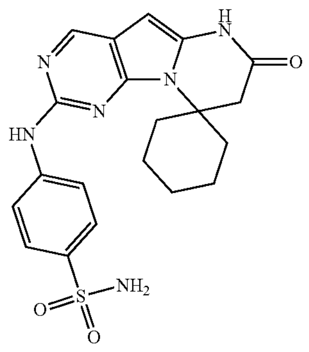

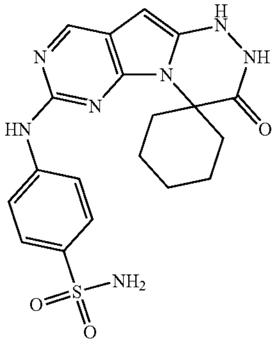

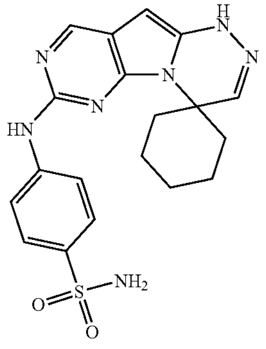

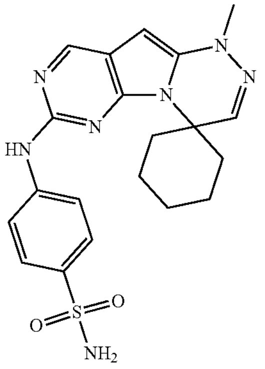

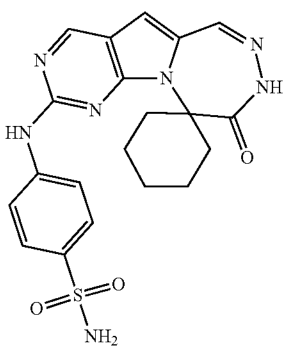

-continued
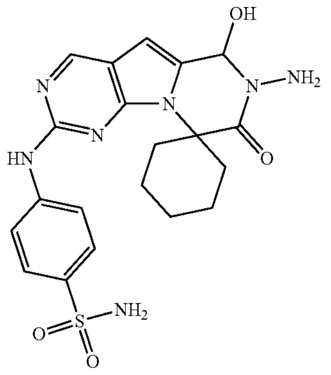
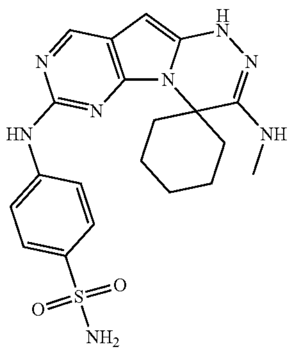
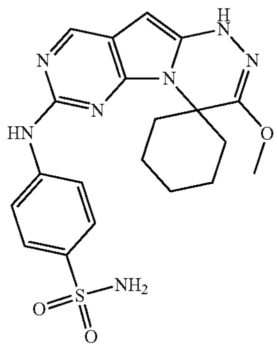
and
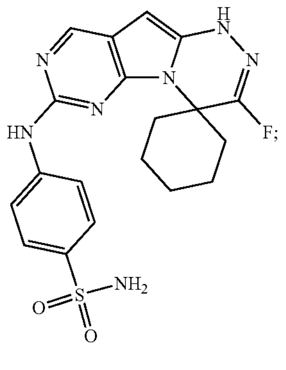
or a pharmaceutically acceptable salt thereof.
78. The compound of embodiment 77 of structure:
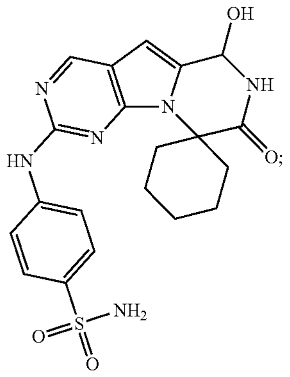 [SMILES: NS(=O)(=O)c1ccc(Nc2ncc3cc4n(c3n2)C2(CCCCC2)C(=O)NC4O)cc1]
or a pharmaceutically acceptable salt thereof.
79. The compound of embodiment 77 of structure:
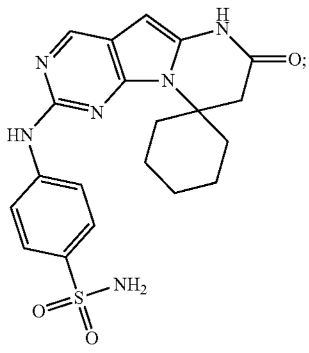 [SMILES: NS(=O)(=O)c1ccc(Nc2ncc3cc4n(c3n2)C2(CCCCC2)CC(=O)N4)cc1]
or a pharmaceutically acceptable salt thereof.
80. The compound of embodiment 77 of structure:
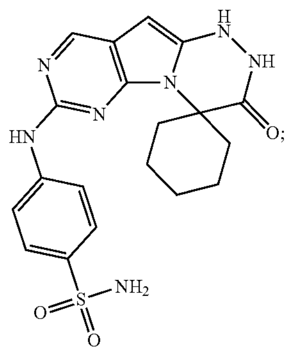 [SMILES: NS(=O)(=O)c1ccc(Nc2ncc3cc4n(c3n2)C2(CCCCC2)C(=O)NN4)cc1]
or a pharmaceutically acceptable salt thereof.

81. The compound of embodiment 77 of structure:

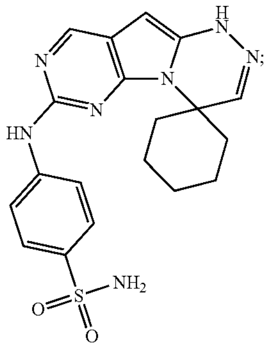 [SMILES: NS(=O)(=O)c1ccc(Nc2ncc3cc4n(c3n2)C2(C=NN4)CCCCC2)cc1]

or a pharmaceutically acceptable salt thereof.

82. The compound of embodiment 77 of structure:

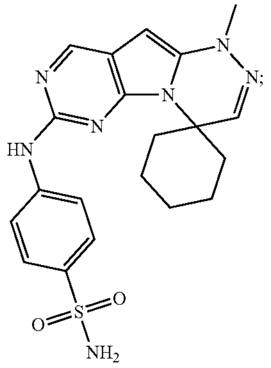 [SMILES: CN1N=CC2(CCCCC2)n2c1cc1cnc(Nc3ccc(S(N)(=O)=O)cc3)nc12]

or a pharmaceutically acceptable salt thereof.

83. The compound of embodiment 77 of structure:

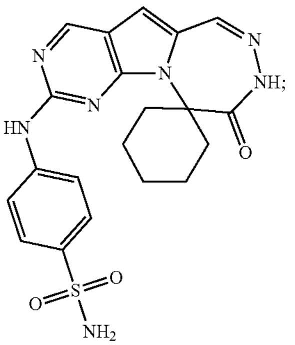 [SMILES: NS(=O)(=O)c1ccc(Nc2ncc3cc4n(c3n2)C2(CCCCC2)C(=O)NN=C4)cc1]

or a pharmaceutically acceptable salt thereof.

84. The compound of embodiment 77 of structure:

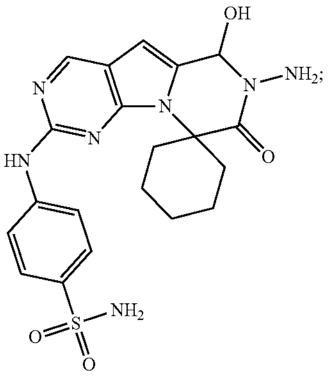 [SMILES: NN1C(=O)C2(CCCCC2)n2c(cc3cnc(Nc4ccc(S(N)(=O)=O)cc4)nc32)C1O]

or a pharmaceutically acceptable salt thereof.

85. The compound of embodiment 77 of structure:

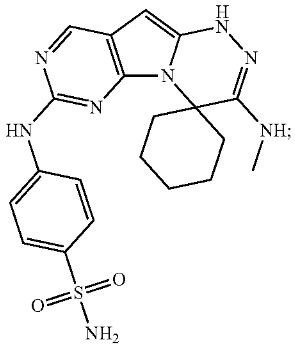 [SMILES: CNC1=NNc2cc3cnc(Nc4ccc(S(N)(=O)=O)cc4)nc3n2C12CCCCC2]

or a pharmaceutically acceptable salt thereof.

86. The compound of embodiment 77 of structure:

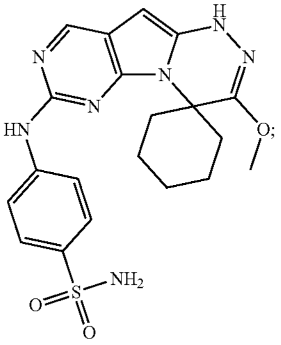 [SMILES: COC1=NNc2cc3cnc(Nc4ccc(S(N)(=O)=O)cc4)nc3n2C12CCCCC2]

or a pharmaceutically acceptable salt thereof.

87. The compound of embodiment 77 of structure:
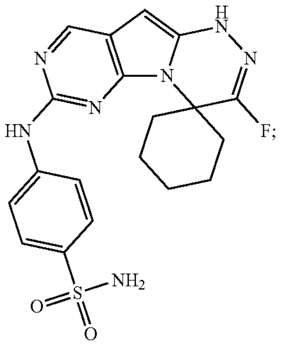 [SMILES: NS(=O)(=O)c1ccc(Nc2ncc3cc4n(c3n2)C2(CCCCC2)C(F)=NN4)cc1]
or a pharmaceutically acceptable salt thereof.
88. The compound of embodiment 1 of structure:
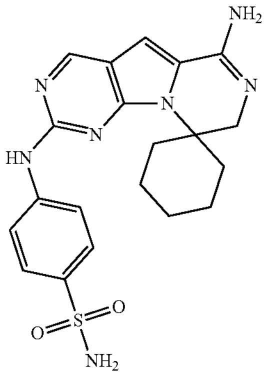
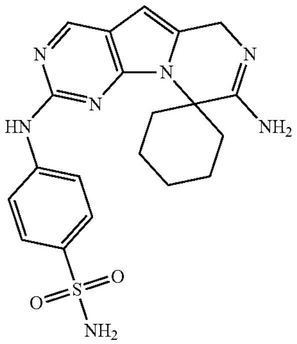
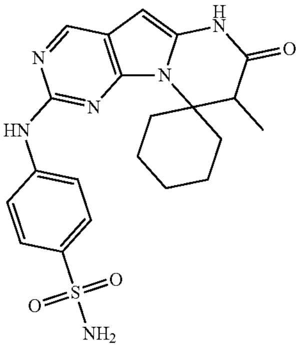
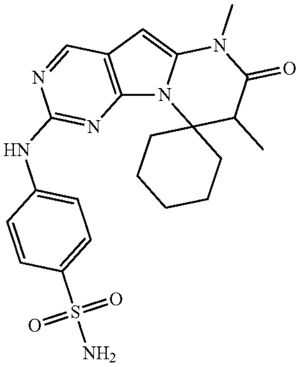
-continued
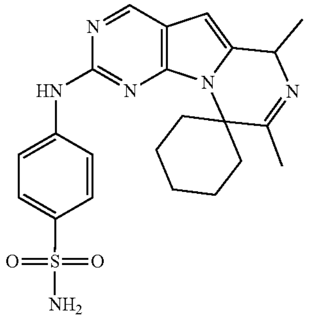
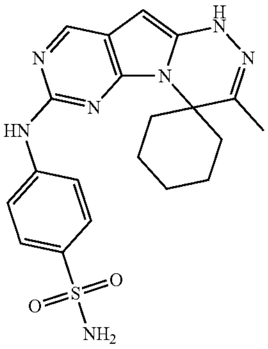
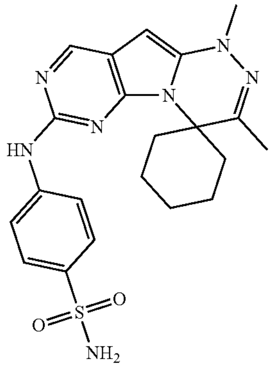
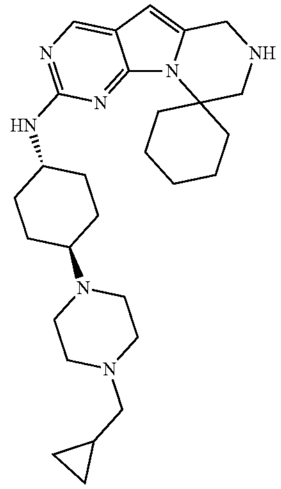
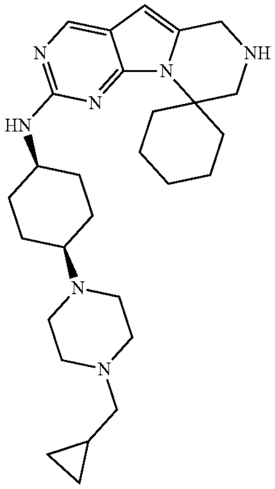
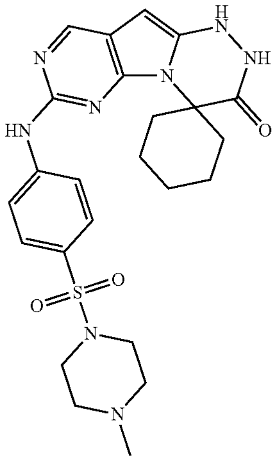
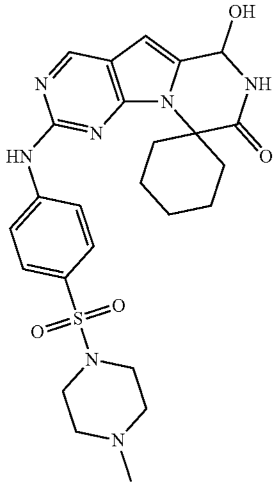

-continued
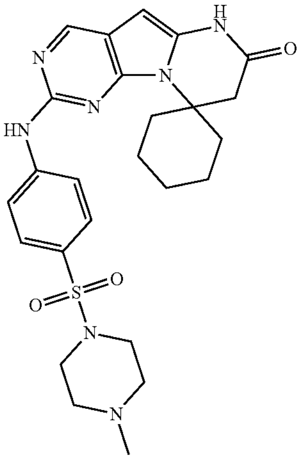
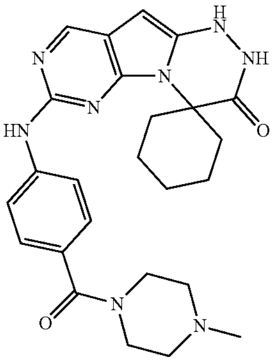
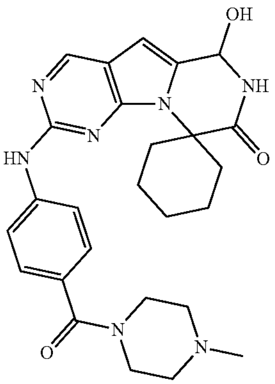
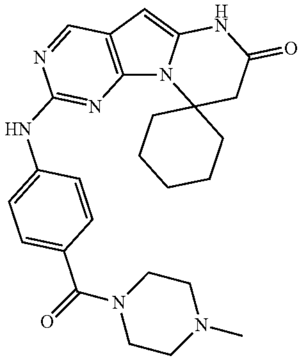
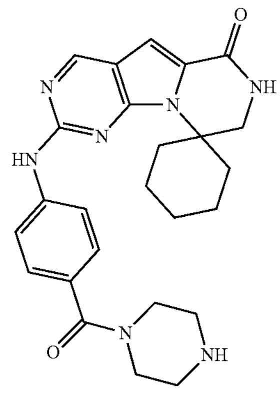
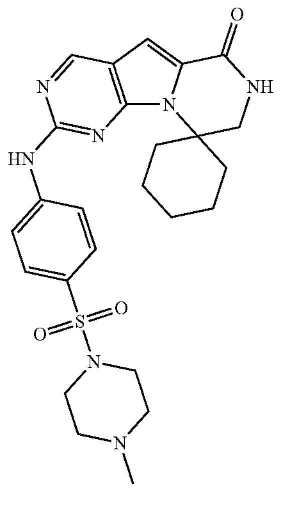
-continued
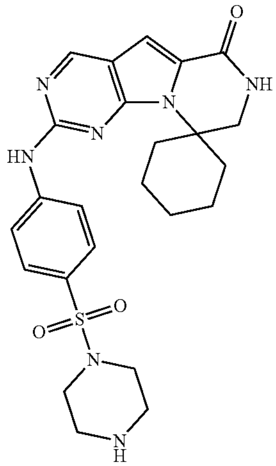
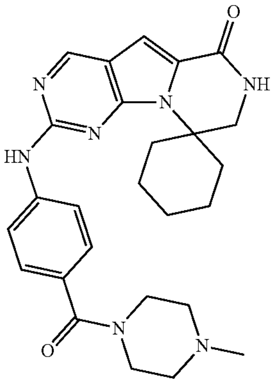
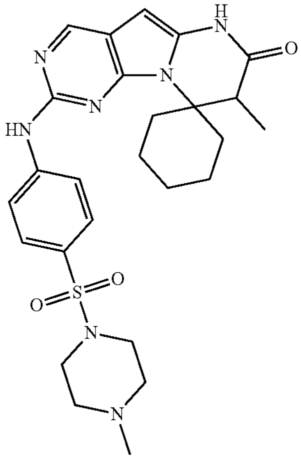
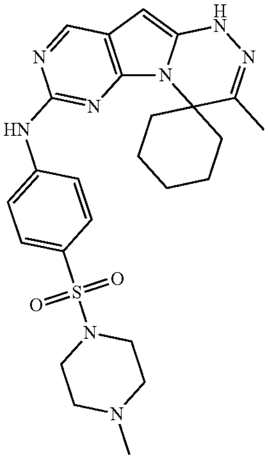
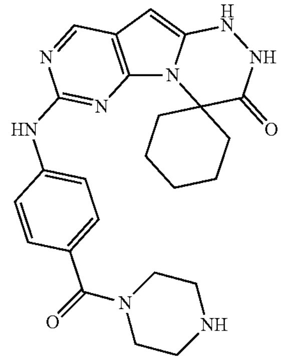
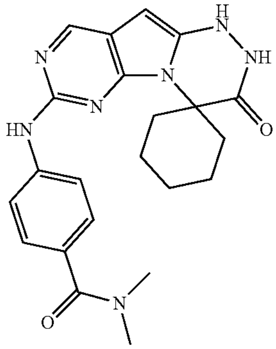
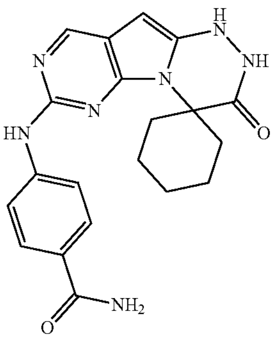
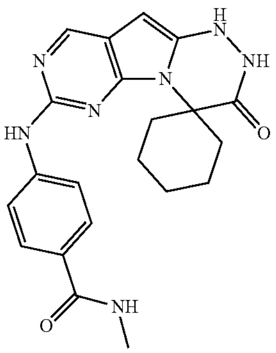

-continued
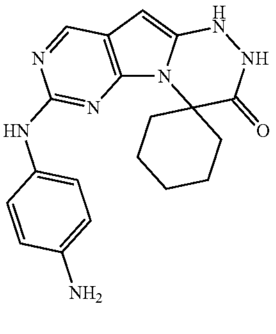
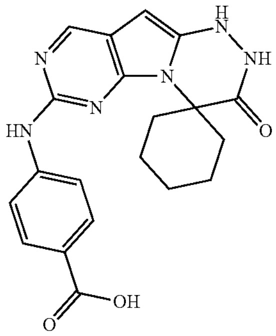
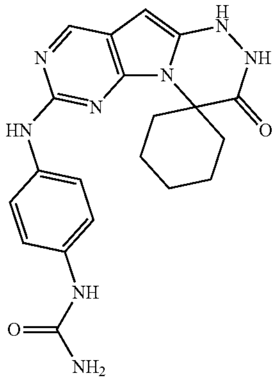
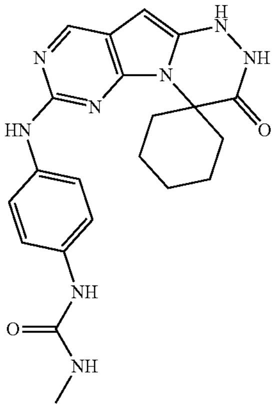
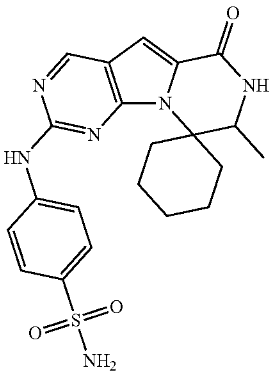
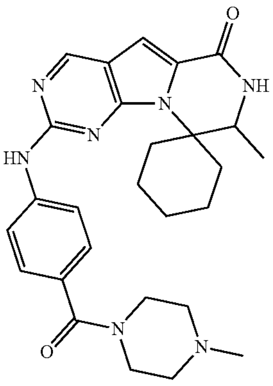
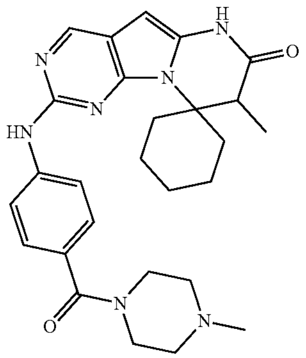
-continued
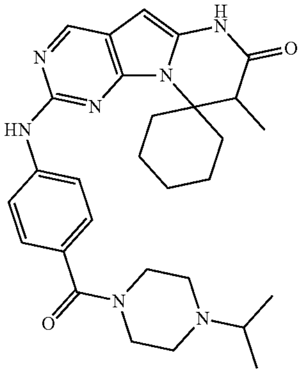
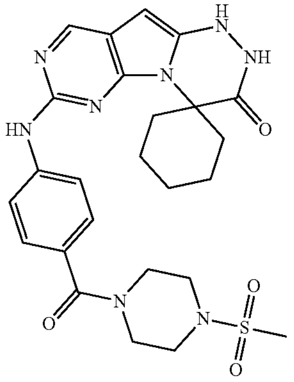
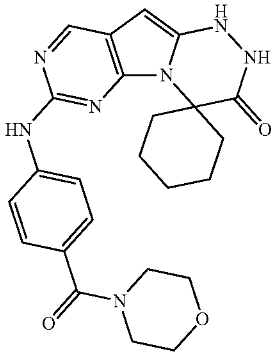
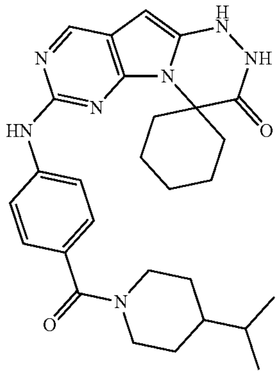
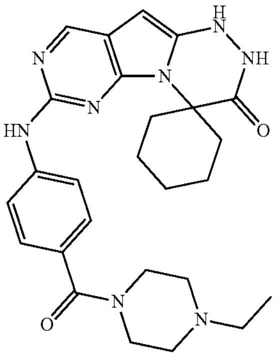
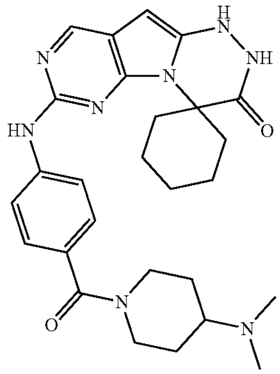
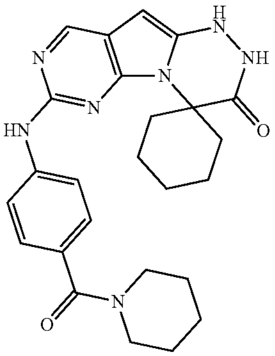

-continued
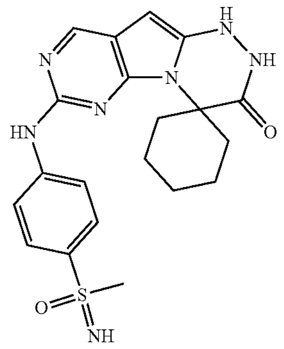
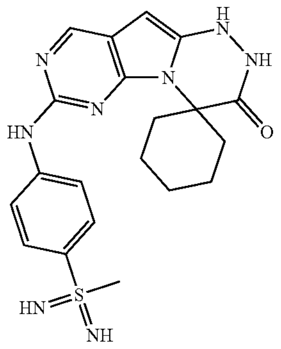
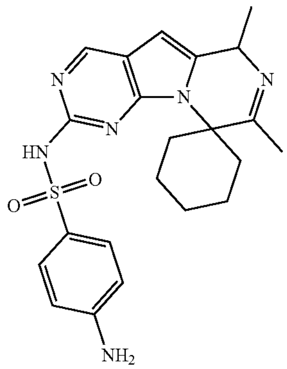
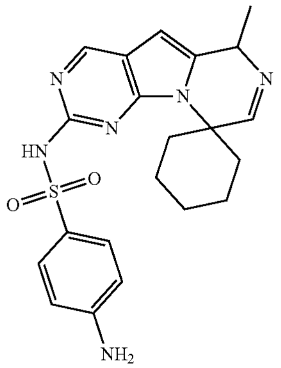
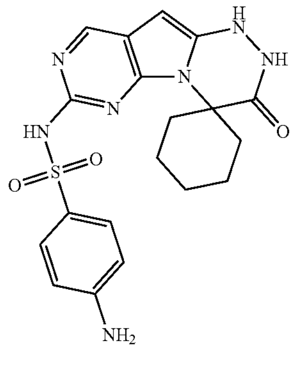
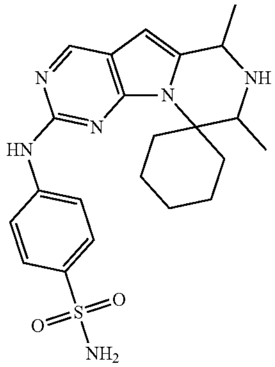
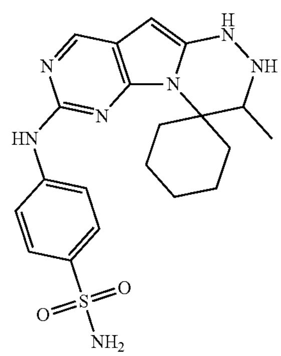
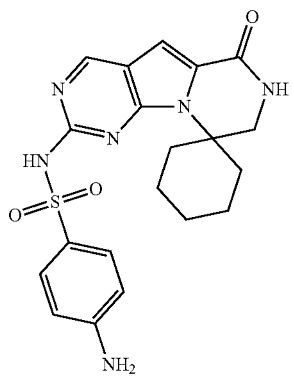
-continued
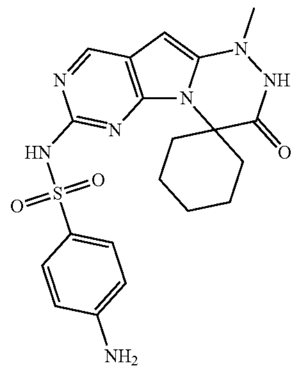
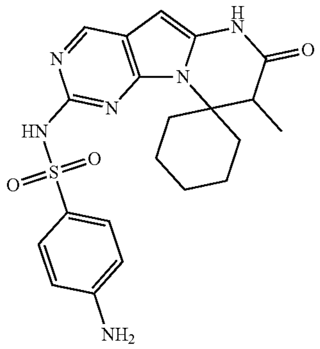
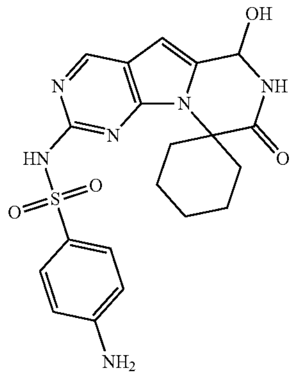
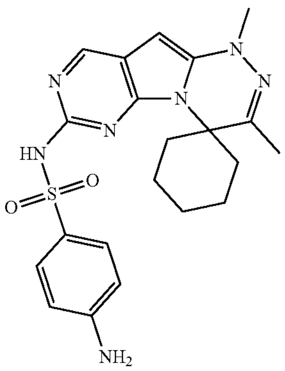
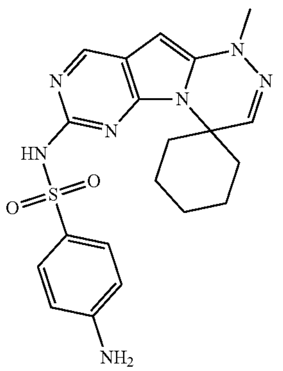
or -continued

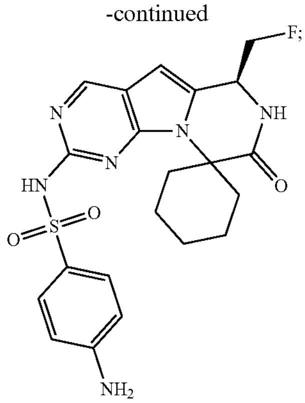

or a pharmaceutically acceptable salt thereof.

89. A method for the treatment of a disorder associated with abnormal cellular proliferation comprising administering an effective amount to a host in need thereof of a compound of any one of embodiments 1-88, optionally in a pharmaceutically acceptable carrier is provided.

90. The method of embodiment 89, wherein the host is a human.

91. The method of embodiment 89 or 90, wherein the disorder is an inflammatory disorder.

92. The method of embodiment 89 or 90, wherein the disorder is a fibrotic disorder.

93. The method of embodiment 89 or 90, wherein the disorder is an autoimmune disorder.

94. The method of embodiment 89 or 90, wherein the disorder is a tumor.

95. The method of embodiment 89 or 90, wherein the disorder is a cancer.

96. The method of embodiment 89 or 90, wherein the disorder is rheumatoid arthritis.

97. In certain embodiments, a method of reducing the effect of chemotherapy on healthy cells in a human being treated for cancer or abnormal cell proliferation, wherein said healthy cells are hematopoietic stem cells or hematopoietic progenitor cells, the method comprising administering to the human an effective amount of a compound of any one of embodiments 1-88, optionally in a pharmaceutically acceptable carrier is provided.

98. A pharmaceutical composition comprising a compound of any one of embodiments 1-88 or pharmaceutically acceptable salt thereof in a pharmaceutically acceptable carrier is provided.

99. The pharmaceutical composition of embodiment 98 for treating a disorder associated with abnormal cellular proliferation.

100. The pharmaceutical composition of embodiment 99, wherein the disorder is an inflammatory disorder.

101. The pharmaceutical composition of embodiment 99, wherein the disorder is a fibrotic disorder.

102. The pharmaceutical composition of embodiment 99, wherein the disorder is an autoimmune disorder.

103. The pharmaceutical composition of embodiment 99, wherein the disorder is a tumor.

104. The pharmaceutical composition of embodiment 99, wherein the disorder is a cancer.

105. The pharmaceutical composition of embodiment 99, wherein the disorder is rheumatoid arthritis.

106. The pharmaceutical composition of embodiment 98 for reducing the effect of chemotherapy on healthy cells in a human being treated for cancer or abnormal cell proliferation, wherein said healthy cells are hematopoietic stem cells or hematopoietic progenitor cells.

107. In certain embodiments, a compound for use in the manufacture of a medicament to treat a disorder associated with abnormal cellular proliferation, wherein the compound is selected from any of embodiments 1-88 or a pharmaceutically acceptable salt thereof is provided.

108. The compound of embodiment 107, wherein the disorder is an inflammatory disorder.

109. The compound of embodiment 107, wherein the disorder is a fibrotic disorder.

110. The compound of embodiment 107, wherein the disorder is an autoimmune disorder.

111. The compound of embodiment 107, wherein the disorder is a tumor.

112. The compound of embodiment 107, wherein the disorder is a cancer.

113. The compound of embodiment 107, wherein the disorder is rheumatoid arthritis.

114. In certain embodiments, a compound for use in the manufacture of a medicament to reduce the effect of chemotherapy on healthy cells in a human being treated for cancer or abnormal cell proliferation, wherein said healthy cells are hematopoietic stem cells or hematopoietic progenitor cells, wherein the compound is selected from any of embodiments 1-88 or a pharmaceutically acceptable salt thereof is provided.

115. In certain embodiments, a use of a compound in the treatment of a disorder associated with abnormal cellular proliferation, wherein the compound is selected from any of embodiments 1-88 or a pharmaceutically acceptable salt thereof is provided.

116. The use of embodiment 115, wherein the disorder is an inflammatory disorder.

117. The use of embodiment 115, wherein the disorder is a fibrotic disorder.

118. The use of embodiment 115, wherein the disorder is an autoimmune disorder.

119. The use of embodiment 115, wherein the disorder is a tumor.

120. The use of embodiment 115, wherein the disorder is a cancer.

121. The use of embodiment 115, wherein the disorder is rheumatoid arthritis.

122. In certain embodiments, a use of a compound in reducing the effect of chemotherapy on healthy cells in a human being treated for cancer or abnormal cell proliferation, wherein said healthy cells are hematopoietic stem cells or hematopoietic progenitor cells, wherein the compound is selected from any of embodiments 1-88 or a pharmaceutically acceptable salt thereof.

Embodiments of the Core

In certain embodiments,

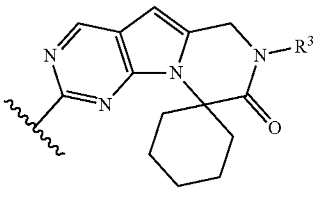

is selected from:
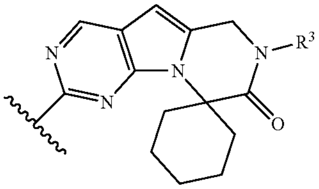
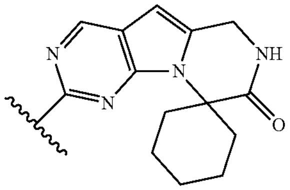
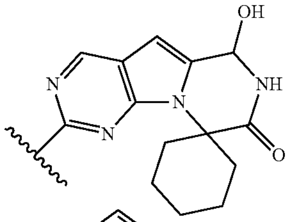
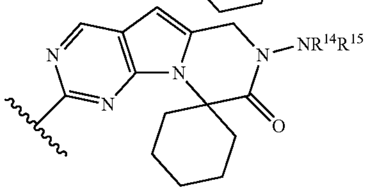
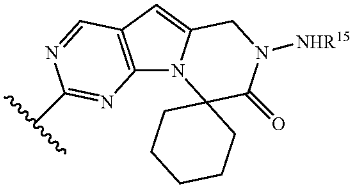
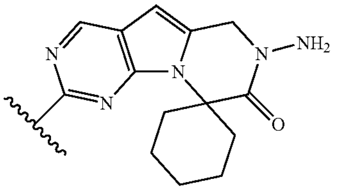
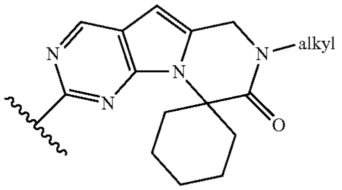
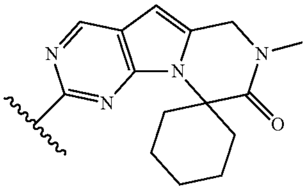
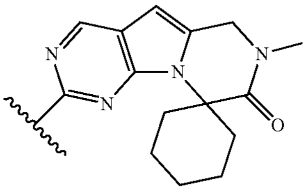
-continued
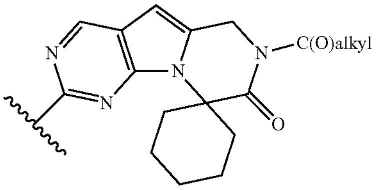
and
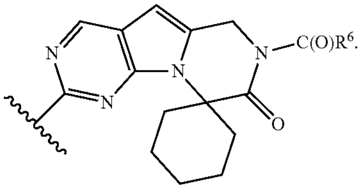
In certain embodiments,
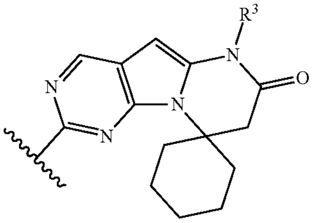
is selected from
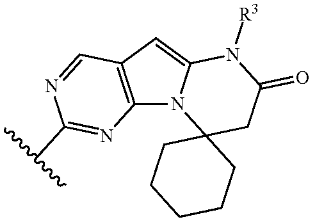
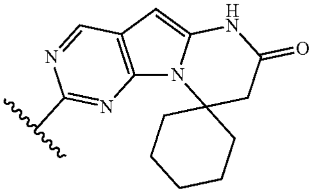
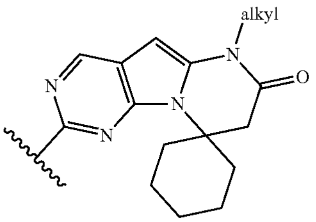
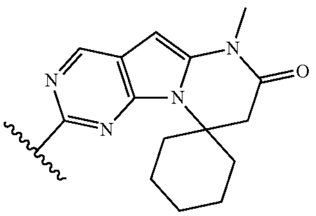

-continued
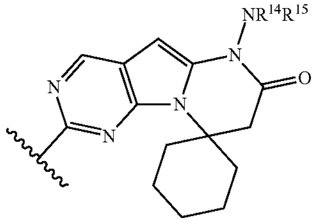
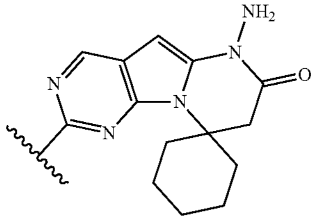
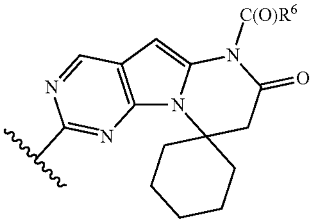
and
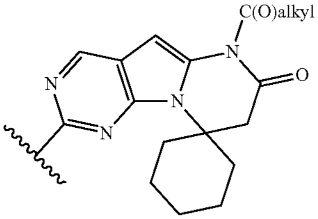
In certain embodiments,
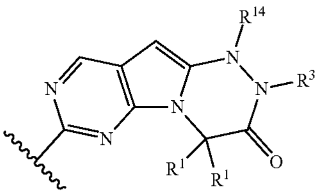
is selected from:
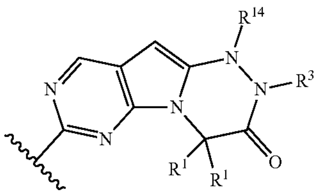
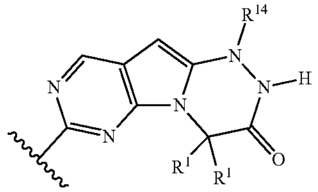
-continued
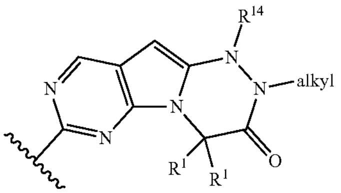
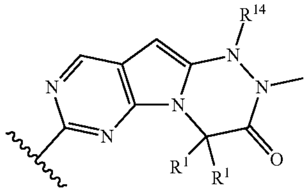
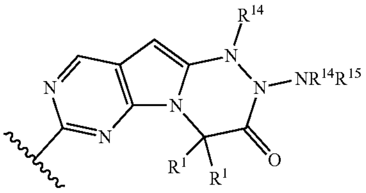
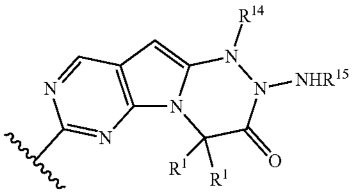
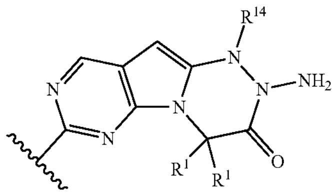
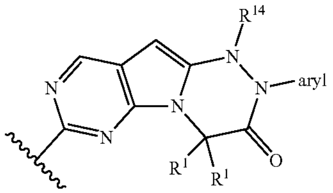
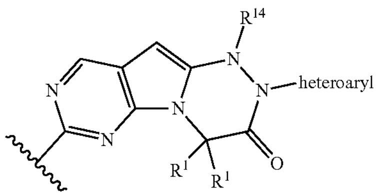
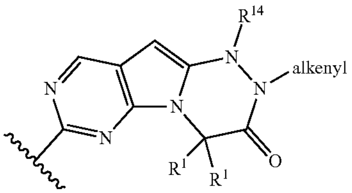

-continued
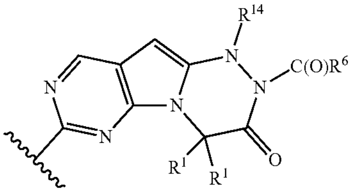
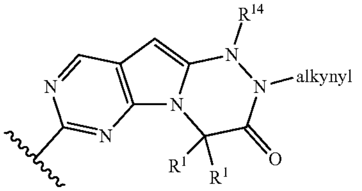
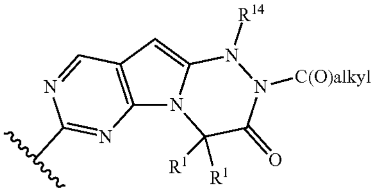
and
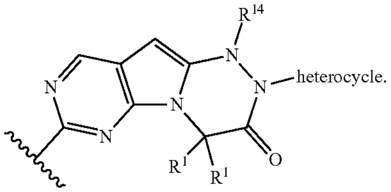
In certain embodiments,
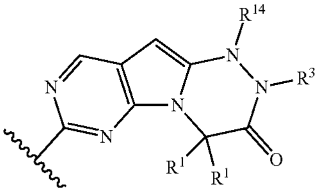
is selected from:
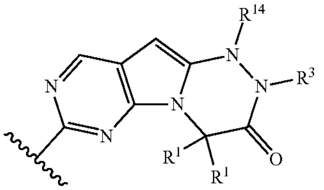
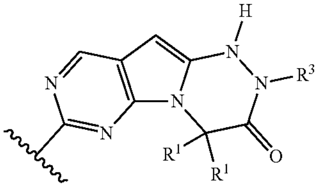
-continued
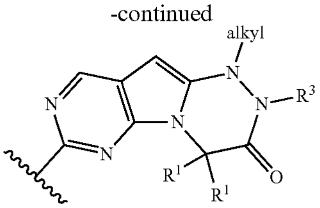
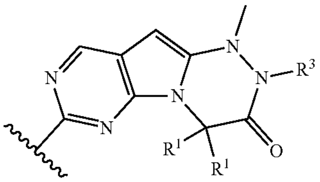
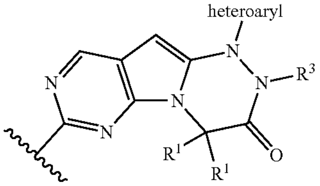
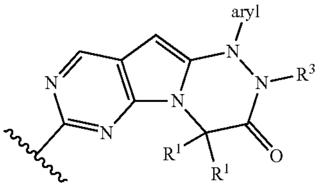
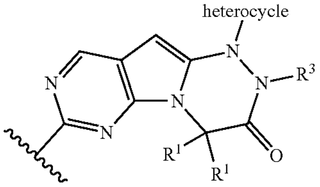
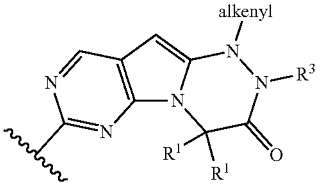
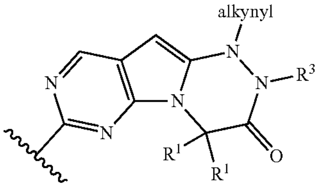
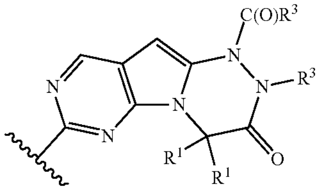
and
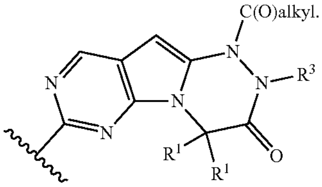

In certain embodiments,
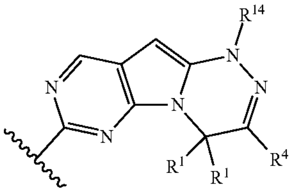
is selected from:
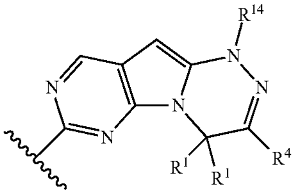
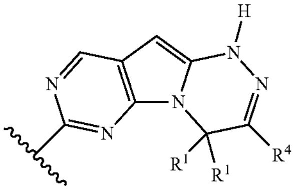
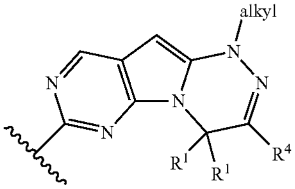
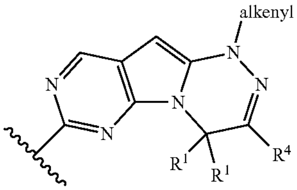
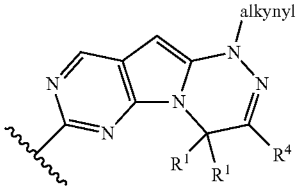
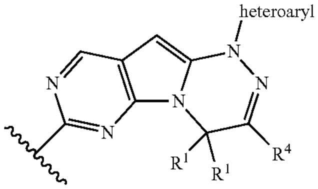
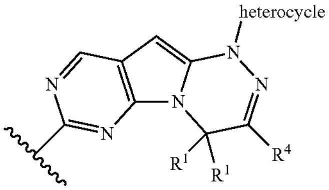
-continued
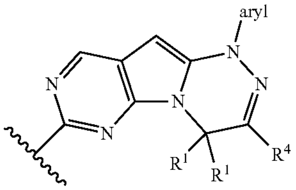
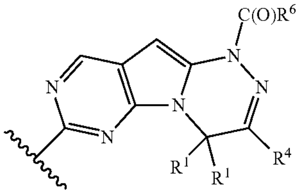
and
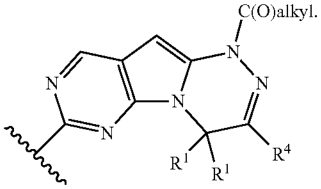
In certain embodiments,
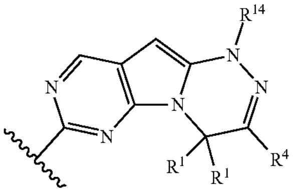
is selected from:
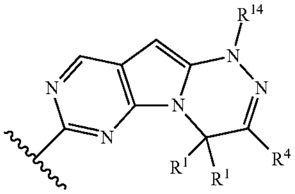
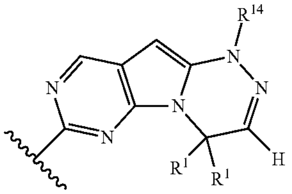
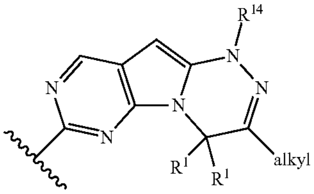

-continued
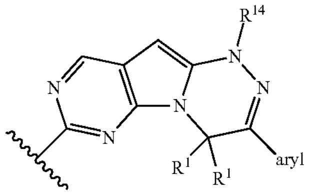
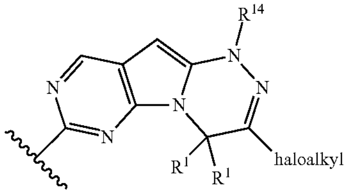
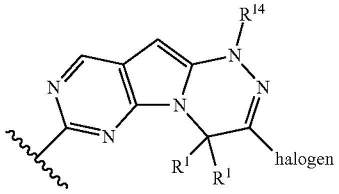
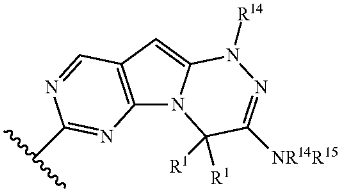
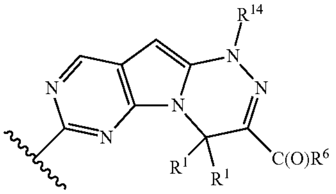
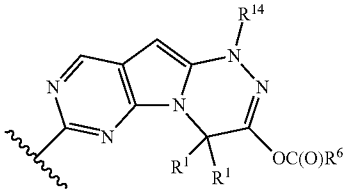
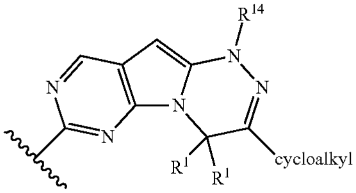
and
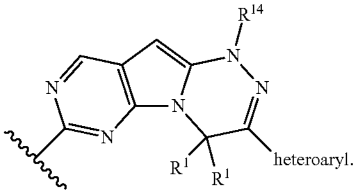
In certain embodiments,
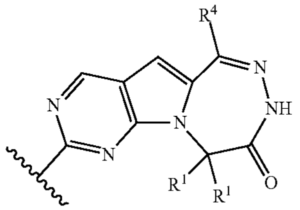
is selected from:
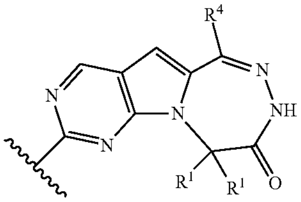
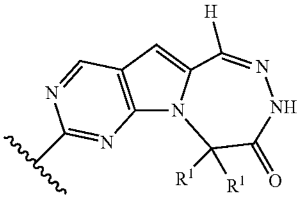
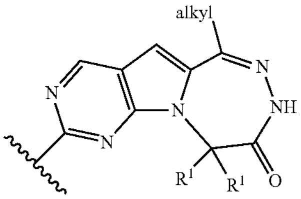
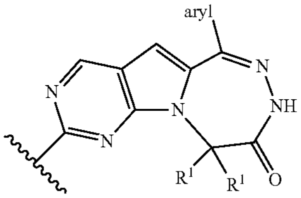
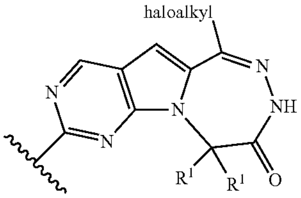
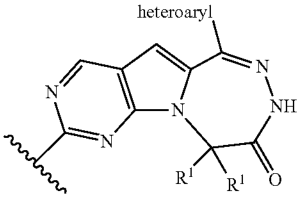
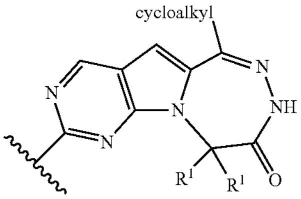

-continued
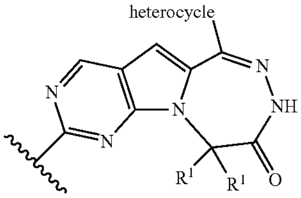
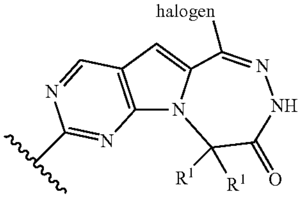
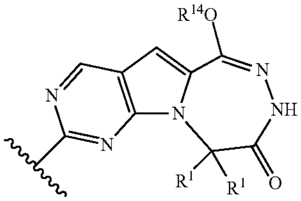
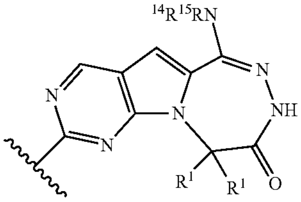
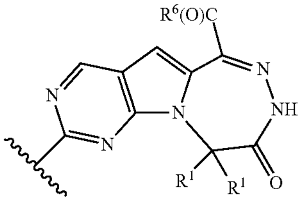
and
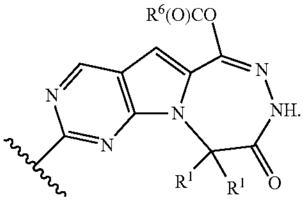
In certain embodiments,
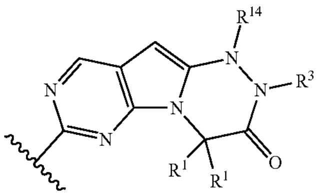
is selected from:
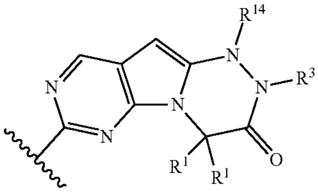
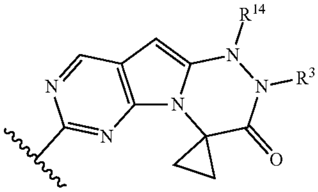
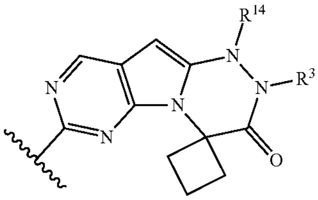
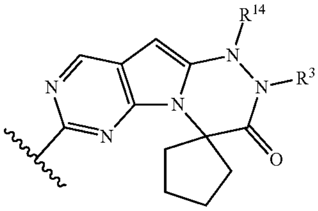
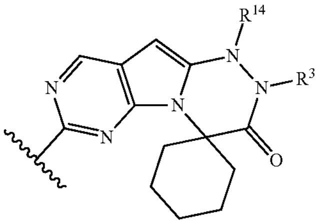
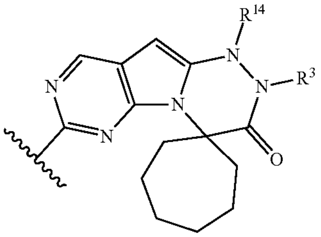
and
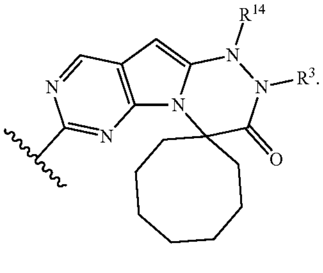

In certain embodiments,
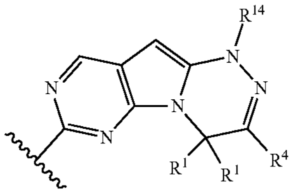
is selected from:
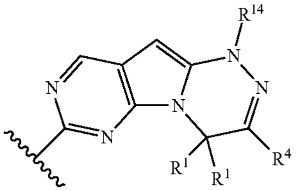
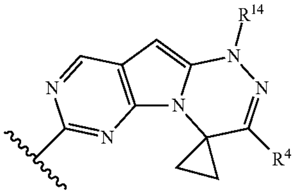
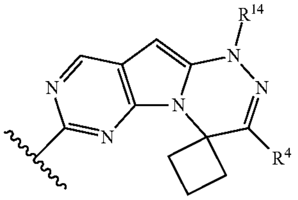
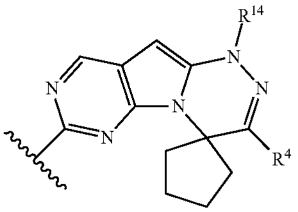
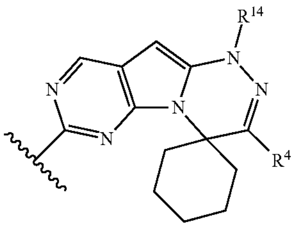
and
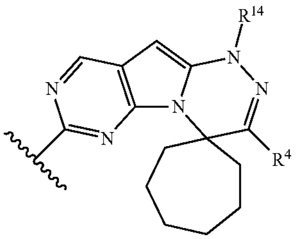
-continued
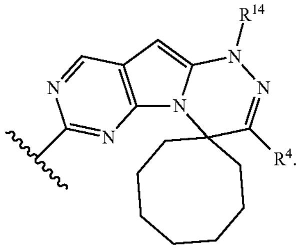
In certain embodiments,
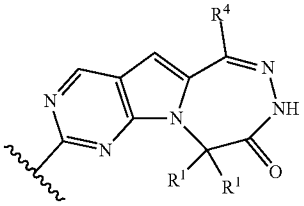
is selected from:
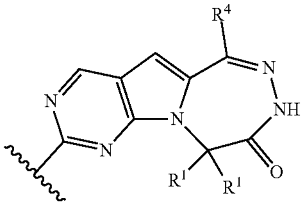
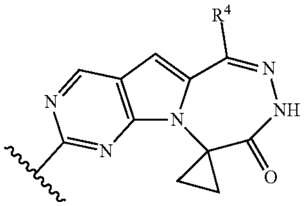
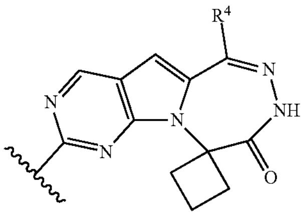
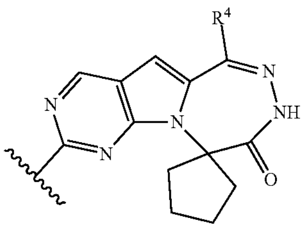

-continued
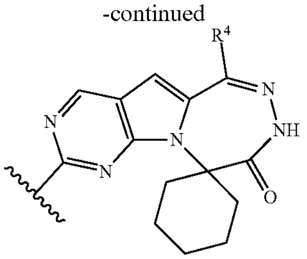
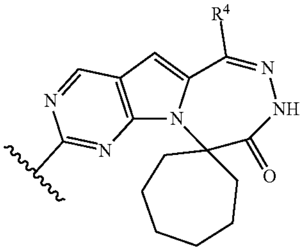
and
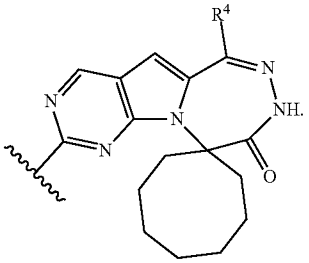
Additional Embodiments
In certain embodiments, the compound of present invention is selected from:
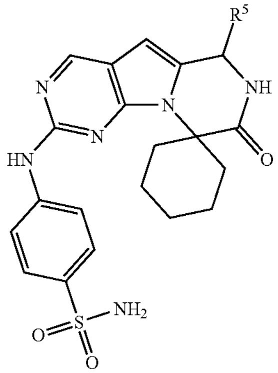
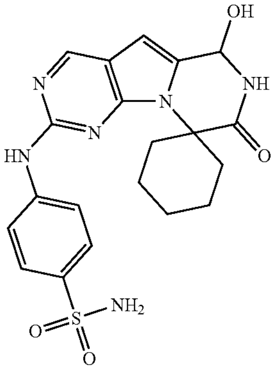
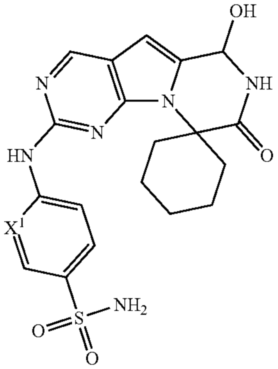
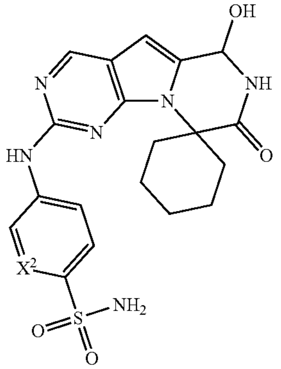
-continued
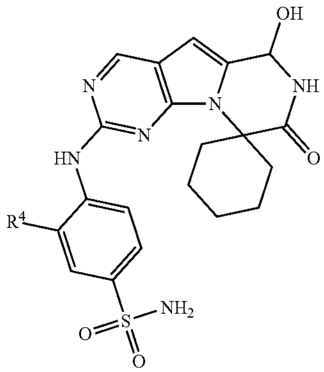
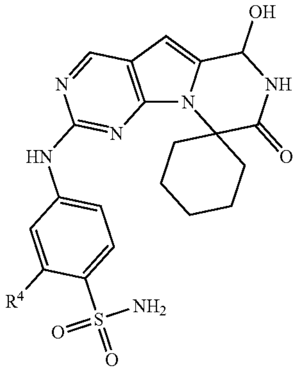
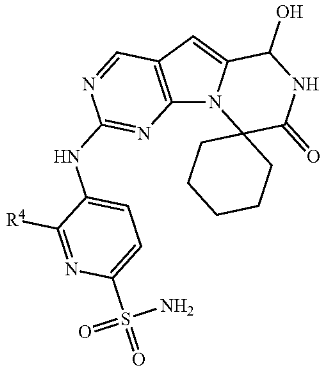
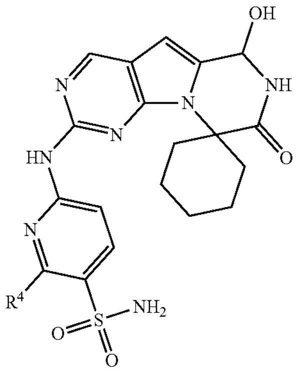

-continued
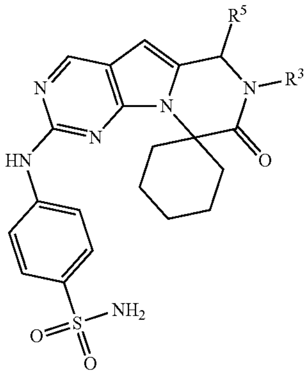
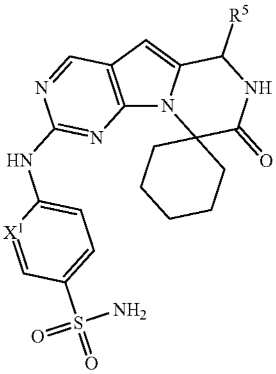
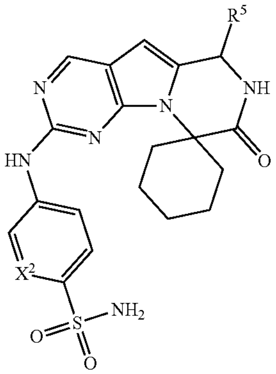
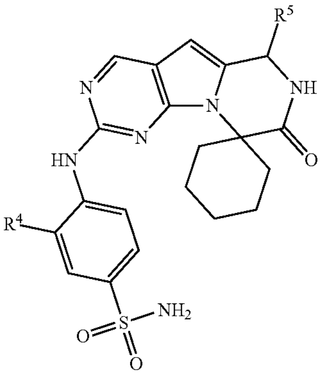
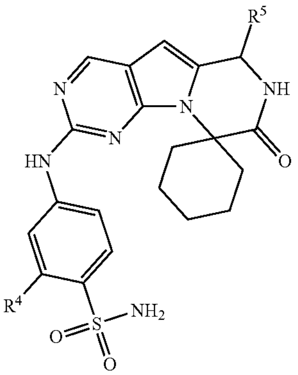
-continued
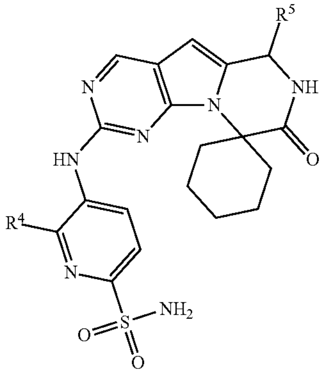
and
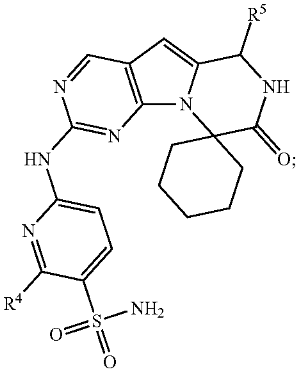
or a pharmaceutically acceptable salt thereof.
In certain embodiments, the compound of present invention is selected from:
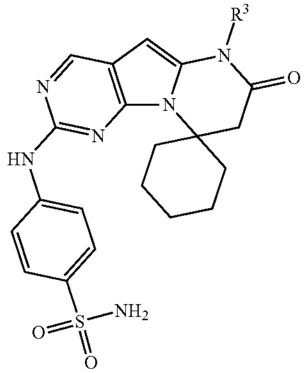
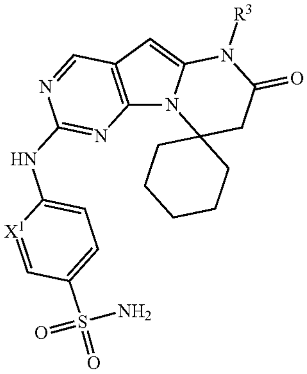

-continued
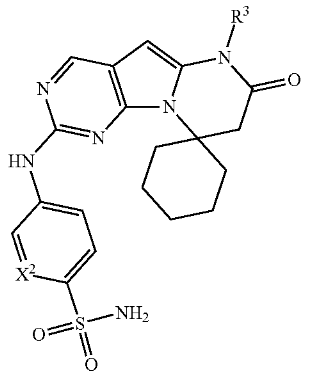
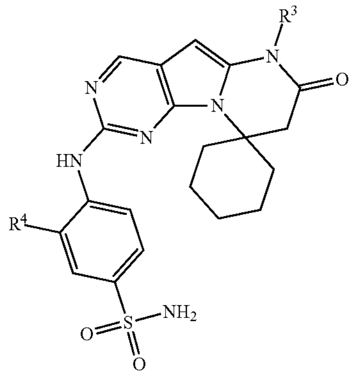
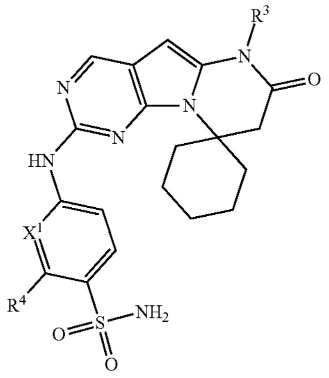
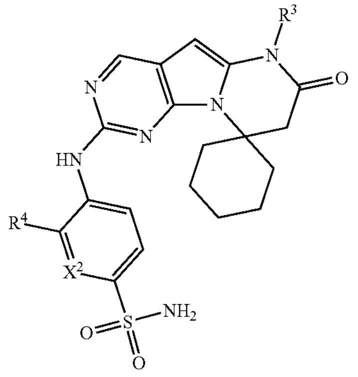
and
-continued
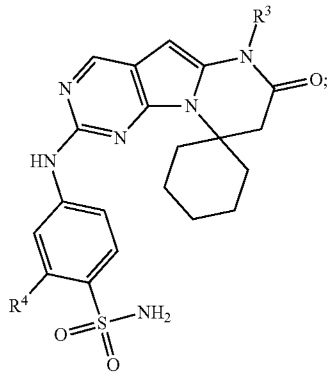
or a pharmaceutically acceptable salt thereof.
In certain embodiments, the compound of present invention is selected from:
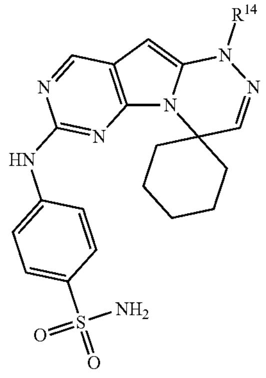
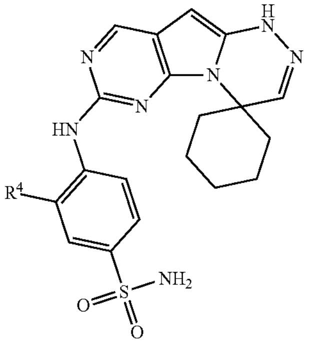
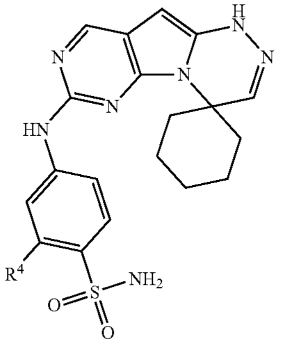

-continued
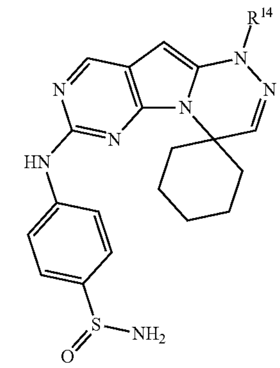
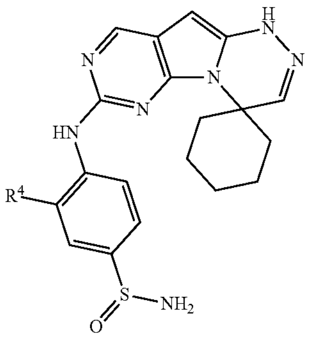
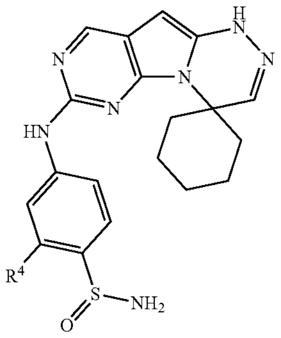
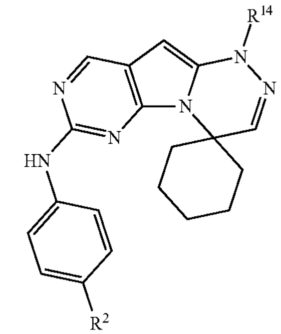
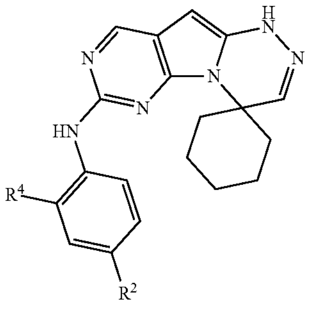
-continued
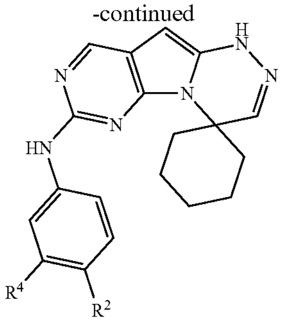
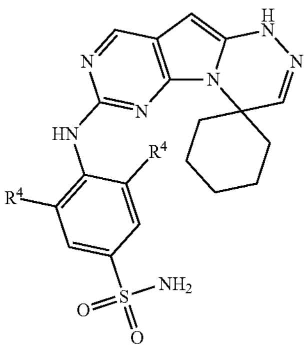
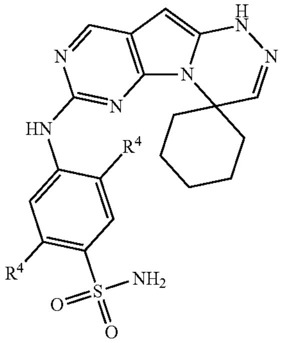
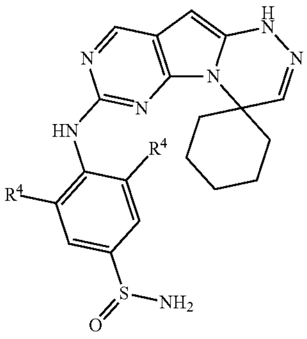
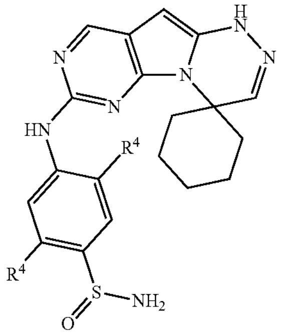

-continued
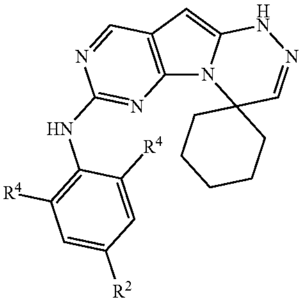
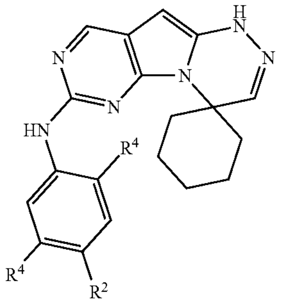
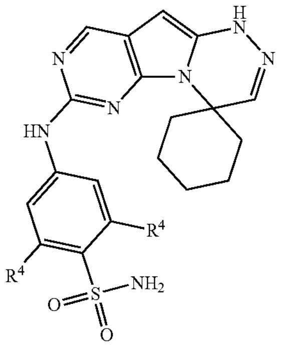
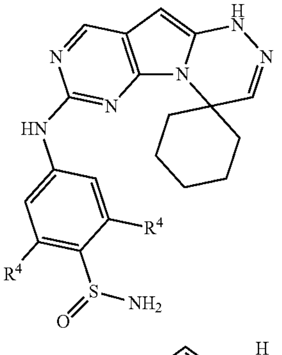
and
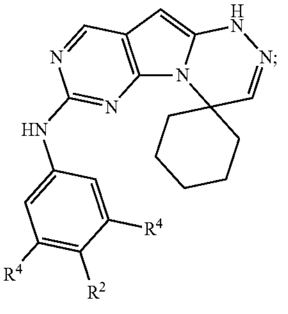
or a pharmaceutically acceptable salt thereof.
In certain embodiments, the compound of present invention is selected from:
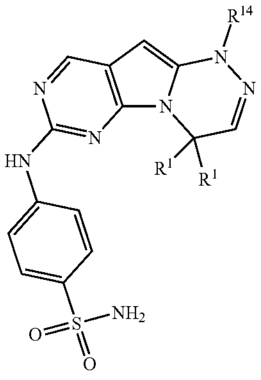
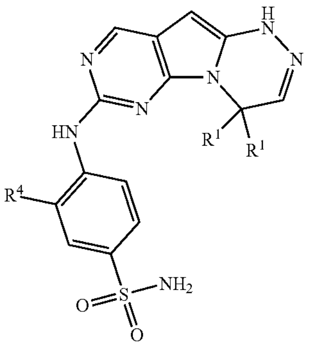
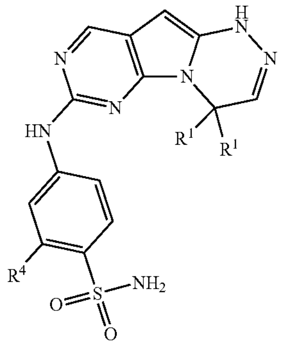
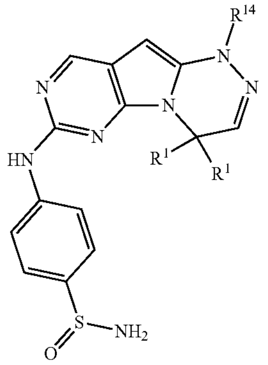
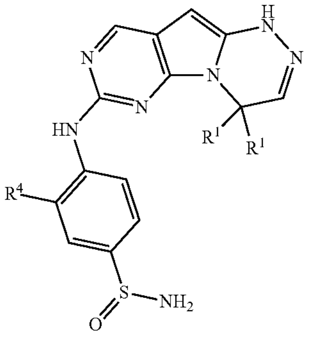
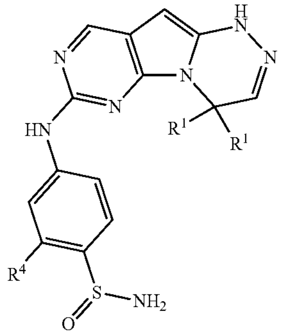
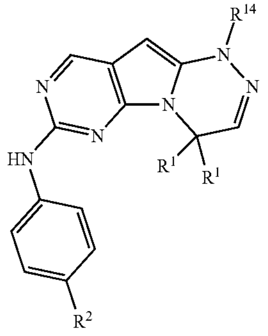

-continued
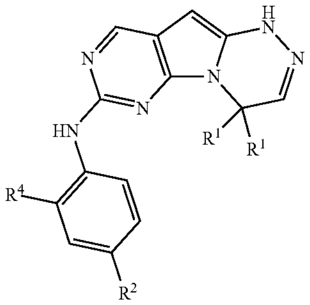
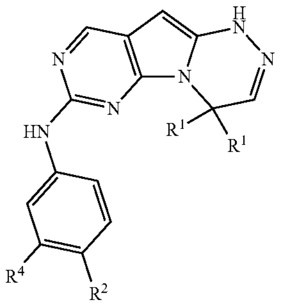
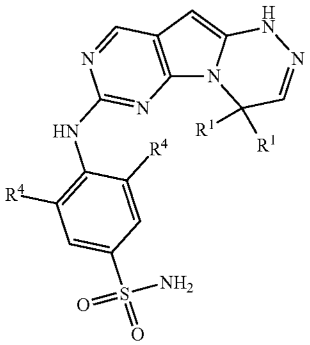
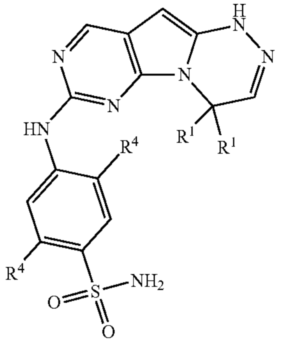
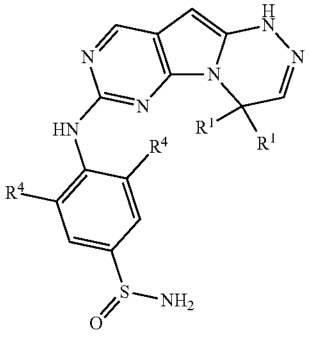
-continued
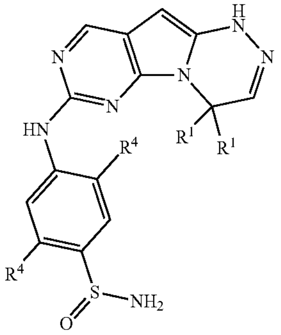
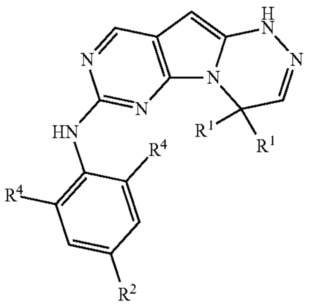
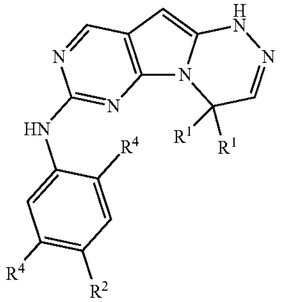
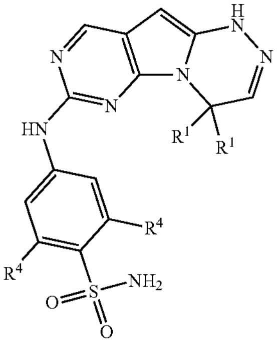
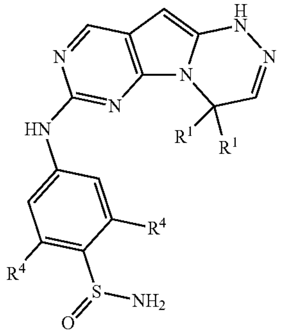
and
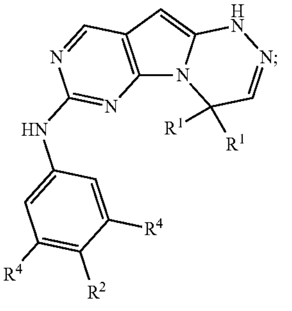
or a pharmaceutically acceptable salt thereof.
In certain embodiments, the compound of present invention is selected from:

-continued
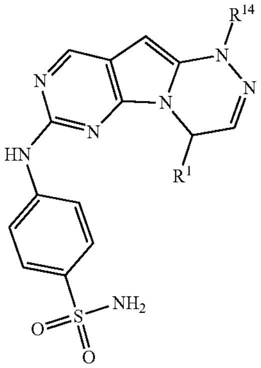
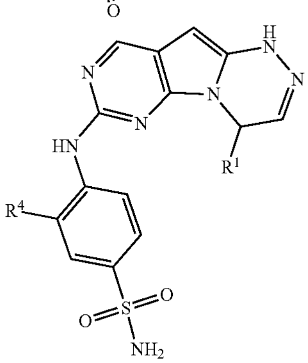
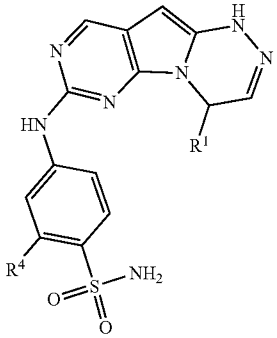
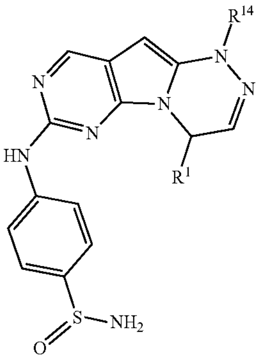
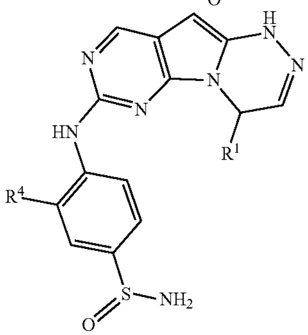
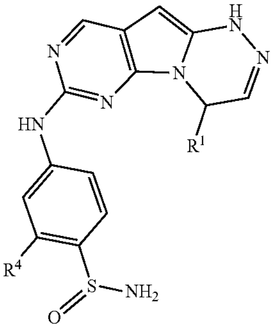
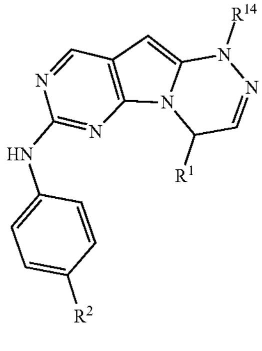
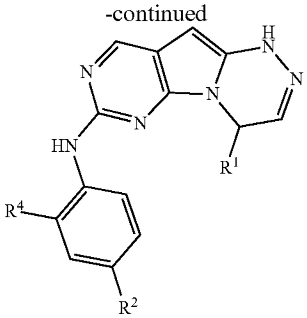
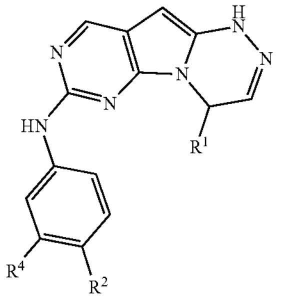
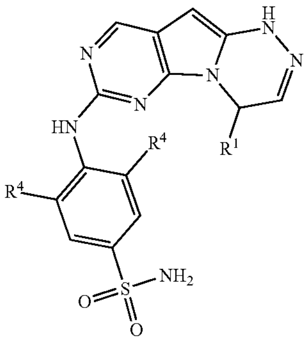
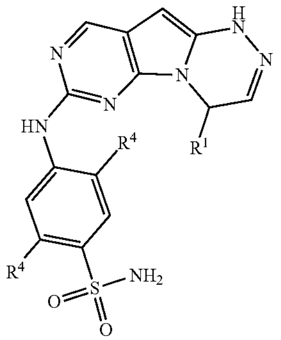
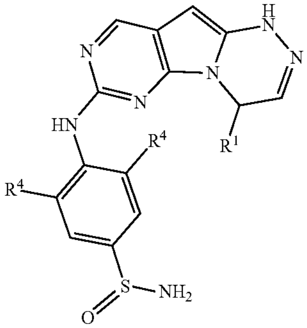

-continued
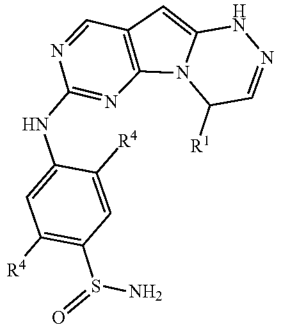
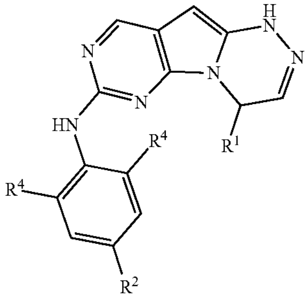
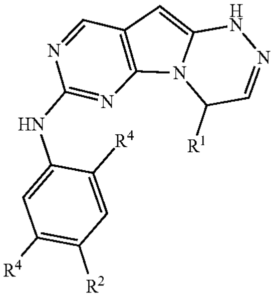
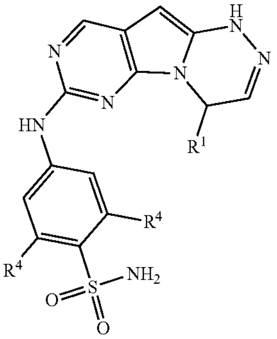
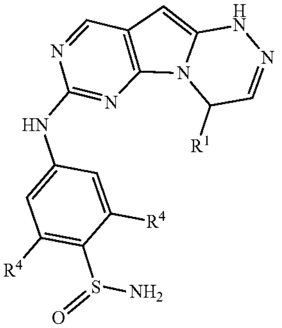
and
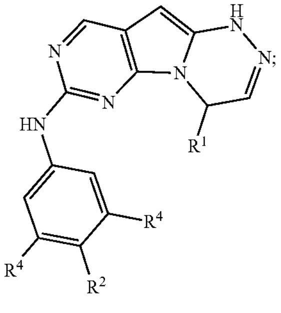
or a pharmaceutically acceptable salt thereof.
In certain embodiments, the compound of present invention is selected from:
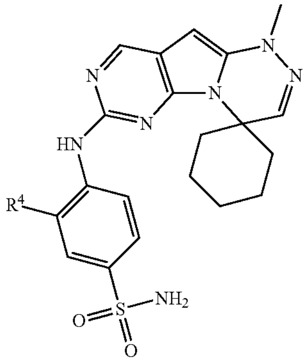
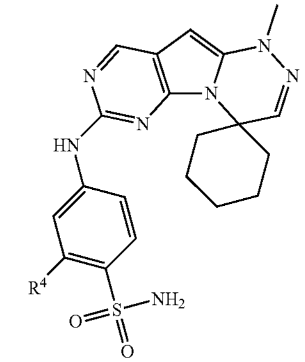
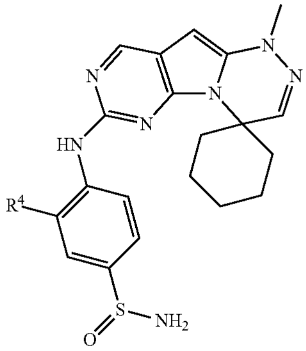
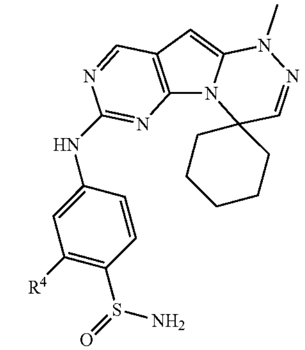

-continued
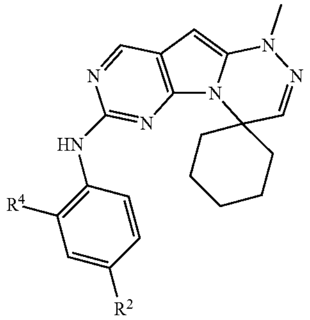
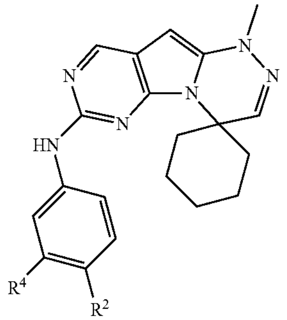
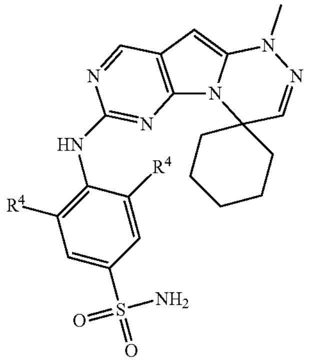
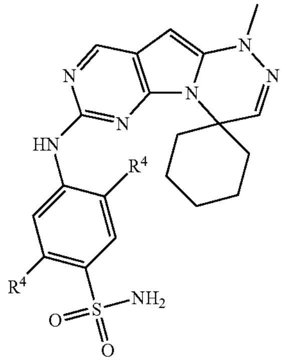
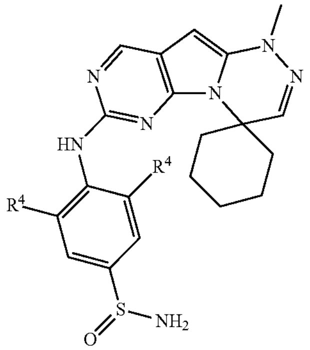
-continued
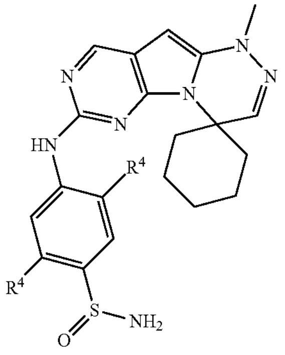
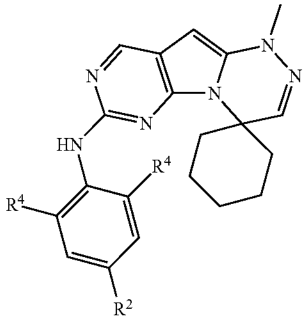
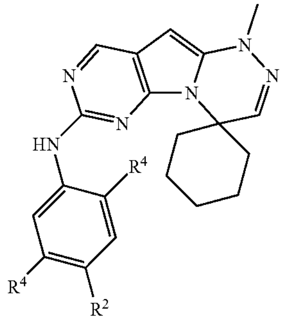
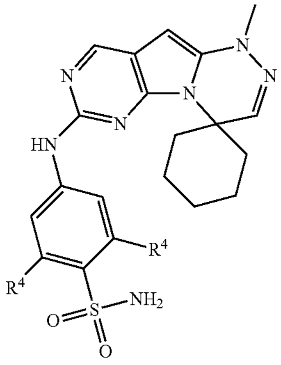
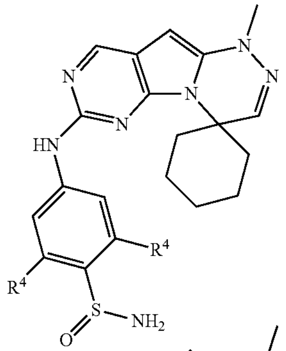
and
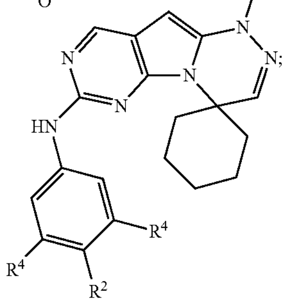
or a pharmaceutically acceptable salt thereof.

In certain embodiments, the compound of present invention is selected from:
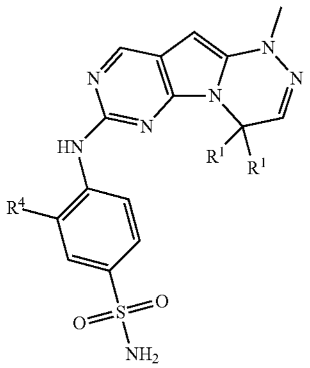
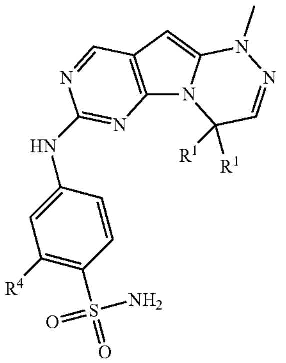
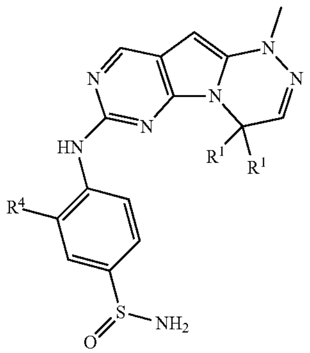
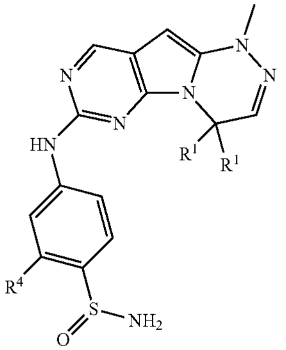
-continued
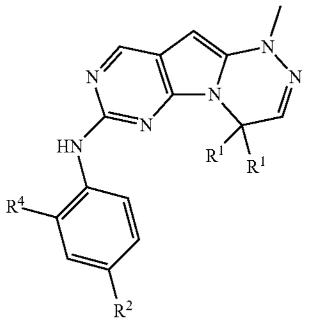
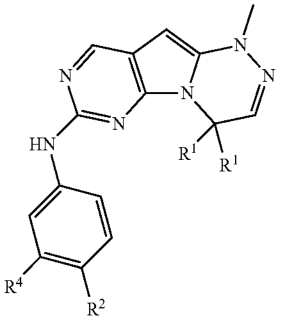
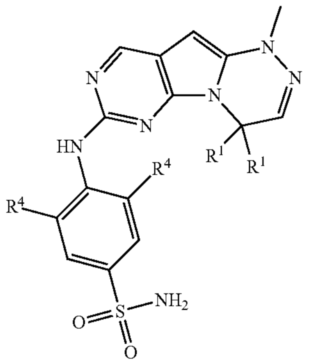
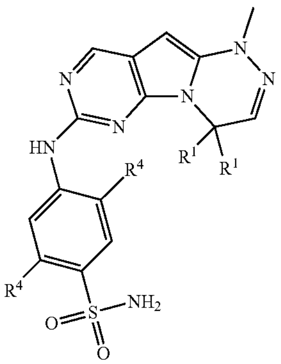
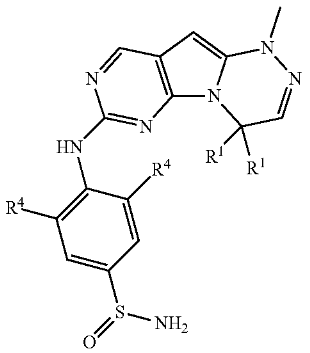

-continued
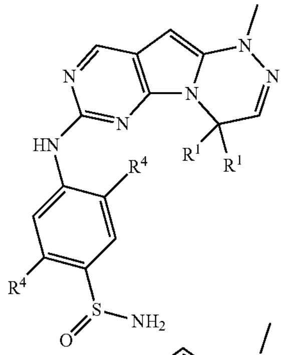
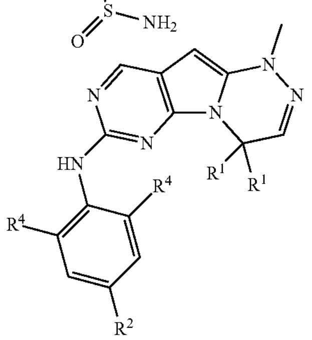
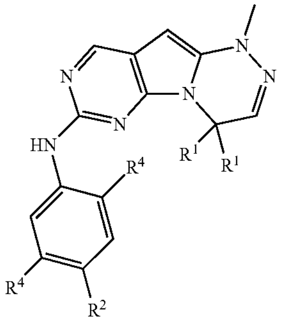
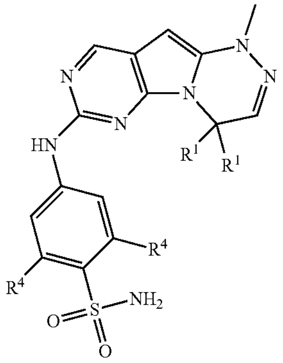
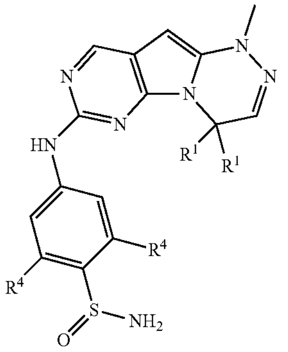
and
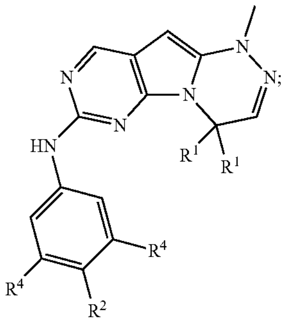
or a pharmaceutically acceptable salt thereof.
In certain embodiments, the compound of present invention is selected from:
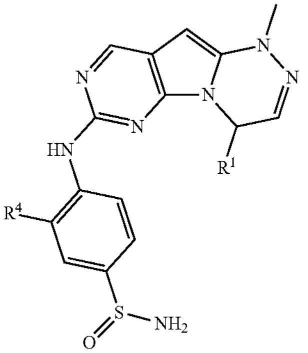
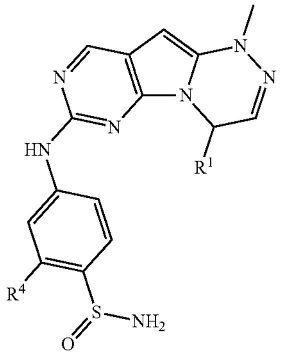
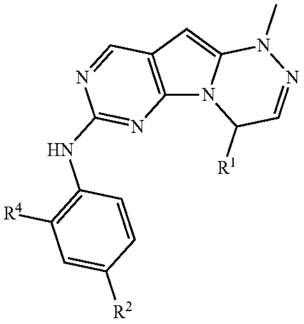
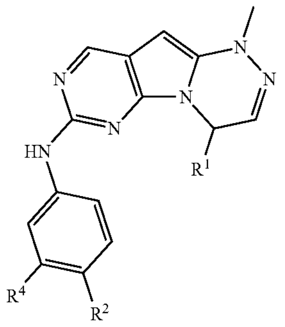

-continued
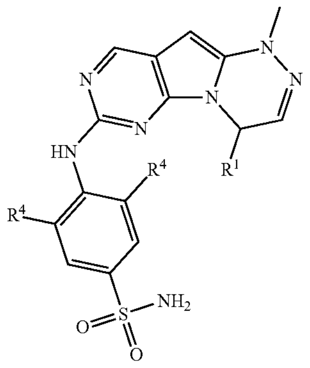
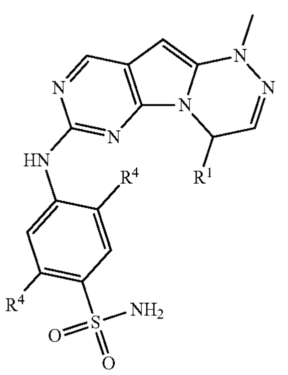
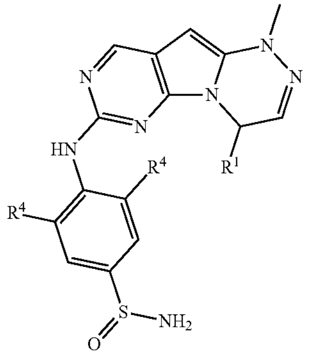
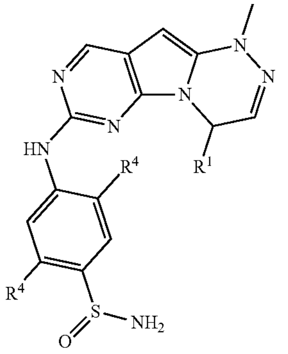
-continued
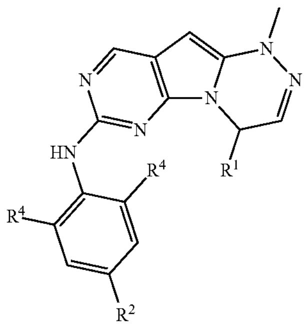
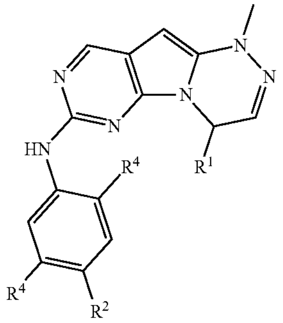
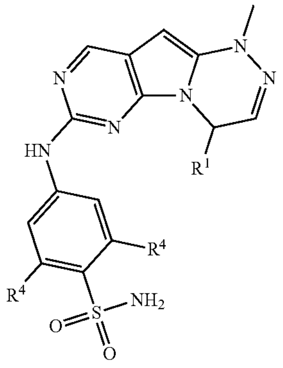
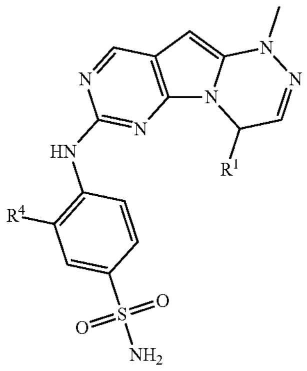

-continued
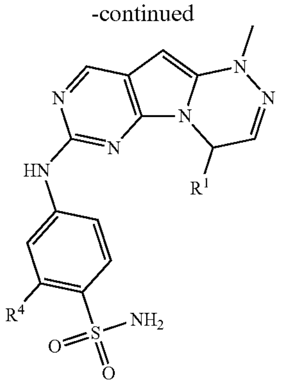
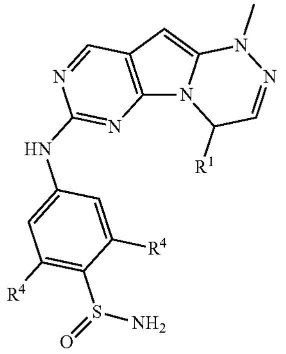
and
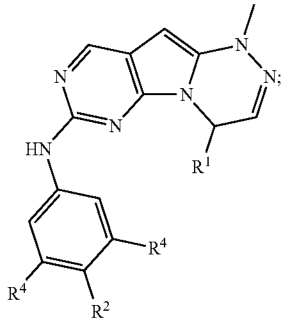
;
or a pharmaceutically acceptable salt thereof.
Non-Limiting Examples of Compounds of the Present Invention
In certain embodiments, the compound of the present invention is selected from:
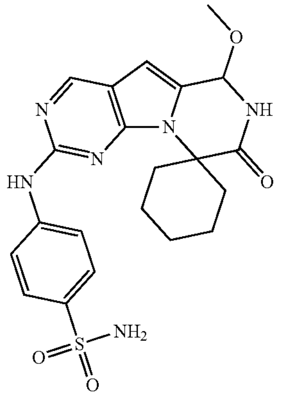
-continued
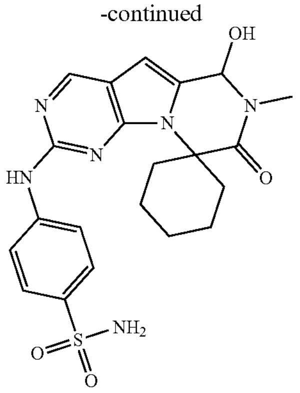
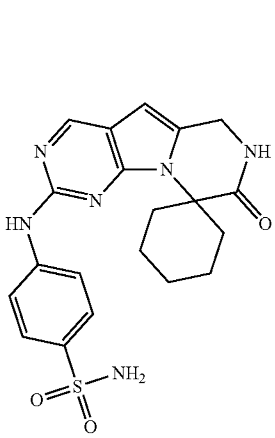
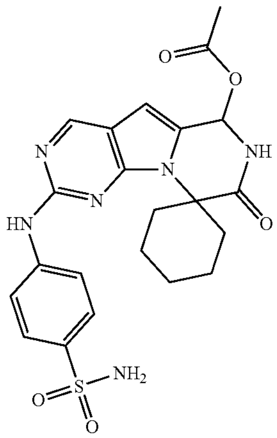
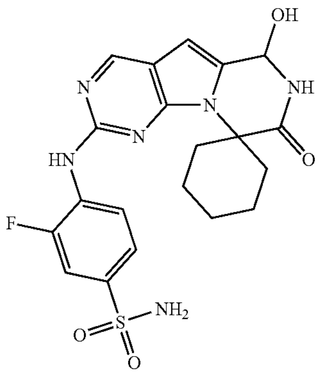
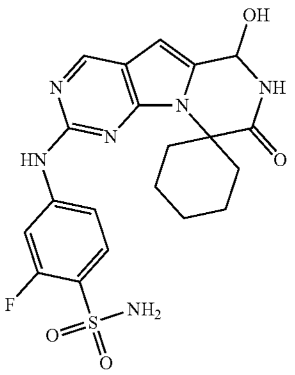

-continued
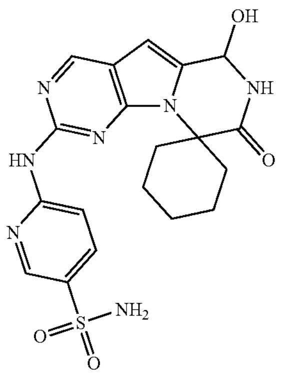
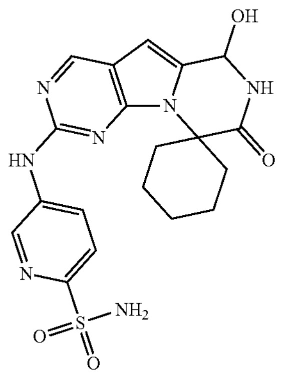
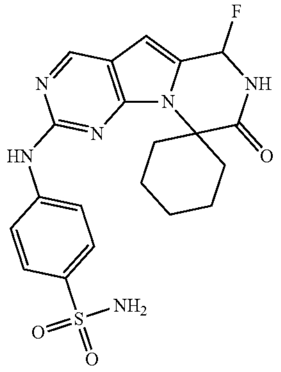
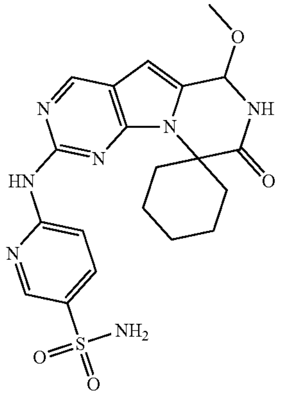
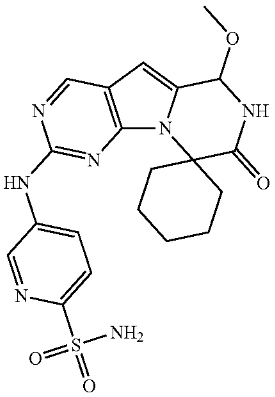
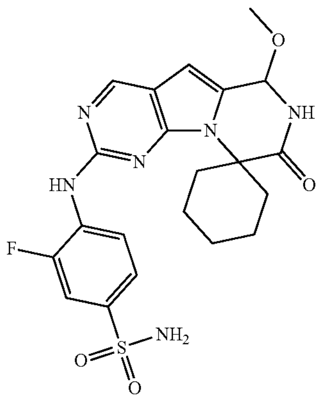
-continued
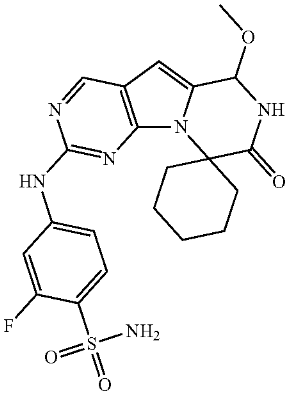
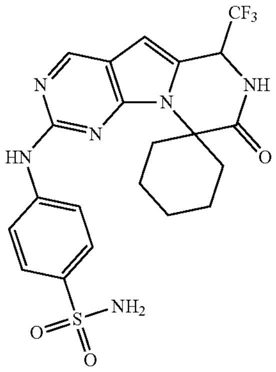
and
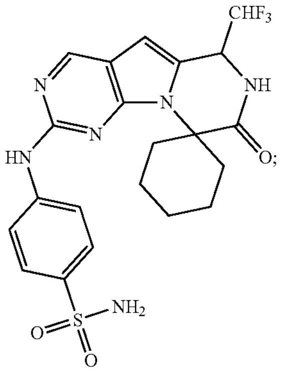
or a pharmaceutically acceptable salt thereof.
In certain embodiments, the compound of the present invention is selected from:
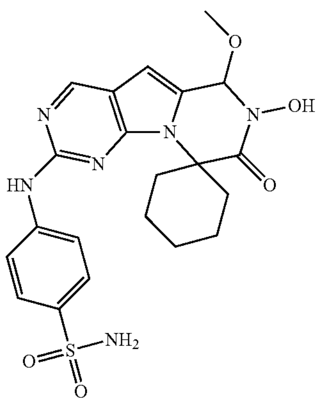

-continued
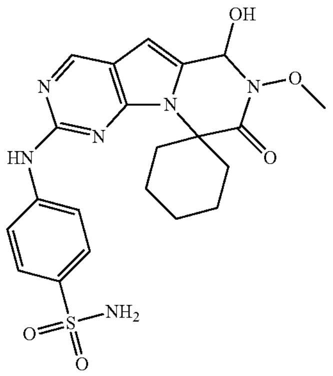
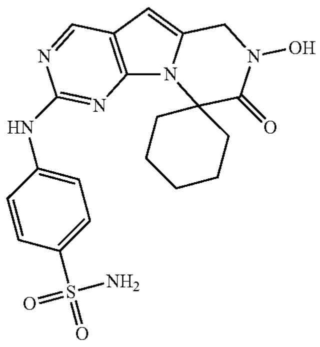
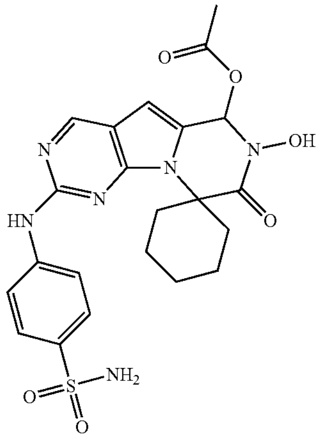
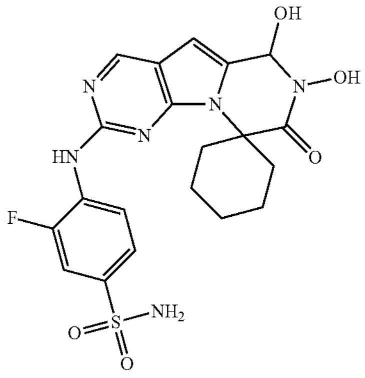
-continued
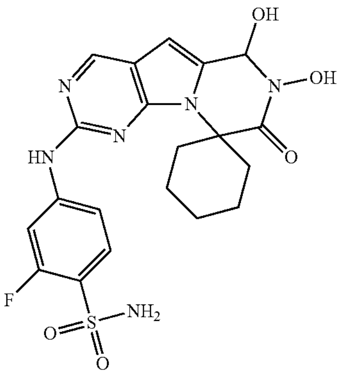
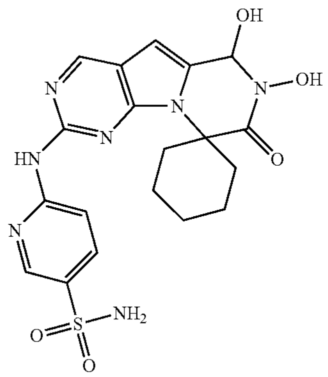
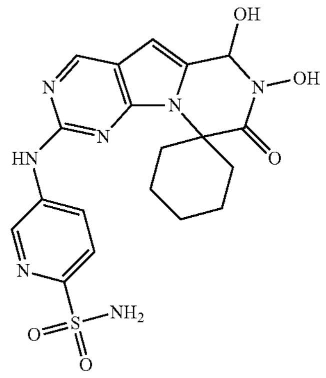
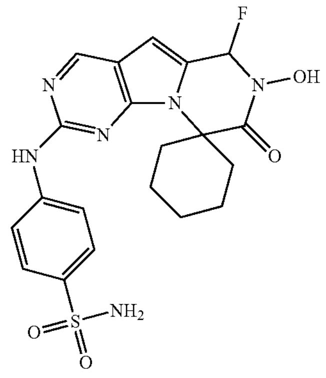

-continued
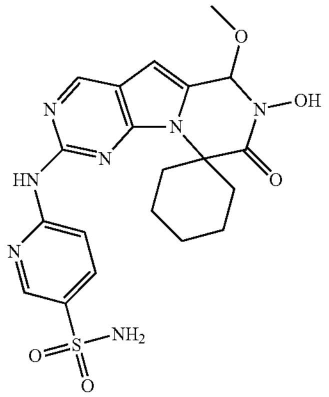
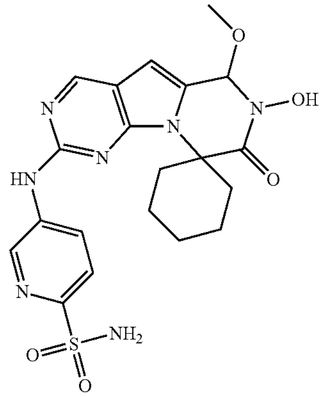
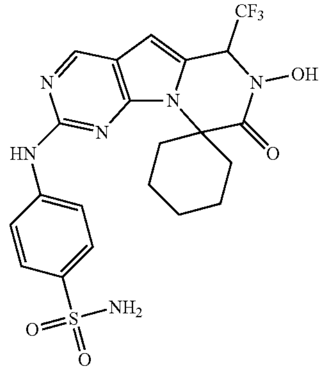
and
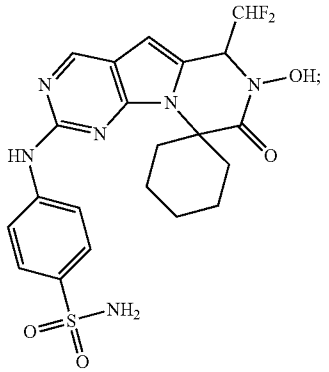
;
or a pharmaceutically acceptable salt thereof.
In certain embodiments, the compound of the present invention is selected from:
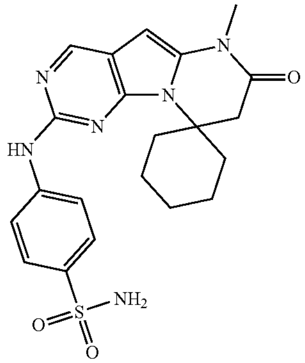
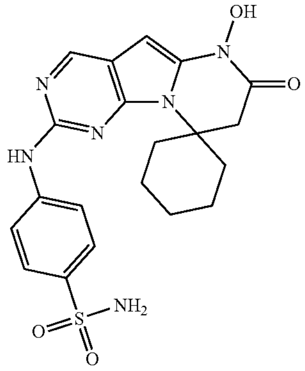
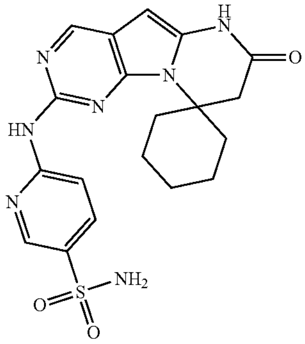
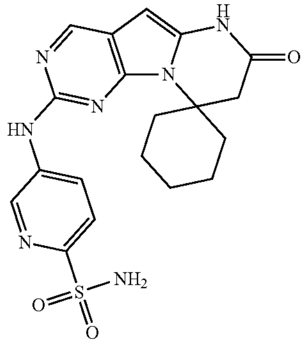

-continued
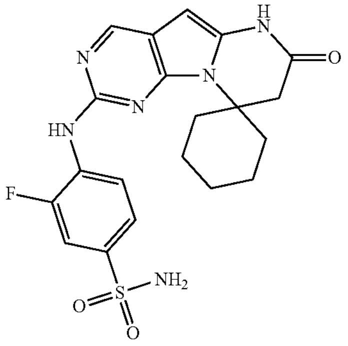
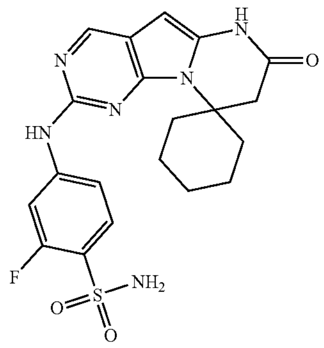
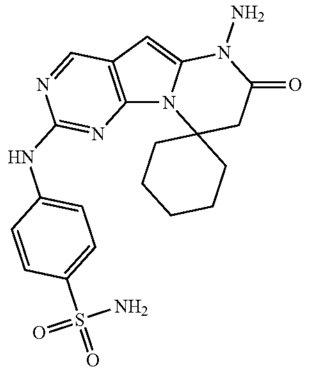
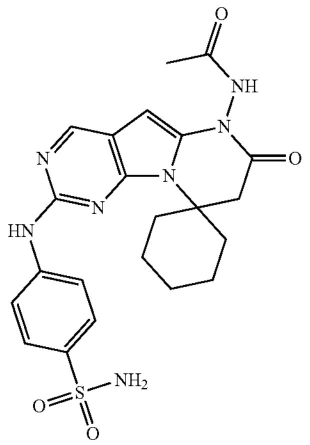
-continued
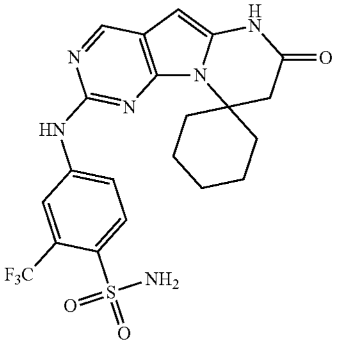
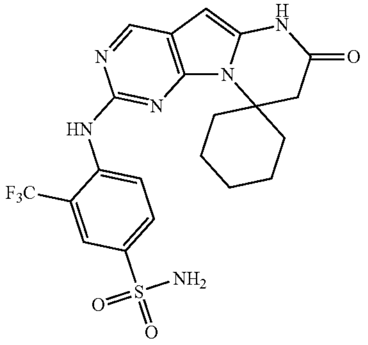
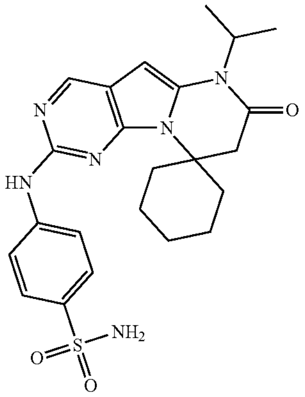
and
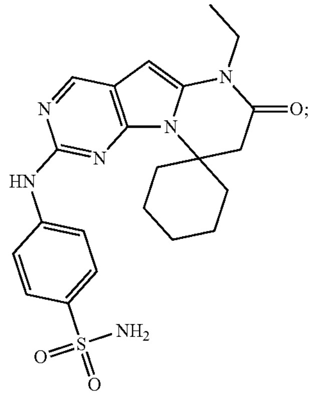
or a pharmaceutically acceptable salt thereof.
In certain embodiments, the compound of the present invention is selected from:

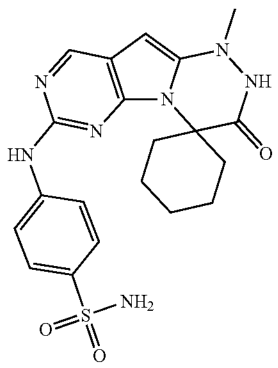
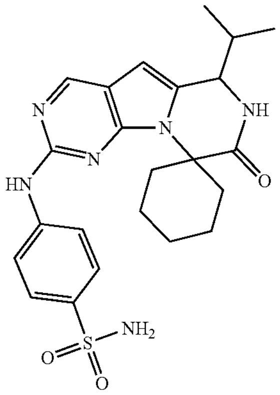
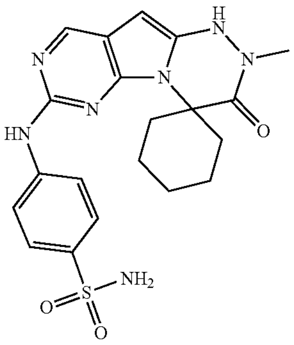
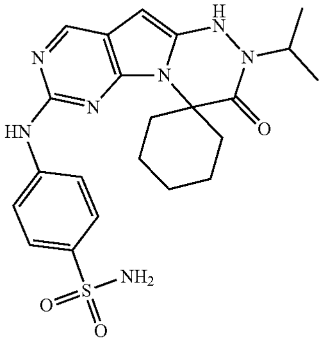
-continued
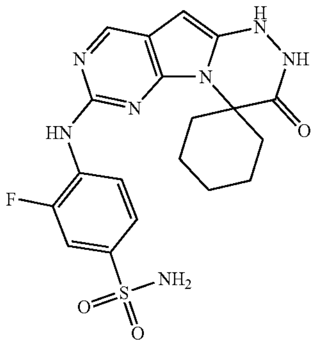
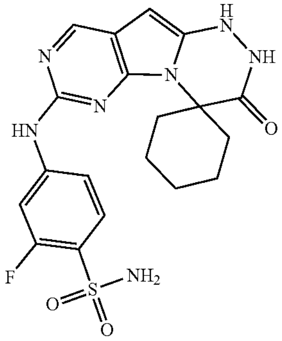
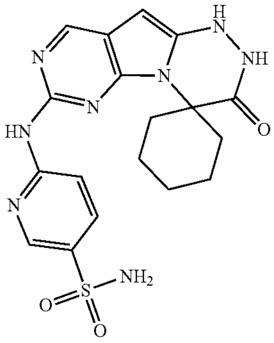
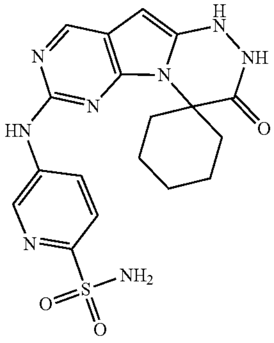
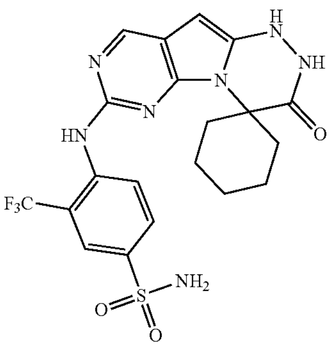

-continued
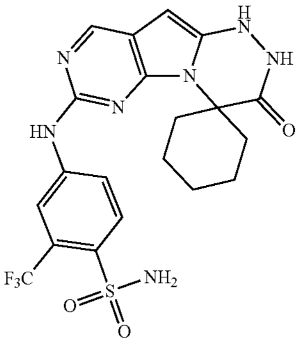
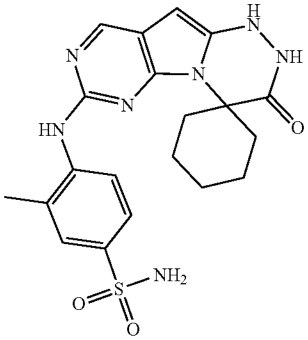
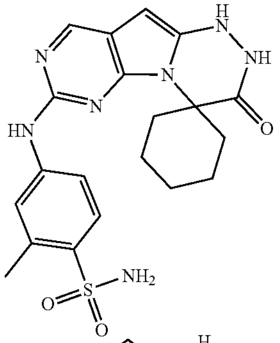
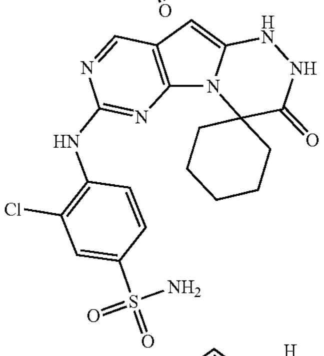
and
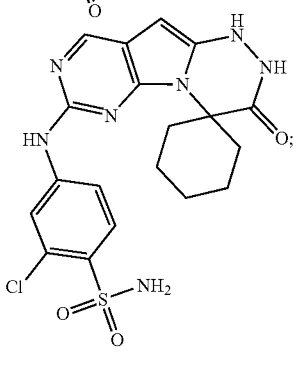
or a pharmaceutically acceptable salt thereof.
In certain embodiments, the compound of the present invention is selected from:
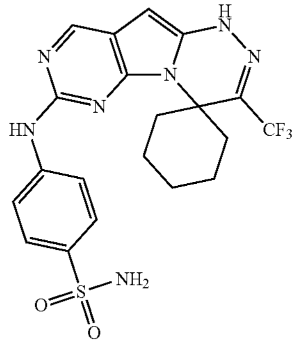
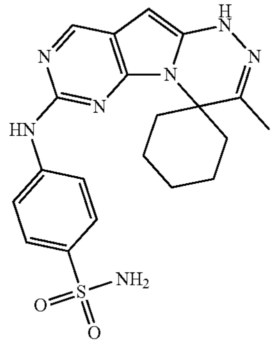
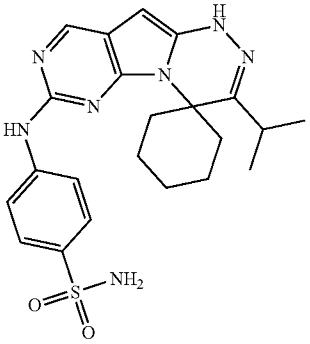
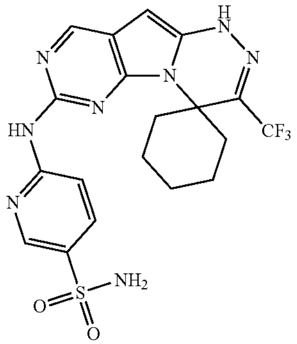
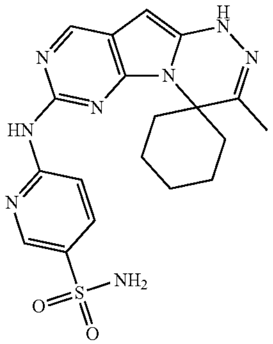
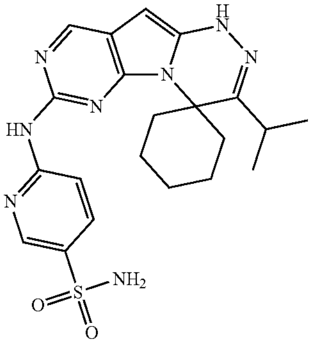

-continued
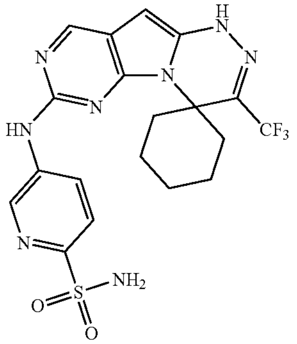
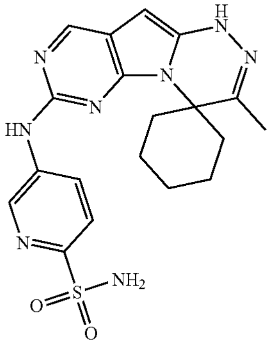
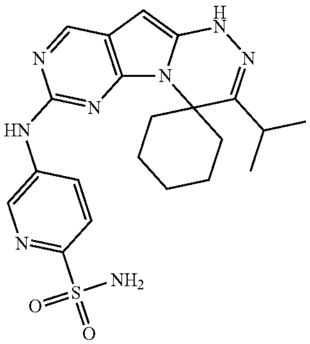
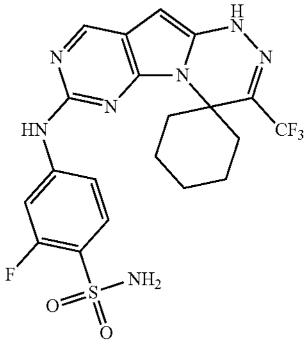
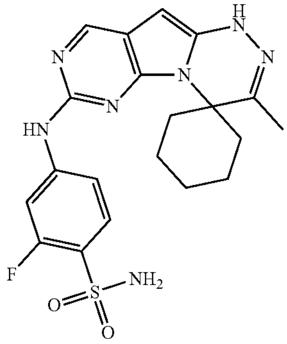
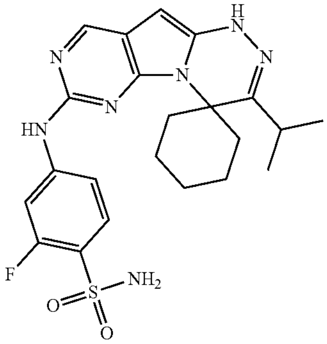
-continued
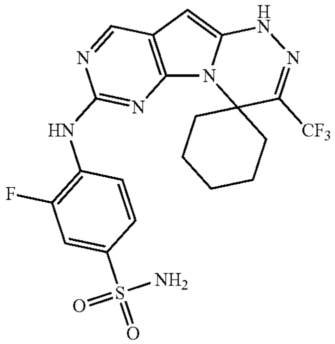
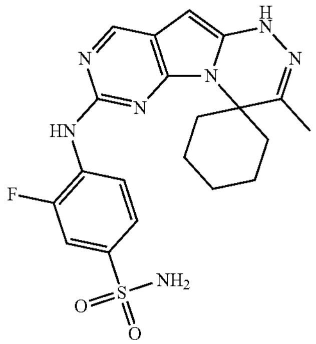
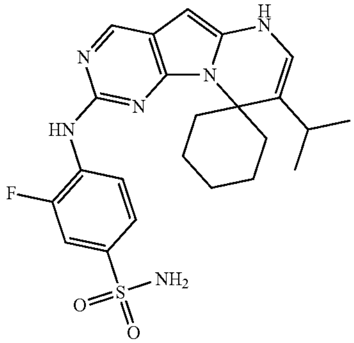
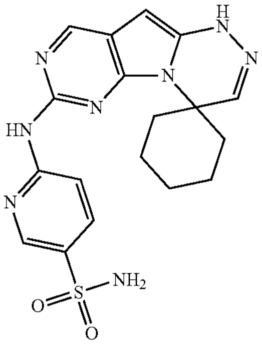
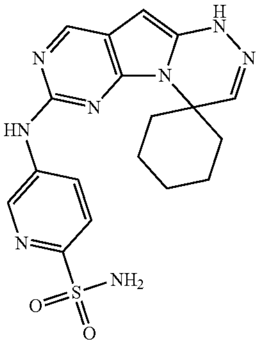
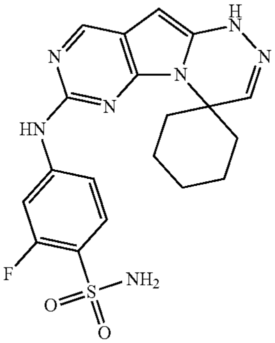
and -continued
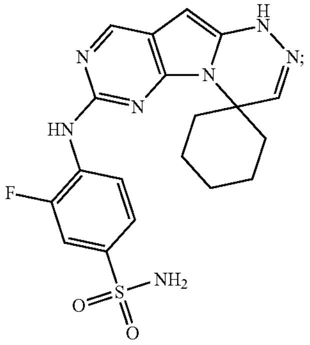
or a pharmaceutically acceptable salt thereof.
In certain embodiments, the compound of the present invention is selected from:
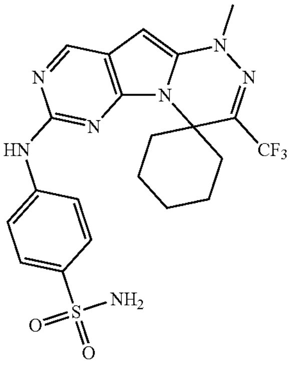
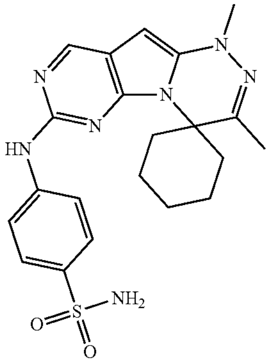
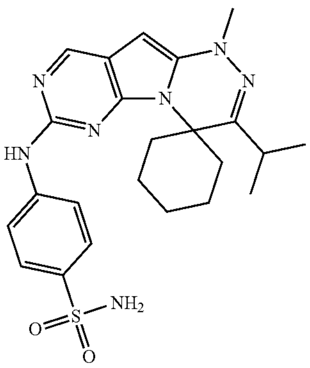
-continued
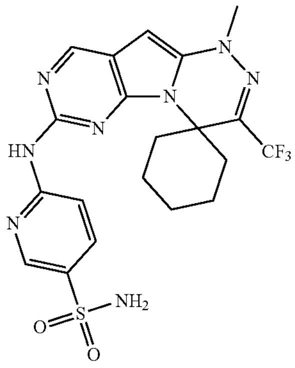
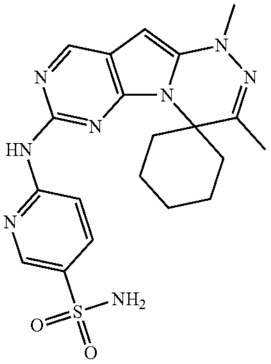
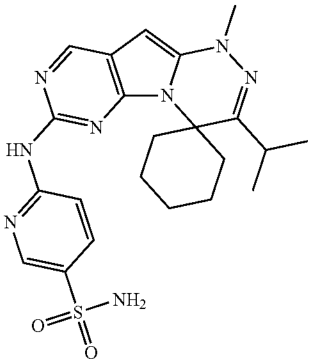
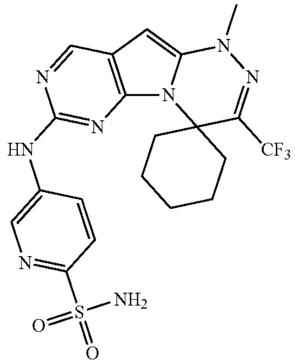

-continued
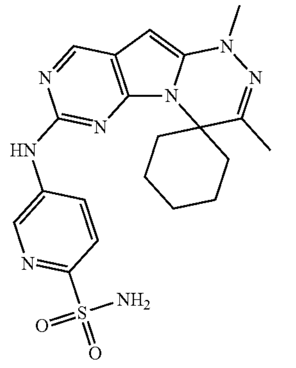
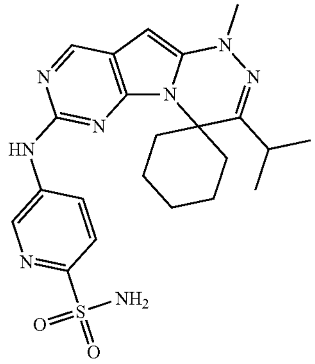
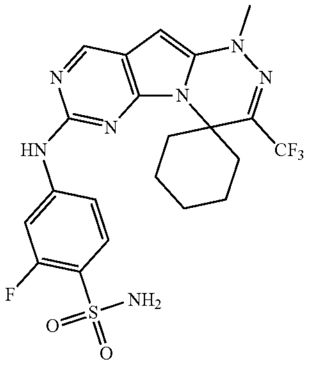
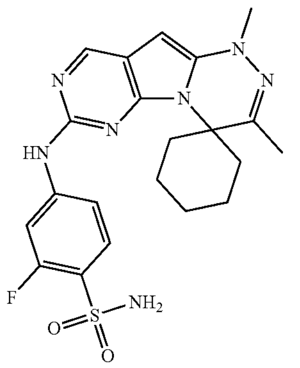
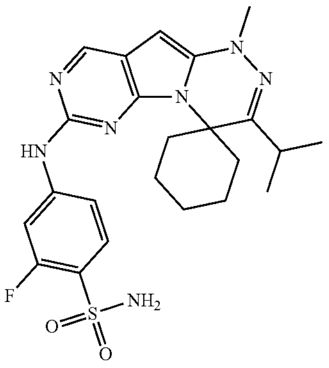
-continued
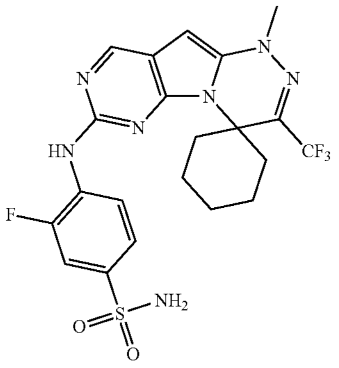
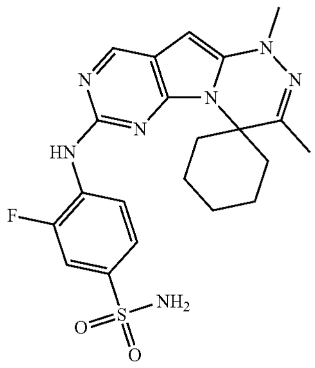
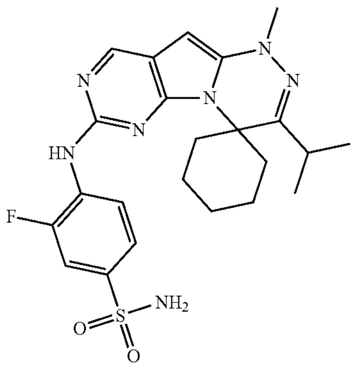

-continued
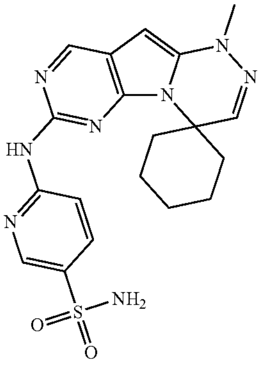
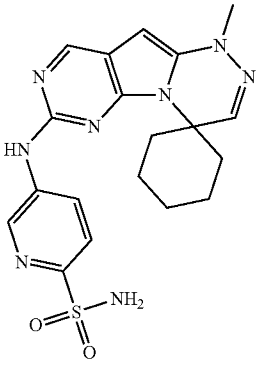
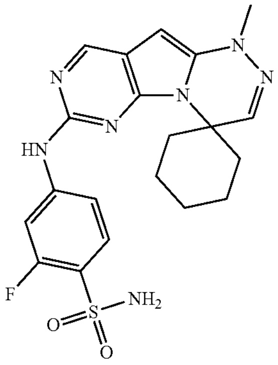
and
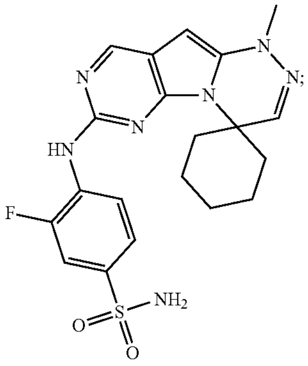
or a pharmaceutically acceptable salt thereof.
In certain embodiments, the compound of the present invention is selected from:
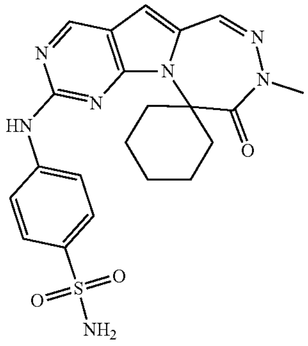
-continued
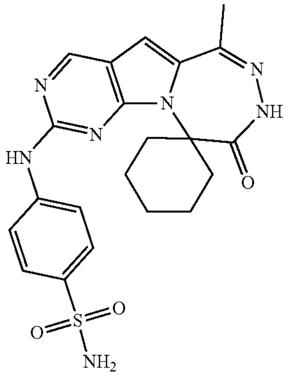
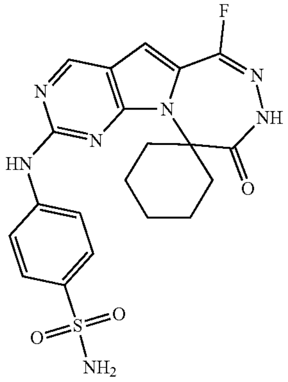
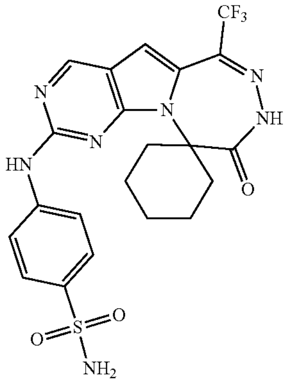
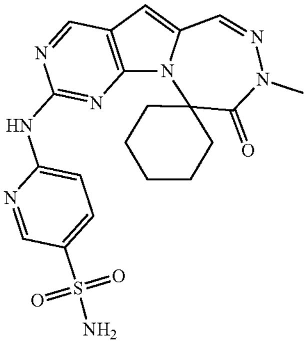

-continued
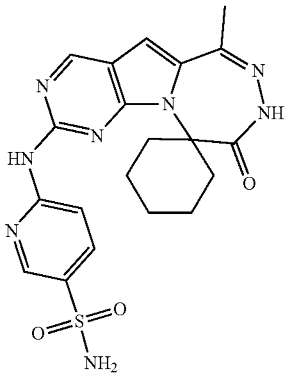
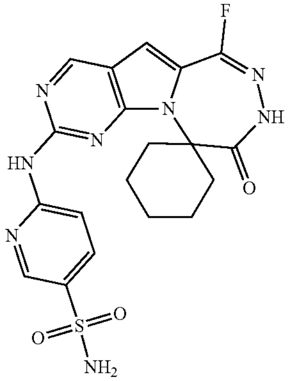
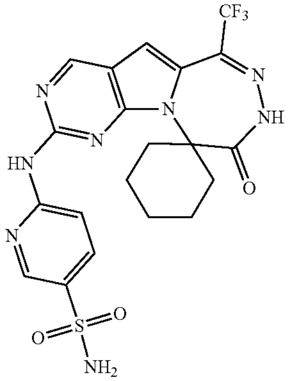
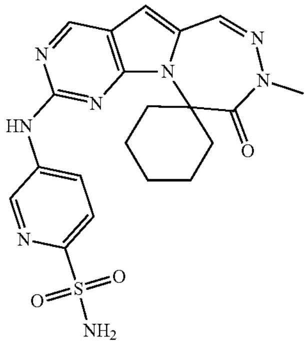
-continued
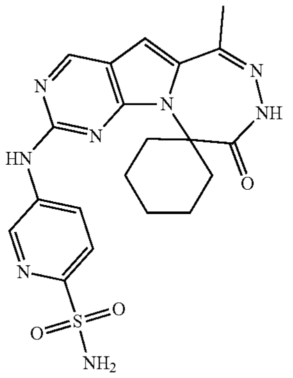
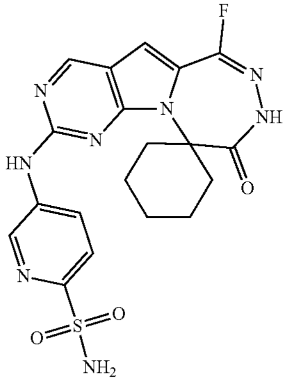
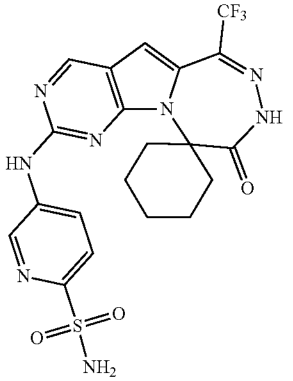
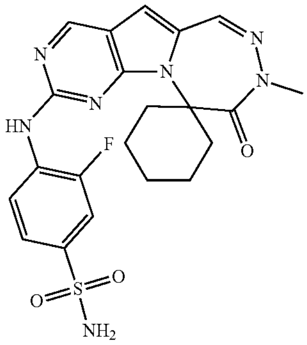

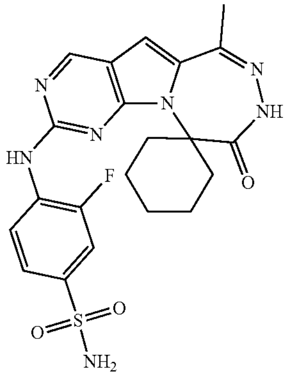
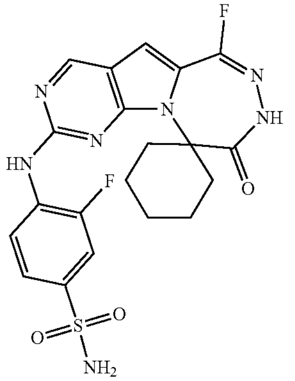
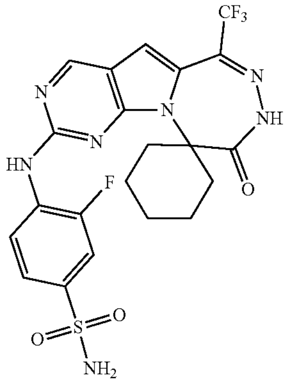
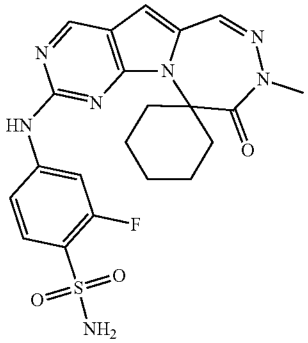
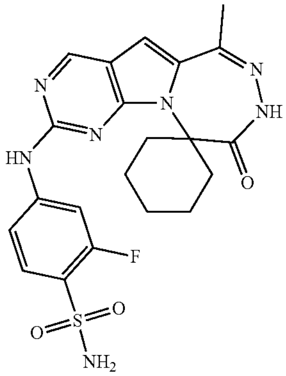
and
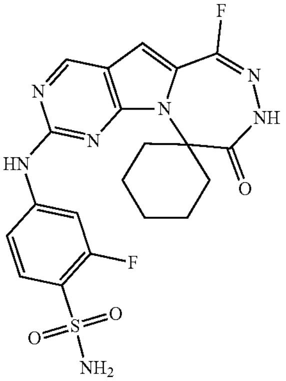
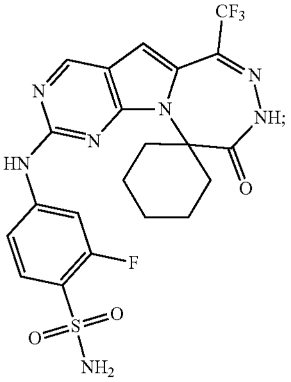
;
or a pharmaceutically acceptable salt thereof.
In certain embodiments, the compound of the present invention is selected from:
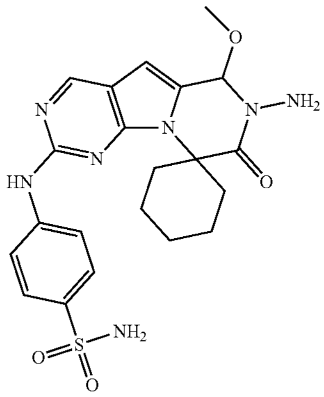

-continued
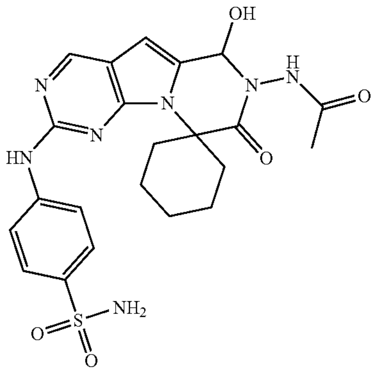
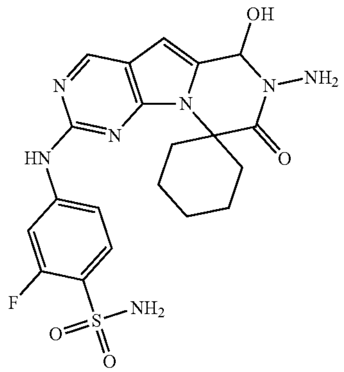
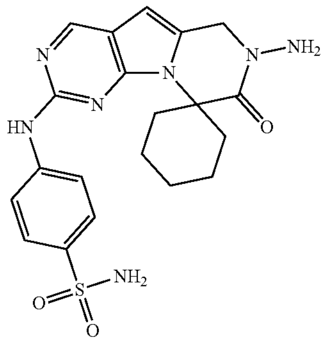
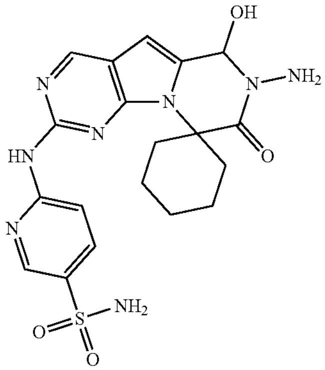
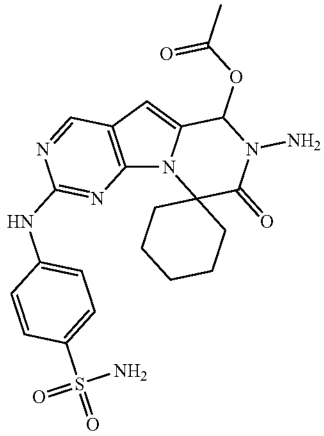
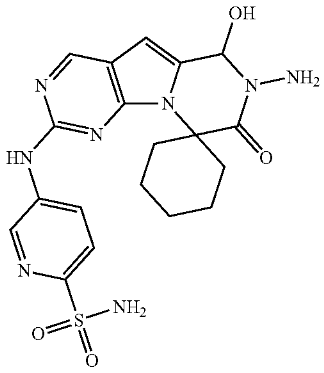
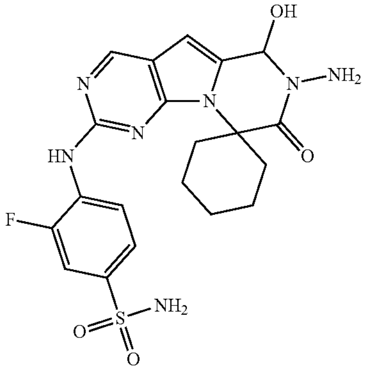
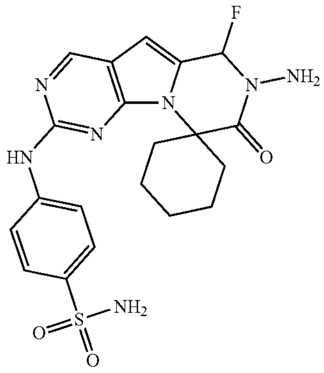
-continued -continued
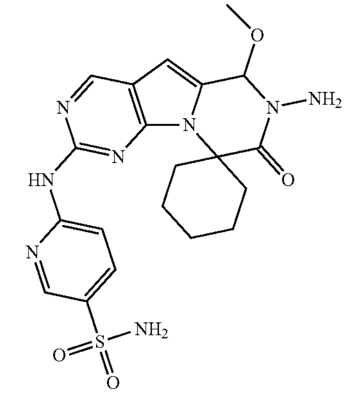
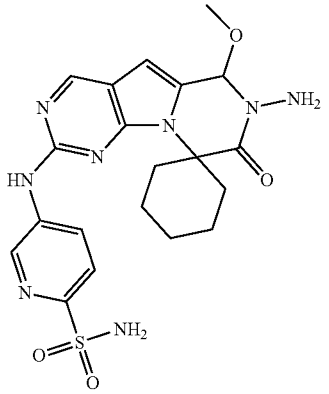
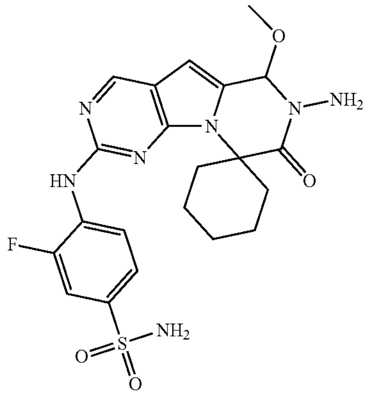
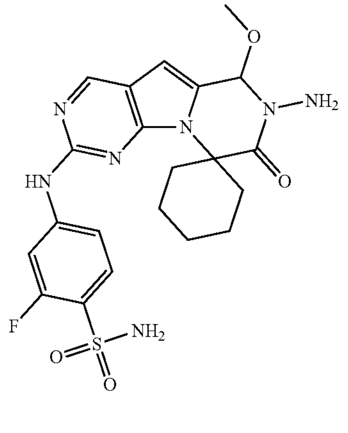
-continued
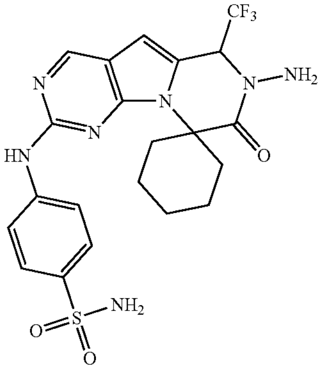
and
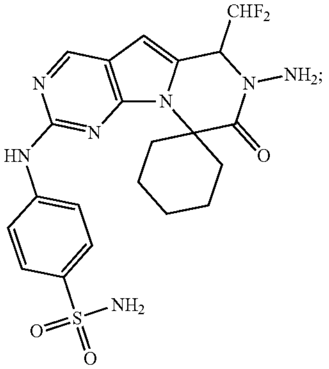 [SMILES: NN1C(=O)C2(CCCCC2)n2c(cc3cnc(Nc4ccc(S(N)(=O)=O)cc4)nc32)C1C(F)F]
or a pharmaceutically acceptable salt thereof.
In certain embodiments, the compound of the present invention is selected from:
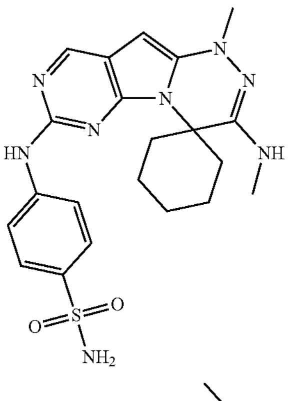
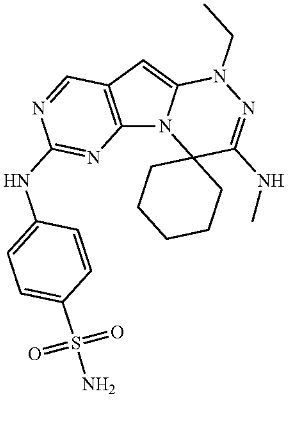

-continued
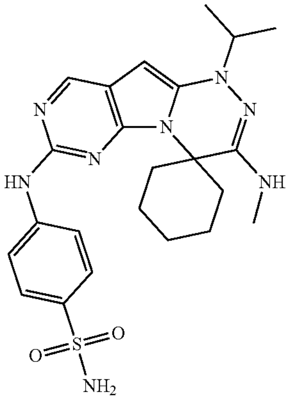
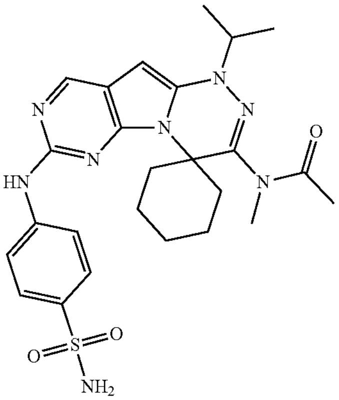
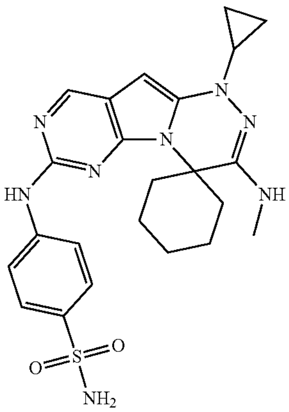
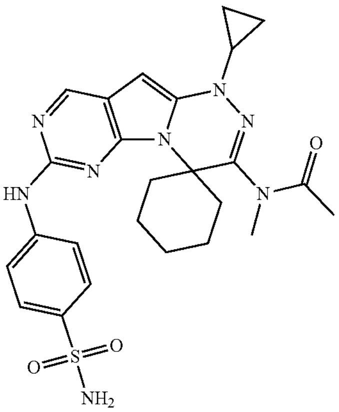
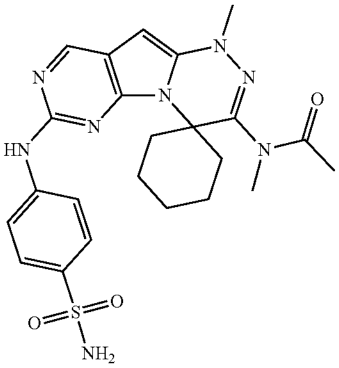
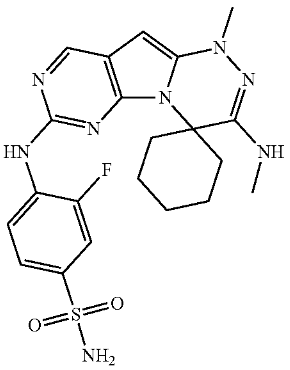
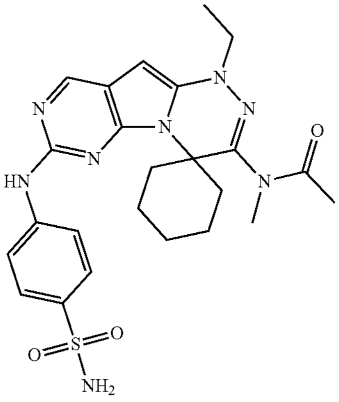
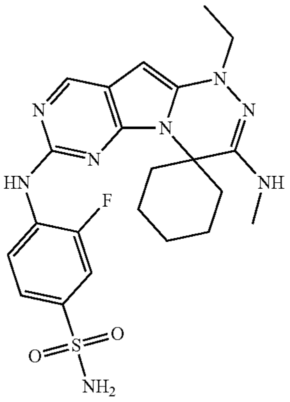

-continued
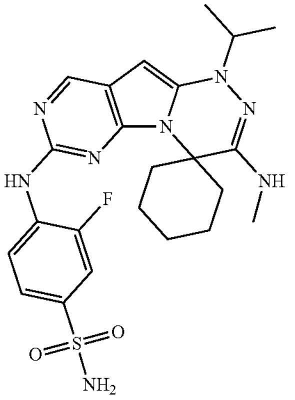
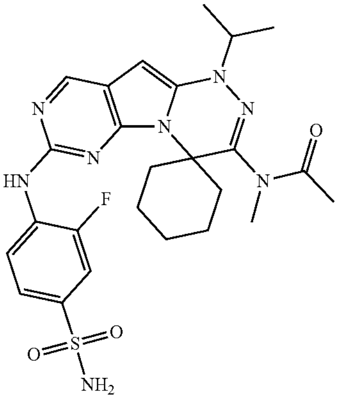
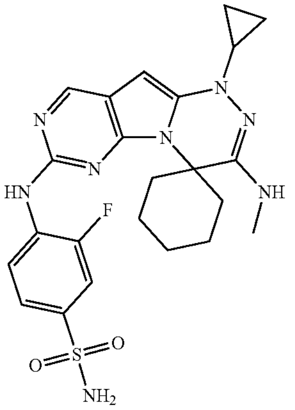
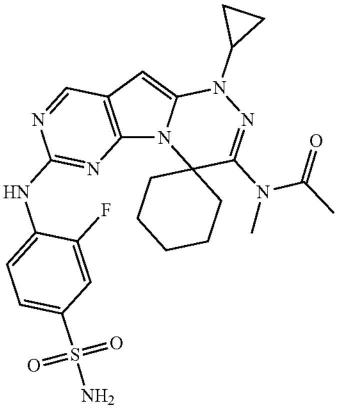
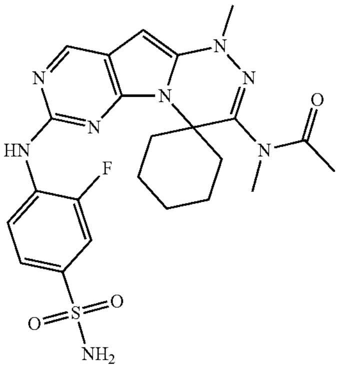
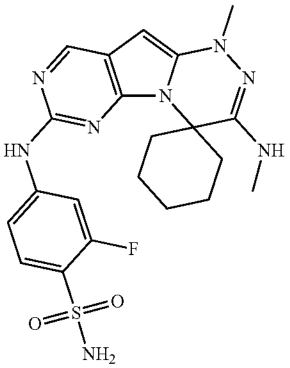
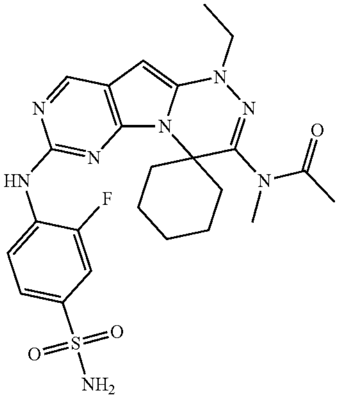
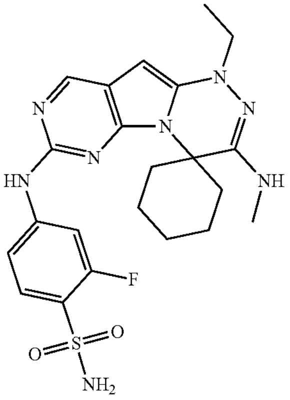
-continued -continued
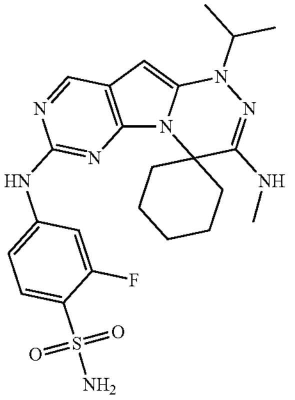
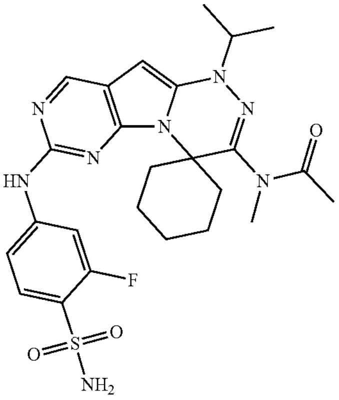
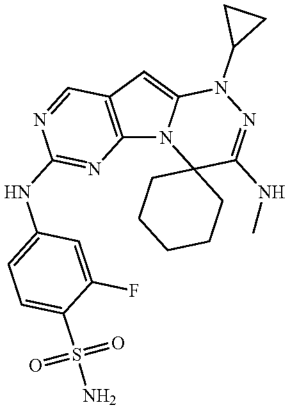
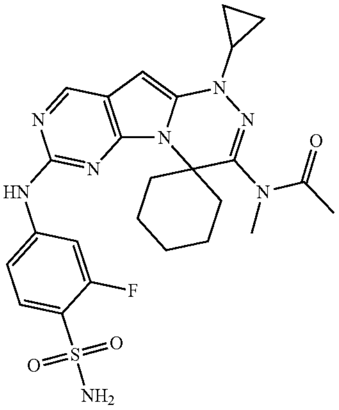
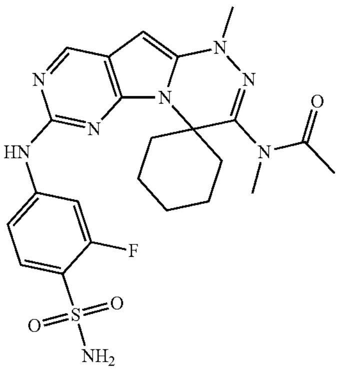
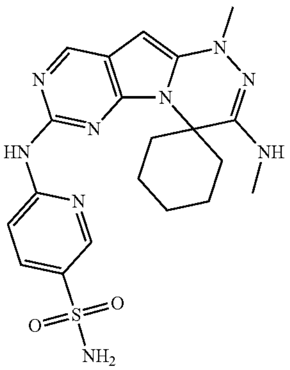
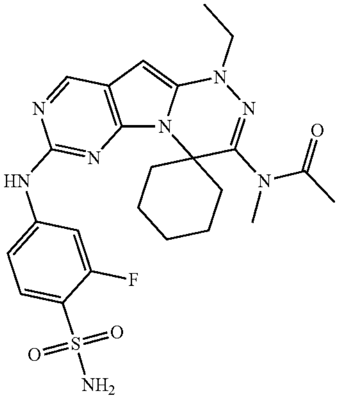
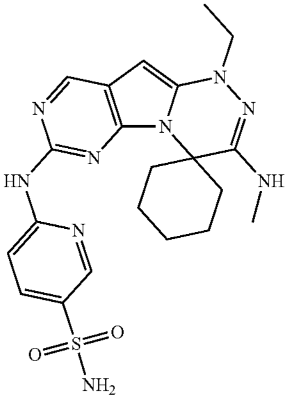
-continued -continued
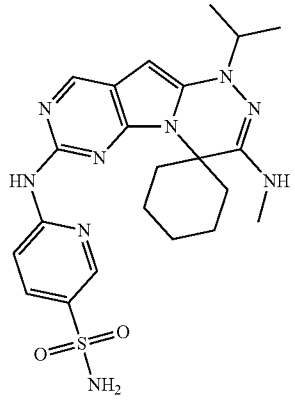
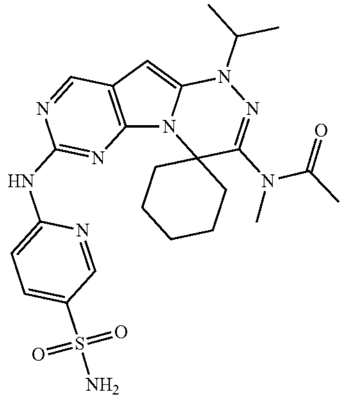
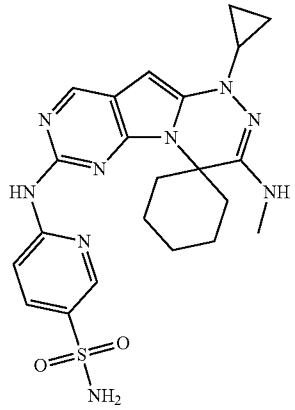
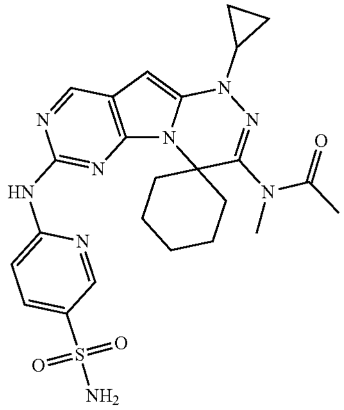
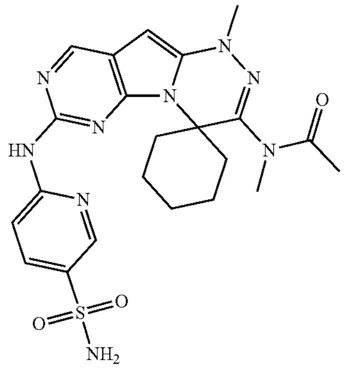
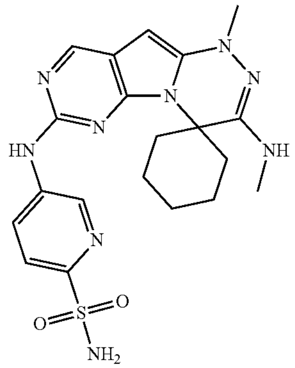
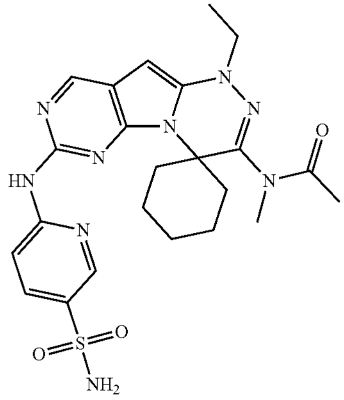
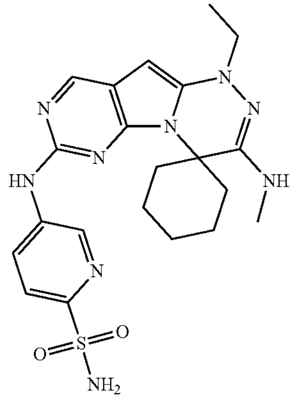

-continued
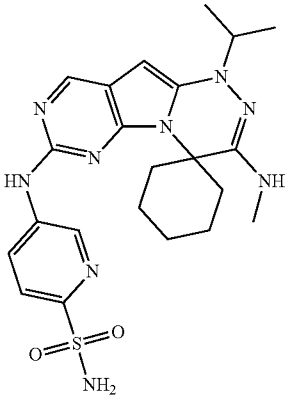
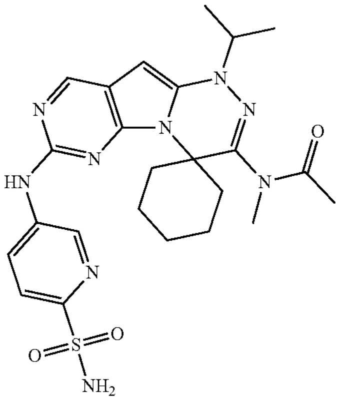
and
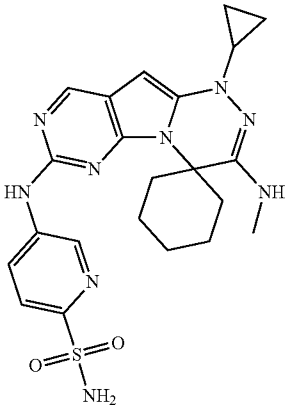
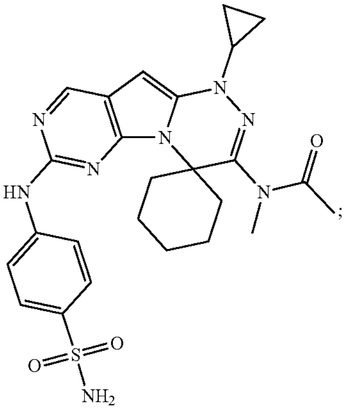
;
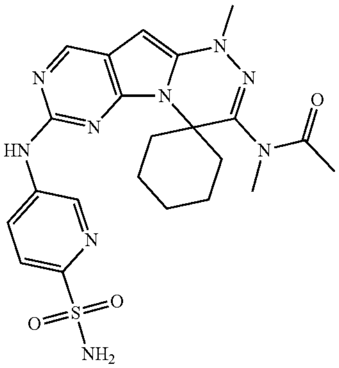
or a pharmaceutically acceptable salt thereof.
In certain embodiments, the compound of the present invention is selected from:
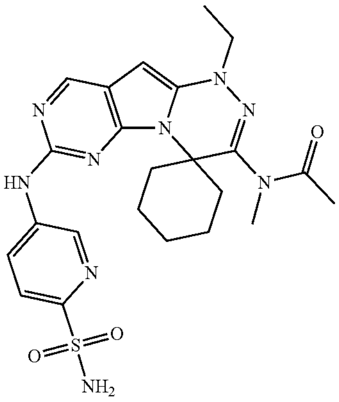
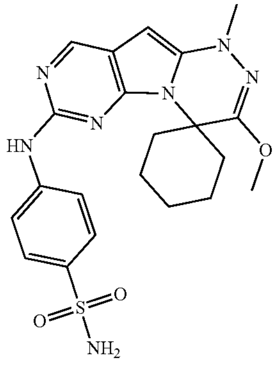
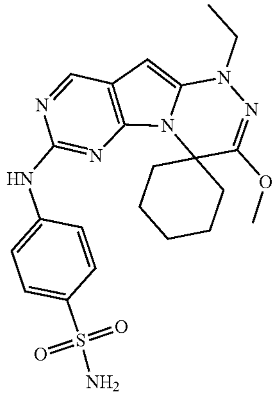

-continued
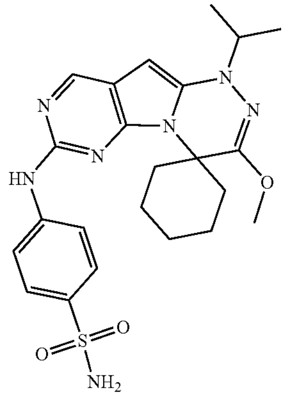
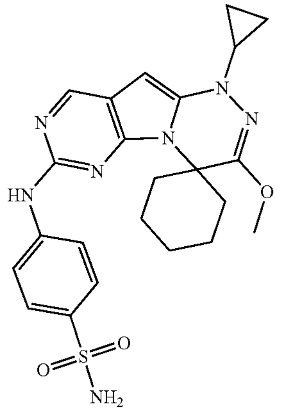
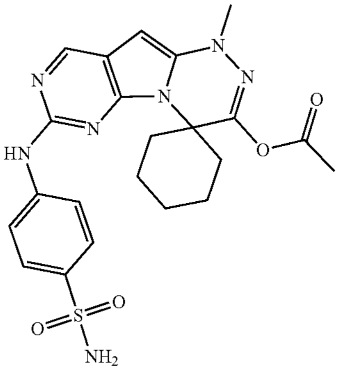
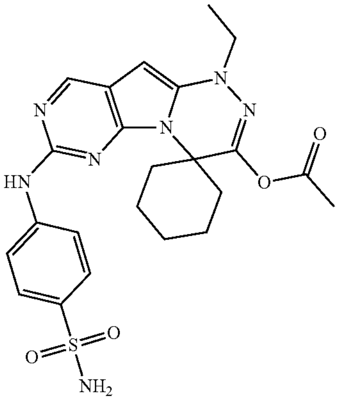
-continued
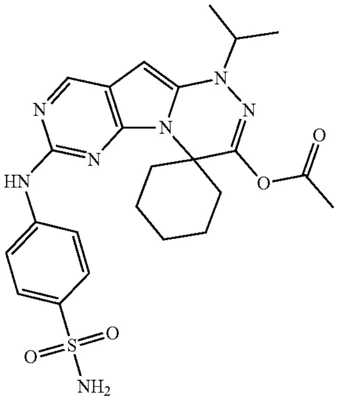
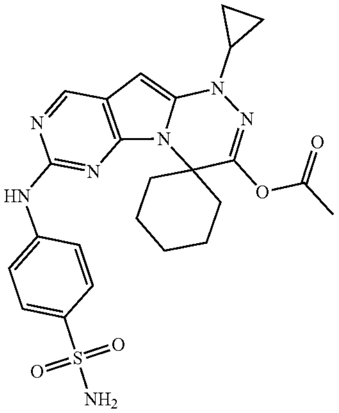
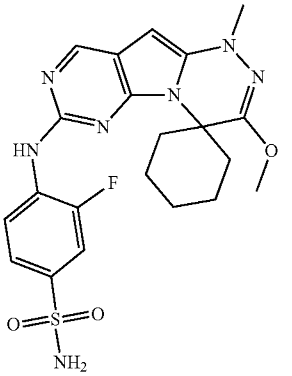
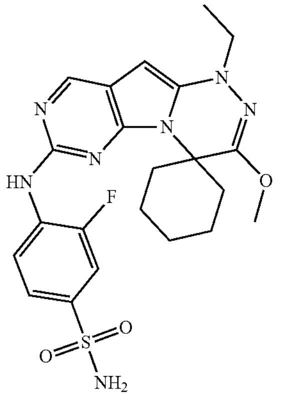

-continued
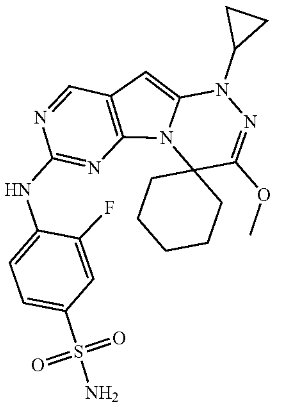
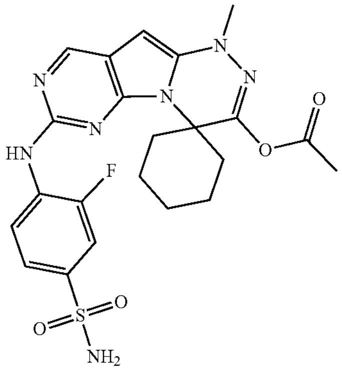
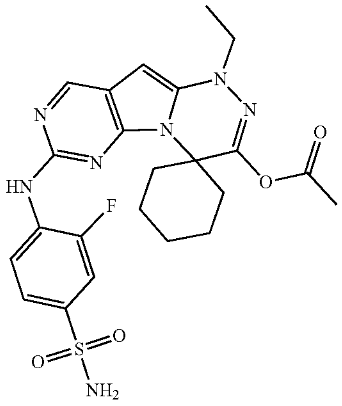
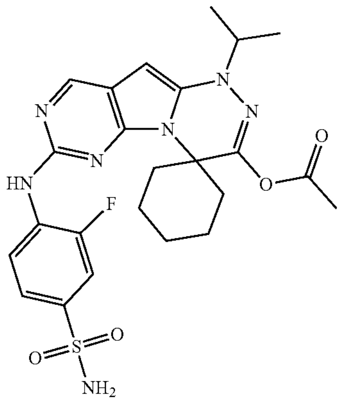
-continued
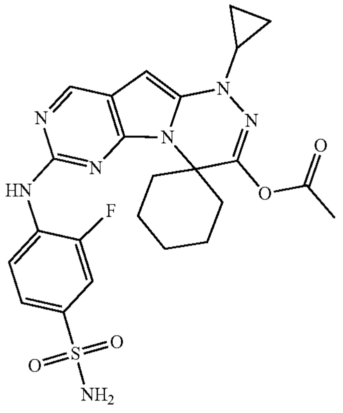
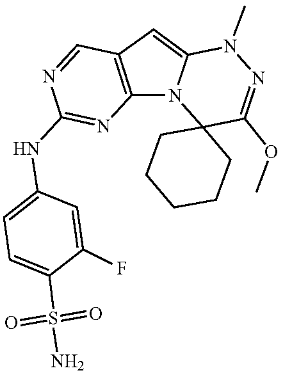
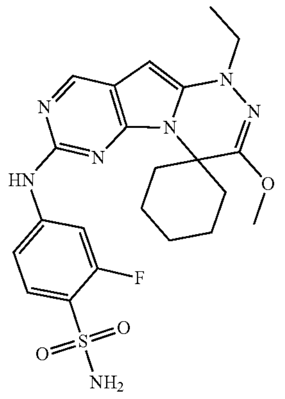
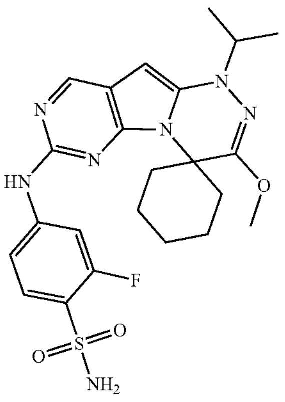

-continued
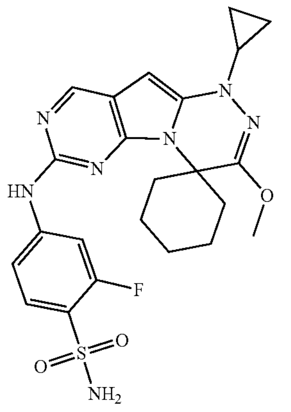
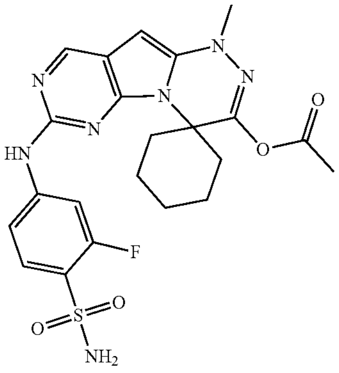
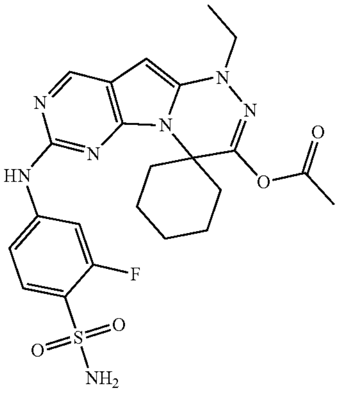
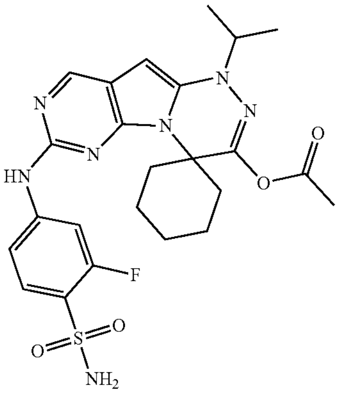
-continued
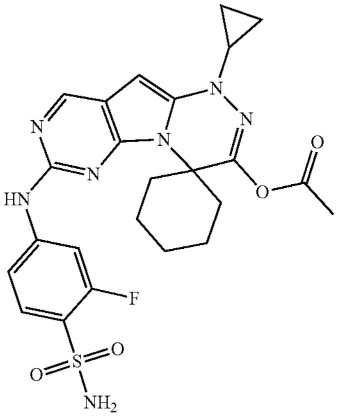
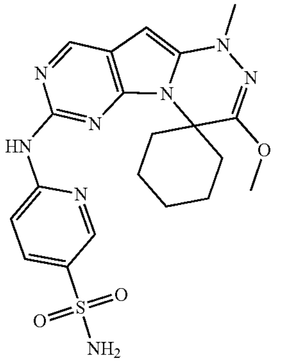
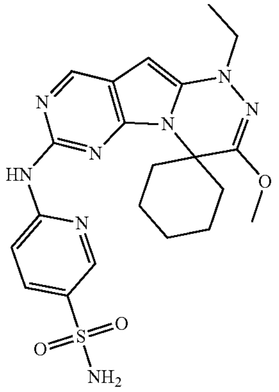
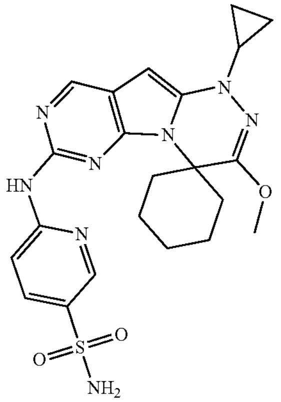
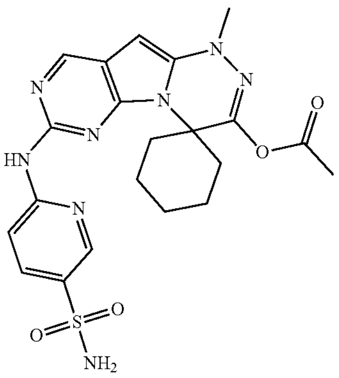 [SMILES: CC(=O)OC1=NN(C)c2cc3cnc(Nc4ccc(S(N)(=O)=O)cn4)nc3n2C12CCCCC2]

-continued
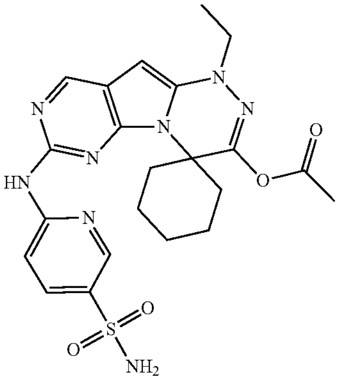
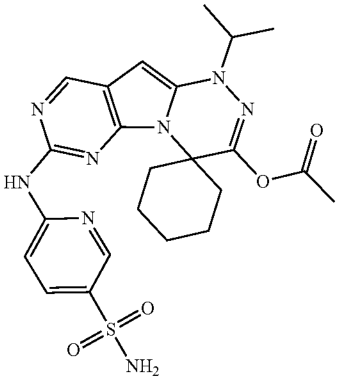
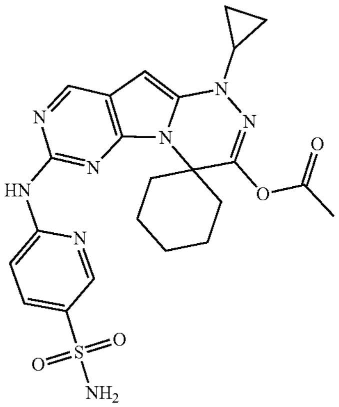
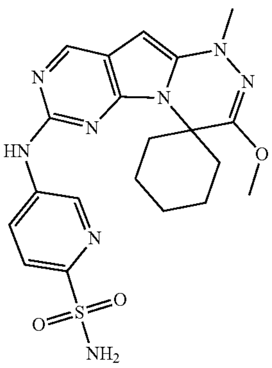
-continued
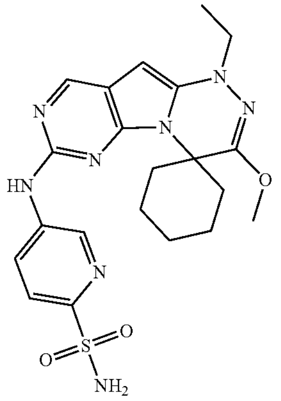
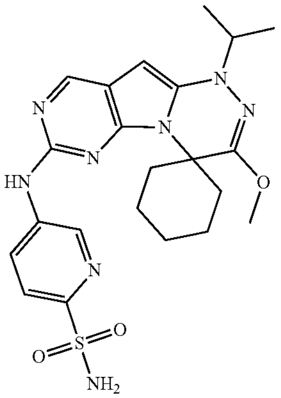
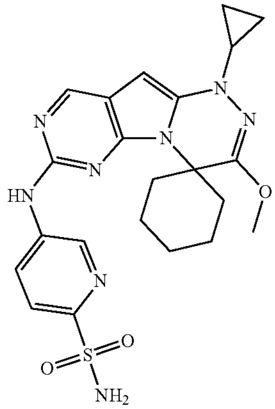
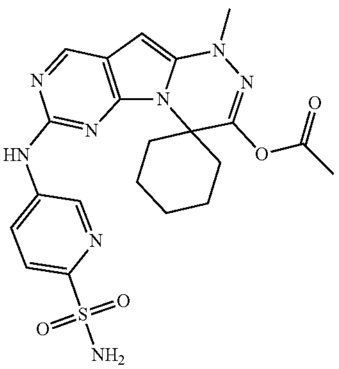

-continued
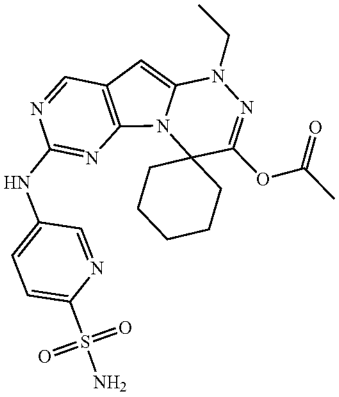
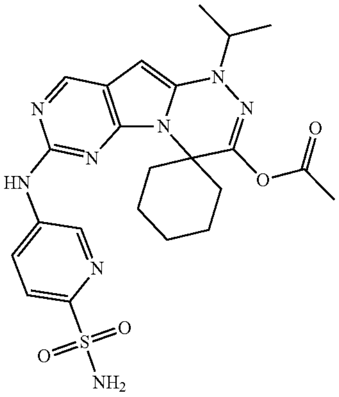
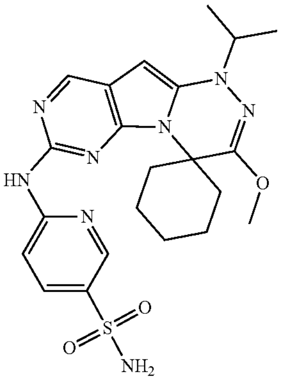
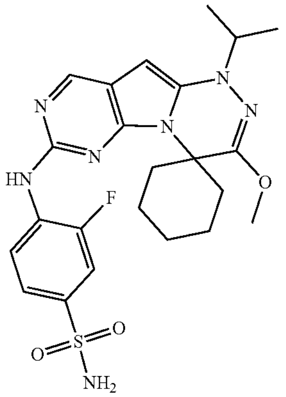
and
-continued
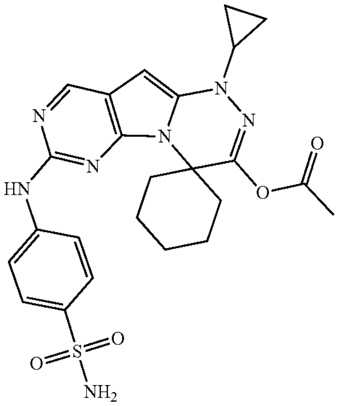
;
or a pharmaceutically acceptable salt thereof.
In certain embodiments, the compound of the present invention is selected from:
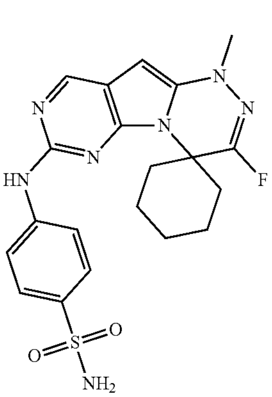
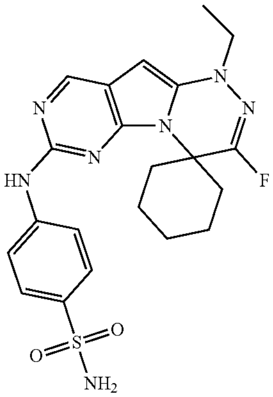
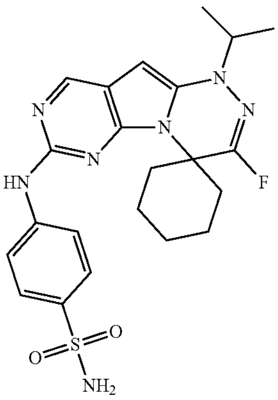
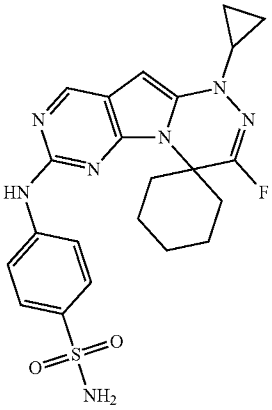

-continued
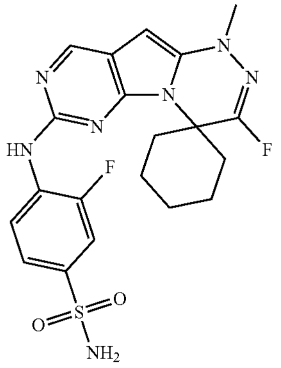
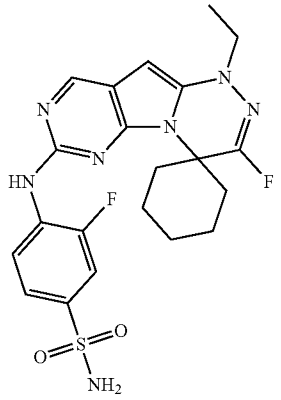
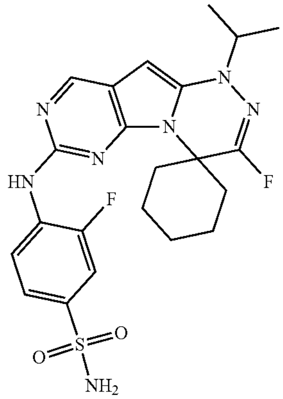
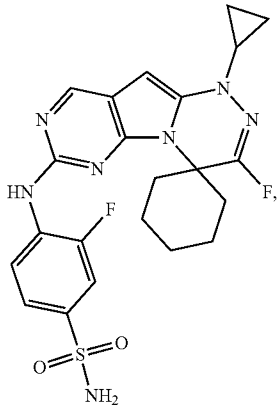
,
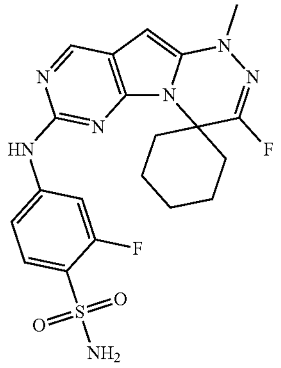
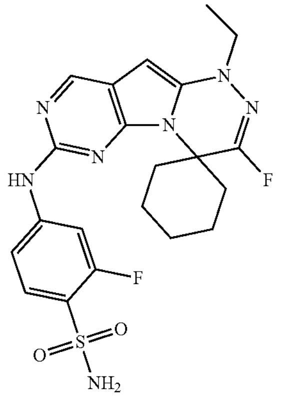
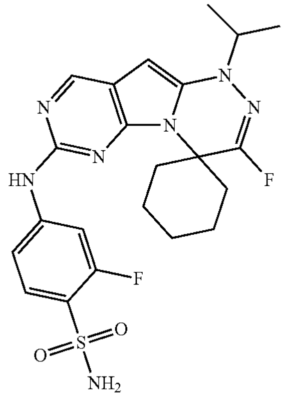
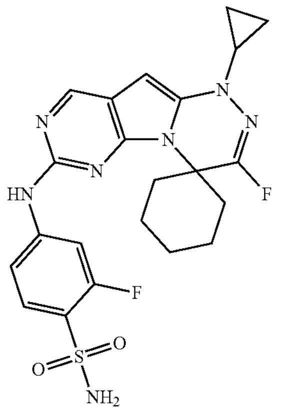
-continued
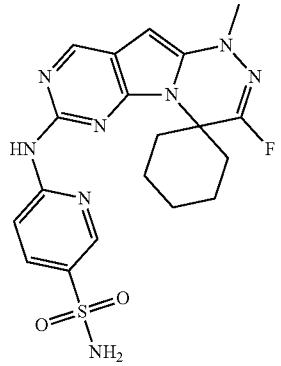
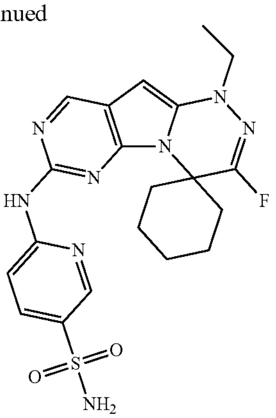
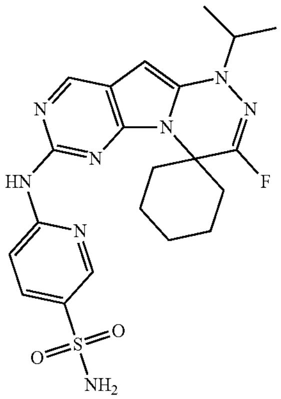
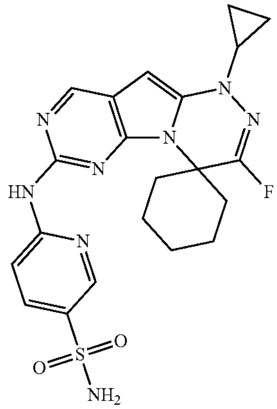
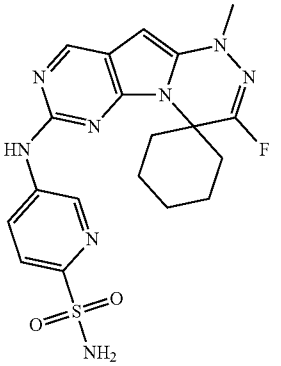
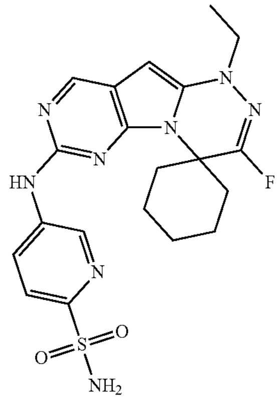
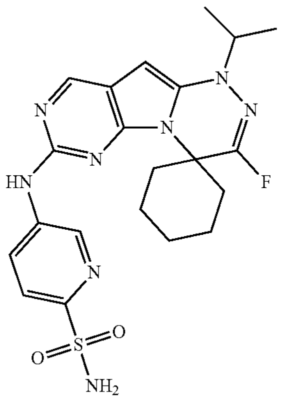
and -continued
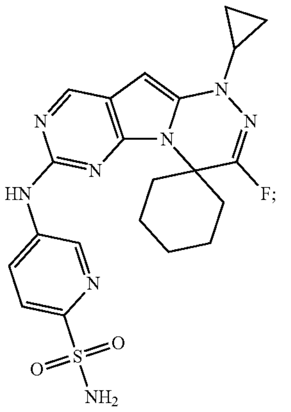
or a pharmaceutically acceptable salt thereof.
In certain embodiments, the compound of the present invention is selected from:
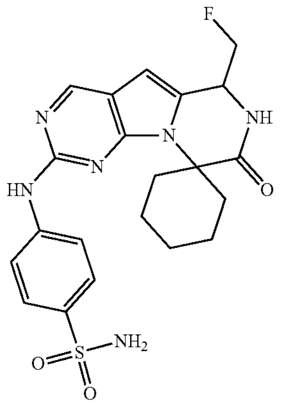
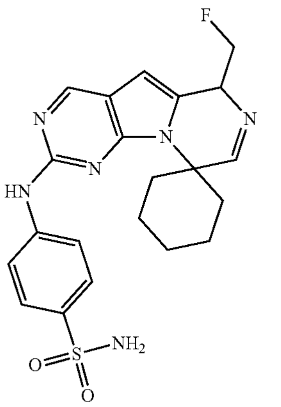
-continued
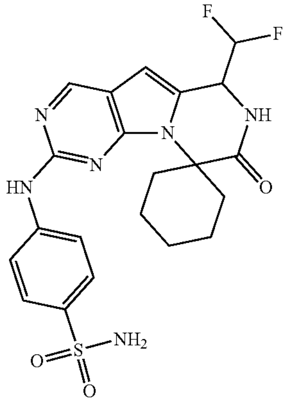
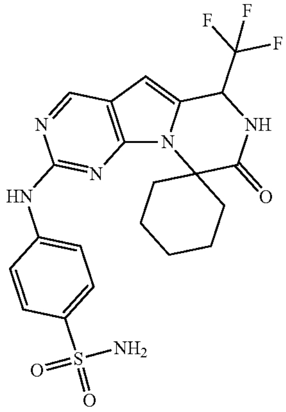
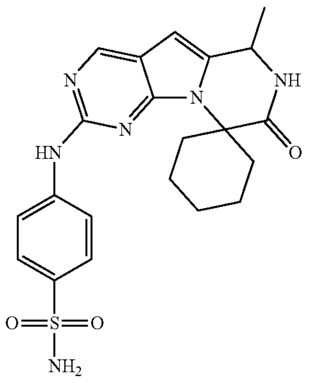
and
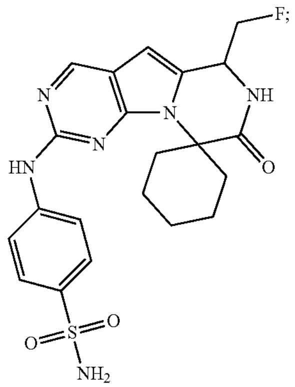
or a pharmaceutically acceptable salt thereof.
In certain embodiments, the compound of the present invention is selected from:

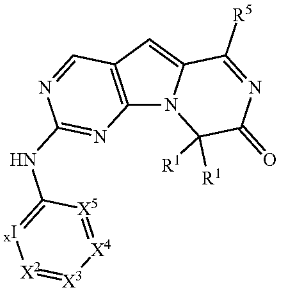
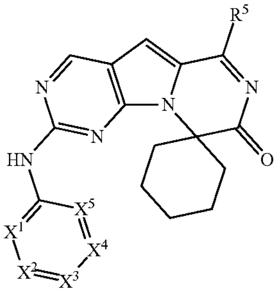
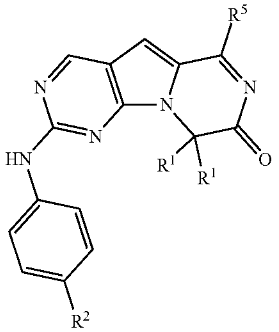
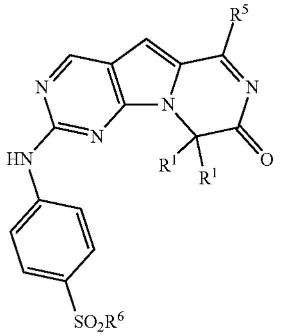
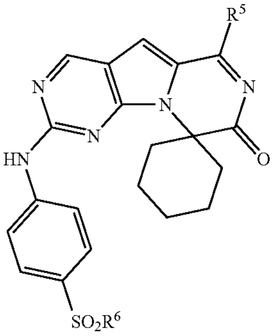
or a pharmaceutically acceptable salt thereof.
In certain embodiments, the compound of the present invention is selected from:
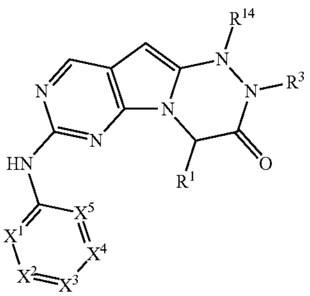
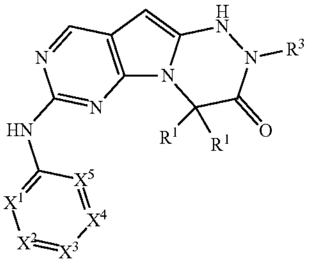
-continued
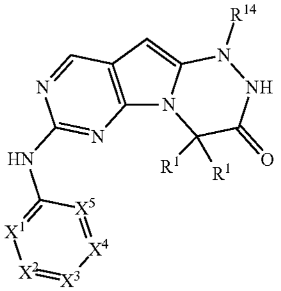
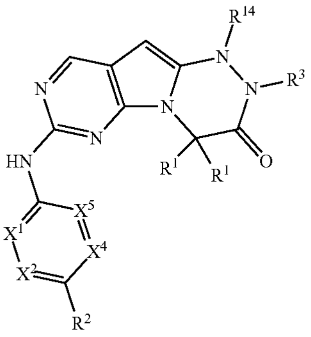
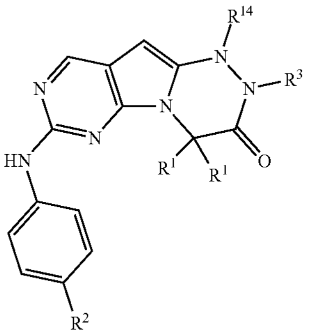
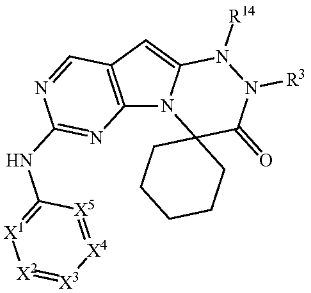
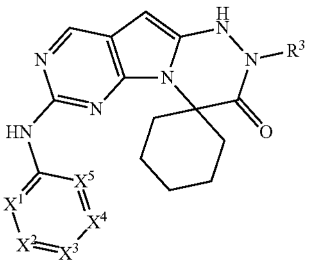

-continued
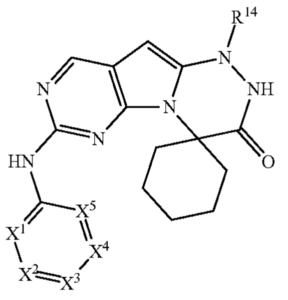
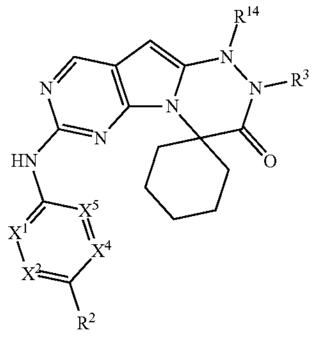
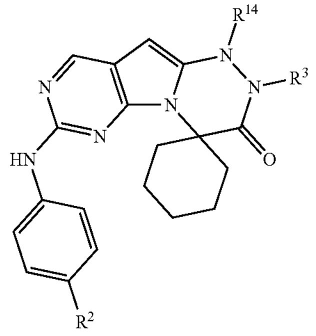
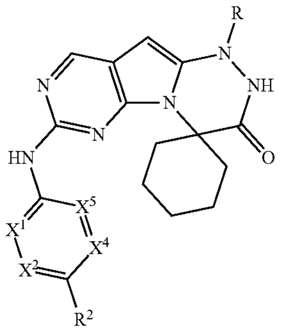
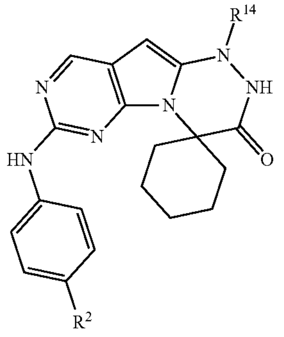
-continued
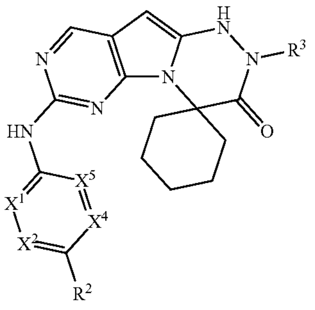
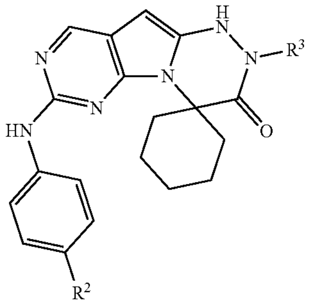
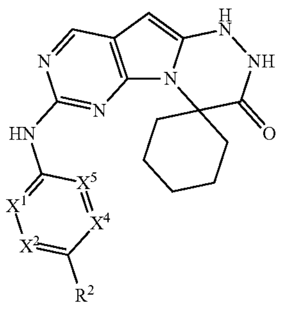
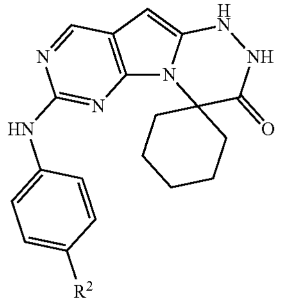
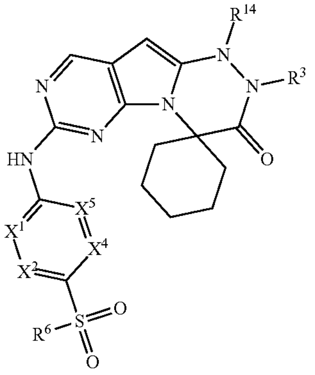

-continued
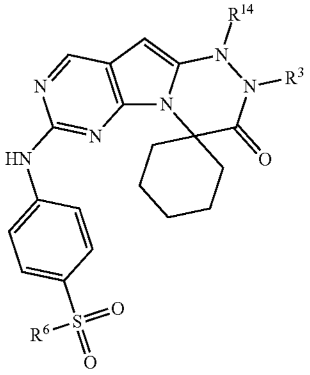
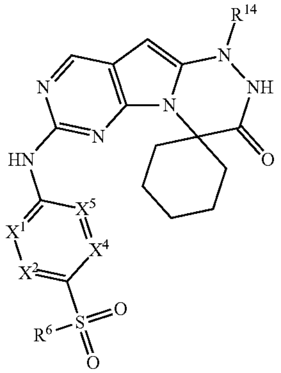
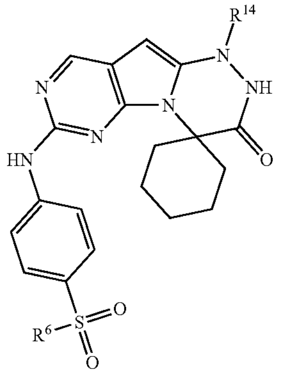
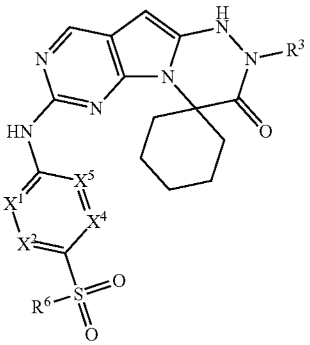
-continued
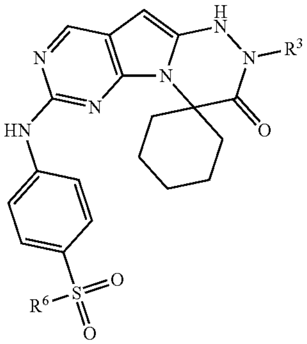
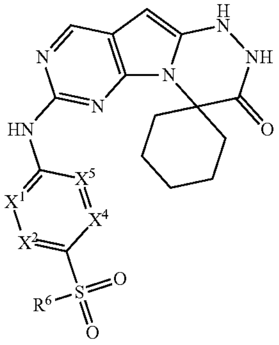
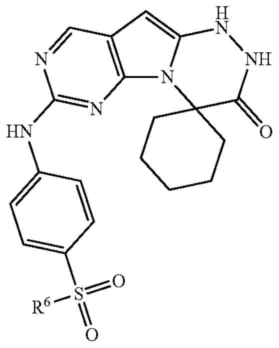
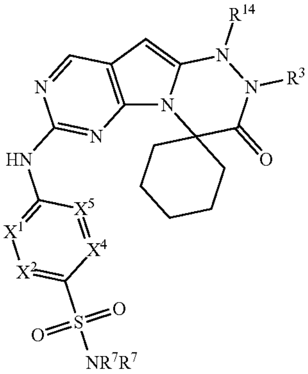

-continued
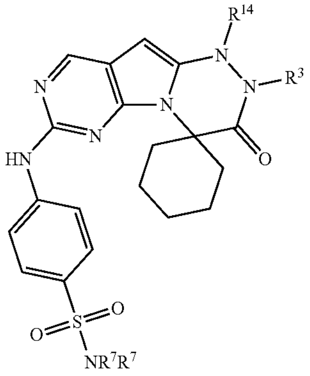
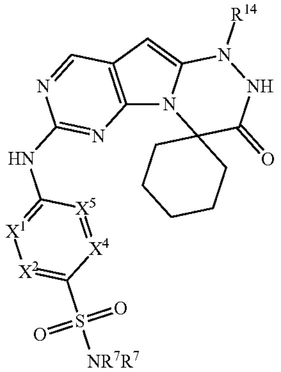
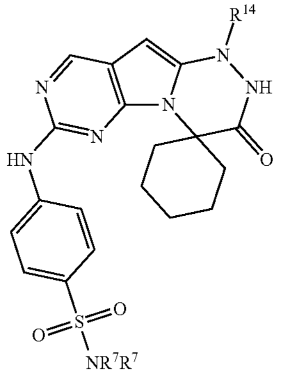
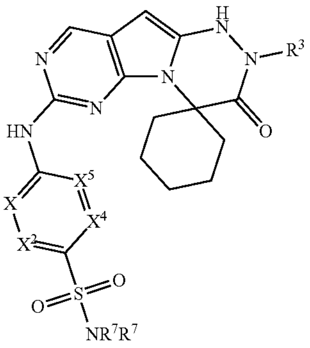
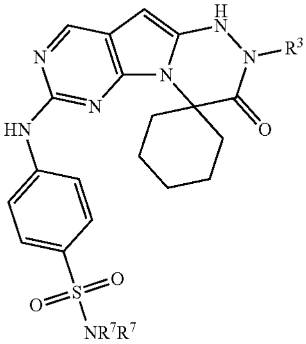
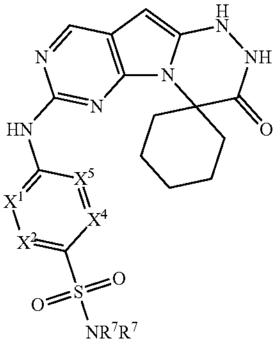
and
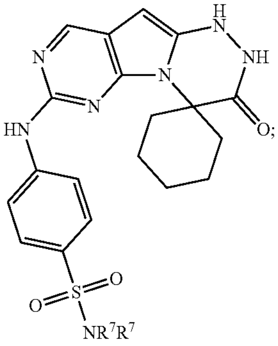
or a pharmaceutically acceptable salt thereof.
In certain embodiments, the compound of the present invention is selected from:
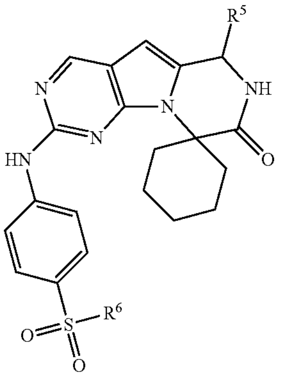

-continued
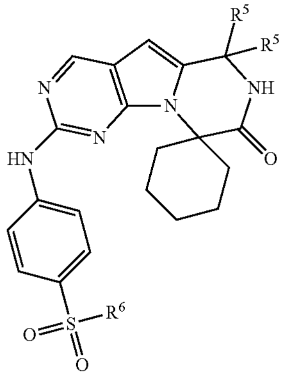
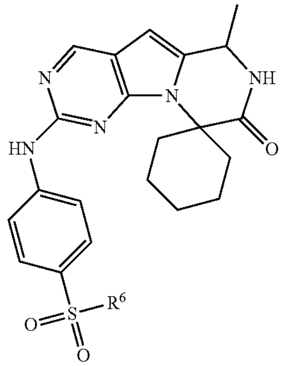
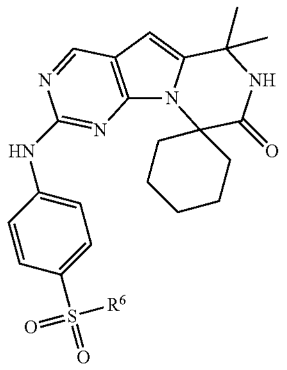
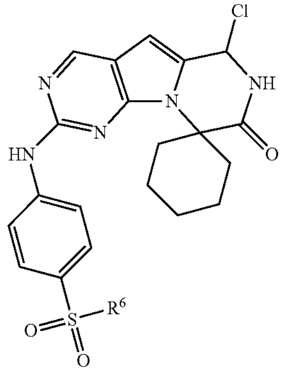
-continued
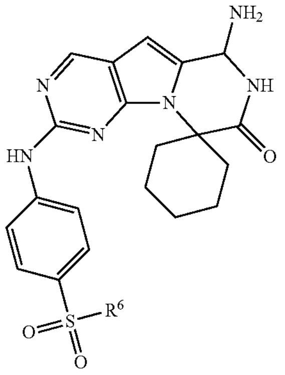
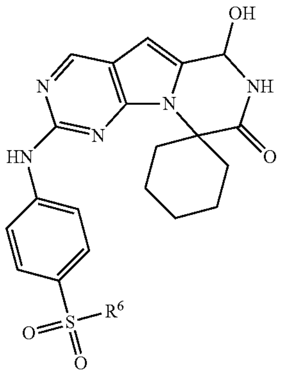
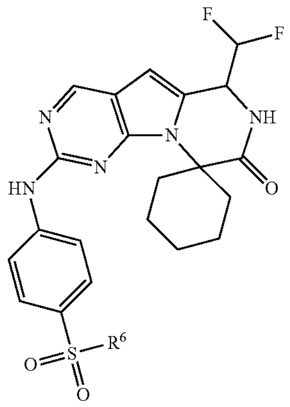
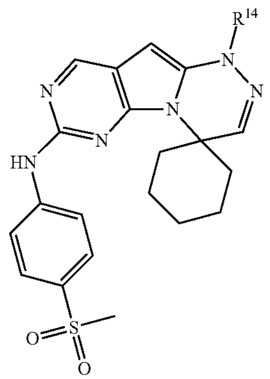

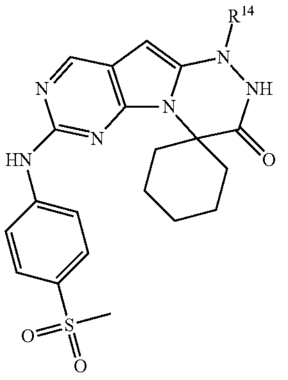
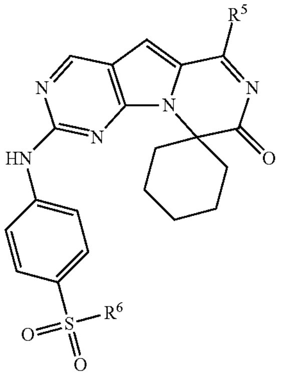
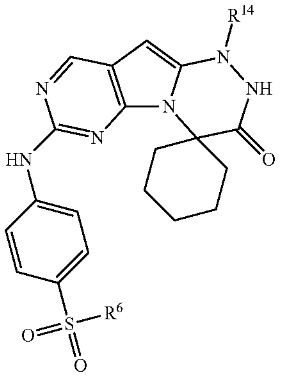
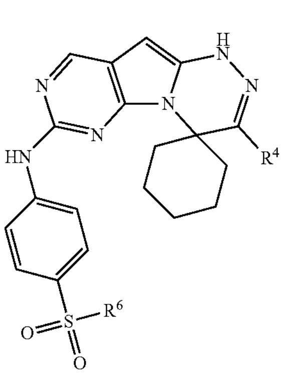
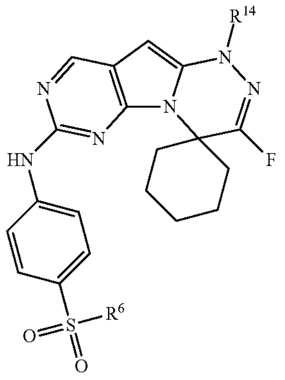
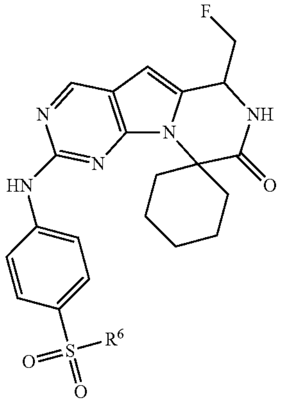
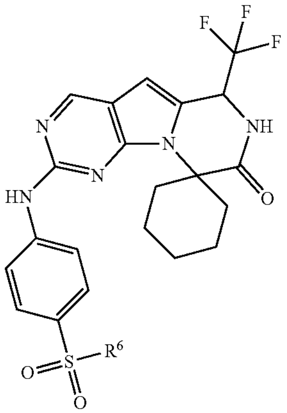
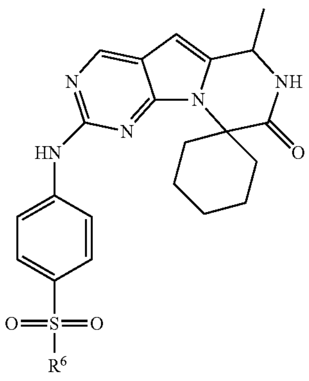
and -continued
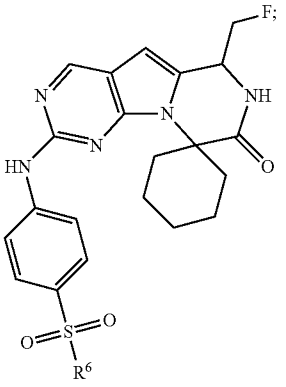
or a pharmaceutically acceptable salt thereof.
In certain embodiments the compound of the present invention is selected from:
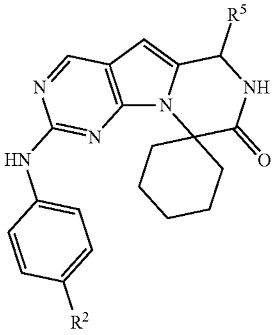
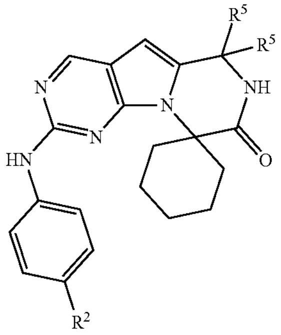
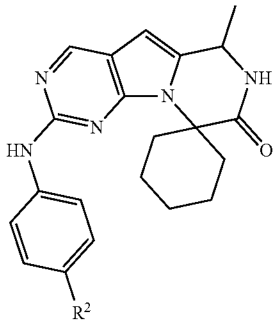
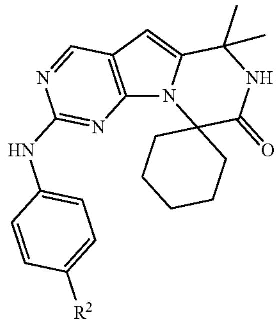
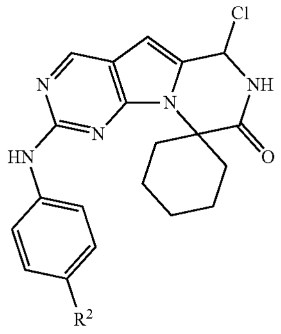
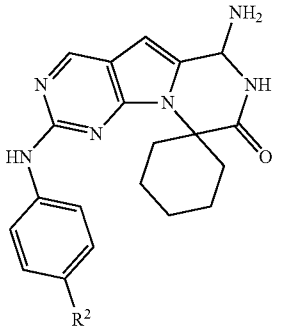
-continued
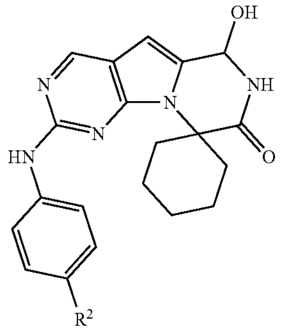
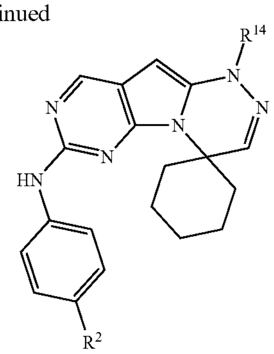
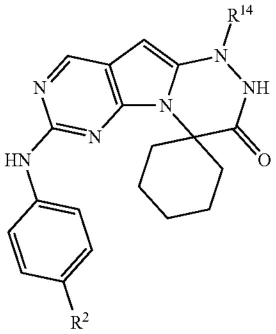
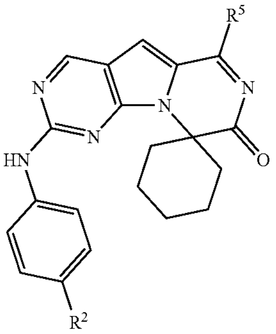
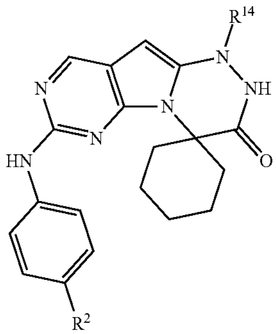
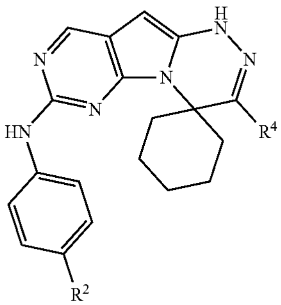
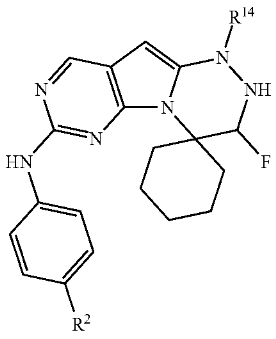
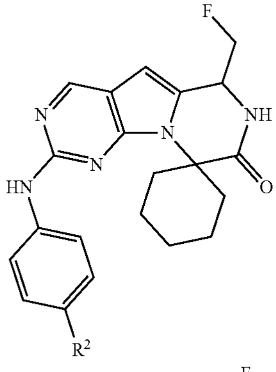
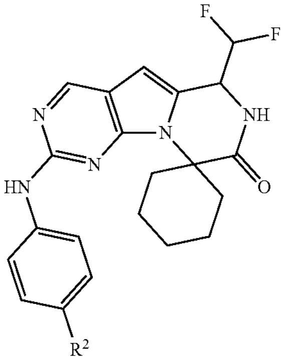
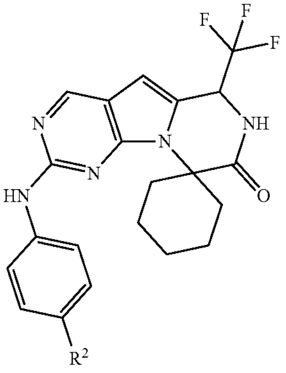

-continued

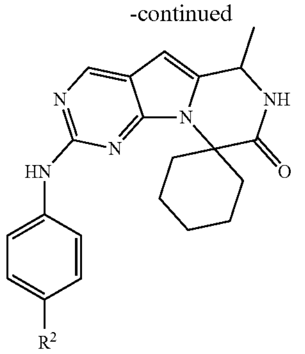

and

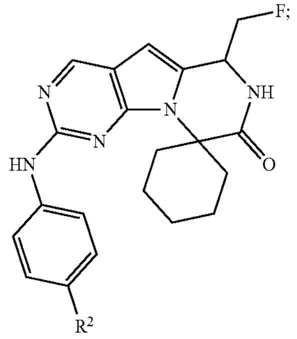

or a pharmaceutically acceptable salt thereof.

II. TERMINOLOGY

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The term "isotopic analog" refers to a compound with at least one isotopic substitution of an atom at an amount above the natural abundance of that isotope. Isotopes are atoms having the same atomic number but different mass numbers, i.e., the same number of protons but a different number of neutrons. Non-limiting examples of isotopic analogs of Compound 1 include:

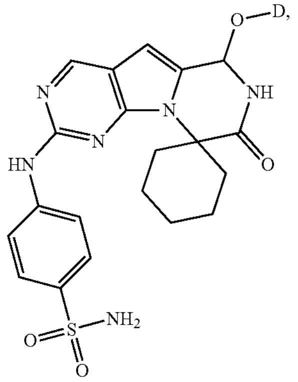

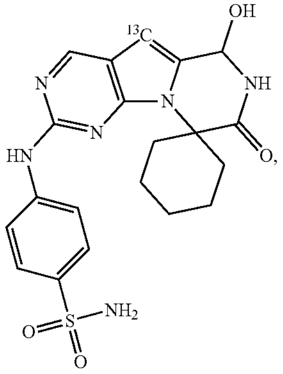

and

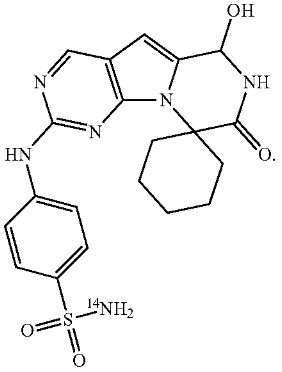

The present invention includes compounds of Formula I, Formula II, Formula III, Formula IV, Formula V, Formula VI, Formula VII, Formula VIII, Formula IX, or Formula X, with at least one desired isotopic substitution of an atom, at an amount above the natural abundance of the isotope, i.e., enriched. In some embodiments, an atom is replaced by its isotope at or near an area of in vivo metabolism, to create an alpha, beta or gamma effect.

Examples of isotopes that can be incorporated into compounds of the invention include isotopes of hydrogen, carbon, nitrogen, oxygen, phosphorous, fluorine, chlorine and iodine such as $^{2}$H, $^{3}$H, $^{11}$C, $^{13}$C, $^{14}$C, $^{15}$N, $^{17}$O, $^{18}$O, $^{18}$F $^{31}$P, $^{32}$p, $^{35}$S, $^{36}$Cl, and $^{125}$1 respectively. In one non-limiting embodiment, isotopically labelled compounds can be used in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of one or more hydrogen atoms for a deuterium atom can be provided in any Formula I, Formula II, Formula III, Formula IV, Formula V, Formula VI, Formula VII, Formula VIII, Formula IX, or Formula X. In one non-limiting embodiment, the substitution of a hydrogen atom for a deuterium atom occurs within a group selected from any of $R^1$, $R^2$, $R^3$, $R^4$, $R^5$, $R^6$, $R^7$, $R^8$, $R^{11}$, $R^{12}$, $R^{13}$, $R^{14}$, $R^1$, $R^{17}$, $R^{18}$, and $R^{19}$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle, wherein the unsubstituted carbons may be deuterated.

The compound of the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)$NH_2$ is attached through carbon of the keto (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, —O-alkyl, haloalkyl, etc. can all be considered to include the cyclic forms of alkyl, unless unambiguously excluded by context.

As used herein "substituted alkyl" refers to an alkyl group that is substituted with the described substituents. If no substituents are explicitly described "substituted alkyl" refers to an alkyl group that is substituted with 1, 2, 3, or 4 substituents independently selected from F, Cl, Br, I, cyano, hydroxy, —O-alkyl, —SH, —Salkyl, —COOH, —COOalkyl, —COalkyl, —COH, —$CONH_2$, —CONHalkyl, —$CON(alkyl)_2$, —OC(O)alkyl, —NHC(O)alkyl, —NalkylC(O)alkyl, nitro, amino, —NHalkyl, $N(alkyl)_2$, cyano, haloalkyl, aryl, heteroaryl, alkenyl, alkynyl, haloalkyl, cycloalkyl, alkyl-aryl, alkyl-heteroaryl, alkyl-cycloalkyl, alkyl-heterocycle, heterocycle, —COOaryl, —COaryl, —CONHaryl, —CON(alkyl)(aryl), —OC(O)aryl, —NHC(O)aryl, —NalkylC(O)aryl, —COOheteroaryl, —COheteroaryl, —CONHheteroaryl, —CON(alkyl)(heteroaryl), —OC(O)heteroaryl, —NHC(O)heteroaryl, —NalkylC(O)heteroaryl, —COOheterocycle, —COheterocycle, —CONHheterocycle, —CON(alkyl)(heterocycle), —OC(O)heterocycle, —NHC(O)heterocycle, and —NalkylC(O)heterocycle.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation. As used herein "substituted alkenyl" can be substituted with the groups described above for alkyl.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation. As used herein "substituted alkynyl" can be substituted with the groups described above for alkyl.

"Halo" and "Halogen" is fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or heterocycle groups wherein the radical or point of attachment is on the aryl ring, and in such instances, the number of carbon atoms continue to designate the number of carbon atoms in the aryl ring system. The one or more fused cycloalkyl or heterocycle groups can be 4 to 7-membered saturated or partially unsaturated cycloalkyl or heterocycle groups. As used herein "substituted aryl" refers to an aryl group that is substituted with the described substituents. If no substituents are explicitly described "substituted aryl" refers to an aryl group that is substituted with 1, 2, 3, or 4 substituents independently selected from F, Cl, Br, I, cyano, hydroxy, —O-alkyl, —SH, —Salkyl, —COOH, —COOalkyl, —COalkyl, —COH, —$CONH_2$, —CONHalkyl, —$CON(alkyl)_2$, —OC(O)alkyl, —NHC(O)alkyl, —NalkylC(O)alkyl, nitro, amino, —NHalkyl, $N(alkyl)_2$, cyano, haloalkyl, aryl, heteroaryl, alkyl, alkenyl, alkynyl, haloalkyl, cycloalkyl, alkyl-aryl, alkyl-heteroaryl, alkyl-cycloalkyl, alkyl-heterocycle, heterocycle, —COOaryl, —COaryl, —CONHaryl, —CON(alkyl)(aryl), —OC(O)aryl, —NHC(O)aryl, —NalkylC(O)aryl, —COOheteroaryl, —COheteroaryl, —CONHheteroaryl, —CON(alkyl)(heteroaryl), —OC(O)heteroaryl, —NHC(O)heteroaryl, —NalkylC(O)heteroaryl, —COOheterocycle, —COheterocycle, —CONHheterocycle, —CON(alkyl)(heterocycle), —OC(O)heterocycle, —NHC(O)heterocycle, and —NalkylC(O)heterocycle.

The terms "heterocyclyl" and "heterocycle" include saturated, and partially saturated heteroatom-containing ring radicals, where the heteroatoms may be selected from nitrogen, sulfur, boron, silicone, and oxygen. Heterocyclic rings comprise monocyclic 3-10 membered rings, as well as 5-16 membered bicyclic ring systems (which can include bridged fused and spiro-fused bicyclic ring systems). It does not include rings containing —O—O—, —O—S— or —S—S— portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl. As used herein "substituted heterocycle" refers to a heterocycle group that is substituted with the described substituents. If no substituents are explicitly described "substituted heterocycle" refers to a heterocycle group that is substituted with 1, 2, 3, or 4 substituents independently selected from oxo, F, Cl, Br, I, cyano, hydroxy, —O-alkyl, —SH, —Salkyl, —COOH, —COOalkyl, —COalkyl, —COH, —$CONH_2$, —CONHalkyl, —$CON(alkyl)_2$, —OC(O)alkyl, —NHC(O)alkyl, —NalkylC(O)alkyl, nitro, amino, —NHalkyl, $N(alkyl)_2$, cyano, haloalkyl, aryl, heteroaryl, alkyl, alkenyl, alkynyl, haloalkyl, cycloalkyl, alkyl-aryl, alkyl-heteroaryl, alkyl-cycloalkyl, alkyl-heterocycle, heterocycle, —COOaryl, —COaryl, —CONHaryl, —CON(alkyl)(aryl), —OC(O)aryl, —NHC(O)aryl, —NalkylC(O)aryl, —COOheteroaryl, —COheteroaryl, —CONHheteroaryl, —CON(alkyl)(heteroaryl), —OC(O)heteroaryl,—NHC(O)heteroaryl, —NalkylC(O)heteroaryl, —COOheterocycle, —CO-heterocycle, —CONHheterocycle, —CON(alkyl)(heterocycle), —OC(O)heterocycle, —NHC(O)heterocycle, and —NalkylC(O)heterocycle.

"Heterocycle" also includes groups wherein the heterocyclic radical is fused/condensed with an aryl or carbocycle radical, wherein the point of attachment is the heterocycle ring. For example, partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms.

The term "heteroaryl" denotes stable aromatic ring systems that contain one or more heteroatoms selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In certain embodiments the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl. As used herein "substituted heteroaryl" refers to a heteroaryl group that is substituted with the described substituents. If no substituents are explicitly described "substituted heteroaryl" refers to a heteroaryl group that is substituted with 1, 2, 3, or 4 substituents independently selected from F, Cl, Br, I, cyano, hydroxy, —O-alkyl, —SH, —Salkyl, —COOH, —COOalkyl, —COalkyl, —COH, —$CONH_2$, —CONHalkyl, —$CON(alkyl)_2$, —OC(O)alkyl, —NHC(O)alkyl, —NalkylC(O)alkyl, nitro, amino, —NHalkyl, $N(alkyl)_2$, cyano, haloalkyl, aryl, heteroaryl, alkyl, alkenyl, alkynyl, haloalkyl, cycloalkyl, alkyl-aryl, alkyl-heteroaryl, alkyl-cycloalkyl, alkyl-heterocycle, heterocycle, —COOaryl, —COaryl, —CONHaryl, —CON(alkyl)(aryl), —OC(O)aryl, —NHC(O)aryl, —NalkylC(O)aryl, —COOheteroaryl, —COheteroaryl, —CONHheteroaryl, —CON(alkyl)(heteroaryl), —OC(O)heteroaryl, —NHC(O)heteroaryl, —NalkylC(O)heteroaryl, —COOheterocycle, —COheterocycle, —CONHheterocycle, —CON(alkyl)(heterocycle), —OC(O)heterocycle, —NHC(O)heterocycle, and —NalkylC(O)heterocycle.

The term "sulfonyl", whether used alone or linked to other terms such as alkylsulfonyl, denotes respectively divalent radicals —$SO_2$—.

"Alkyl-heterocycle" is an alkyl group as defined herein with a heterocycle substituent. Examples include but are not limited to, piperidylmethyl and morpholinylethyl.

"Alkyl-aryl" is an alkyl group as defined herein with an aryl substituent. Non-limiting examples of alkyl-aryl groups include:

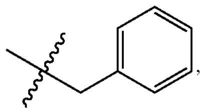,
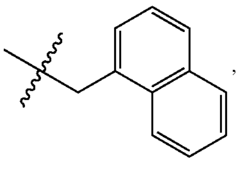,
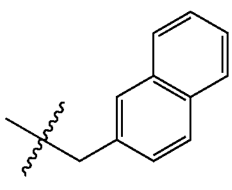, and
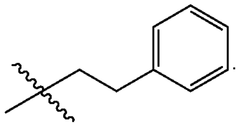.

"Alkyl-heteroaryl" is an alkyl group as defined herein with a heteroaryl substituent. Non-limiting examples of alkyl-heteroaryl groups include:

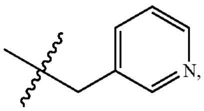,
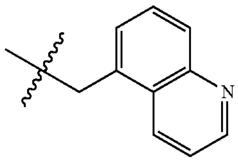,
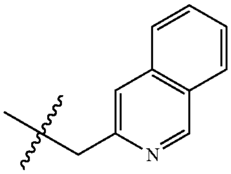, and
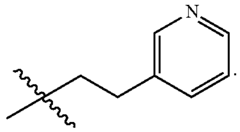.

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double or triple bonds. In an alternative embodiment, "cycloalkyl" also includes ring systems wherein the cycloalkyl ring, as defined above, is fused with one heterocycle, aryl or heteroaryl ring wherein the point of attachment is on the cycloalkyl ring, and in such instances, the number of carbons continue to designate the number of carbons in the carbocyclic ring system. In an alternative embodiment, each instance of cycloalkyl is optionally substituted with one or more substituents. In certain embodiments, the cycloalkyl group is an unsubstituted $C_{3-14}$ cycloalkyl.

"Alkyl-cycloalkyl" is an alkyl group as defined herein with a cycloalkyl substituent. Non-limiting examples of alkyl-cycloalkyl groups include:

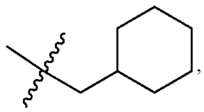, 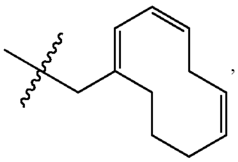,

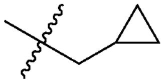, and 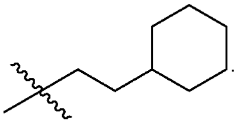.

The term "oxo" as used herein contemplates an oxygen atom attached with a double bond.

"Intrinsic resistance," also known as primary resistance, as used herein, refers to a condition wherein a cancer is not responsive to the inhibitory effects of initial CDK4/6 inhibitor treatment. Mutations and conditions associated with CDK4/6 inhibitor intrinsic resistance include, but are not limited to: increased activity of cyclin-dependent kinase 1 (CDK1); increased activity of cyclin-dependent kinase 2 (CDK2); loss, deficiency, or absence of retinoblastoma tumor suppressor protein (Rb)(Rb-null); high levels of p16Ink4a expression; high levels of MYC expression; increased expression of cyclin E1, cyclin E2, and cyclin A; and combinations thereof. The cancer may be characterized by reduced expression of the retinoblastoma tumor suppressor protein or a retinoblastoma family member protein or proteins (such as, but not limited to p107 and p130). In certain embodiments, a tumor or cancer that is intrinsically resistant to selective CDK4/6 inhibitor inhibition is a tumor or cancer whose cell population, as a whole, does not experience substantial G1 cell-cycle arrest when exposed to a selective CDK4/6 inhibitor. In certain embodiments, a tumor or cancer that is intrinsically resistant to CDK4/6 inhibitor inhibition is a tumor or cancer who has a cell population wherein less than 25%, 20%, 15%, 10%, or 5% of its cells experience G1 cell-cycle arrest when exposed to a selective CDK4/6 inhibitor.

"Acquired resistance," as used herein, refers to a condition wherein a cancer that was or is initially sensitive to the inhibitory effects of at least one selective CDK4/6 inhibitor becomes non-responsive or less-responsive over time to the effects of that selective CDK4/6 inhibitor. Without wishing to be bound by any one theory, it is believed that acquired resistance to CDK4/6 inhibitors occurs due to one or more additional mutations or genetic alterations in bypass signaling that develops after the onset of CDK4/6 inhibitor treatment regimen. For example, non-limiting exemplary causes of acquired resistance to CDK4/6 inhibitors may be a result of: the development of one or more genetic aberrations associated with "intrinsic resistance." In addition, other non-limiting exemplary causes of acquired resistance to CDK4/6 inhibitors may include an increase in cyclin E expression; CCNE1/2 amplification; E2F amplification; CDK2 amplification; amplification of CDK6; amplification of CDK4; p16 amplification; WEE1 overexpression; MDM2 overexpression; CDK7 overexpression; loss of FZR1; HDAC activation; activation of the FGFR pathway; activation of the PI3K/AKT/mTOR pathway; loss of ER or PR expression; higher transcriptional activity of AP-1; epithelial-mesenchymal transition; Smad 3 suppression; autophagy activation; Rb 1-loss or inactivating RB1 mutations; or a combination thereof A general review of CDK4/6 resistant mechanisms can be found, for example, in Pandey et al., Molecular mechanisms of resistance to CDK4/6 inhibitors in breast cancer: A review. Int. J. Cancer: 00,1-10 (2019), incorporated herein by reference. In certain embodiments, a tumor or cancer that has acquired resistance to selective CDK4/6 inhibitor inhibition is a tumor or cancer whose cell population, as a whole, no longer experiences substantial G1 cell-cycle arrest when exposed to a selective CDK4/6 inhibitor, resulting in disease progression. In certain embodiments, a tumor or cancer that has acquired resistance to CDK4/6 inhibitor inhibition is a tumor or cancer who has a cell population wherein less than 50%, 40%, 30% 20%, 15%, 10%, or 5% of its cells experience G1 cell-cycle arrest when exposed to a selective CDK4/6 inhibitor, leading to disease progression.

Determining intrinsic resistance to selective CDK4/6 inhibitors, for example by determining the loss or absence of retinoblastoma (Rb) tumor suppressor protein (Rb-null), can be determined through any of the standard assays known to one of ordinary skill in the art. For example, Rb-status in a cancer can be determined by, for example but not limited to, Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of described herein was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer".

Alternatively, molecular genetic testing may be used for determination of retinoblastoma gene status. Molecular genetic testing for retinoblastoma includes the following as described in Lohmann and Gallie "Retinoblastoma. Gene Reviews" (2010) or Parsam et al. "A comprehensive, sensitive and economical approach for the detection of mutations in the RB1 gene in retinoblastoma" Journal of Genetics, 88(4), 517-527 (2009).

Increased activity of CDK1 or CDK2, high levels of MYC expression, increased cyclin E and increased cyclin A can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line, or surrogate tissue sample that is utilized e.g., for example Western Blot and ELISA may be used with any or all types of tissues, cell lines, or surrogate tissues, whereas the IHC method would be more appropriate wherein the tissue utilized in the methods was a tumor biopsy. FACs analysis would be most applicable to samples that were single cell suspensions such as cell lines and isolated peripheral blood mononuclear cells.

Numerous methods can be utilized to measure markers believed to contribute to CDK4/6 inhibitor acquired resistance. Current methods include immunohistochemistry (IHC), immunocytochemistry, mass spectrometry. An alternative method includes the use of immunofluorescence (IF) and image analysis to determine the relative abundance of a protein of interest in formalin-fixed, paraffin-embedded (FFPE) tissue samples. The most frequently used methods for determining gene expression levels is immunohistochemistry (IHC), although western blot allows for assessment of total as well as isoform-specific expression. mRNA from the gene of interest can also be measured by reverse transcription polymerase chain reaction (RT-PCR).

Immunohistochemistry (IHC) and immunocytochemistry (ICC) are techniques employed to localize expression and are dependent on specific epitope-antibody interactions. IHC refers to the use of tissue sections, whereas ICC describes the use of cultured cells or cell suspensions. In both methods, positive staining is visualized using a molecular label, which can be fluorescent or chromogenic. Briefly, samples are fixed to preserve cellular integrity and then subjected to incubation with blocking reagents to prevent non-specific binding of the antibodies. Samples are subsequently incubated with primary and secondary antibodies, and the signal is visualized for microscopic analysis.

The western blot technique uses three elements to identify specific proteins from a complex mixture of proteins extracted from cells: separation by size, transfer to a solid support, and marking target protein using a proper primary and secondary antibody to visualize. The most common version of this method is immunoblotting. This technique is used to detect specific proteins in a given sample of tissue homogenate or extract. The sample of proteins is first electrophoresed by SDS-PAGE to separate the proteins based on molecular weight. The proteins are then transferred to a membrane where they are probed using antibodies specific to the target protein.

Genomic alterations and mRNA expression can be determined through fluorescence in situ hybridization (FISH), targeted sequencing, and microarray analysis. Commonly mutated genes, as well as differentially expressed and co-expressed genes can be identified. Fluorescence in situ hybridization (FISH) is a cytogenic technique used for the detection and localization of RNA sequences within tissues or cells. It is particularly important for defining the spatial-temporal patterns of gene expression. FISH relies on fluorescent probes that bind to complementary sequences of the RNA of interest. A series of hybridization steps are performed to achieve signal amplification of the target of interest. This amplification is then viewed using a fluorescent microscope. This technique can be used on formalin-fixed paraffin embedded (FFPE) tissue, frozen tissues, fresh tissues, cells and circulating tumor cells.

Targeted RNA-sequencing (RNA-Seq) is a highly accurate method for selecting and sequencing specific transcripts of interest. It offers both quantitative and qualitative information. Targeted RNA-Seq can be achieved via either enrichment or amplicon-based approaches, both of which enable gene expression analysis in a focused set of genes of interest. Enrichment assays also provide the ability to detect both known and novel gene fusion partners in many sample types, including formalin-fixed paraffin-embedded (FFPE) tissue. RNA enrichment provides quantitative expression information as well as the detection of small variants and gene fusions.

In a microarray analysis, mRNA molecules are typically collected from both an experimental sample and a reference sample. For example, the reference sample could be collected from a healthy individual, and the experimental sample could be collected from an individual with a disease such as cancer. The two mRNA samples are then converted into complementary DNA (cDNA), and each sample is labeled with a fluorescent probe of a different color. The experimental cDNA sample may be labeled with a red fluorescent dye, whereas the reference cDNA may be labeled with a green fluorescent dye. The two samples are then mixed together and allowed to hybridize to the microarray slide. Following hybridization, the microarray is scanned to measure the expression of each gene printed on the slide. If the expression of a particular gene is higher in the experimental sample than in the reference sample, then the corresponding spot on the microarray appears red. In contrast, if the expression in the experimental sample is lower than in the reference sample, then the spot appears green. Finally, if there is equal expression in the two samples, then the spot appears yellow. The data gathered through microarrays can be used to create gene expression profiles, which show simultaneous changes in the expression of many genes in response to a particular condition or treatment.

The term "selective CDK4/6 inhibitor" used in the context of the compounds described herein includes compounds that inhibit CDK4 activity, CDK6 activity, or both CDK4 and CDK6 activity at an IC50 molar concentration at least about 300, or 400, or 500, or 1000, or 1500, or 1800, or 2000, or 5000, or 10,000 times less than the IC50 molar concentration necessary to inhibit to the same degree of CDK2 activity in a standard phosphorylation assay.

The term "N-Oxide" used in the context of the compounds described herein refers to the oxidated form of the molecule where the oxidation occurs on a nitrogen. Any nitrogen on any of the molecules described herein can be oxidized.

As non-limiting embodiments, the N-oxide of Compound 1 may be:

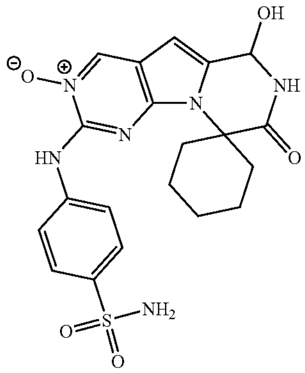

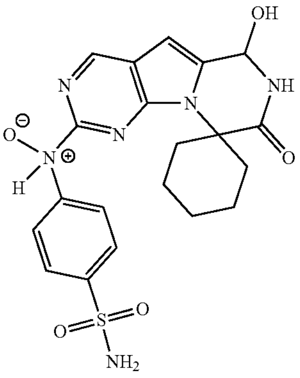

or

-continued

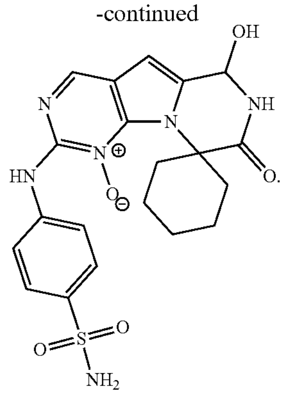

In certain embodiments, any of the active compounds can be provided in a N-oxide form to a patient in need thereof. In certain embodiments, an N-oxide of an active compound or a precursor of the active compound is used in a manufacturing scheme. In other embodiments, the N-oxide is a metabolite of administration of one of the active compounds herein, and may have independent activity. Using techniques known to the person having ordinary skill in the art an N-oxide can be formed by treating the compound of interest with an oxidizing agent, for example a suitable peroxyacid or peroxide, to generate an N-oxide compound. For example, a heteroaryl group, for example a pyrimidine group, can be treated with an oxidizing agent such as sodium percarbonate in the presence of a metal catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

III. METHODS OF TREATMENT

In certain aspects, a method of treating a proliferative disorder in a host, including a human, is provided comprising administering an effective amount of a compound of Formula I, Formula II, Formula III, Formula IV, Formula V, Formula VI, Formula VII, Formula VIII, Formula IX, or Formula X or its pharmaceutically acceptable salt, N-oxide, deuterated derivative, and/or a pharmaceutically acceptable composition thereof as described herein optionally in a pharmaceutically acceptable carrier. Non-limiting examples of disorders include tumors, cancers, disorders related to abnormal cellular proliferation, inflammatory disorders, immune disorders, and autoimmune disorders. In certain embodiments, the disorder is mediated by CDK2, CDK4, CDK6, or CDK9. In certain embodiments, the disorder is mediated by CDK2. In certain embodiments, the disorder is mediated by CDK4. In certain embodiments the disorder is mediated by CDK6. In certain embodiments, the disorder is mediated by CDK9.

A compound of Formula I, Formula II, Formula III, Formula IV, Formula V, Formula VI, Formula VII, Formula VIII, Formula IX, or Formula X, is useful as therapeutic agents when administered in an effective amount to a host, including a human, to treat a tumor, cancer (solid, non-solid, diffuse, hematological, etc.), abnormal cellular proliferation, immune disorder, inflammatory disorder, blood disorder, a myelo- or lymphoproliferative disorder such as B-or T-cell lymphomas, multiple myeloma, breast cancer, prostate cancer, AML, ALL, CLL, myelodysplastic syndrome (MDS), mesothelioma, renal cell carcinoma (RCC), cholangiocarcinoma, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn's Disease, Addison disease, Celiac disease, dermatomyositis, Graves' disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

In certain embodiments, the compound of the present invention is used to treat breast cancer. In certain embodiments, the breast cancer is HR+ and HER2−. In certain embodiments, the breast cancer is HR− and HER2+.

In certain embodiments, the compound of the present invention is used to treat non-small cell lung cancer (NSCLC). In certain embodiments, the NSCLC has an EGFR mutation. In certain embodiments, the NSCLC has an EGFR mutation and an EGFR inhibitor failed (e.g. $2^{nd}$ line therapy). In certain embodiments, an ALK inhibitor failed (e.g. $2^{nd}$ line therapy). In certain embodiments, the NSCLC has an KRAS mutation.

In certain embodiments, the compound of the present invention is used to treat prostate cancer. In certain embodiments, the prostate cancer is castration resistant. In certain embodiments, a prior chemotherapeutic agent already failed (e.g. $2^{nd}$ line therapy).

In certain embodiments, the compound of the present invention is used to treat lymphoma. In certain embodiments, the lymphoma is mantel cell lymphoma (MCL), marginal zone lymphoma (MZL), chronic lymphocytic leukemia (CLL), follicular lymphoma (FL), or diffuse large B-cell lymphoma (DLBCL). In certain embodiments, a prior chemotherapeutic agent already failed (e.g. $2^{nd}$ line therapy).

In certain embodiments, the compound of the present invention is used to treat melanoma. In certain embodiments, the melanoma has a BRAF mutation.

In certain embodiments, the compound of the present invention is used to treat RAS mutated cancer. In certain embodiments, the RAS mutated cancer is colon cancer (CLC). In certain embodiments, the RAS mutated cancer is pancreatic cancer. In certain embodiments, the RAS mutated cancer is cholangiocarcinoma.

In certain embodiments, the compound of the present invention is used to treat a gastrointestinal stromal tumor (GIST). In certain embodiments, the treatment with imatinib or sunitinib already failed (e.g. $2^{nd}$ line therapy).

Exemplary proliferative disorders include, but are not limited to, benign growths, neoplasms, tumors, cancer (Rb positive or Rb negative), autoimmune disorders, inflammatory disorders graft-versus-host rejection, and fibrotic disorders.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AIL) (e.g., B-cell AIL, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CVL), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

In certain embodiments, the condition treated with a Formula I, Formula II, Formula III, Formula IV, Formula V, Formula VI, Formula VII, Formula VIII, Formula IX, or Formula X, is a disorder related to abnormal cellular proliferation.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis.

Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments, a compound of the present invention and its pharmaceutically acceptable derivatives or pharmaceutically acceptable formulations containing these compounds are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment, compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, head, kidney, neck, leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, Ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In another aspect, a method of increasing BIM expression (e.g., BCLC2L11 expression) is provided to induce apoptosis in a cell comprising contacting a compound of the present invention or a pharmaceutically acceptable composition, salt, or isotopic analog thereof with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is downregulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., Nat. Med. (2012) 18:521-528.

In yet another aspect, a method of treating a condition associated with angiogenesis is provided, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of the present invention or a pharmaceutically acceptable composition, salt, or isotopic analog thereof.

In certain embodiments, the condition associated with angiogenesis is macular degeneration. In certain embodiments, provided is a method of treating macular degeneration comprising administering to a subject in need thereof a compound of the present invention or a pharmaceutically acceptable composition, salt, or isotopic analog thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, a method of treating obesity is provided comprising administering to a subject in need thereof a compound of the present invention or a pharmaceutically acceptable composition, salt, or isotopic analog thereof.

In certain embodiments, the condition associated with angiogenesis is atherosclerosis. In certain embodiments, provided is a method of treating atherosclerosis comprising administering to a subject in need thereof a compound of the present invention or a pharmaceutically acceptable composition, salt, or isotopic analog thereof.

In certain embodiments, the condition associated with angiogenesis is a proliferative disorder. In certain embodiments, provided is a method of treating a proliferative disorder comprising administering to a subject in need thereof a compound of the present invention or a pharmaceutically acceptable composition, salt, or isotopic analog thereof.

IV. METHODS TO REDUCE THE SIDE EFFECTS RELATED TO CHEMOTHERAPY

In certain embodiments, compounds of the present invention decrease the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

In certain embodiments, the subject has been exposed to a chemotherapeutic agent, and, using a compound described herein, the subject's CDK4/6-replication dependent healthy cells are placed in G1 arrest following exposure in order to mitigate, for example, DNA damage. In certain embodiments, the compound is administered at least 1%2 hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure.

In certain embodiments, the compound can allow for dose intensification (e.g., more therapy can be given in a fixed period of time) in medically related chemotherapies, which will translate to better efficacy. Therefore, the presently disclosed methods can result in chemotherapy regimens that are less toxic and more effective.

In some embodiments, the use of a compound described herein may result in reduced or be substantially free of off-target effects, for example, related to inhibition of kinases other than CDK4 and/or CDK6 and/or CDK2. Furthermore, in certain embodiments, the use of the compounds described herein should not induce cell cycle arrest in CDK4/6 replication independent cells.

In some embodiments, the use of a compound described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non-estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

V. METHODS TO TREAT ABNORMAL PROLIFERATION OF T-CELLS, B-CELLS AND/OR NK-CELLS

In certain aspects, the invention includes the use of an effective amount of a compound described herein, or its pharmaceutically acceptable salt, or isotopic analog thereof optionally in a pharmaceutical composition, to treat a host, typically a human, with a selected cancer, tumor, hyperproliferative condition or an inflammatory or immune disorder. Some of the disclosed compounds are highly active against T-cell proliferation. Given the paucity of drugs for T-cell cancers and abnormal proliferation, the identification of such uses represents a substantial improvement in the medical therapy for these diseases.

Abnormal proliferation of T-cells, B-cells, and/or NK-cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (a palliative agent) or a decrease in the underlying disease (a disease modifying agent).

Examples include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sezary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In certain embodiments, a compound disclosed herein, or its salt, or isotopic analog thereof can be used in an effective amount to treat a host, for example a human, with a lymphoma or lymphocytic or myelocytic proliferation disorder or abnormality. For example, the compounds as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non- Cleaved Cell Lymphoma); Chronic Lymphocytic Leukemia/ Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, a compound disclosed herein, or its salt, or isotopic analog thereof can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, a compound disclosed herein, or its salt, or isotopic analog thereof can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In certain embodiments, a compound disclosed herein, or its salt, or isotopic analog thereof can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JML); hairy cell leukemia (HCL); acute promyelocytic leukemia (a subtype of AML); large granular lymphocytic leukemia; or Adult T-cell chronic leukemia. In certain embodiments, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

VI. PHARMACEUTICAL COMPOSITIONS AND DOSAGE FORMS

An active compound described herein, or its salt, or isotopic analog thereof can be administered in an effective amount to a host to treat any of the disorders described herein using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In certain embodiments, the dosage is at about or greater than 0.1, 0.5, 1, 5, 10, 25, 50, 75, 100, 125, 150, 175, or 200 mg/kg. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 M, 5 M, 10 M, 20 M, 30 M, or 40 M.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

In some embodiments, compounds disclosed herein or used as described are administered once a day (QD), twice a day (BID), or three times a day (TID). In some embodiments, compounds disclosed herein or used as described are administered at least once a day for at least 21 days, at least 24 days, at least 28 days, at least 35 days, at least 45 days, at least 60 days, at least 75 days, at least 90 days, at least 120 days, at least 180 days, or longer.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intramuscular, inhalation, intra-aortal, intracranial, subdermal, intraperitoneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

In accordance with the presently disclosed methods, an oral administration can be in any desired form such as a solid, gel or liquid, including a solution, suspension, or emulsion. In some embodiments, the compounds or salts are administered by inhalation, intravenously, or intramuscularly as a liposomal suspension. When administered through inhalation the active compound or salt may be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may sometimes be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup.

Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration, a pharmaceutical composition can take the form of a solution suspension, tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In certain embodiments, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. In certain embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VII. COMBINATION THERAPY

The disclosed compounds of Formula I, Formula II, Formula III, Formula IV, Formula V, Formula VI, Formula VII, Formula VIII, Formula IX, or Formula X, can be used in an effective amount alone or in combination with another compound of the present invention or another bioactive agent (therapeutic agent) to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" or "therapeutic agent" is used to describe an agent, other than the selected compound according to the present invention, which can be used in combination or alternation with a compound of the present invention to achieve a desired result of therapy. In certain embodiments, the compound of the present invention and the bioactive agent are administered in a manner that they are active in vivo during overlapping time periods, for example, have time-period overlapping $C_{max}$, $T_{max}$, AUC or another pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In certain aspects of this embodiment, the bioactive agent is a chemotherapeutic.

In another aspect of this embodiment, the bioactive agent is a growth factor.

In certain aspects of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or another inhibitor. In certain aspects, the immune modulator is an antibody, such as a monoclonal antibody.

Immune Checkpoint Inhibitors

Immune checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combinations thereof. In some embodiments, an immune checkpoint inhibitor is administered in an effective amount in combination with a compound described herein to treat a cancer, including but not limited to, Hodgkin lymphoma, melanoma, non-small cell lung cancer, including NSCLC with EGFR or ALK genomic tumor aberrations, squamous cell carcinoma of the head and neck, small cell lung cancer, hepatocellular carcinoma, renal cell carcinoma, urothelial carcinoma, colorectal cancer, colorectal cancer, hepatocellular carcinoma, renal cell carcinoma, small-cell lung carcinoma, bladder carcinoma, B-cell lymphoma, gastric cancer, cervical cancer, liver cancer, advanced Merkel cell carcinoma, esophageal squamous cell carcinoma, or ovarian cancer.

In certain embodiments, the immune checkpoint inhibitor is a PD-1 inhibitor that blocks the interaction of PD-1 and PD-L1 by binding to the PD-1 receptor, and in turn inhibits immune suppression. In certain embodiments, the immune checkpoint inhibitor is a PD-1 immune checkpoint inhibitor selected from nivolumab (Opdivo®), pembrolizumab (Keytruda®), pidilizumab, (AMP-224 (AstraZeneca and MedImmune), PF-06801591 (Pfizer), MEDIO680 (AstraZeneca), PDR001 (Novartis), cemiplimad/REGN2810 (Libtayo® Regeneron), MGA012 (MacroGenics), BGB-A317 (BeiGene) SHR-12-1 (Jiangsu Hengrui Medicine Company and Incyte Corporation), TSR-042 (Tesaro), and the PD-L1/VISTA inhibitor CA-170 (Curis Inc.).

In certain embodiments, the immune checkpoint inhibitor is the PD-1 immune checkpoint inhibitor nivolumab (Opdivo®) administered in an effective amount with a compound described herein for the treatment of Hodgkin lymphoma, melanoma, non-small cell lung cancer, including NSCLC with EGFR or ALK genomic tumor aberrations, squamous cell carcinoma of the head and neck, small cell lung cancer, hepatocellular carcinoma, renal cell carcinoma, squamous cell carcinoma, urothelial carcinoma, colorectal cancer, colorectal cancer, hepatocellular carcinoma, or ovarian cancer. Nivolumab has been FDA approved for the use of Hodgkin lymphoma, melanoma, non-small cell lung cancer, including NSCLC with EGFR or ALK genomic tumor aberrations, squamous cell carcinoma of the head and neck, small cell lung cancer, hepatocellular carcinoma, renal cell carcinoma, squamous cell carcinoma, urothelial carcinoma, colorectal cancer, progressive classical Hodgkin lymphoma (cHL), colorectal cancer, urothelial cancer, squamous cell carcinoma of the head and neck, or ovarian cancer. In another aspect of this embodiment, the immune checkpoint inhibitor is the PD-1 immune checkpoint inhibitor pembrolizumab (Keytruda®) administered in an effective amount for the treatment of melanoma, non-small cell lung cancer, small cell lung cancer, head and neck cancer, bladder cancer, urothelial carcinoma, renal cell carcinoma, classical Hodgkin lymphoma, gastric cancer, cervical cancer, liver cancer, primary mediastinal B-cell lymphoma, advanced Merkel cell carcinoma, esophageal squamous cell carcinoma, or urothelial cancer. In an additional aspect of this embodiment, the immune checkpoint inhibitor is the PD-1 immune checkpoint inhibitor pidilizumab (Medivation) administered in an effective amount for refractory diffuse large B-cell lymphoma (DLBCL) or metastatic melanoma. In an additional aspect of this embodiment, the immune checkpoint inhibitor is the PD-1 immune checkpoint inhibitor cemiplimab (Libtayo/Regeneron) administered in an effective amount for cutaneous squamous cell carcinoma.

In certain embodiments, the immune checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, atezolizumab, durvalumab, KN035CA-170 (Curis Inc.), and LY3300054 (Eli Lilly). In certain embodiments, the PD-L1 inhibitor is atezolizumab. In certain embodiments, the PD-L1 inhibitor blocks the interaction between PD-L1 and CD80 to inhibit immune suppression.

In certain embodiments, the immune checkpoint inhibitor is the PD-L1 immune checkpoint inhibitor atezolizumab (Tecentriq®) administered in an effective amount for the treatment of metastatic bladder cancer, small cell lung cancer, metastatic melanoma, metastatic non-small cell lung cancer, or metastatic renal cell carcinoma. In another aspect of this embodiment, the immune checkpoint inhibitor is durvalumab (Imfinzi®; AstraZeneca and MedImmune) administered in an effective amount for the treatment of small cell lung cancer, non-small cell lung cancer, or bladder cancer. In certain embodiments, the immune checkpoint inhibitor is the PD-L1 immune checkpoint inhibitor avelumab (Bavencio®; EMD Serono/Pfizer) administered in an effective amount for the treatment of Merkel cell carcinoma or urothelial carcinoma. In yet another aspect of the embodiment, the immune checkpoint inhibitor is KN035 (Alphamab) administered in an effective amount for the treatment of PD-L1 positive solid tumors.

In certain aspects of this embodiment, the immune checkpoint inhibitor is a CTLA-4 immune checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In certain embodiments, the CTLA-4 immune checkpoint inhibitor is ipilimumab (Yervoy®) administered in an effective amount for the treatment of metastatic melanoma, adjuvant melanoma, or non-small cell lung cancer.

In another embodiment, the immune checkpoint inhibitor is a LAG-3 immune checkpoint inhibitor. Examples of LAG-3 immune checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGDO13 (MacroGenics). In yet another aspect of this embodiment, the immune checkpoint inhibitor is a TIM-3 immune checkpoint inhibitor. A specific TIM-3 inhibitor includes, but is not limited to, TSR-022 (Tesaro).

Other immune checkpoint inhibitors for use in the invention described herein include, but are not limited to, B7-H3/CD276 immune checkpoint inhibitors such as MGA217, indoleamine 2,3-dioxygenase (IDO) immune checkpoint inhibitors such as Indoximod and INCB024360, killer immunoglobulin-like receptors (KIRs) immune checkpoint inhibitors such as Lirilumab (BMS-986015), carcinoembryonic antigen cell adhesion molecule (CEACAM) inhibitors (e.g., CEACAM-1, -3 and/or -5). Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10:1371/journal.pone.0021146), or cross-reacts with CEACAM-1 and CEACAM-5 as described in, e.g., WO 2013/054331 and US 2014/0271618. Still other checkpoint inhibitors can be molecules directed to B and T lymphocyte attenuator molecule (BTLA), for example as described in Zhang et al., Monoclonal antibodies to B and T lymphocyte attenuator (BTLA) have no effect on in vitro B cell proliferation and act to inhibit in vitro T cell proliferation when presented in a cis, but not trans, format relative to the activating stimulus, Clin Exp Immunol. 2011 January; 163(1): 77-87.

Chemotherapeutic Agents

As contemplated herein, a CDK inhibitor described herein can be in combination with any standard chemotherapeutic agent treatment modality. In certain embodiments, a CDK inhibitor described herein can be in combination with any standard chemotherapeutic agent treatment modality and in further combination with an immune checkpoint inhibitor.

In certain embodiments, the chemotherapeutic agent is toxic to immune effector cells. In certain embodiments the chemotherapeutic agent inhibits cell growth. In certain embodiments, the cytotoxic chemotherapeutic agent administered is a DNA damaging chemotherapeutic agent. In certain embodiments, the chemotherapeutic agent is a protein synthesis inhibitor, a DNA-damaging chemotherapeutic, an alkylating agent, a topoisomerase inhibitor, an RNA synthesis inhibitor, a DNA complex binder, a thiolate alkylating agent, a guanine alkylating agent, a tubulin binder, DNA polymerase inhibitor, an anticancer enzyme, RAC1 inhibitor, thymidylate synthase inhibitor, oxazophosphorine compound, integrin inhibitor such as cilengitide, camptothecin or homocamptothecin, antifolate or a folate antimetabolite.

In some embodiments, the additional therapeutic agent is selected from elotuzumab, rituximab, lenalidomide, cytarabine, daratumumab, adalimumab, idealisib, gilteritinib, glasdegib, valaciclovir, acalabrutinib, ibrutinib, midostaurin, ruxolitinib, bortezomib, lapatinib, bendamstine, enzalutamide, azacitadine, obinutuzumab, decitabine, erdafitinib, and venetoclax.

In certain embodiments, the additional therapeutic agent is trastuzumab. In certain embodiments the additional therapeutic agent is lapatinib. In certain embodiments, the compound of the present invention is dosed with 2, 3, or 4 additional therapeutic agents. In certain embodiments, there are 2 additional therapeutic agents. In certain embodiments, the two additional therapeutic agents are lapatinib and trastuzumab.

In certain embodiments, the additional therapeutic agent is osimertinib mesylate (Tagrisso®).

In certain embodiments, the additional therapeutic agent is alectinib (Alecensa®).

In certain embodiments, the additional therapeutic agent is a MEK inhibitor.

In certain embodiments, the additional therapeutic agent is an Androgen Receptor ligand.

In certain embodiments, the additional therapeutic agent is a BTK inhibitor, for example but not limited to ibrutinib (Imbruvica®) or acalabrutinib (Calquence®).

In certain embodiments, the additional therapeutic agents are a MEK inhibitor and a RAF inhibitor In certain embodiments, the additional therapeutic agent is a RAF inhibitor.

In certain embodiments, the additional therapeutic agent is regorafenib.

Cytotoxic Chemotherapeutic Agents

Cytotoxic, DNA-damaging chemotherapeutic agents tend to be non-specific and, particularly at high doses, toxic to normal, rapidly dividing cells such as HSPC and immune effector cells. As used herein the term "DNA-damaging" chemotherapy or chemotherapeutic agent refers to treatment with a cytostatic or cytotoxic agent (i.e., a compound) to reduce or eliminate the growth or proliferation of undesirable cells, for example cancer cells, wherein the cytotoxic effect of the agent can be the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect. Such compounds include, but are not limited to, DNA damaging compounds that can kill cells. "DNA damaging" chemotherapeutic agents include, but are not limited to, alkylating agents, DNA intercalators, protein synthesis inhibitors, inhibitors of DNA or RNA synthesis, DNA base analogs, topoisomerase inhibitors, telomerase inhibitors, and telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylol melamine; nitrogen mustards such as chlorambucil, chlornaphazine, cyclophosphamide, estramustine, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine. Other DNA-damaging chemotherapeutic agents include daunorubicin, doxorubicin, idarubicin, epirubicin, mitomycin, and streptozocin. Chemotherapeutic antimetabolites include gemcitabine, mercaptopurine, thioguanine, cladribine, fludarabine phosphate, fluorouracil (5-FU), floxuridine, cytarabine, pentostatin, methotrexate, azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis, include alkylating agents such as dimethyl sulfate, nitrogen and sulfur mustards; intercalating agents, such as acridine dyes, actinomycins, anthracenes, benzopyrene, ethidium bromide, propidium diiodide-intertwining; and other agents, such as distamycin and netropsin. Topoisomerase inhibitors, such as irinotecan, teniposide, coumermycin, nalidixic acid, novobiocin, and oxolinic acid; inhibitors of cell division, including colcemide, mitoxantrone, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

In certain embodiments, the chemotherapeutic agent is a DNA complex binder such as camptothecin, or etoposide; a thiolate alkylating agent such as nitrosourea, BCNU, CCNU, ACNU, or fotesmustine; a guanine alkylating agent such as temozolomide, a tubulin binder such as vinblastine, vincristine, vinorelbine, vinflunine, cryptophycin 52, halichondrins, such as halichondrin B, dolastatins, such as dolastatin 10 and dolastatin 15, hemiasterlins, such as hemiasterlin A and hemiasterlin B, colchicine, combrestatins, 2-methoxyestradiol, E7010, paclitaxel, docetaxel, epothilone, discodermolide; a DNA polymerase inhibitor such as cytarabine; an anticancer enzyme such as asparaginase; a Rac1 inhibitor such as 6-thioguanine; a thymidylate synthase inhibitor such as capecitabine or 5-FU; a oxazophosphorine compound such as Cytoxan; a integrin inhibitor such as cilengitide; an antifolate such as pralatrexate; a folate antimetabolite such as pemetrexed; or a camptothecin or homocamptothecin such as diflomotecan.

In certain embodiments, the topoisomerase inhibitor is a type I inhibitor. In another embodiment the topoisomerase inhibitor is a type II inhibitor.

Other DNA-damaging chemotherapeutic agents whose toxic effects can be mitigated by the presently disclosed selective CDK4/6 inhibitors include, but are not limited to, cisplatin, hydrogen peroxide, carboplatin, procarbazine, ifosfamide, bleomycin, plicamycin, taxol, transplatinum, thiotepa, oxaliplatin, and the like, and similar acting-type agents. In certain embodiments, the DNA damaging chemotherapeutic agent is selected from the group consisting of cisplatin, carboplatin, camptothecin, and etoposide.

Other suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®), liposomal vincristine (Marqibo®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Prednisone, and Dexamethasone (Decadron). Examples of additional suitable chemotherapeutic agents include but are not limited to 5-fluorouracil, dacarbazine, alkylating agents, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), bleomycin sulfate, calicheamicin, cytochalasin B, dactinomycin (formerly actinomycin), daunorubicin HCl, daunorubicin citrate, denileukin diftitox, dihydroxy anthracin dione, Docetaxel, doxorubicin HCl, E. coli L-asparaginase, Erwinia L-asparaginase, etoposide citrovorum factor, etoposide phosphate, gemcitabine HCl, idarubicin HCl, interferon α-2b, irinotecan HCl, maytansinoid, mechlorethamine HCl, melphalan HCl, mithramycin, mitomycin C, mitotane, polifeprosan 20 with carmustine implant, procarbazine HCl, streptozotocin, teniposide, thiotepa, topotecan HCl, valrubicin, vinblastine sulfate, vincristine sulfate, and vinorelbine tartrate.

Additional cytotoxic chemotherapeutic agents for use with the present invention include: epirubicin, abraxane, taxotere, epothilone, tafluposide, vismodegib, azacytidine, doxifluridine, vindesine, and vinorelbine.

In certain embodiments, the chemotherapeutic agent is not an aromatase inhibitor. In certain embodiments the chemotherapeutic agent is not a steroid. In certain embodiments the chemotherapeutic agent is not a BCR-ABL inhibitor.

In certain embodiments, the chemotherapeutic agent is a DNA complex binder. In certain embodiments the chemotherapeutic agent is a tubulin binder. In certain embodiments the chemotherapeutic agent is an alkylating agent. In certain embodiments the chemotherapeutic agent is a thiolate alkylating agent.

Additional Chemotherapeutic Agents

Additional chemotherapeutic agents that may be used as described herein may include 2-methoxyestradiol or 2ME2, finasunate, etaracizumab (MEDI-522), HLL1, huN901-DM1, atiprimod, saquinavir mesylate, ritonavir, nelfinavir mesylate, indinavir sulfate, plitidepsin, P276-00, tipifarnib, lenalidomide, thalidomide, pomalidomide, simvastatin, and celecoxib. Chemotherapeutic agents useful in the present invention include, but are not limited to, Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

Additional chemotherapeutic agents contemplated include, but are not limited to, a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, campath 1H, a SIP receptor modulator, a dual mTORC1 and mTORC2 inhibitor, eg. Vistusertib (AZD2014), e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3@), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, dexamethasone, ISAtx-247, SDZ ASM 981 (pimecrolimus, Elidel®), Abatacept, belatacept, LFA3lg, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, dasatinib (Sprycel®) nilotinib (Tasigna®), bosutinib (Bosulif®), Imatinib mesylate (Gleevec®) and ponatinib (Iclusig™) amifostine, dolasetron mesylate, dronabinol, epoetin-α, etidronate, filgrastim, fluconazole, goserelin acetate, gramicidin D, granisetron, leucovorin calcium, lidocaine, Mesna, ondansetron HCl, pilocarpine HCl, porfimer sodium, vatalanib, 1-dehydrotestosterone, allopurinol sodium, Betamethasone, sodium phosphate and betamethasone acetate, calcium leucovorin, conjugated estrogens, Dexrazoxane, Dibromomannitol, esterified estrogens, estradiol, estramustine phosphate sodium, ethinyl estradiol, flutamide, folinic acid, glucocorticoids, leuprolide acetate, levamisole HCl, medroxyprogesterone acetate, megestrol acetate, methyltestosterone, nilutamide, octreotide acetate, pamidronate disodium, procaine, propranolol, testolactone, tetracaine, toremifene citrate, and sargramostim.

In certain embodiments the chemotherapeutic agent is an estrogen receptor ligands such as tamoxifen, raloxifene, fulvestrant, anordrin, bazedoxifene, broparestriol, chlorotrianisene, clomiphene citrate, cyclofenil, lasofoxifene, ormeloxifene, or toremifene; an androgen receptor ligand such as bicalutamide, enzalutamide, apalutamide, cyproterone acetate, chlormadinone acetate, spironolactone, canrenone, drospirenone, ketoconazole, topilutamide, abiraterone acetate, or cimetidine; an aromatase inhibitor such as letrozole, anastrozole, or exemestane; an anti-inflammatory such as prednisone; an oxidase inhibitor such as allopurinol; an anticancer antibody; an anticancer monoclonal antibody; an antibody against CD40 such as lucatumumab or dacetuzumab; an antibody against CD20 such as rituximab; an antibody that binds CD52 such as alemtuzumab; an antibody that binds integrin such as volociximab or natalizumab; an antibody against interleukin-6 receptor such as tocilizumab; an interleukin-2 memetic such as aldesleukin; an antibody that targets IGF1 like figitumumab; an antibody that targets DR4 such as mapatumumab; an antibody that targets TRAIL-$R^2$ such as lexatumumab or dulanermin; a fusion protein such as atacicept; a B cell inhibitor such as atacicept; a proteasome inhibitor such as carfilzomib, bortezomib, or marizomib; a HSP90 inhibitor such as tanespimycin; a HDAC inhibitor such as vorinostat, belinostat or panobinostat; a MAPK ligand such as talmapimod; a PKC inhibitor such as enzastaurin; a HER2 receptor ligand such as trastuzumab, lapatinib, or pertuzumab; an EGFR inhibitor such as gefitinib, erlotinib, cetuximab, panitumumab, or vandetanib; a natural product such as romidepsin; a retinoid such as bexarotene, tretinoin, or alitretinoin; a receptor tyrosine kinase (RTK) inhibitor such as sunitinib, regorafenib, or pazopanib; or a VEGF inhibitor such as ziv-aflibercept, bevacizumab or dovitinib.

In certain embodiments, the combinations of a CDK4/6 inhibitor, chemotherapeutic agent, and immune checkpoint inhibitor is further combined with the use of hematopoietic growth factors including, but not limited to, granulocyte colony stimulating factor (G-CSF, for example, sold as Neupogen® (filgrastim), Neulasta® (peg-filgrastim), or lenograstim), granulocyte-macrophage colony stimulating factor (GM-CSF, for example sold as molgramostim and sargramostim (Leukine®)), M-CSF (macrophage colony stimulating factor), Thrombopoietin (megakaryocyte growth development factor (MGDF), for example sold as Romiplostim® and Eltrombopag®) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-0 sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO).

Additional active compounds contemplated herein, particularly in the treatment of abnormal tissue of the female reproductive system such as breast, ovarian, endometrial, or uterine cancer include a CDK9 inhibitor described herein in combination with an estrogen inhibitor including but not limited to a SERM (selective estrogen receptor modulator), a SERD (selective estrogen receptor degrader), a complete estrogen receptor degrader, or another form of partial or complete estrogen antagonist. Partial anti-estrogens include raloxifene and tamoxifen retain some estrogen-like effects. Complete anti-estrogens include fulvestrant. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, WO2017/100712, WO2017/100715, WO2018/081168, and WO2018/148576 assigned to G1 Therapeutics, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, arzoxifene, bazedoxifene, broparestriol, clomiphene citrate, cyclofenil, droloxifene, endoxifen, idoxifene, lasofoxifene, ormeloxifene, pipendoxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, delmadinone acetate, dydrogesterone, medroxyprogesterone acetate, megestrol acetate, nomegestrol acetate, norethisterone acetate, progesterone, and spironolactone. Additional non-limiting examples of anti-estrogen compounds include: SERDS such as fulvestrant, rintodestrant (G1T48), brilanestrant (GDC0810), elacestrant (RAD1901), etacstil (GW5638), GW7604, AZD9496, GDC-0927, GDC9545 (RG6171), LSZ102, and SAR439859.

In certain embodiments, the SERD compound of the Formula described in WO 2017/100712,

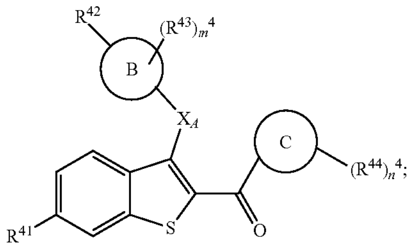

or a pharmaceutically acceptable salt thereof wherein:

$m^4$ is 0, 1, 2, 3, or 4;

$n^4$ is 0, 1, 2, 3,or 4;

$X_A$ is selected from —O—, —$CH_2$—, —S—, —NH—, —NMe-, —$CF_2$—, and $C_3$cycloalkyl;

Ring B is phenyl, naphthyl, quinolinyl, 5- or 6-membered monocyclic heteroaryl or 7-, 8-, 9- or 10 membered bicyclic heterocycle;

Ring C is phenyl, thienyl, 5- or 6-membered monocyclic heteroaryl or 7-, 8-, 9- or 10-membered bicyclic heterocycle;

$R^{41}$ is selected from hydroxyl, hydrogen, halogen, —O($C_1$-$C_6$ alkyl), —OC(O)($C_1$-$C_6$ alkyl), —OC(O) $C_6$H5, —OC(O)O($C_1$-$C_6$ alkyl), —OC(O)O$C_6H_5$ and —$OSO_2$($C_2$-$C_6$ alkyl);

$R^{42}$ is selected from —CH═CHCOOH, —NH(CO) COOH, —COOH, —$C_2$-$C_6$alkenylene-COOH and —$C_2$-$C_6$alkynylene-COOH;

$R^{43}$ is independently selected at each occurrence from hydrogen, halogen, —CN, —$NO_2$, —$C_1$-$C_6$alkyl and —$C_1$-$C_6$fluoroalkyl; and $R^{44}$ is independently selected at each occurrence from hydrogen, halogen, hydroxyl, —$C_1$-$C_6$alkyl, —$C_1$-$C_6$fluoroalkyl, —CN, —O($C_1$-$C_6$alkyl), and —O($C_1$-$C_6$fluoroalkyl).

Non-limiting examples of SERDS for use in the present invention include:

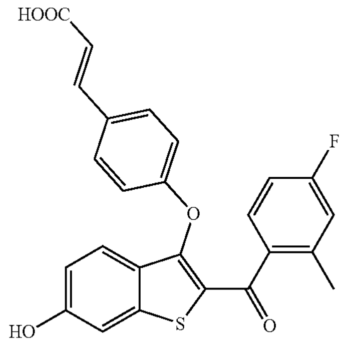

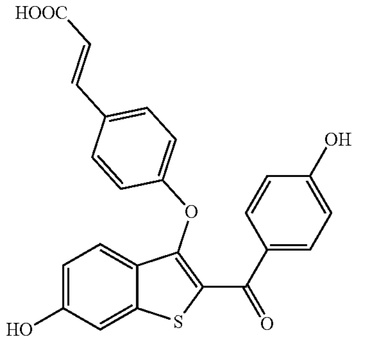

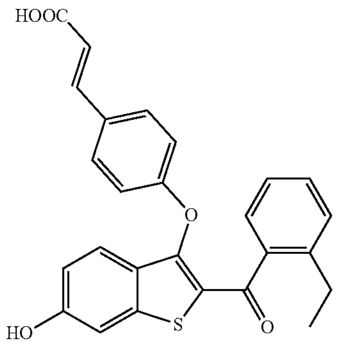

-continued

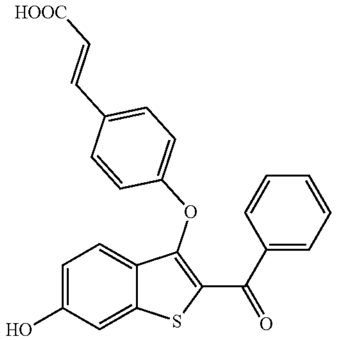

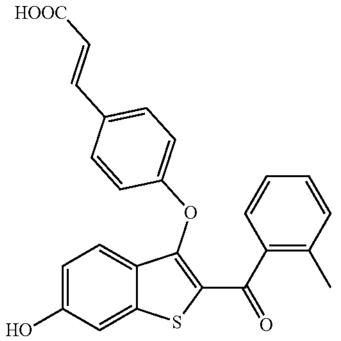

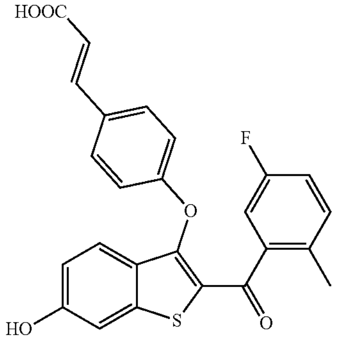

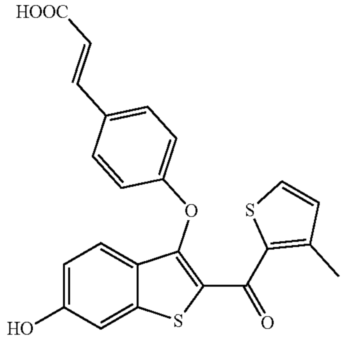

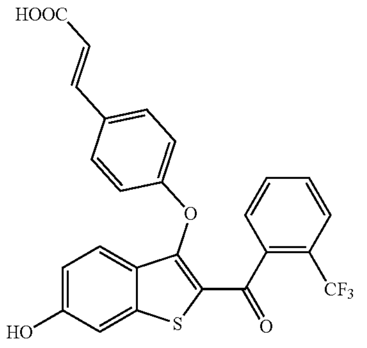

-continued
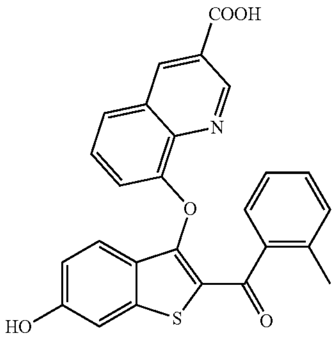
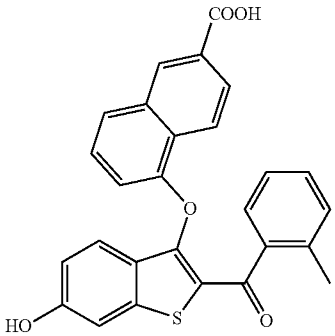
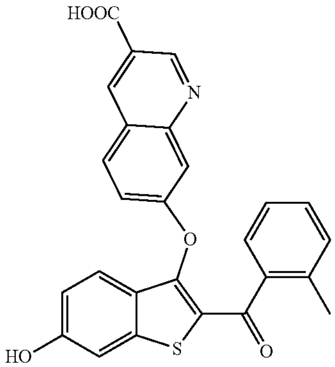
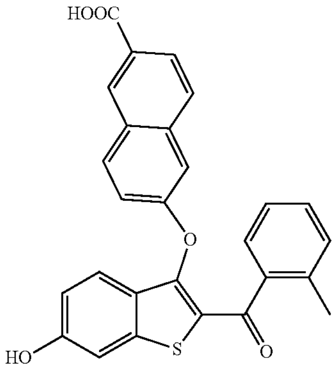
-continued
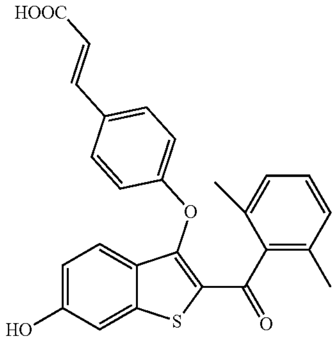
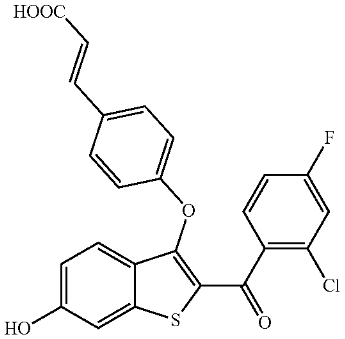
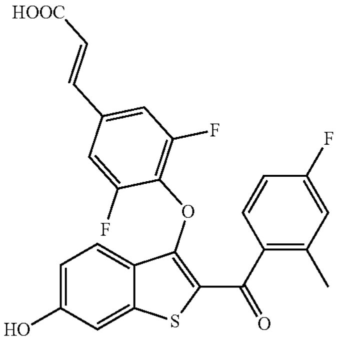
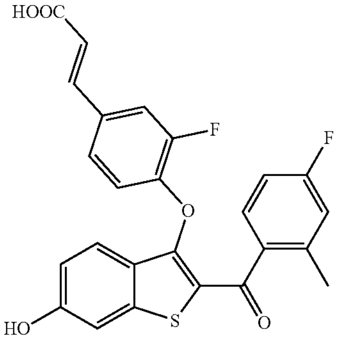
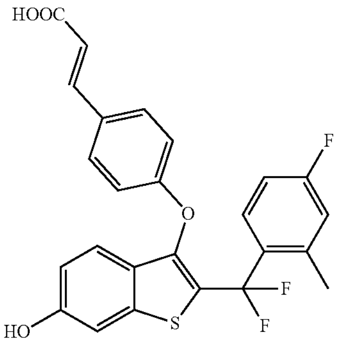

-continued

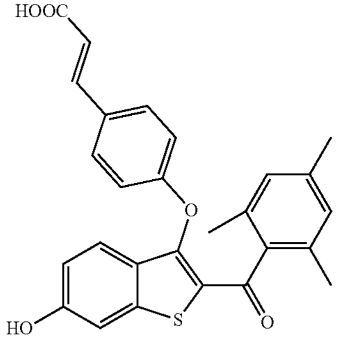

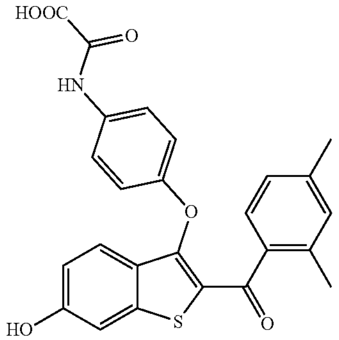

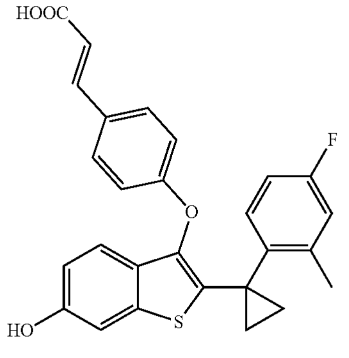

and

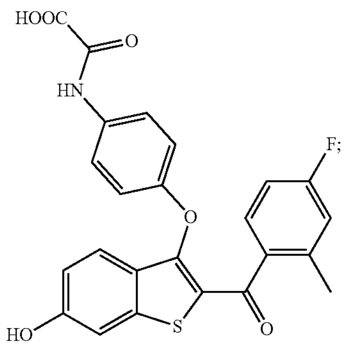 [SMILES: Cc1cc(F)ccc1C(=O)c1sc2cc(O)ccc2c1Oc1ccc(NC(=O)C(=O)O)cc1]

or a pharmaceutically acceptable salt thereof.

In certain embodiments, the SERD is:

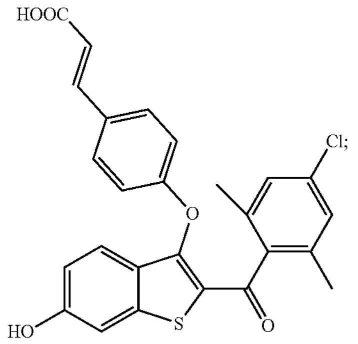 [SMILES: Cc1cc(Cl)cc(C)c1C(=O)c1sc2cc(O)ccc2c1Oc1ccc(/C=C/C(=O)O)cc1]

or a pharmaceutically acceptable salt thereof.

In certain embodiments, the SERD is:

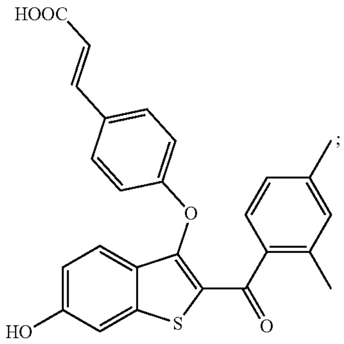 [SMILES: Cc1ccc(C(=O)c2sc3cc(O)ccc3c2Oc2ccc(/C=C/C(=O)O)cc2)c(C)c1]

or a pharmaceutically acceptable salt thereof.

In certain embodiments, the SERD is:

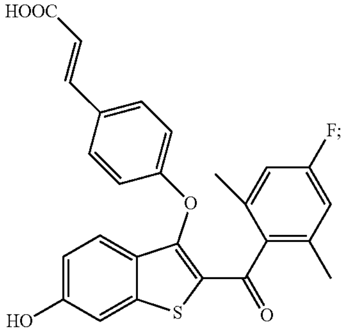 [SMILES: Cc1cc(F)cc(C)c1C(=O)c1sc2cc(O)ccc2c1Oc1ccc(/C=C/C(=O)O)cc1]

or a pharmaceutically acceptable salt thereof.

Additional chemotherapeutic agents contemplated herein, particularly in the treatment of abnormal tissue of the male reproductive system such as prostate or testicular cancer, include, but are not limited to, an androgen (such as testosterone) inhibitor including but not limited to a selective androgen receptor modulator, a selective androgen receptor degrader, a complete androgen receptor degrader, or another form of partial or complete androgen antagonist. In certain embodiments, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: chlormadinone acetate, spironolactone, canrenone, drospirenone, ketoconazole, topilutamide, abiraterone acetate, and cimetidine.

The chemotherapeutic agent may include a kinase inhibitor, including but not limited to a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3, 5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl]acetate (also known as sonolisib)), and the structure described in WO2014/071109 having the formula:

BTK inhibitors are well known. Examples of BTK inhibitors include ibrutinib (also known as PCI-32765)(Imbruvica™) (1-[(3R)-3-[4-amino-3-(4-phenoxy-phenyl)pyrazolo[3,4-d]pyrimidin-1-yl]piperidin-1-yl]prop-2-en-1-one), acalabrutinib (Calquence®), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), BGB-3111, and other molecules capable of inhibiting BTK activity, for example those BTK inhibitors disclosed in Akinleye et al, Journal of Hematology & Oncology, 2013, 6:59, the entirety of which is incorporated herein by reference.

Syk inhibitors are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), $R^{09021}$ (6-[(1R,2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

The chemotherapeutic agent can also be a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl] methyl]piperazin-1-yl]-N-[[3-nitro-4-[[(tetrahydro-2H-pyran-4-yl)methyl]amino]phenyl]sulfonyl]-2-[(1H-pyrrolo [2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl) phenyl)sulfonyl)benzamide), GX15-070 (obatoclax mesylate, (2Z)-2-[(5Z)-5-[(3,5-dimethyl-1H-pyrrol-2-yl) methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl] phenyl]-2,3,4-trihydroxy-5-[[2-(1-methylethyl)phenyl] methyl]benzamide), Apogossypolone (ApoG2), or G3139 (Oblimersen).

Additional chemotherapeutic agents for use in the methods contemplated herein include, but are not limited to, midazolam, MEK inhibitors, RAS inhibitors, ERK inhibitors, ALK inhibitors, HSP inhibitors (for example, HSP70 and HSP 90 inhibitors, or a combination thereof), RAF inhibitors, apoptotic compounds, topoisomerase inhibitors, AKT inhibitors, including but not limited to, MK-2206, GSK690693, Perifosine, (KRX-0401), GDC-0068, Triciribine, AZD5363, Honokiol, PF-04691502, and Miltefosine, or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of MEK inhibitors include but are not limited to trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-l(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEAl19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/$CH_{4987655}$ (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

Known ERK inhibitors include SCH772984 (Merck/Schering-Plough), VTX-11e (Vertex), DEL-22379, Ulixertinib (BVD-523, VRT752271), GDC-0994, FR 180204, XMD8-92, and ERK5-IN-1.

Raf inhibitors are well known, and include, for example, Vemurafinib (N-[3-[[5-(4-Chlorophenyl)-1H-pyrrolo[2,3-b] pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP—BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2, 3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3(trifluoroMethyl) phenyl]aMino]carbonyl]aMino]phenoxy]-N-Methyl-2pyridinecarboxaMide 1-Oxide).

Known topoisomerase I inhibitors useful in the present invention include (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride (topotecan), (S)-4-ethyl-4-hydroxy-1H-pyrano[3',4':6,7]indolizino[1,2- b]quinoline-3,14-(4H,12H)-dione (camptothecin), (1S,9S)-1-Amino-9-ethyl-5-fluoro-1,2,3,9,12,15-hexahydro-9-hydroxy-4-methyl-10H,13H-benzo(de)pyrano(3',4':6,7) indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4':6,7]indolizino[1,2-b] quinoline-3,15(1H,13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino [1,2-b]quinoline-9,12(3H,8H)-dione (lurtotecan), (4S)-4-Ethyl-4-hydroxy-11-[2-[(1-methylethyl)amino]ethyl]-1H-pyrano[3,4:6,7]indolizino[1,2-b]quinoline-3,14(4H,12H)-dione (belotecan), 6-((1,3-dihydroxypropan-2-yl)amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylamino-ethyl)-2,3-methylenedioxy-5H-dibenzo(c,h)(1,6)naphthyridin-6-one (topovale), benzo[6,7]indolizino[1,2-b]quinolin-11(13H)-one (rosettacin), (S)-4-ethyl-4-hydroxy-11-(2-(trimethylsilyl)ethyl)-1H-pyrano[3',4':6,7]indolizino[1,2-b] quinoline-3,14(4H,12H)-dione (cositecan), tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino [1,2-b]quinolin-4-yl}N,N',N'',N'''-{methanetetrayltetrakis [methylenepoly(oxyethylene)oxy(1-oxoethylene)]} tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-((4-methylpiperidin-1-yl) methyl)-4,5-dihydrooxepino[3',4':6,7]indolizino[1,2-b]quinoline-3,15(1H,13H)-dione (elmotecan).

In certain embodiments, the chemotherapeutic agent is not an aromatase inhibitor. In certain embodiments, the chemotherapeutic agent is not an estrogen or androgen receptor agonist or antagonist.

Growth Factors

In certain embodiments, the combination of a CDK4/6 inhibitor, chemotherapeutic agent, and checkpoint inhibitor is further combined with the use of hematopoietic growth factors including, but not limited to, granulocyte colony stimulating factor (G-CSF, for example, sold as Neupogen (filgrastim), Neulasta (peg-filgrastim), or lenograstim), granulocyte-macrophage colony stimulating factor (GM-CSF, for example sold as molgramostim and sargramostim (Leukine)), M-CSF (macrophage colony stimulating factor), Thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO).

CDK4/6 Inhibitors

The present invention also provides advantageous methods to treat a patient with a selective CDK4/6 inhibitor resistant cancer, which includes administering an effective amount of a compound of Formula I, Formula II, Formula III, Formula IV, Formula V, Formula VI, Formula VII, Formula VIII, Formula IX, or Formula X or a pharmaceutically acceptable composition, salt, or isotopic analog thereof. In certain aspects, a compound of the present invention is used to treat a patient with a cancer intrinsically resistant to selective CDK4/6 inhibition. In certain aspects, a compound of the present invention, is used to treat a patient with a cancer that has acquired resistance to one or more selective CDK4/6 inhibitors. In certain aspects, a compound of the present invention, is administered in combination with a selective CDK4/6 inhibitor to a patient with a selective CDK4/6 inhibition responsive cancer in order to extend the therapeutic effectiveness of the selective CDK4/6 inhibitor. In certain aspects, a compound of the present invention, is administered in combination with a selective CDK4/6 inhibitor to a patient with a selective CDK4/6 inhibition responsive cancer, wherein the patient is selective CDK4/6 inhibitor naïve. Selective CDK4/6 inhibitors for use in combination with a compound of the present invention include, but are not limited to, palbociclib, abemaciclib, ribociclib, trilaciclib, SHR6390, and lerociclib.

In certain embodiments, the selective CDK4/6 inhibitor is Palbociclib:

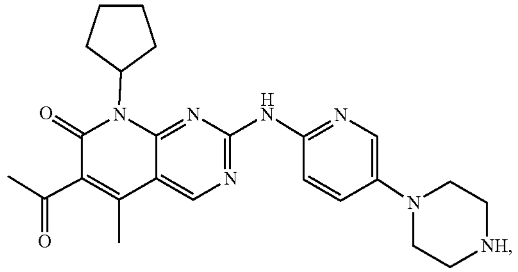 [SMILES: CC(=O)c1c(C)c2cnc(Nc3ccc(N4CCNCC4)cn3)nc2n(C2CCCC2)c1=O]

or a pharmaceutically acceptable salt thereof.

In certain embodiments, the selective CDK4/6 inhibitor is abemaciclib:

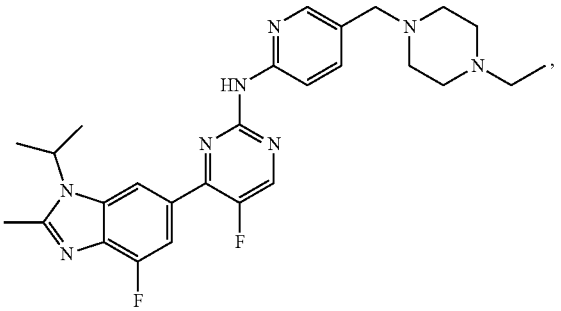 [SMILES: CCN1CCN(Cc2ccc(Nc3ncc(F)c(-c4cc(F)c5nc(C)n(C(C)C)c5c4)n3)nc2)CC1]

or a pharmaceutically acceptable salt thereof.

In certain embodiments, the selective CDK4/6 inhibitor is ribociclib:

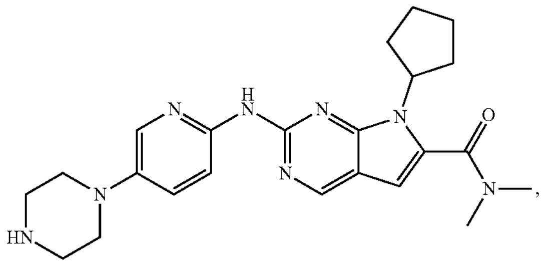 [SMILES: CN(C)C(=O)c1cc2cnc(Nc3ccc(N4CCNCC4)cn3)nc2n1C1CCCC1]

or a pharmaceutically acceptable salt thereof.

In certain embodiments, the selective CDK4/6 inhibitor is lerociclib:

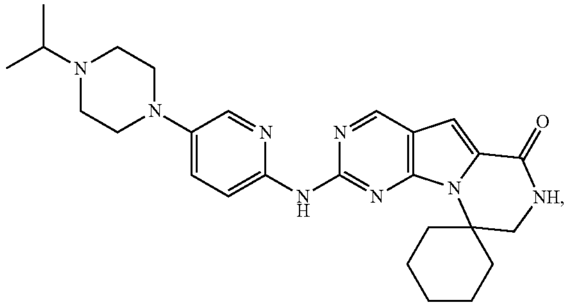 [SMILES: CC(C)N1CCN(c2ccc(Nc3ncc4cc5n(c4n3)C3(CCCCC3)CNC5=O)nc2)CC1]

or a pharmaceutically acceptable salt thereof.

In certain embodiments, the selective CDK4/6 inhibitor is trilaciclib:

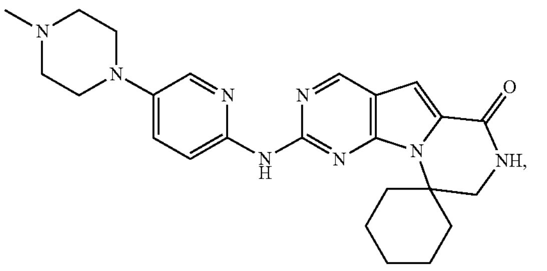 [SMILES: CN1CCN(c2ccc(Nc3ncc4cc5n(c4n3)C3(CCCCC3)CNC5=O)nc2)CC1]

or a pharmaceutically acceptable salt thereof.

In certain embodiments, the selective CDK4/6 inhibitor is SHR 6390.

In certain embodiments, the selective CDK4/6 inhibitor is selected from an inhibitor described in, for example, U.S. Pat. Nos. 8,822,683; 8,598,197; 8,598,186; 8,691,830; 8,829,102; 8,822,683; 9,102,682; 9,499,564; 9,481,591; and 9,260,442, filed by Tavares and Strum and assigned to G1 Therapeutics describe a class of N-(heteroaryl)-pyrrolo[3,2-d]pyrimidin-2-amine cyclin dependent kinase inhibitors including those of the formula (with variables as defined therein):

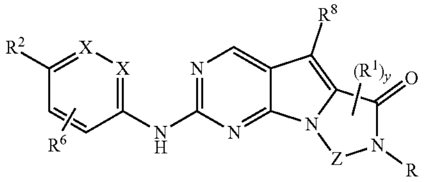

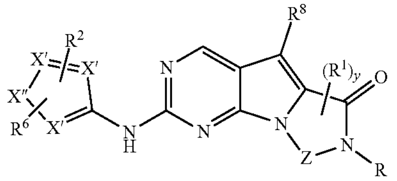

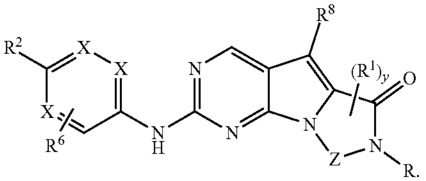

In certain embodiments, the selective CDK4/6 inhibitor is selected from an inhibitor described in, for example, U.S. Pat. Nos. 9,464,092, 9,487,530, and 9,527,857 which are also assigned to G1 Therapeutics describe the use of the above pyrimidine-based agents in the treatment of cancer.

In certain embodiments, the selective CDK4/6 inhibitor is selected from an inhibitor described in, for example, WO 2013/148748 (U.S. Ser. No. 61/617,657) titled "Lactam Kinase Inhibitors", WO 2013/163239 (U.S. Ser. No. 61/638,491) titled "Synthesis of Lactams" and WO 2015/061407 filed by Tavares and also assigned to G1 Therapeutics describes the synthesis of N-(heteroaryl)-pyrrolo[3,2-d]pyrimidin-2-amines and their use as lactam kinase inhibitors.

In certain embodiments, the selective CDK4/6 inhibitor is selected from an inhibitor described in, for example. WO 2014/144326 filed by Strum et al. and assigned to G1 Therapeutics describes compounds and methods for protection of normal cells during chemotherapy using pyrimidine-based CDK4/6 inhibitors. WO 2014/144596 filed by Strum et al. and assigned to G1 Therapeutics describes compounds and methods for protection of hematopoietic stem and progenitor cells against ionizing radiation using pyrimidine-based CDK4/6 inhibitors. WO 2014/144847 filed by Strum et al. and assigned to G1 Therapeutics describes HSPC-sparing treatments of abnormal cellular proliferation using pyrimidine-based CDK4/6 inhibitors. WO 2014/144740 filed by Strum et al. and assigned to G1 Therapeutics describes highly active anti-neoplastic and anti-proliferative pyrimidine-based CDK 4/6 inhibitors. WO 2015/161285 filed by Strum et al. and assigned to G1 Therapeutics describes tricyclic pyrimidine-based CDK inhibitors for use in radioprotection. WO 2015/161287 filed by Strum et al. and assigned to G1 Therapeutics describes tricyclic pyrimidine-based CDK inhibitors for the protection of cells during chemotherapy. WO 2015/161283 filed by Strum et al. and assigned to G1 Therapeutics describes tricyclic pyrimidine-based CDK inhibitors for use in HSPC-sparing treatments of RB-positive abnormal cellular proliferation. WO 2015/161288 filed by Strum et al. and assigned to G1 Therapeutics describes tricyclic pyrimidine-based CDK inhibitors for use as anti-neoplastic and anti-proliferative agents. WO 2016/040858 filed by Strum et al. and assigned to G1 Therapeutics describes the use of combinations of pyrimidine-based CDK4/6 inhibitors with other anti-neoplastic agents. WO 2016/040848 filed by Strum et al. and assigned to G1 Therapeutics describes compounds and methods for treating certain Rb-negative cancers with CDK4/6 inhibitors and topoisomerase inhibitors.

VIII. EXAMPLES

Example 1

General Methods:

Compounds of the present invention with stereocenters are drawn racemic for convenience. One skilled in the art will recognize that pure enantiomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in certain embodiments. A wide variety of chiral stationary phases are commercially available.

Representative Synthesis

General

Unless otherwise noted, all reagents were used without further purification. $^1$H NMR spectra were obtained in DMSO-$d_6$ or $CD_3OD$ at room temperature on a Bruker 300 MHz instrument. When more than one conformer was detected, the chemical shifts for the most abundant one is reported. Chemical shifts of $^1$H NMR spectra were recorded in parts per million (ppm) on the 6 scale from an internal standard of residual solvent. Splitting patterns are designed as s, singlet; d, doublet; t, triplet; q, quartet; m, multiplet; brs, broad. LC-MS conditions are described below:

General LC/MS Method:

| | |
|---|---|
| Column: | Agilent Zorbax XDB C18 4.6 × 50 mm, 3.5 μm |
| Mobile phase: | Solvent A: 0.1% in formic acid water<br>Solvent B: MeOH |
| Flow rate: | 1.0 mL/min |
| Run time/Gradient: | 2 min (20%-90% B), then 3 min @90% B |
| Temperature: | 30° C. |

General HPLC Method:

| | |
|---|---|
| Column: | Agilent SB-C18 4.6 × 150 mm, 3.5 μm |
| Mobile phase: | Solvent A: 0.02% in TFA water<br>Solvent B: MeOH |
| Flow rate: | 1.0 mL/min |
| Run time/Gradient: | 0.5 min @10% B, 9.5 min gradient @10%-90% B, then 10 min @90% B, |
| Temperature: | 30° C. |

General Preparative HPLC Method:

| | |
|---|---|
| Column: | Phenomenex Luna 5u 100A, 21.2 × 250 mm, 5 μm |
| Mobile phase: | Solvent A: Water<br>Solvent B: MeOH |
| Flow rate: | 10 mL/min |
| Run time/Gradient: | 1 min @20% B, 30 min gradient @20%-80% B, then 10 min @90% B |
| Temperature: | Ambient |

The following abbreviations are used below: PE=petroleum ether, EA=ethyl acetate, DMSO=dimethyl sulfoxide, DMP=Dess-Martin reagent, DMF=N, N-dimethylacetamide, MeOH=methanol, MTBE=methyl tert-butyl ether, DCM=dichloromethane, TEA=triethylamine, DIPEA=diisopropylethylamine, DIEA=N, N-Diisopropylethylamine, $N_2H_4 \cdot H_2O$=hydrated hydrazine, TFA=trifluoroacetic acid, TLC=thin layer chromatography, $B_2Pin_2$=bis(pinacolato)diboron, AcOK=potassium acetate, $N_2$=nitrogen gas, $Pd(OAc)_2$=palladium(II) acetate, EtOAc=ethyl acetate, $Na_2SO_4$=sodium sulfate, $SOCl_2$=thionyl chloride, $NaHCO_3$=sodium bicarbonate, $Na_2CO_3$=sodium carbonate, $NaS_2O_3$=sodium thiosulfate, $MgSO_4$=magnesium sulfate, RT=room temperature, THF=tetrahydrofuran, DMAC=dimethylacetamide, t-BuOH=tert-butyl alcohol, DBU=1,8-diazabicyclo[5.4.0]undec-7-ene, CuI=copper (I) iodide, TBAF=tetra-n-butylammonium fluoride, $Pd(PPh_3)_2Cl_2$=bis(triphenylphosphine)palladium(II) dichloride, $Pd(OAc)_2$=palladium(II) acetate, n-BuLi=n-butyllithium, $NH_4Cl$=ammonium chloride, $Cs_2CO_3$=cesium carbonate, EA=ethyl acetate, MeCN=Acetonitrile, NBS=N-bromosuccinimide, $K_2CO_3$=potassium carbonate, CPBA=meta-chloroperoxybenzoic acid.

Scheme 1. Synthesis of 4-((6'-hydroxy-8'-oxo-7',8'-dihydro-6'H-spiro [cyclohexane-1,9'-pyrazino[1',2':1,5]pyrrolo[2,3-d]pyrimidin]-2'-yl)amino) benzenesulfonamide Compound 1

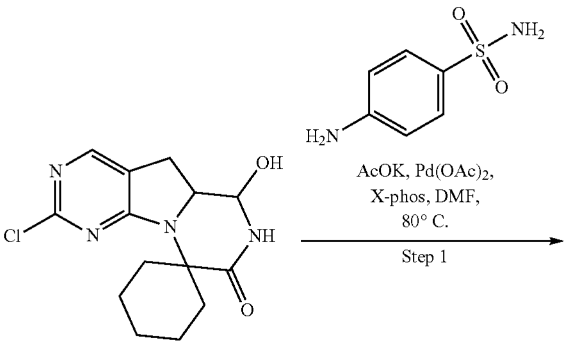

1

-continued

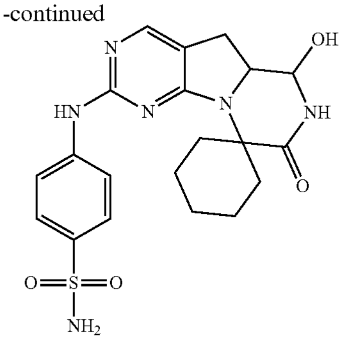

Compound 1

Step 1: To a solution of intermediate 1 (100 mg, 0.33 mmol) in DMF (4 mL), under $N_2$ atmosphere, was added 4-aminobenzenesulfonamide (67.3 mg, 0.39 mmol), AcOK (95.8 mg, 0.98 mmol), $Pd(OAc)_2$ (7.3 mg, 0.03 mmol) and X-phos (62.2 mg, 0.13 mmol). The solution was stirred at 80° C. for 3 hours, then the reaction mixture was cooled to room temperature, quenched with water (10 mL) and extracted with EtOAc (10 mL×3). The combined organic phase was washed with brine (5 mL×2), dried over $Na_2SO_4$ and concentrated in vacuo. The resulting residue was purified by preparative TLC to afford Compound 1 (2.5 mg, 0.006 mmol). MS (ESI+): m/z 443 $[M+H]^+$. $^1H$ NMR (300 MHz, DMSO-d6): δ9.97 (s, 1H), 8.82 (s, 1H), 8.75 (d, J=3.9 Hz, 1H), 8.02 (d, J=9.0 Hz, 2H), 7.73 (d, J=9.0 Hz, 2H), 7.19 (s, 2H), 6.55 (d, J=6.6 Hz, 1H), 6.50 (s, 1H), 5.90-5.85 (m, 1H), 2.75-2.65 (m, 2H), 2.31-2.17 (m, 2H), 1.95-1.62 (m, 6H).

Scheme 2. Synthesis of 4-((7'-oxo-7',8'-dihydro-6'H-spiro[cyclohexane-1,9'-pyrrolo[1,5-a:2,3-d']dipyrimidin]-2'-yl)amino)benzenesulfonamide Compound 2

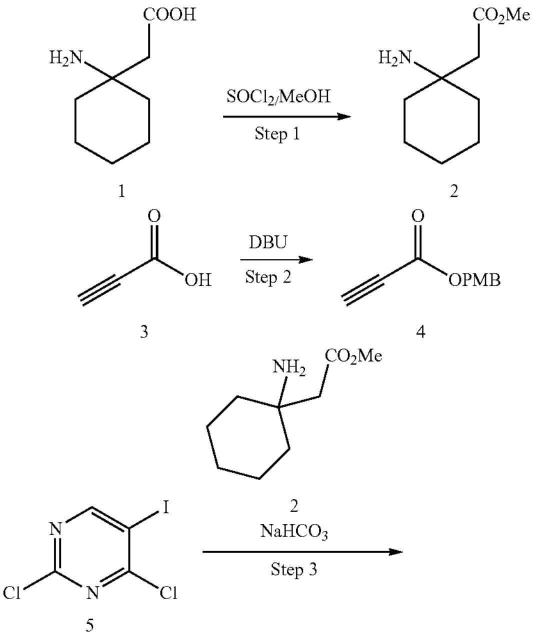

-continued

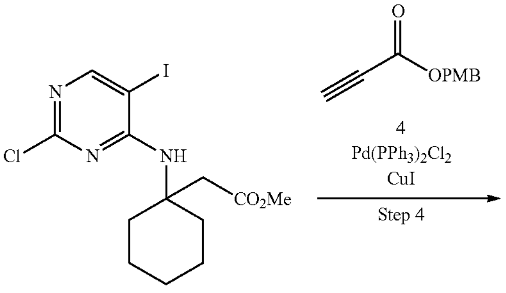

6

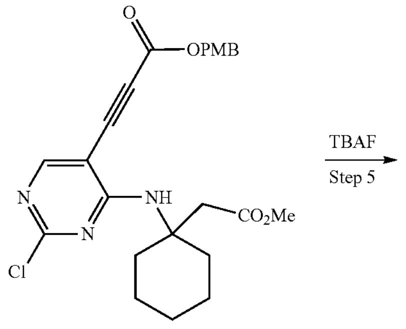

7

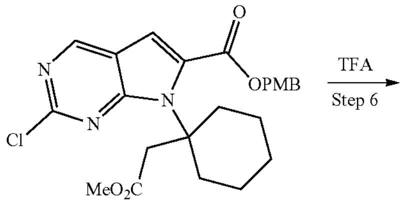

8

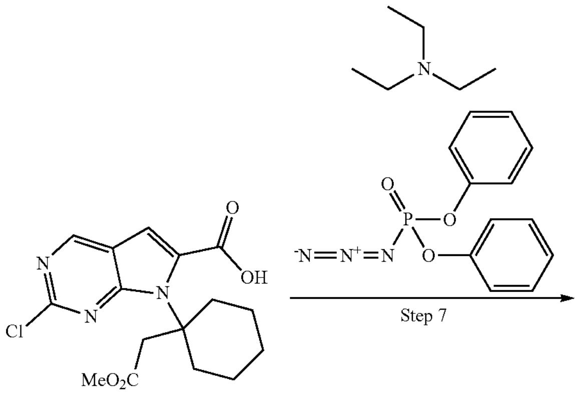

9

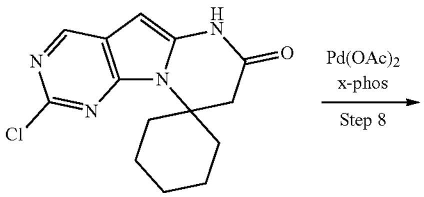

10

-continued

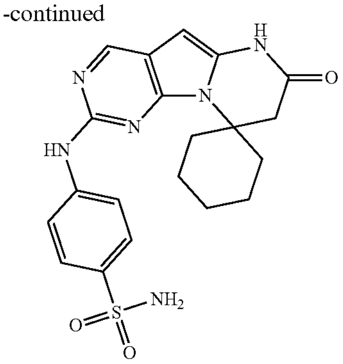

Compound 2

Step 1: To a mixture of intermediate 1 (12 g, 76.33 mmol) in MeOH (120 mL) was added dropwise $SOCl_2$ (10 mL). The reaction was stirred at 40° C. overnight. The reaction was concentrated in vacuo. The resulting residue was neutralized with aq. $Na_2CO_3$ solution to pH ~8 and extracted with DCM (50 mL×5). The combined organic phase was concentrated to afford intermediate 2 (12 g, 70.08 mmol). LC-MS (ESI+): m/z 172 [M+H]+.

Step 2: To a solution of intermediate 3 (10 g, 142.76 mmol) in DCM (150 mL) was added DBU (23 g, 151.08 mmol) dropwise at 0° C. over 30 min. After addition, the reaction solution was stirred at room temperature for 2 hours. Then 1-(chloromethyl)-4-methoxybenzene (20 g, 127.71 mmol) was added to the reaction solution. The reaction was stirred at room temperature for 2 days. The reaction was quenched with saturated aqueous sodium bicarbonate solution (100 mL). The organic phase was dried over $Na_2SO_4$, filtered and concentrated in vacuo. The resulting residue was purified by silica gel column chromatography to afford intermediate 4 (14 g, 73.61 mmol).

Step 3: To a solution of intermediate 5 (25 g, 90.95 mmol) in DMAc (100 mL) was added intermediate 2 (12 g, 70.08 mmol) and $NaHCO_3$ (20 g, 238.07 mmol). The reaction mixture was stirred at 60° C. for 12 hours. After cooled to room temperature, the reaction mixture was quenched with water (200 mL) and extracted with EtOAc (100 mL×2). The organic layer was separated and washed with brine, dried over $MgSO_4$, filtered and concentrated in vacuo. The resulting crude product was purified by column chromatography to afford intermediate 6 (14 g, 34.17 mmol). LC-MS (ESI+): m/z 410 [M+H]+.

Step 4: To a solution of intermediate 6 (14 g, 34.17 mmol) in THE (200 mL), under $N_2$ atmosphere, was added CuI (647 mg, 3.40 mmol), $Pd(PPh_3)_2Cl_2$ (1.2 g, 1.71 mmol) and TEA (6.9 g, 68.19 mmol). Then a solution of intermediate 4 (8 g, 42.06 mmol) in THE (20 mL), was added dropwise to the reaction mixture, over 15 min. The mixture was stirred at room temperature overnight, then the reaction mixture was concentrated in vacuo. The resulting residue was purified by silica gel column chromatography to afford intermediate 7 (5 g, 10.59 mmol). LC-MS (ESI+): m/z 472 [M+H]+.

Step 5: To a solution of intermediate 7 (5 g, 10.59 mmol) in THE (30 mL), under $N_2$ atmosphere, was added TBAF (30 mL, 1 M in THF) at 60° C. The mixture was stirred at 60° C. for 2 hours, then the reaction was quenched with water (100 mL) and extracted with EtOAc (50 mL×2). The combined organic phase was washed with brine (50 mL), dried over $Na_2SO_4$, filtered and concentrated in vacuo. The resulting residue was purified by silica gel column chromatography to afford intermediate 8 (1 g, 2.12 mmol). LC-MS (ESI+): m/z 472 [M+H]+.

Step 6: To a solution of intermediate 8 (1 g, 2.12 mmol) in DCM (9 mL) was added TFA (3 mL) at RT. The reaction was stirred at room temperature overnight. The reaction solution was concentrated in vacuo. The resulting residue was purified by silica gel column chromatography to afford intermediate 9 (380 mg, 1.08 mmol). LC-MS (ESI+): m/z 352 [M+H]+.

Step 7: To a solution of intermediate 9 (160 mg, 0.46 mmol) in t-BuOH (5 mL) was added 4A cular sieve (100 mg). The mixture was stirred at RT for 30 min. Then to the mixture was added triethylamine (90 mg, 0.89 mmol) and diphenyl phosphorazidate (240 mg, 0.0.87 mmol). The mixture was stirred at 80° C. for 4 hours, then the reaction mixture was filtered and the filtrate concentrated in vacuo. The resulting residue was purified by silica gel column chromatography to afford intermediate 10 (30 mg, 0.10 mmol). LC-MS (ESI+): m/z 291 [M+H]+.

Step 8: To a solution of 4-aminobenzenesulfonamide (40 mg, 0.23 mmol) in DMF (4 mL), under $N_2$ atmosphere, was added intermediate 10 (57 mg, 0.20 mmol), $Pd(OAc)_2$ (8 mg, 0.036 mmol), X-Phos (20 mg, 0.042 mmol) and AcOK (50 mg, 0.51 mmol). The mixture was stirred at 80° C. for 4 hours, the reaction mixture was cooled to room temperature, quenched with water (5 mL) and extracted with EtOAc/THF=1/1 (5 mL×3). The combined organic phase was dried over $Na_2SO_4$, concentrated in vacuo. The resulting residue was purified by preparative TLC to afford Compound 2 (4.2 mg, 0.01 mmol). LC-MS (ESI+): m/z 427 [M+H]+; 1H NMR (300 MHz, DMSO-d6): δ11.05 (s, 1H), 9.72 (s, 1H), 8.53 (s, 1H), 7.91 (d, J=9.0 Hz, 2H), 7.69 (d, J=9.0 Hz, 2H), 7.15 (s, 1H), 5.68 (s, 1H), 5.32 (s, 1H), 3.02-2.95 (m, 4H), 2.05-1.95 (m, 2H), 1.85-1.81 (m, 2H), 1.60-1.50 (m, 4H).

Scheme 3. Synthesis of 4-((3'-oxo-2',3'-dihydro-1'H-spiro[cyclohexane-1,4'-pyrimido[5',4':4,5]pyrrolo[2,1-c][1,2,4]triazin]-7'-yl)amino)benzenesulfonamide Compound 3

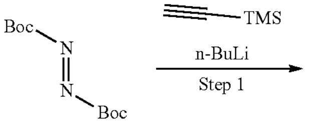

1

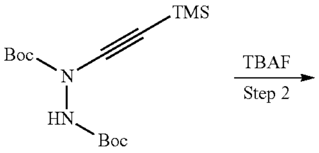

2

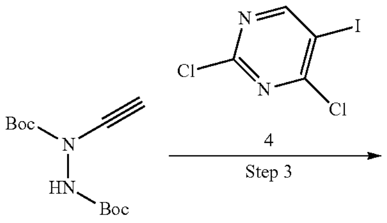

4

3

-continued

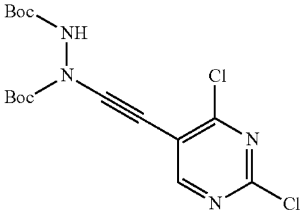

5

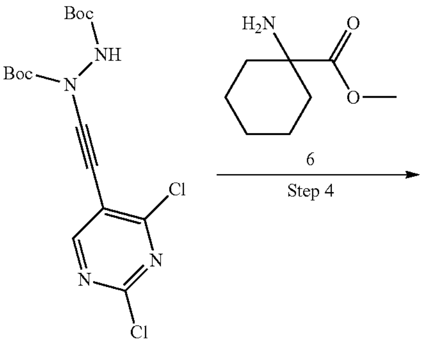

6

5

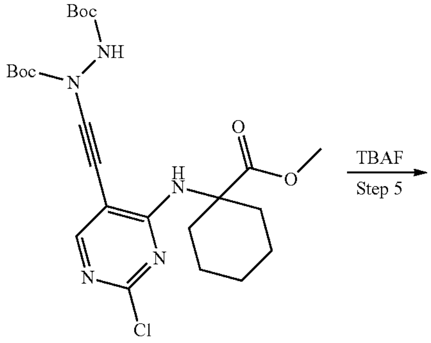

7

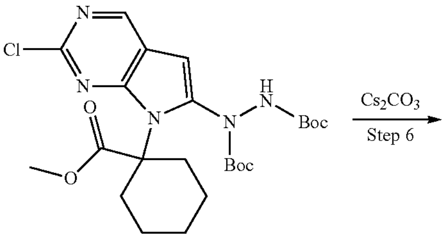

8

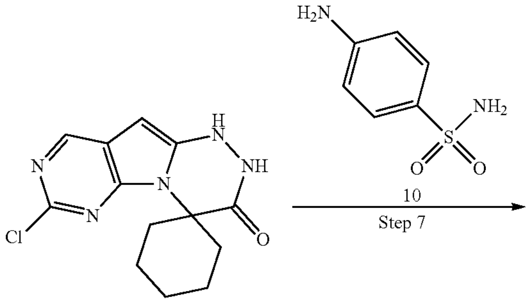

10

9

-continued

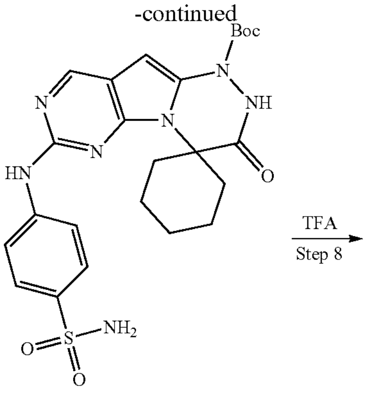

11

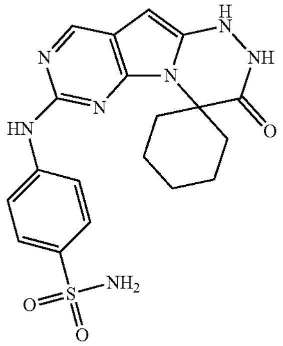

Compound 3

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of intermediate 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford intermediate 2 (60 g, 182.83 mmol) as oil.

Step 2: To a solution of intermediate 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford intermediate 3 (36 g, 140.55 mmol).

Step 3: To a solution of intermediate 3, intermediate 4, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford intermediate 5 (28 g, 69.64 mmol). LC-MS (ESI+): m/z 403 [M+H]+.

Step 4: To a solution of intermediate 5 (2 g, 4.97 mmol) in DMF (20 mL), under $N_2$ atmosphere, was added intermediate 6 (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford intermediate 7 (1.2 g, 2.29 mmol). LC-MS (ESI+): m/z 524 [M+H]+.

Step 5: To a solution of intermediate 7 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford intermediate 8 (300 mg, 0.57 mmol). LC-MS (ESI+): m/z 524 [M+H]+.

Step 6: To a solution of intermediate 8 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford intermediate 9 (320 mg, 0.82 mmol). LC-MS (ESI+): m/z 392 [M+H]+.

Step 7: To a solution of intermediate 9 (50 mg, 0.13 mmol) in DMF (2 mL), under $N_2$ atmosphere, was added intermediate 10 (24 mg, 0.14 mmol), $Pd(OAc)_2$ (2.8 mg, 0.013 mmol), X-Phos (24 mg, 0.05 mmol) and AcOK (38 mg, 0.38 mmol). The reaction was stirred at 80° C. for 5 hours. The reaction mixture was cooled to room temperature, quenched with water (20 mL), and extracted with DCM:MeOH=10:1 (20 mL×3). The combined organic phase was dried over $MgSO_4$, filtered and concentrated in vacuo. The resulting residue was purified by preparative TLC to afford intermediate 11 (43 mg, 0.082 mmol). LC-MS (ESI+): m/z 528 [M+H]+.

Step 8: To a solution of intermediate 11 (20 mg, 0.038 mmol) in DCM (2 mL) was added TFA (0.2 mL). The reaction was stirred at RT for 2 hours. The reaction mixture was quenched with saturated $NaHCO_3$ solution (10 mL), and extracted with DCM:MeOH=10:1 (10 mL×3). The combined organic phase was dried over $MgSO_4$, filtered and concentrated in vacuo. The resulting residue was purified by preparative TLC to afford Compound 3 (2.1 mg, 0.005 mmol). LC-MS (ESI+): m/z 428 [M+H]+; 1H NMR (300 MHz, CD30D): 58.48 (s, 1H), 7.92 (d, J=9.0 Hz, 2H), 7.80 (d, J=9.0 Hz, 2H), 5.80 (s, 1H), 2.49-2.38 (m, 2H), 2.15-1.97 (m, 6H), 1.90-1.81 (m, 1H), 1.70-1.61 (m, 1H).

Scheme 4. Synthesis of 4-((1'H-spiro[cyclohexane-1,4'-pyrimido[5',4':4,5]pyrrolo [2,1-c][1,2,4]triazin]-7'-yl)amino)benzenesulfonamide Compound 4

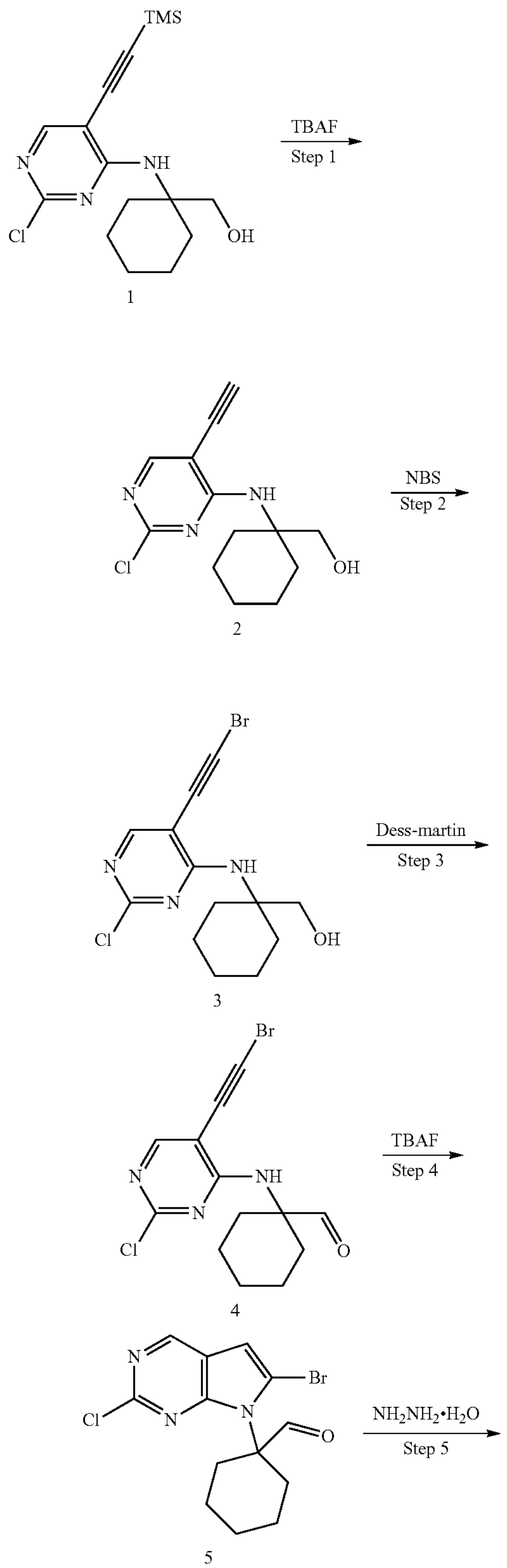

-continued

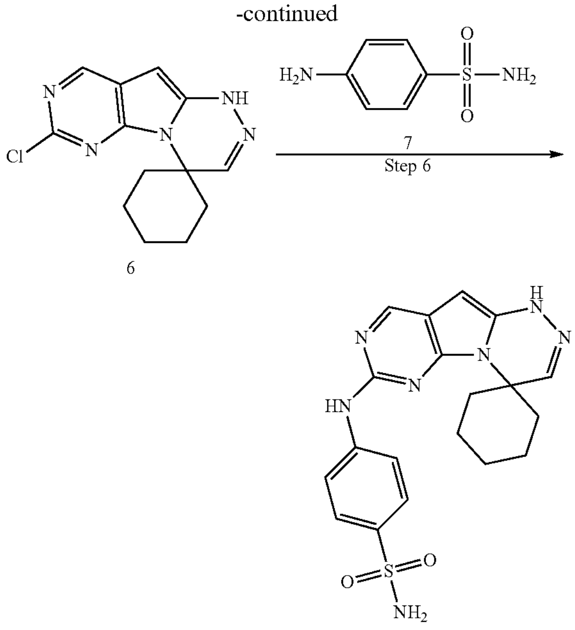

Compound 4

Step 1: To a solution of intermediate 1 (300 mg, 0.89 mmol) in THE (20 mL) was added TBAF trihydrate (50 mg, 0.16 mmol) at −10° C. After the addition, the reaction was stirred at −10° C. for 5 min. The reaction mixture was quenched with saturated $NH_4Cl$ solution (30 mL), and extracted with EA (20 mL×2). The combined organic phase was dried over $Na_2SO_4$, filtered and concentrated in vacuo to afford intermediate 2 (220 mg, 0.83 mmol). LC-MS (ESI+): m/z 266 $[M+H]^+$.

Step 2: To a solution of intermediate 2 (200 mg, 0.83 mmol) in MeCN (20 mL) was added NBS (200 mg, 1.12 mmol) and DBU (170 mg, 1.12 mmol) at room temperature. After the addition, the reaction was stirred at RT for 30 min. The reaction mixture was quenched with water (100 mL), and extracted with EA (50 mL×2). The combined organic phase was dried over $Na_2SO_4$, filtered and concentrated in vacuo. The resulting residue was purified by column chromatography to afford intermediate 3 (200 mg, 0.58 mmol). LC-MS (ESI+): m/z 344/346 $[M+H]^+$.

Step 3: To a solution of intermediate 3 (75 mg, 0.22 mmol) in DCM (5 mL) was added Dess-Martin Reagent (100 mg, 0.24 mmol) at room temperature, After the addition, the reaction was stirred at room temperature for 10 min. The reaction mixture was quenched with saturated $Na_2S203$ solution (10 mL) and saturated $NaHCO_3$ solution (10 mL), and extracted with DCM (20 mL×2). The combined organic phase was dried over $Na_2SO_4$, filtered and concentrated in vacuo. The resulting residue was purified by silica column chromatography to afford intermediate 4 (50 mg, 0.15 mmol). LC-MS (ESI+): m/z 342/344 [M+H]+.

Step 4: To a solution of intermediate 4 (400 mg, 1.17 mmol) in THE (40 mL) was added TBAF trihydrate (1 g, 3.17 mmol) at room temperature. After the addition, the reaction was stirred at RT for 30 min. The reaction mixture was quenched with water (100 mL), and extracted with EA (50 mL×2). The combined organic phase was dried over $Na_2SO_4$, filtered and concentrated in vacuo. The resulting residue was purified by silica column chromatography to afford intermediate 5 (260 mg, 0.77 mmol) as a white solid.

Step 5: To a solution of intermediate 5 (300 mg, 0.88 mmol) in THE (5 mL) was added hydrazinehydrate diamidhydrate (2 mL) and $K_2CO_3$ (200 mg, 1.45 mmol). After addition, the reaction was stirred at 40° C. for 1 hour. The reaction mixture was quenched with water (20 mL), and extracted with EA (20 mL×3). The combined organic phase was dried over $Na_2SO_4$, filtered and concentrated in vacuo. The resulting residue was purified by silica column chromatography to afford intermediate 6 (200 mg, 0.73 mmol). LC-MS (ESI+): m/z 276/278 [M+H]+.

Step 6: To a solution of intermediate 6 (20 mg, 0.07 mmol) in DMF (2 mL), under $N_2$ atmosphere, was added intermediate 7 (15 mg, 0.09 mmol), $Pd(OAc)_2$ (1.9 mg, 0.01 mmol), X-Phos (14 mg, 0.03 mmol) and AcOK (21 mg, 0.22 mmol). The reaction was stirred at 80° C. for 5 hours. The reaction mixture was cooled to room temperature, quenched with water (5 mL), and extracted with DCM:MeOH=10:1 (5 mL×3). The combined organic phase was dried over $MgSO_4$, filtered and concentrated in vacuo. The resulting residue was purified by preparative TLC to afford Compound 4 (3.9 mg, 0.01 mmol). LC-MS (ESI+): m/z 412 [M+H]+; 1H NMR (300 MHz, DMSO-d6): δ 10.71 (s, 1H), 9.77 (s, 1H), 8.45 (s, 1H), 7.95 (d, J=8.7 Hz, 2H), 7.70 (d, J=8.7 Hz, 2H), 7.20 (s, 1H), 7.16 (s, 1H), 5.41 (s, 1H), 3.12-3.05 (m, 2H), 1.98-1.87 (m, 4H), 1.85-1.75 (m, 4H).

Scheme 5. Synthesis of 4-((9'-oxo-8',9'-dihydrospiro[cyclohexane-1,10'-pyrimido[5',4':4,5]pyrrolo[2,1-d][1,2,5]triazepin]-2'-yl)amino)benzenesulfonamide Compound 6

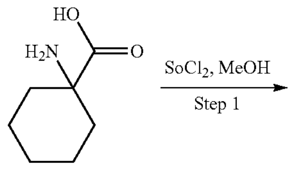

1

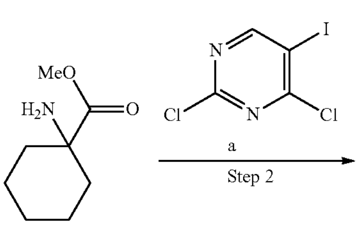

2

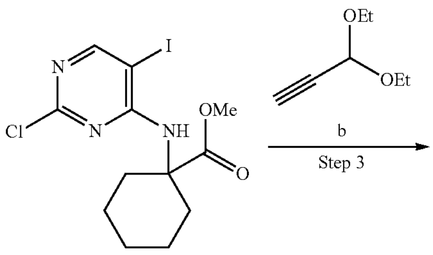

3

-continued

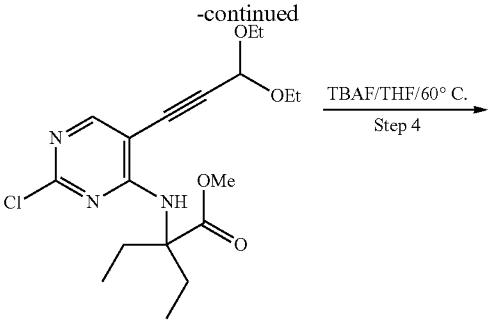

4

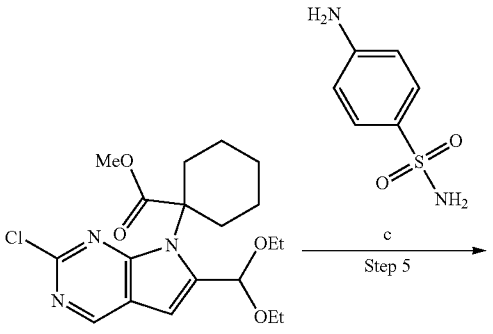

5

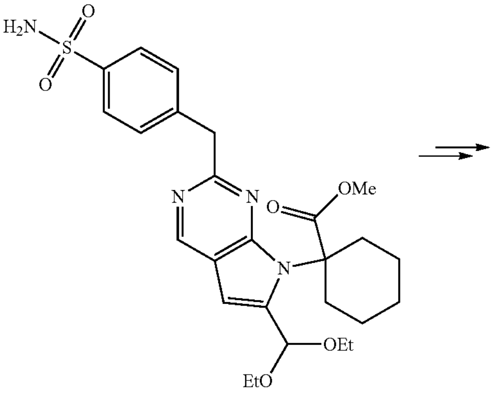

6

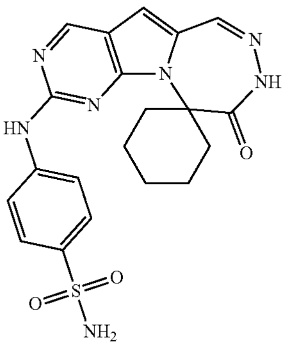

Compound 6

Step 1: Thionyl chloride was added to a solution of intermediate 1 (10 g) in methanol and the reaction was then allowed to stir overnight. After purification intermediate 2 (5.47 g) was obtained.

Step 2: Sodium bicarbonate was added to a solution of intermediate 2 (5.47 g) in DMAC and the reaction was then allowed to stir overnight at 90° C. After purification intermediate 3 (6.25 g) was obtained.

Step 3: To a solution of intermediate 3 (500 mg) in THF was added DIEA and then compound b, $PdCl_2(PPh_3)_2$, and CuI were added. The reaction was then allowed to stir overnight at 30° C. After purification intermediate 4 (410 mg) was obtained.

Step 4: TBAF was added to a solution of intermediate 4 (20 mg) in THF and the reaction was then allowed to stir overnight at 60° C. After purification intermediate 5 (8 mg) was obtained.

Step 5: Compound c, $Pd(OAc)_2$, X-phos, and AcOK was added to a solution of intermediate 5 (50 mg) in DMF. The reaction was then allowed to stir at 70° C. for 4 hours. The MS peak of the desired product was detected by LC-MS. After purification intermediate 6 (10 mg) was obtained.

Scheme 6 Synthesis of Cyclic Imine Intermediates and Compound 24

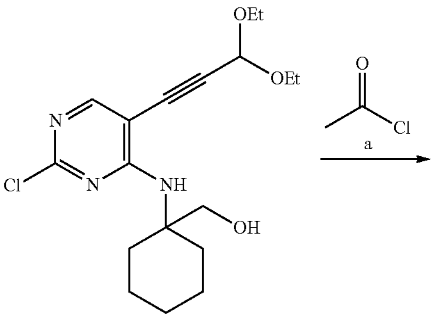

1

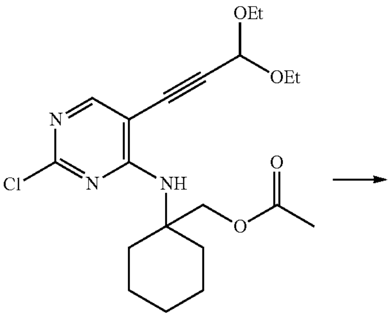

2

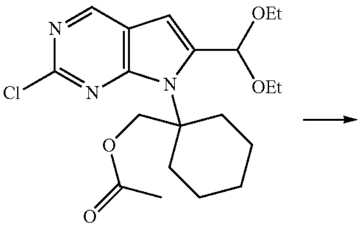

3

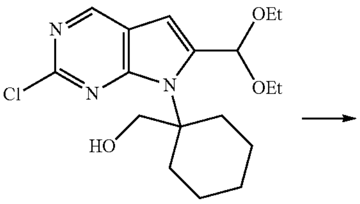

4

-continued

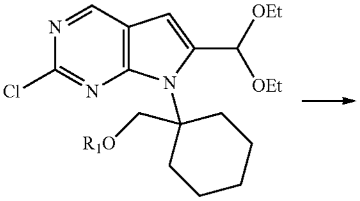

5

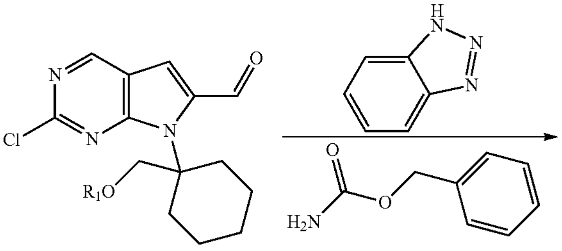

6

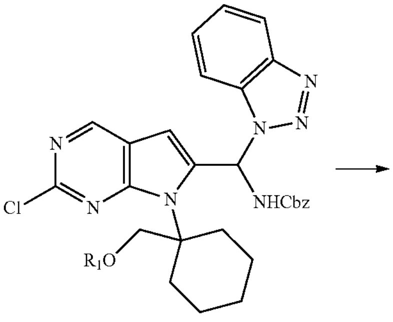

7

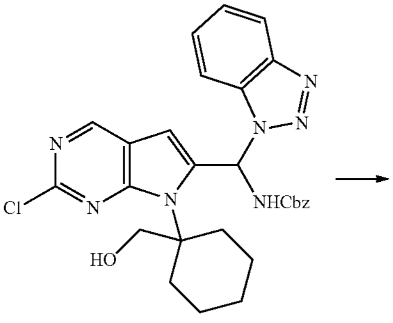

8

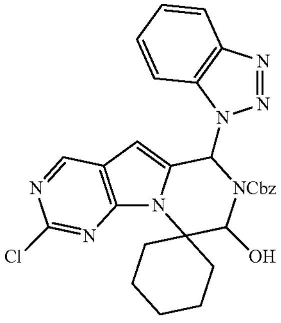

9

-continued
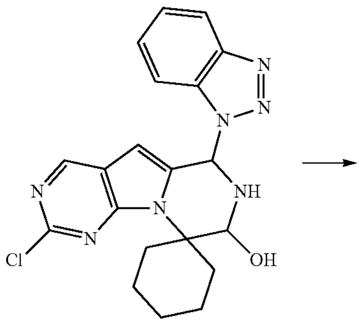
10
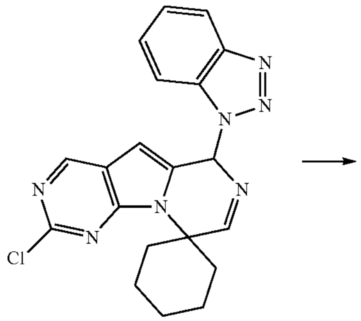
11
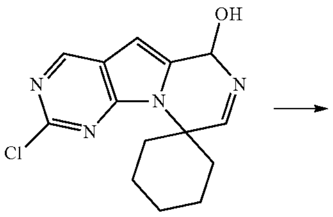
12
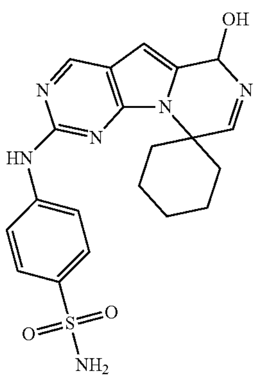
Scheme 7. Synthesis of 4-((1'-methyl-3'-oxo-2',3'-dihydro-1'H-spiro[cyclohexane-1,4'-pyrimido[5',4':4,5]pyrrolo[2,1-c][1,2,4]triazin]-7'-yl)amino)benzenesulfonamide Compound 12
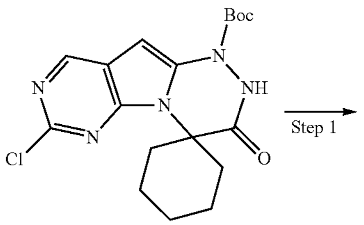
1
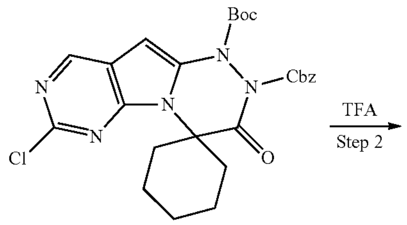
2
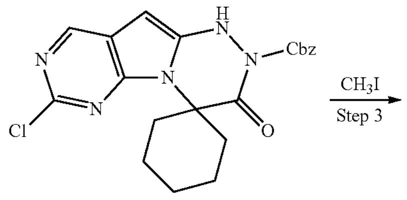
3
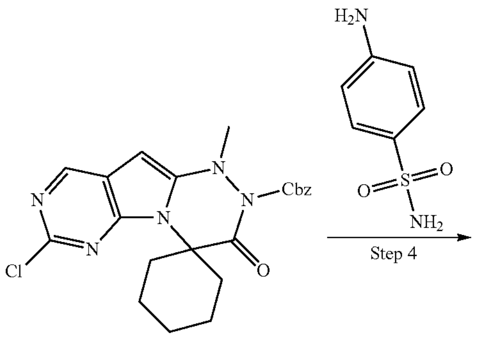
4
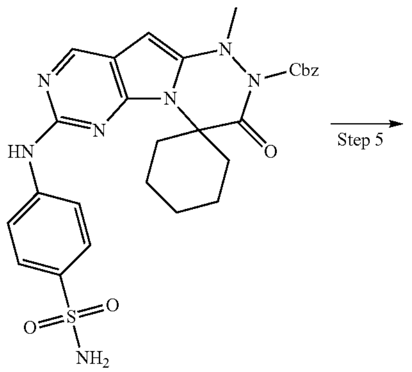
5

-continued

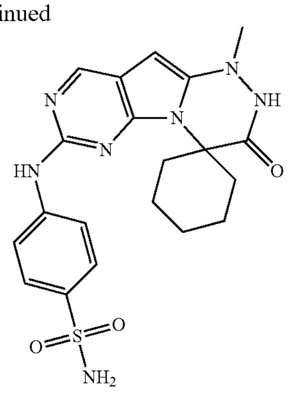

Compound 12

Step 1: 200 mg of 1 was converted to 2 using Cbz-Cl/NaH/THF/0° C./0.5 h. After purification, 220 mg of 2 was obtained.

Step 2: 210 mg of 2 was converted to 3 using TFA/DCM/RT/30 min. After purification, 150 mg of 3 was obtained.

Step 3: 130 mg of 3 was converted to 4 using NaH/THF/0° C./2 h. The starting material was consumed. After purification, 80 mg of 4 was obtained.

Step 4 and Step 5: 20 mg of 4 was converted to 5 using Pd(OAc)2/x-phos/AcOK/DMF/85° C./4 h. The starting material was consumed. TLC was clean. The MS peak of Compound 12 was detected by LC-MS significantly. After purification, 7.3 mg of Compound 12 was obtained.

Scheme 8. Synthesis of (R)-4-((6'-(fluoromethyl)-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide Compound 18

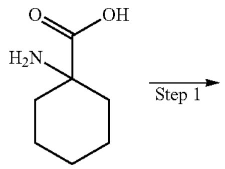

1

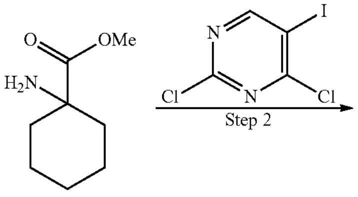

2

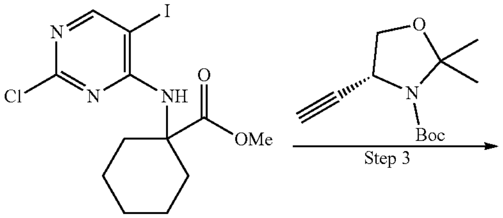

3

-continued

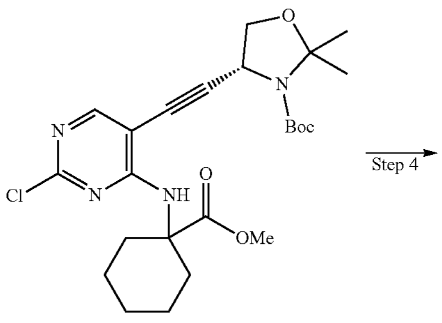

4

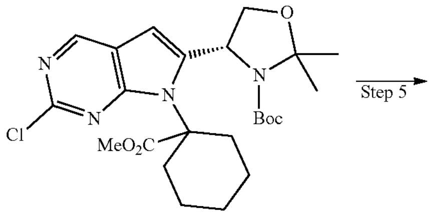

5

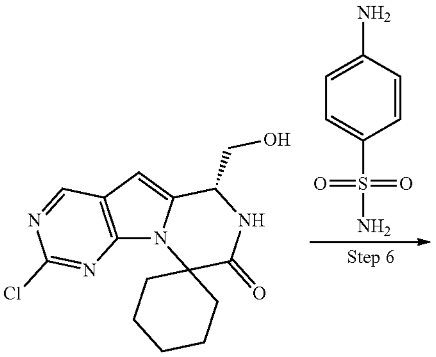

6

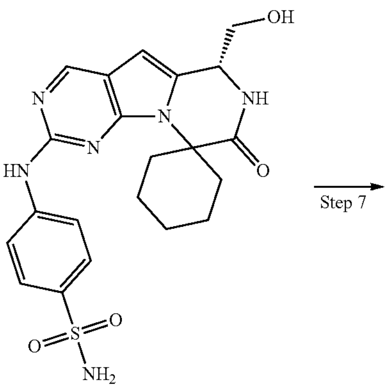

7

-continued

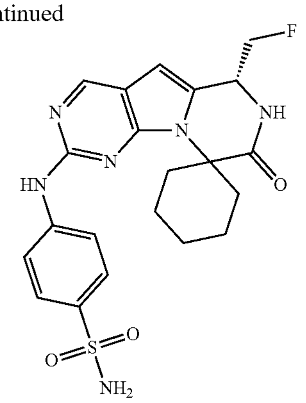

Compound 18

Step 6: 500 mg of 6 was converted to 7 using $Pd(OAc)_2$/X-Phos/KOAc/DMF/80° C./4 h. After purification, 315 mg of 7 was obtained.

Step 7: 70 mg of 7 was converted to Compound 18 using DAST/THF/0° C.~RT/3 h. After purification with the one above, 3.0 mg of Compound 18 was obtained.

Scheme 9. Synthesis of (S)-4-((6'-methyl-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide Compound 19

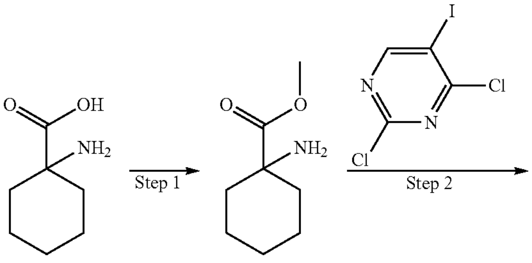

1
2

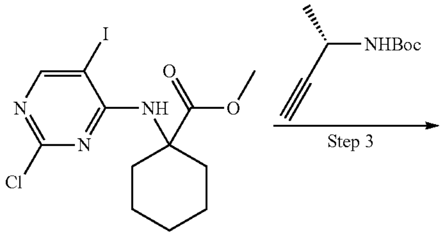

3

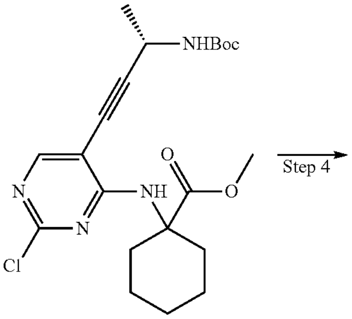

4

-continued

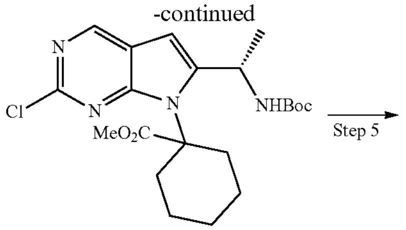

5

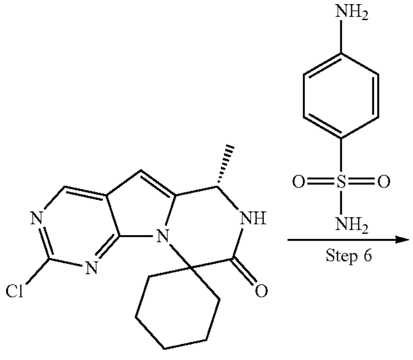

6

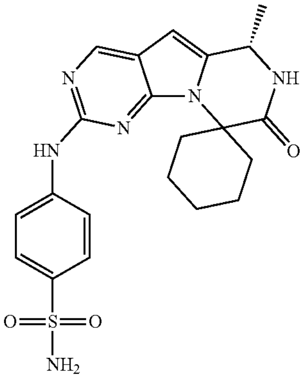

Compound 19

Step 1: 20 g of 1 was converted to 2 using $SOCl_2$/MeOH/reflux rt/overnight. After purification, 17.7 g of 2 was obtained.

Step 2: 17.7 g of 2 was converted to 3 using $NaHCO_3$/DMAc/70° C./overnight. After purification, 22 g of 3 was obtained.

Step 3: 5.5 g of 3 was converted to 4 using CuI/$PdCl_2(PPh_3)_2$/TEA/THF/RT/overnight. After purification, 4.5 g of 4 was obtained.

Step 4: 500 mg of 4 was converted to 5 using $Cs_2CO_3$/DMF/rt/overnight. After purification, 195 mg of 5 was obtained.

Step 5: 165 mg of 5 was converted to 6 using TFA/DCM/RT/30 min. After purification, 100 mg of 6 was obtained.

Step 6: 30 mg of 6 was converted to Compound 19 using $Pd(OAc)_2$/x-phos/AcOK/DMF/80° C./3 h. A major new spot was observed by TLC. After purification, 3.4 mg of Compound 19 was obtained. H-NMR and LC-MS are good.

Scheme 10 Synthesis of R-4-((6'-methyl-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide Compound 22

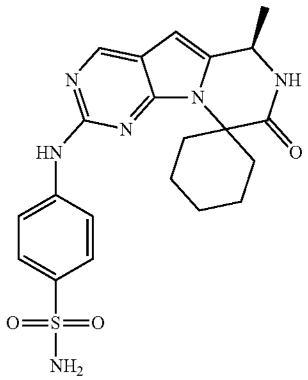 [SMILES: C[C@H]1NC(=O)C2(CCCCC2)n2c1cc1cnc(Nc3ccc(S(N)(=O)=O)cc3)nc12]

Compound 22 is made in an analogous manner to Compound 19, instead using the R-enantiomer of the propargyl amine reagent in step 3.

Scheme 11 Synthesis of 4-((6'-amino-8'H-spiro[cyclohexane-1,9'-pyrazino[1',2':1,5]pyrrolo[2,3-d]pyrimidin]-2'-yl)amino)benzenesulfonamide Compound 40

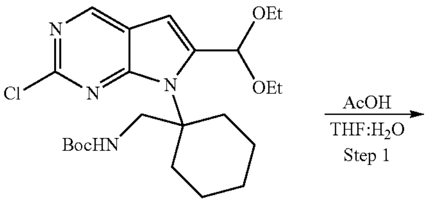

1

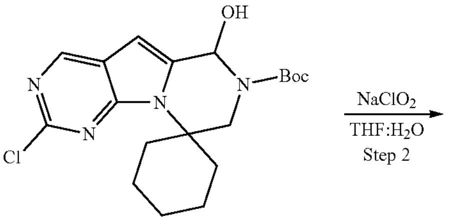

2

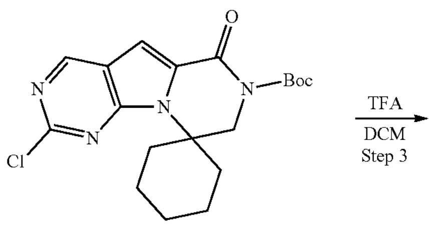

3

-continued

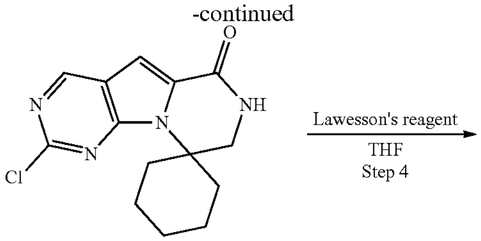

4

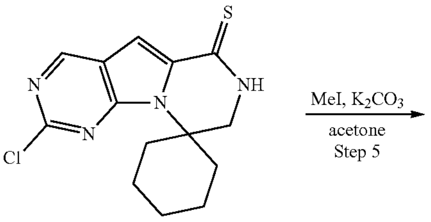

5

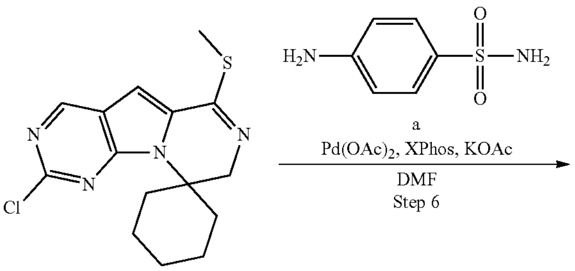

6

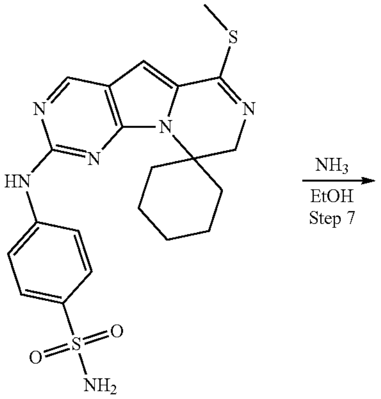

7

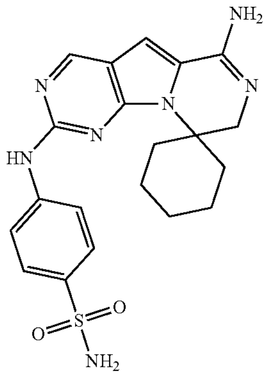

Step 1: 2.6 g of 1 was converted to 2 using HOAc/THF/$H_2O$/60° C./overnight. After purification, 2 g of 2 was obtained.

Step 2: 2 g of 2 was converted to 3 using $NaCl_2O$/THF/$H_2O$/RT/overnight. Some of the starting material remained. After purification, 1.5 g of 3 was obtained.

Step 3: 1.5 g of 3 was converted to 4 using TFA/DCM/RT/0.5 h. After purification, 1.0 g of 4 was obtained.

Step 4: 500 mg of 4 was converted to 5 using Lawesson reagent/THF/reflux/2 h. The starting material was consumed. After purification, 200 mg of 5 was obtained.

Step 5: 240 mg of 5 was converted to 6 using MeI/$K_2CO_3$/acetone/RT/overnight. After purification, 100 mg of 6 was obtained.

Step 6: 90 mg of 6 was converted to 7 using a/Pd$(OAc)_2$/X-Phos/AcOK/DMF/90° C./3 h. After purification, 60 mg of 7 was obtained.

Step 7: 40 mg of 7 was converted to Compound 40 using $NH_3$/EtOH/70° C./8 h. After purification, 13.5 mg of Compound 40 was obtained.

Scheme 12 Synthesis of 4-((8'-amino-6'H-spiro[cyclohexane-1,9'-pyrazino[1',2':1,5]pyrrolo[2,3-d]pyrimidin]-2'-yl)amino)benzenesulfonamide Compound 41

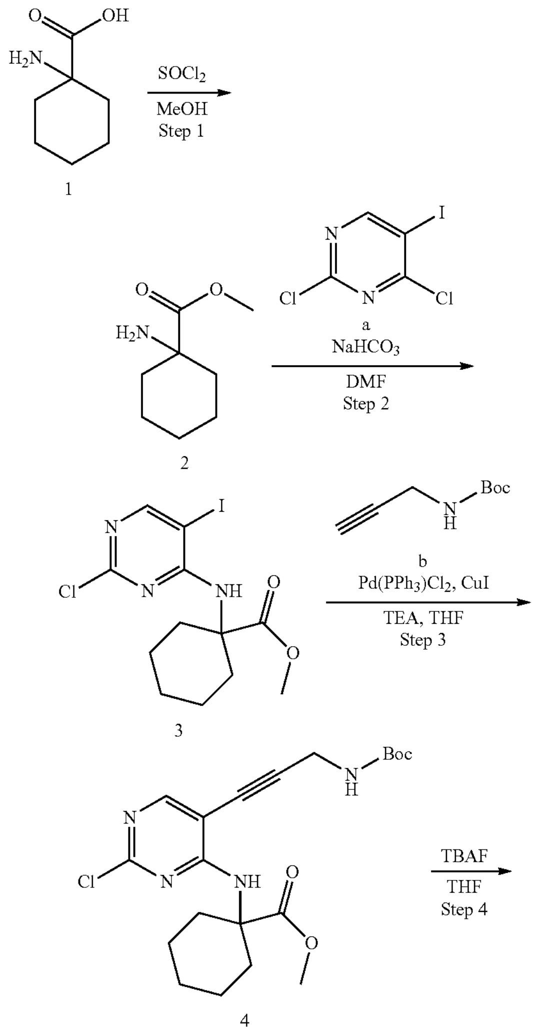

-continued

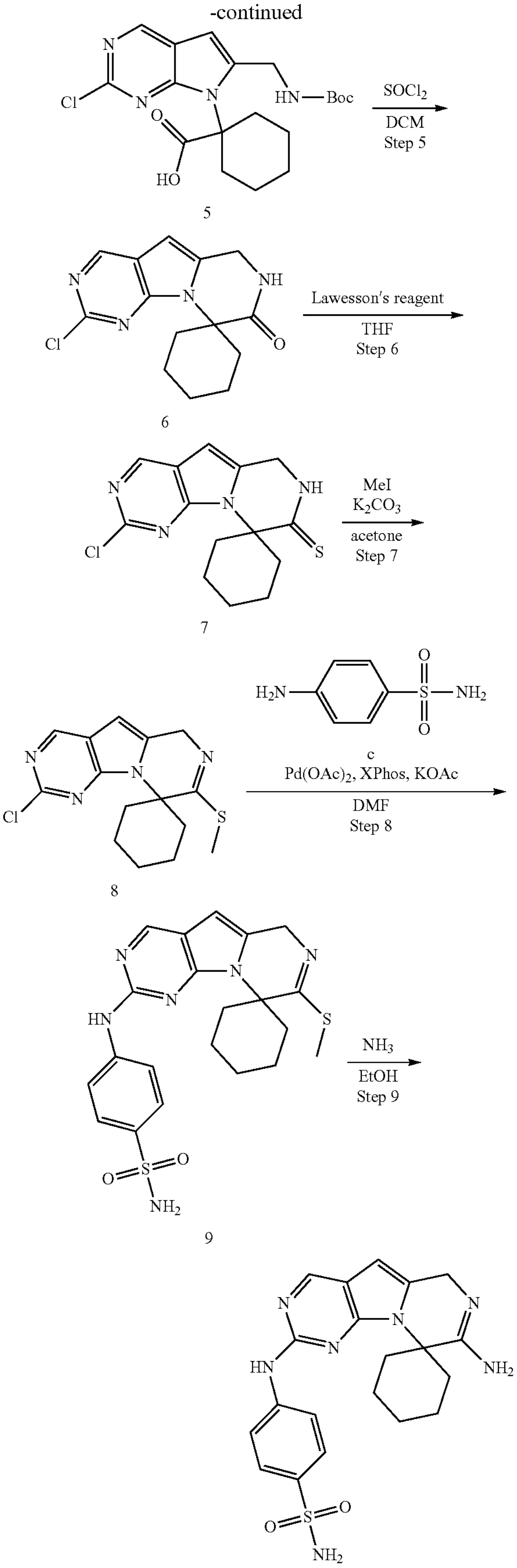

Step 1: 50 g of impure 1 was converted to 2 using $SOCl_2$/MeOH/RT/overnight. After purification, 45 g of 2 was obtained.

Step 2: 15 g of 2 was converted to 3 using a/DMF/$NaHCO_3$/60° C./overnight. After purification, 13 g of 3 was obtained.

Step 3: 13 g of 3 was converted to 4 using b/CuI/Pd$(PPh_3)_2Cl_2$/TEA/TIF/RT/3 h. After purification, 12 g of 4 was obtained.

Step 4: 6 g of 4 was converted to 5 using TBAF/THF/60° C./3 h. After purification, 3 g of 5 was obtained.

Step 5: 3 g of 5 was converted to 6 using $SOCl_2$/DCM/RT/3 h. After purification, 1 g of 6 was obtained.

Step 6: 950 mg of 6 was converted to 7 using Lawesson's reagent/toluene/reflux/4 h. After purification, 250 mg of 7 was obtained.

Step 7: 250 mg of 7 was converted to 8 using MeI/$K_2CO_3$/acetone/rt/overnight. After purification, 200 mg of 8 was obtained.

Step 8: 100 mg of 8 was converted to 9 using a/Pd$(OAc)_2$/Xphos/KOAc/DMF/90° C./4 h. After purification 60 mg of 9 was obtained.

Step 9: 30 mg of 9 was converted to Compound 41 using $NH_3$/EtOH/80° C./overnight. After purification, 5.2 mg of Compound 41 was obtained.

Scheme 13 Synthesis of 4-((6',8'-dimethyl-7',8'-dihydro-6'H-spiro[cyclohexane-1,9'-pyrazino[1',2':1,5]pyrrolo[2,3-d]pyrimidin]-2'-yl)amino)benzenesulfonamide Compound 85

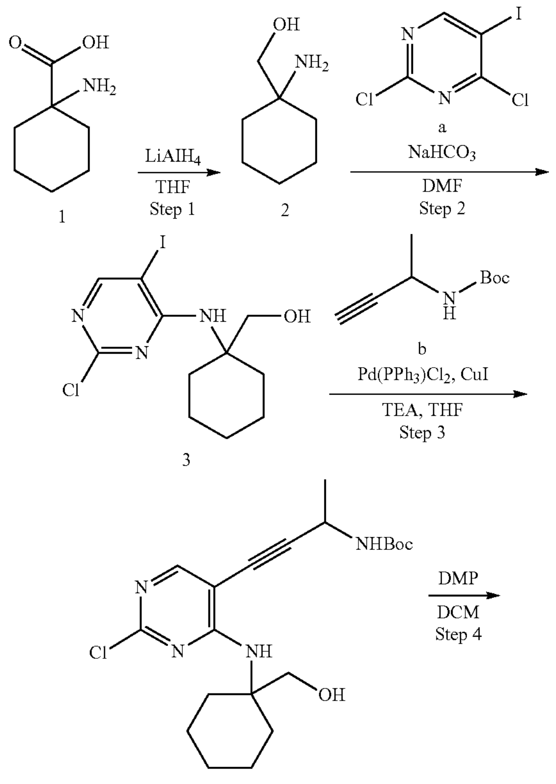

1 2 3 4

-continued

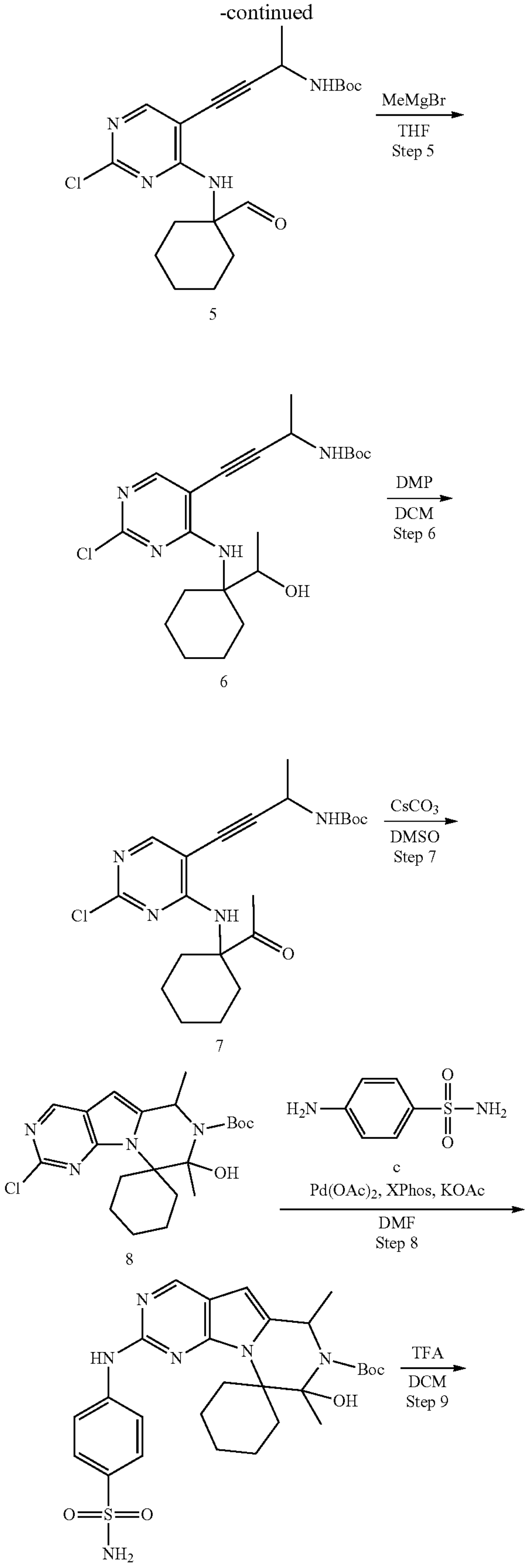

5 6 7 8 9

-continued

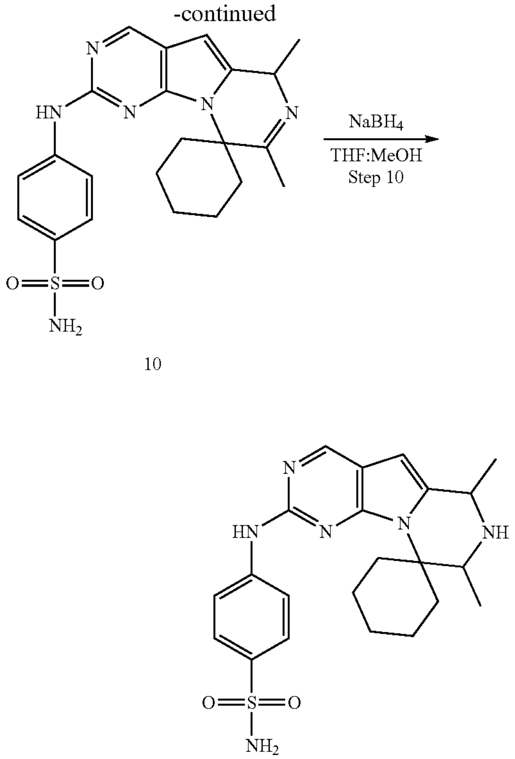

10

Step 1: 50 g of 1 was converted to 2 using $LiAlH_4$/THF/RT/overnight. After purification, 42.7 g of 2 was obtained.

Step 2: 42.7 g of 2 was converted to 3 using a/$NaHCO_3$/DMAC/60° C./overnight. Purification, 76.5 g of 3 was obtained.

Step 3: 14.4 g of 3 was converted to 4 using b/CuI/$PdCl_2(PPh_3)_2$/$Et_3N$/THF/rt/overnight. After purification, 16.3 g of 4 was obtained.

Step 4: 5 g of 4 was converted to 5 using Dess-Martin reagent/DCM/0° C.-RT/2 h. After purification, 3.6 g of 5 was obtained.

Step 5: 3.8 g of 5 was converted to 6 using $CH_3MgBr$/THF/−78° C.-RT/2 h. After purification, 3.86 g of 6 was obtained.

Step 6: 400 mg of 6 was converted to 7 using Dess-martin reagent/DCM/0° C.-RT/2 h. After purification, 310 mg of 7 was obtained.

Step 7: 310 mg of 7 was converted to 8 using $Cs_2CO_3$/DMSO/RT/40° C./4 h. After purification, 180 mg of 8 was obtained.

Step 8: 180 mg of 8 was converted to 9 using a (1.2 eq)/AcOK (3 eq)/$Pd(OAc)_2$ (0.1 eq)/X-phos (0.4 eq)/DMF/85° C./3.5 h. After purification, 290 mg of 9 was obtained.

Step 9: 290 mg of 9 was converted to 10 using TFA/DCM/RT/2 h. After purification, 100 mg of was obtained.

Step 10: 80 mg of 10 was converted to Compound 85 using $NaBH_4$/THF/MeOH/RT/0.5 h. After purification, 19.3 mg of Compound 85 was obtained.

Scheme 14 Synthesis of 4-((8'-methyl-7'-oxo-7',8'-dihydro-6'H-spiro[cyclohexane-1,9'-pyrrolo[1,5-a:2,3-d']dipyrimidin]-2'-yl)amino)benzenesulfonamide Compound 42

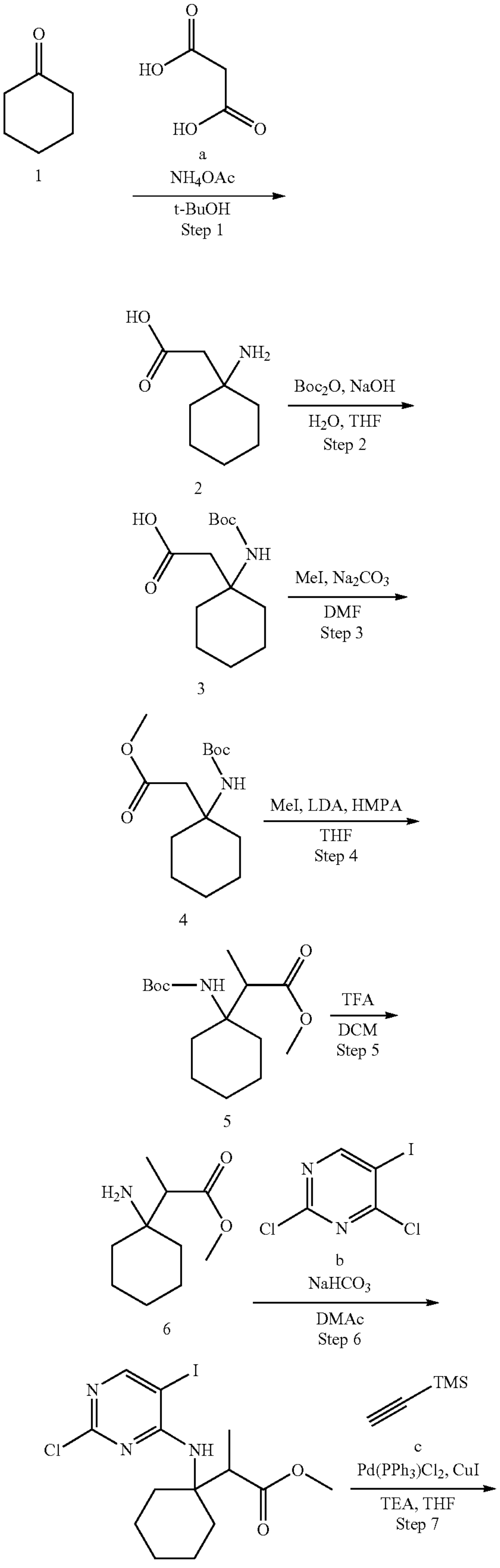

-continued

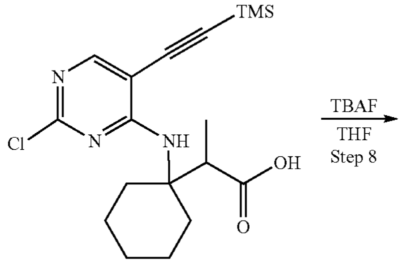

8

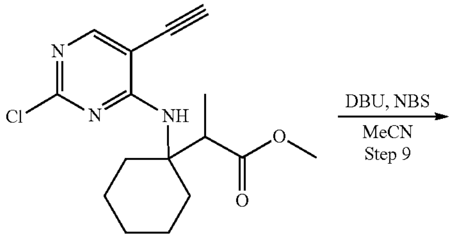

9

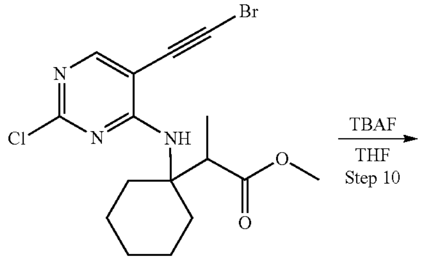

10

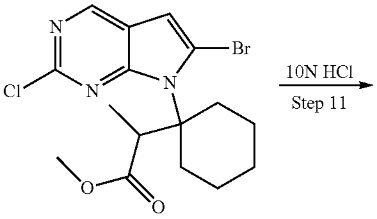

11

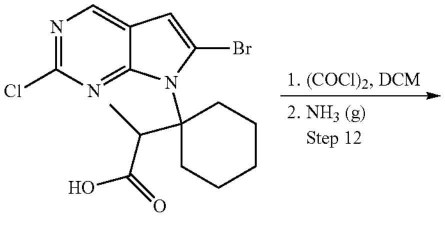

12

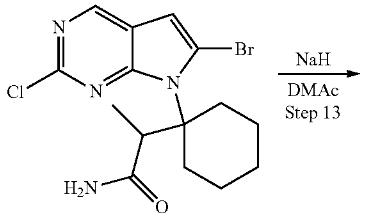

13

-continued

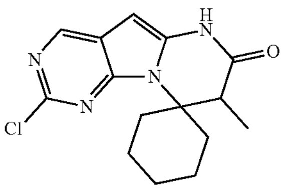

14

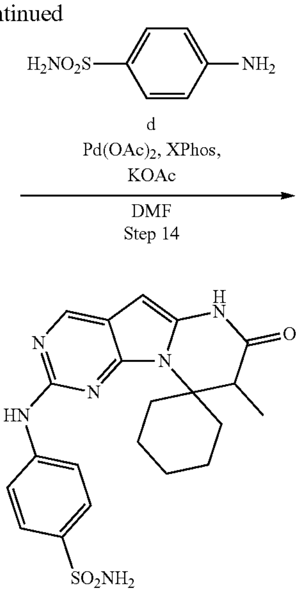

Step 1: 20 g of 1 was converted to 2 using a/$NH_4OAc$/t-BuOH/135° C./3.5 h. After purification, 19.7 g of 2 was obtained.

Step 2: 20 g of 2 was converted to 3 using $Boc_2O$/NaOH/$H_2O$/THF/RT/4 h. After purification, 21 g of 3 was obtained.

Step 3: 21 g of 3 was converted to 4 using $Na_2CO_3$/MeI/DMF/RT/2 h. After purification, 19 g of 4 was obtained.

Step 4: 14 g of 4 was converted to 5 using MeI/LDA/HMPA/THF/−78° C.-RT/3 h. After purification, 14 g of impure 5 was obtained (mixed with some of the starting material 4 and dimethyl byproduct).

Step 5: 14 g of impure 5 was converted to 6 using TFA/DCM/RT/3 h. After simple workup, 7.1 g of crude 6 was obtained.

Step 6: 7.1 g of 6 was converted to 7 using b/$NaHCO_3$/DMAc/60° C./overnight. After purification, 3.0 g of 7 was obtained.

Step 7: 2.87 g of 7 was converted to 8 using c/$Pd(PPh_3)_2Cl_2$/CuI/DIEA/THF/RT/2 h. After purification, 1.78 g of 8 was obtained.

Step 8: 1.7 g of 8 was converted to 9 using TBAF/THF/0° C./5 min. After purification, 1.4 g of 9 was obtained.

Step 9: 1.15 g of 9 was converted to 10 using DBU/NBS/acetonitrile/0° C./10 min. After workup, 1.5 g of crude 10 was obtained.

Step 10: 1.5 g of crude 10 was converted to 11 using TBAF/THF/10° C./1 h. After purification, 430 mg of pure 11 and 350 mg of impure 11 were obtained.

Step 11: 400 mg of 11 was converted to 12 using HCl (10 N)/70° C./6 h. After purification, 150 mg of 12 was obtained.

Step 12: 150 mg of 12 was converted to 13 using oxalyl chloride/DCM/RT/1 h. Then the reaction was concentrated and treated with $NH_3$ (g). After purification, 155 mg of 13 was obtained.

Step 13: 155 mg of 13 was converted to 14 using NaH/DMAc/0° C.-RT/30 min. After purification, 85 mg of 14 was obtained.

Step 14: 10 mg of 14 was converted to Compound 42 using d/$Pd(OAc)_2$/X-phos/KOAc/DMF/60° C./4 h. After purification, 3.2 mg of Compound 42 was obtained.

Scheme 15 Synthesis of 4-((6',8'-dimethyl-7'-oxo-7',8'-dihydro-6'H-spiro[cyclohexane-1,9'-pyrrolo[1,5-a:2,3-d']dipyrimidin]-2'-yl)amino)benzenesulfonamide Compound 42
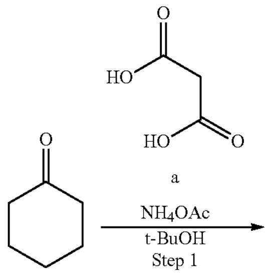
1
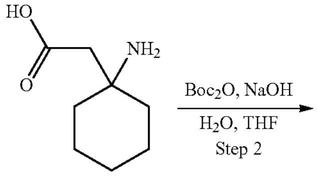
2
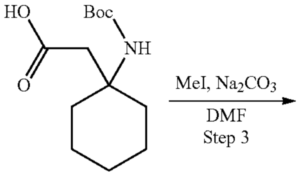
3
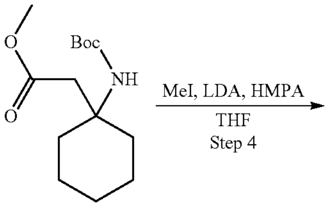
4
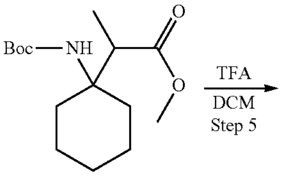
5
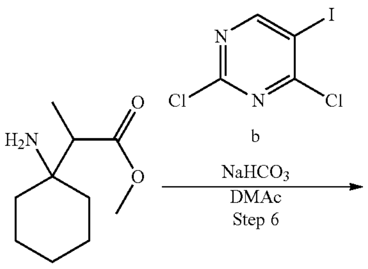
6
-continued
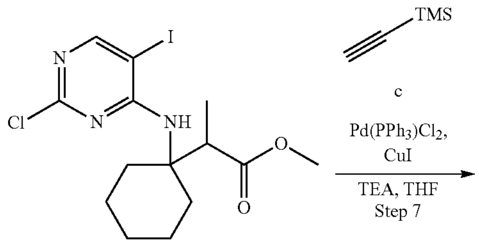
7
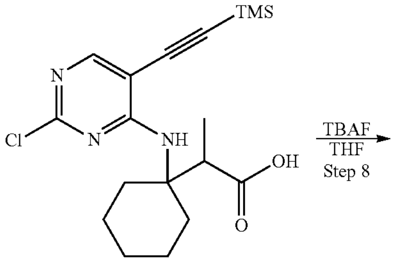
8
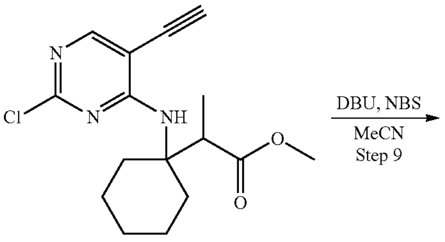
9
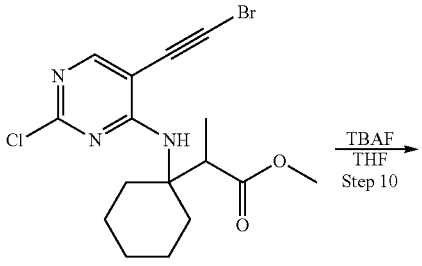
10
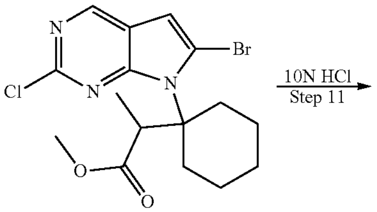
11
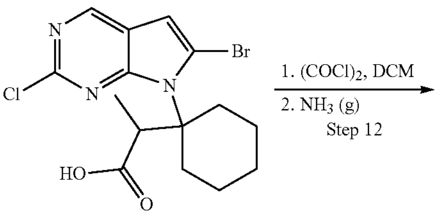
12

-continued

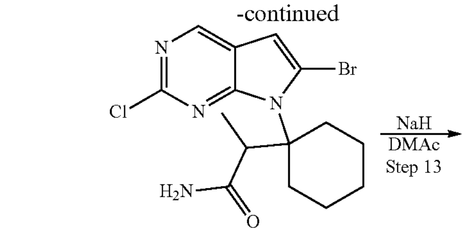

13

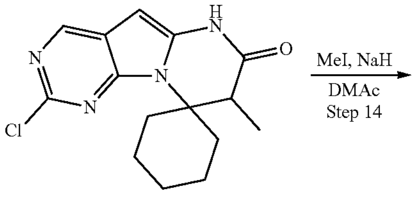

14

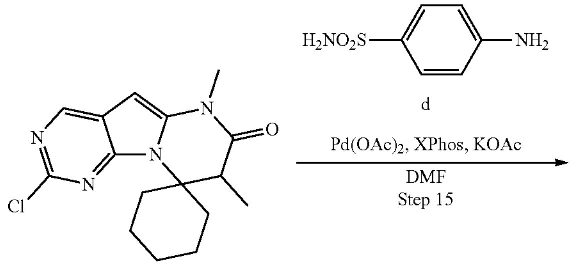

15

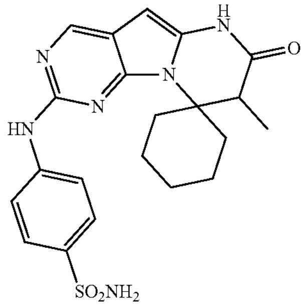

Step 1: 20 g of 1 was converted to 2 using a/$NH_4OAc$/t-BuOH/135° C./3.5 h. After purification, 19.7 g of 2 was obtained.

Step 2: 20 g of 2 was converted to 3 using $Boc_2O$/NaOH/$H_2O$/THF/RT/4 h. After purification, 21 g of 3 was obtained.

Step 3: 21 g of 3 was converted to 4 using $Na_2CO_3$/MeI/DMF/RT/2 h. After purification, 19 g of 4 was obtained.

Step 4: 14 g of 4 was converted to 5 using MeI/LDA/HMIPA/THF/−78° C.-RT/3 h. After purification, 14 g of impure 5 was obtained (mixed with some of the starting material 4 and dimethyl byproduct).

Step 5: 14 g of impure 5 was converted to 6 using TFA/DCM/RT/3 h. After simple workup, 7.1 g of crude 6 was obtained.

Step 6: 7.1 g of 6 was converted to 7 using b/$NaHCO_3$/DMAc/60° C./overnight. After purification, 3.0 g of 7 was obtained.

Step 7: 2.87 g of 7 was converted to 8 using c/Pd($PPh_3$)$_2Cl_2$/CuI/DIEA/THF/RT/2 h. After purification, 1.78 g of 8 was obtained.

Step 8: 1.7 g of 8 was converted to 9 using TBAF/THF/0° C./5 min. After purification, 1.4 g of 9 was obtained.

Step 9: 1.15 g of 9 was converted to 10 using DBU/NBS/acetonitrile/0° C./10 min. After workup, 1.5 g of crude 10 was obtained.

Step 10: 1.5 g of crude 10 was converted to 11 using TBAF/THF/10° C./1 h. After purification, 430 mg of pure 11 and 350 mg of impure 11 were obtained.

Step 11: 400 mg of 11 was converted to 12 using HCl (10 N)/70° C./6 h. After purification, 150 mg of 12 was obtained.

Step 12: 150 mg of 12 was converted to 13 using oxalyl chloride/DCM/RT/1 h. Then the reaction was concentrated and treated with $NH_3$ (g). After purification, 155 mg of 13 was obtained.

Step 13: 155 mg of 13 was converted to 14 using NaH/DMAc/0° C.-RT/30 min. After purification, 85 mg of 14 was obtained.

Step 14: 40 mg of 14 was converted to 15 using CH3I/NaH/DMAc/0° C.-RT/30 min. After purification, 30 mg of 15 was obtained.

Step 15: 30 mg of 15 was converted to Compound 42 using d/Pd$(OAc)_2$/X-phos/KOAc/DMF/60° C./4 h. After purification, 5 mg of Compound 42 was obtained.

Scheme 16 Synthesis of 4-((1',3'-dimethyl-1'H-spiro[cyclohexane-1,4'-pyrimido[5',4':4,5]pyrrolo[2,1-c][1,2,4]triazin]-7'-yl)amino)benzenesulfonamide Compound 46

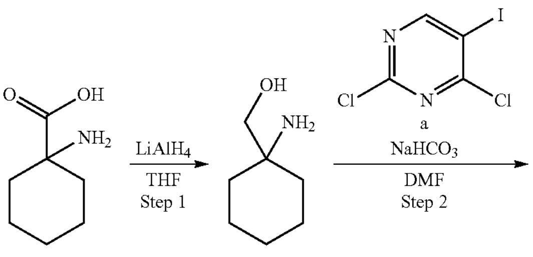

1

2

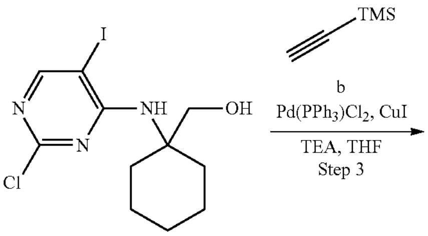

3

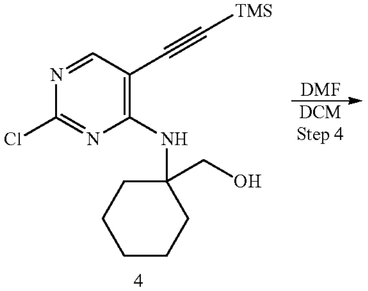

4

-continued

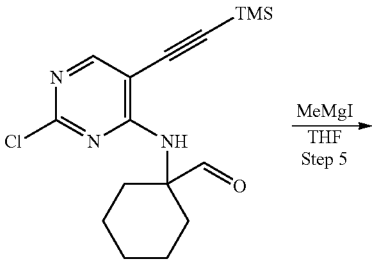

5

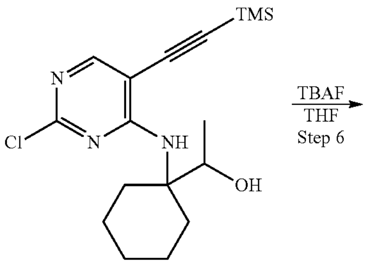

6

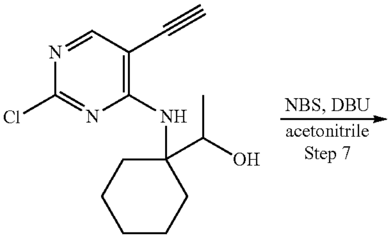

7

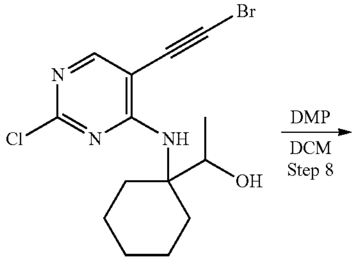

8

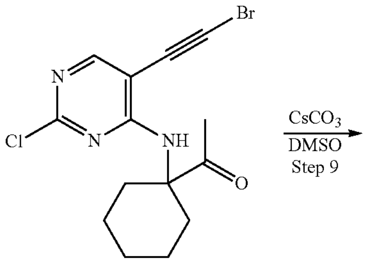

9

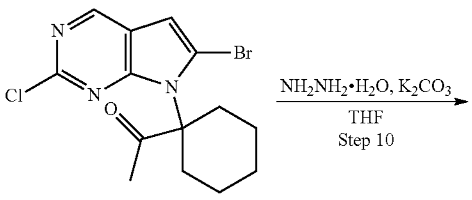

10

-continued

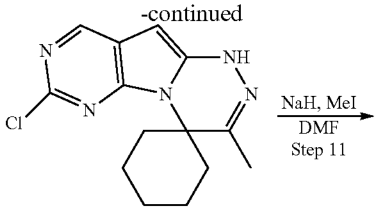

11

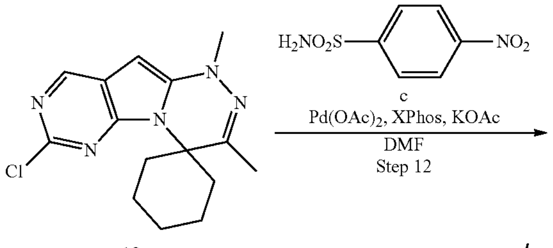

12

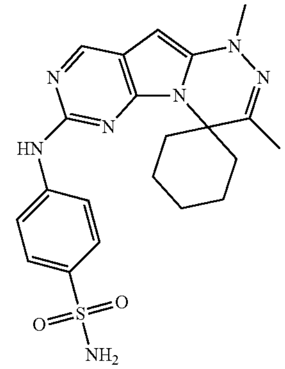 [SMILES: CC1=NN(C)c2cc3cnc(Nc4ccc(S(N)(=O)=O)cc4)nc3n2C12CCCCC2]

Step 1: 100.0 g of 1 was converted to 2 using $LiAlH_4$/THF/40° C.-rt/overnight. After workup, 89 g of 2 was obtained.

Step 2: 42.7 g of 2 was converted to 3 using a/$NaHCO_3$/DMAC/60° C./overnight. Purification, 76.5 g of 3 was obtained.

Step 3: 20 g of 3 was converted to 4 using b/TEA/$PdCl_2(PPh_3)_2$/CuI/THF/r.t/3 h. After purification, 13 g of 4 was obtained.

Step 4: 14.39 g of 4 was converted to 5 using Dess-Martin reagent/DCM/RT/1 h. After purification, 11 g of 5 was obtained.

Step 5: 11.0 g of 5 was converted to 6 using $CH_3MgI$/THF/−75° C.-RT/2 h. After purification, 9.0 g of 6 was obtained.

Step 6: 9.0 g of 6 was converted to 7 using TBAF/THF/−20° C./20 min. After purification, 6.8 g of 7 was obtained.

Step 7: 6.8 g of 7 was converted to 8 using NBS/DBU/MeCN/RT/20 min. After purification, 8.7 g of 8 was obtained.

Step 8: 8.7 g of 8 was converted to 9 using Dess-Martin reagent/DCM/RT/1 h. After purification, 5.8 g of 9 was obtained.

Step 9: 4.2 g of 9 was converted to 10 using $Cs_2CO_3$/DMSO/RT/15 min. After purification, 1.4 g of 10 was obtained.

Step 10: 1.4 g of 10 was converted to 11 using $NH_2NH_2 \cdot H_2O$/THF/$K_2CO_3$/RT/overnight. After purification, 700 mg of 11 was obtained.

Step 11: 100 mg of 11 was converted to 12 using CH3I/NaH/DMF/30° C./1 h. After purification, 107 mg of 12 was obtained.

Step 12: 40 mg of 12 was converted to Compound 46 using c/$Pd(OAc)_2$/X-Phos/KOAc/DMF/80° C./overnight. After purification, 24.7 mg of Compound 46 was obtained.

Scheme 17 Synthesis of N-((1r,4r)-4-(4-(cyclopropylmethyl)piperazin-1-yl)cyclohexyl)-7',8'-dihydro-6'H-spiro[cyclohexane-1,9'-pyrazino[1',2':1,5]pyrrolo[2,3-d]pyrimidin]-2'-amine Compound 47

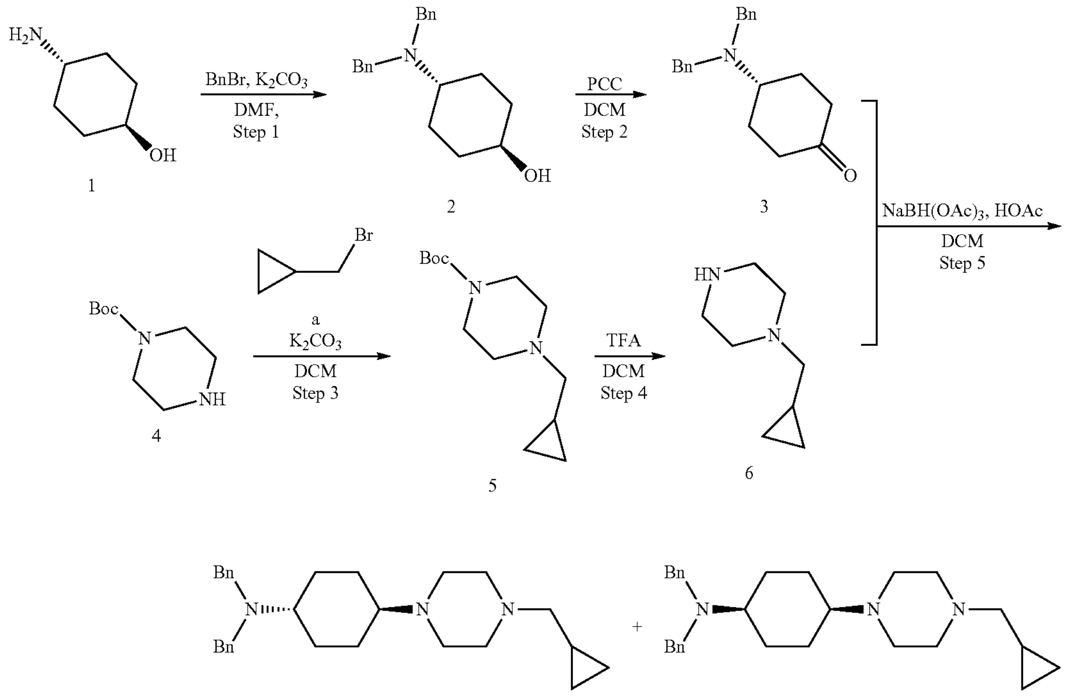

1 2 3 4 5 6 7 8

Step 1: 25.0 g of 1 was converted to 2 using $BnBr/K_2CO_3$/DMF/rt/overnight. After purification, 43 g of 2 was obtained.

Step 2: 42 g of 2 was converted to 3 using PCC/DCM/RT/overnight. After purification, 35.4 g of 3 was obtained.

Step 3: 25.0 g of 4 was converted to 5 using $a/K_2CO_3$/DCM/RT/overnight. After purification, 26.8 g of 5 was obtained.

Step 4: 26.8 g of 5 was converted to 6 using TFA/DCM/RT/2.5 h. After purification, 12.0 g of 6 was obtained.

Step 5: 660 mg of 3 was converted to 7 using 6/NaBH$(OAc)_3$/HOAc/DCM/RT/overnight. After purification, 240 mg of 7 and 160 mg of impure 8 were obtained.

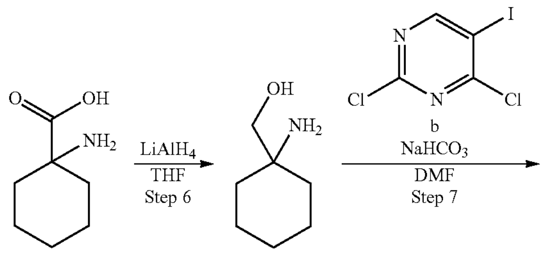

1' 2'

-continued

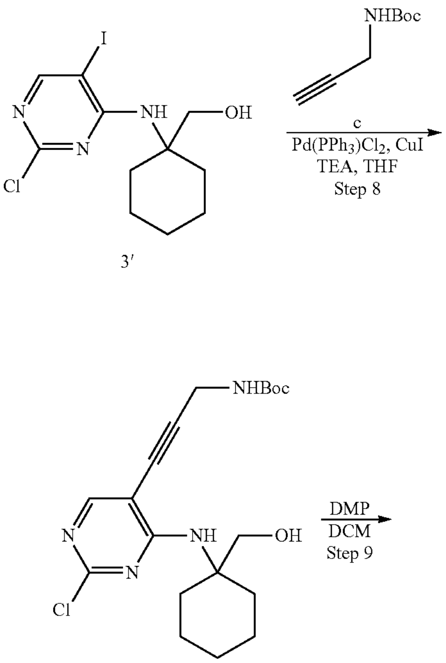

3' 4'

-continued

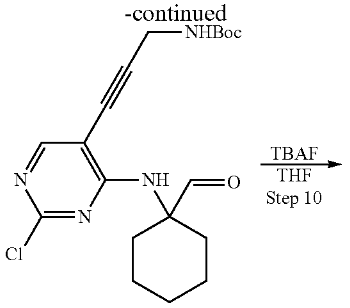

5'

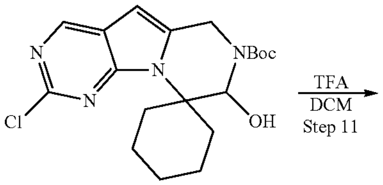

6'

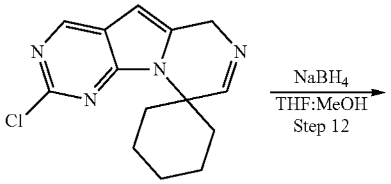

7'

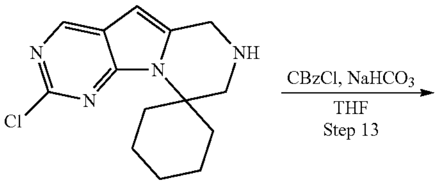

8'

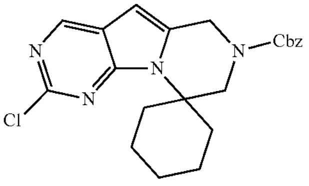

d

Step 6: 100.0 g of 1' was converted to 2' using $LiAlH_4$/THF/40° C.-rt/overnight. After workup, 89 g of 2' was obtained.

Step 7: 42.7 g of 2' was converted to 3' using b/$NaHCO_3$/DMAC/60° C./overnight. Purification, 76.5 g of 3' was obtained.

Step 8: 5.0 g of 3' was converted 4' using c/$PdCl_2(PPh_3)_2$/CuI/TEA/THF/RT/overnight. After purification, 4.8 g of 4' was obtained.

Step 9: 4.8 g of 4' was converted to 5' using Dess-Martin reagent/DCM/RT/overnight. After purification, 4.0 g of 5' was obtained.

Step 10: 3.5 g of 5' was converted to 6' using TBAF/THF/60° C./1.5 h. After purification, after purification, 600 mg of 6' was obtained.

Step 11: 600 mg of 6' was converted to 7' using TFA/DCM/RT/2 h. After purification, 200 mg of 7' was obtained.

Step 12: 1.3 g of 7' (TLC showed the purity became a little bit lower over a week) was converted to 8' using $NaBH_4$/MeOH/THF/r.t/3 h. After purification, 300 mg of 8' was obtained.

Step 13: 300 mg of 8' was converted to d using Cbz-Cl/$NaHCO_3$/THF/RT/30 min. After purification, 300 mg of d was obtained.

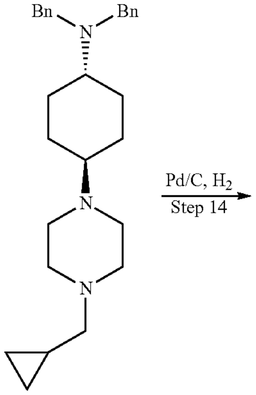

7

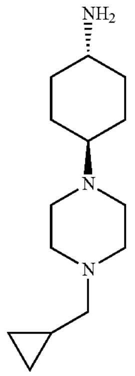

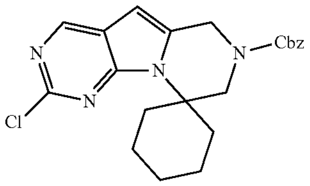

d

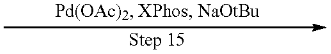

9

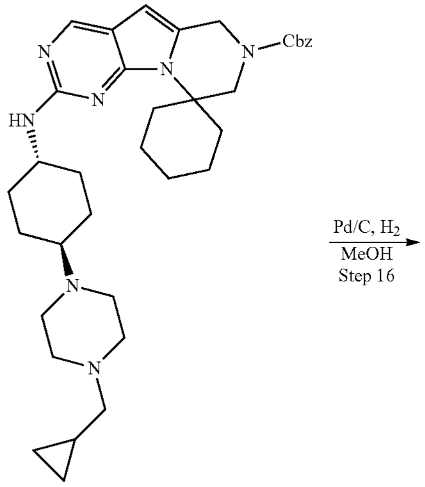

11

-continued

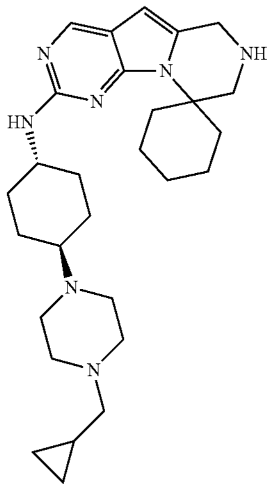 [SMILES: c1nc(N[C@H]2CC[C@H](N3CCN(CC4CC4)CC3)CC2)nc2c1cc1n2C2(CCCCC2)CNC1]

Step 14: 200 mg of 7 was converted to 9 using $H_2$/Pd/C/RT/overnight. After purification, 100 mg of 9 was obtained.

Step 15: 50 mg of 9 was converted to 11 using d/t-BuONa/X-phos/Pd(OAc)$_{2/60°}$ C./1 h. The MS peak of the desired product was detected by LC-MS. After purification, 14.7 mg of 11 was obtained.

Step 16: 14.7 mg of 11 was converted to Compound 47 using $H_2$/Pd/C/MeOH/RT/1 h. After purification, 2.7 mg of Compound 47 was obtained.

Scheme 18 Synthesis of N-((1s,4s)-4-(4-(cyclopropylmethyl)piperazin-1-yl)cyclohexyl)-7',8'-dihydro-6'H-spiro[cyclohexane-1,9'-pyrazino[1',2':1,5]pyrrolo[2,3-d]pyrimidin]-2'-amine Compound 48

Step 1: 25.0 g of 1 was converted to 2 using BnBr/$K_2CO_3$/DMF/rt/overnight. After purification, 43 g of 2 was obtained.

Step 2: 42 g of 2 was converted to 3 using PCC/DCM/RT/overnight. After purification, 35.4 g of 3 was obtained.

Step 3: 25.0 g of 4 was converted to 5 using a/$K_2CO_3$/DCM/RT/overnight. After purification, 26.8 g of 5 was obtained.

Step 4: 26.8 g of 5 was converted to 6 using TFA/DCM/RT/2.5 h. After purification, 12.0 g of 6 was obtained.

Step 5: 660 mg of 3 was converted to 7 using 6/NaBH(OAc)$_3$/HOAc/DCM/RT/overnight. After purification, 240 mg of 7 and 160 mg of impure 8 were obtained.

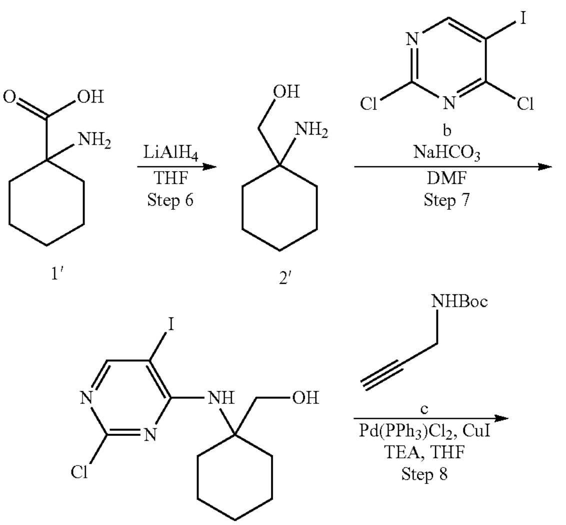

1'

2'

3'

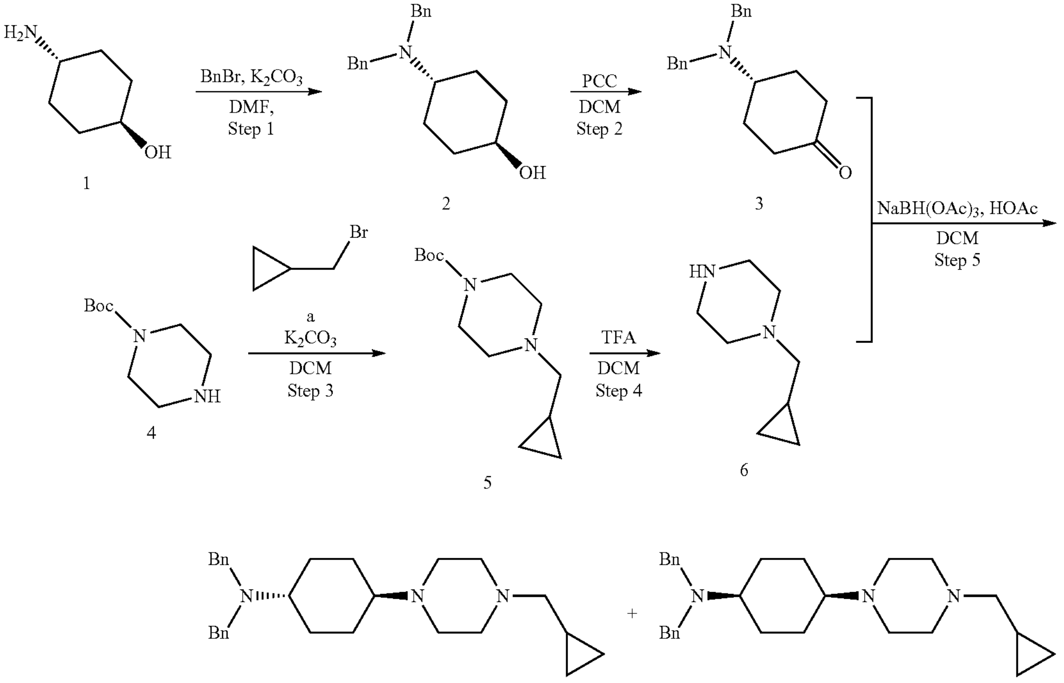

1

2

3

4

5

6

7

8

-continued

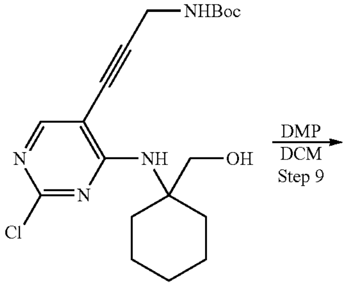

4'

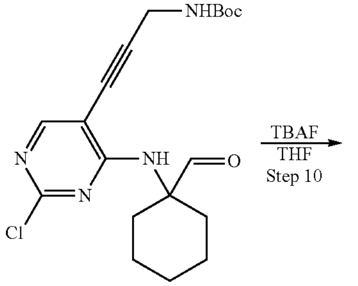

5'

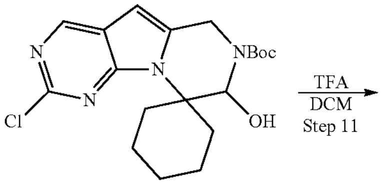

6'

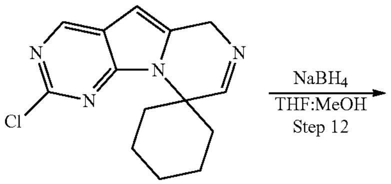

7'

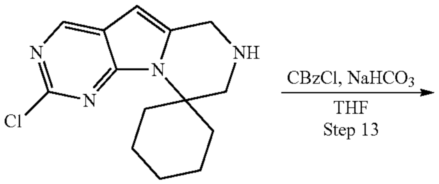

8'

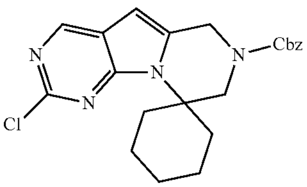

d

Step 6: 100.0 g of 1' was converted to 2' using $LiAlH_4$/THF/40° C.-rt/overnight. After workup, 89 g of 2' was obtained.

Step 7: 42.7 g of 2' was converted to 3' using b/$NaHCO_3$/DMAC/60° C./overnight. Purification, 76.5 g of 3' was obtained.

Step 8: 5.0 g of 3' was converted 4' using c/$PdCl_2(PPh_3)_2$/CuI/TEA/THF/RT/overnight. After purification, 4.8 g of 4' was obtained.

Step 9: 4.8 g of 4' was converted to 5' using Dess-Martin reagent/DCM/RT/overnight. After purification, 4.0 g of 5' was obtained.

Step 10: 3.5 g of 5' was converted to 6' using TBAF/THF/60° C./1.5 h. After purification, after purification, 600 mg of 6' was obtained.

Step 11: 600 mg of 6' was converted to 7' using TFA/DCM/RT/2 h. After purification, 200 mg of 7' was obtained.

Step 12: 1.3 g of 7' (TLC showed the purity became a little bit lower over a week) was converted to 8' using $NaBH_4$/MeOH/THF/r.t/3 h. After purification, 300 mg of 8' was obtained.

Step 13: 300 mg of 8' was converted to d using Cbz-Cl/$NaHCO_3$/THF/RT/30 min. After purification, 300 mg of d was obtained.

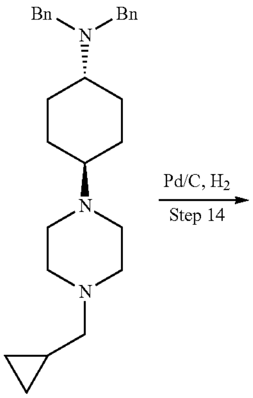

8

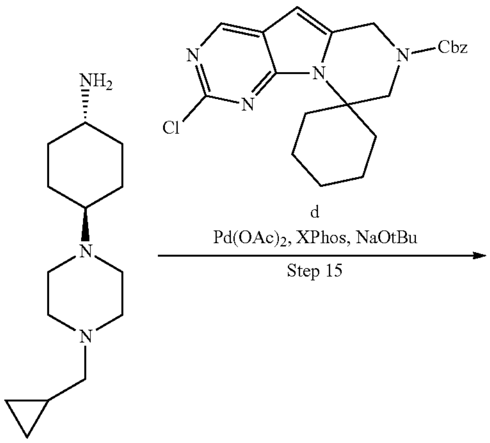

d

10

-continued

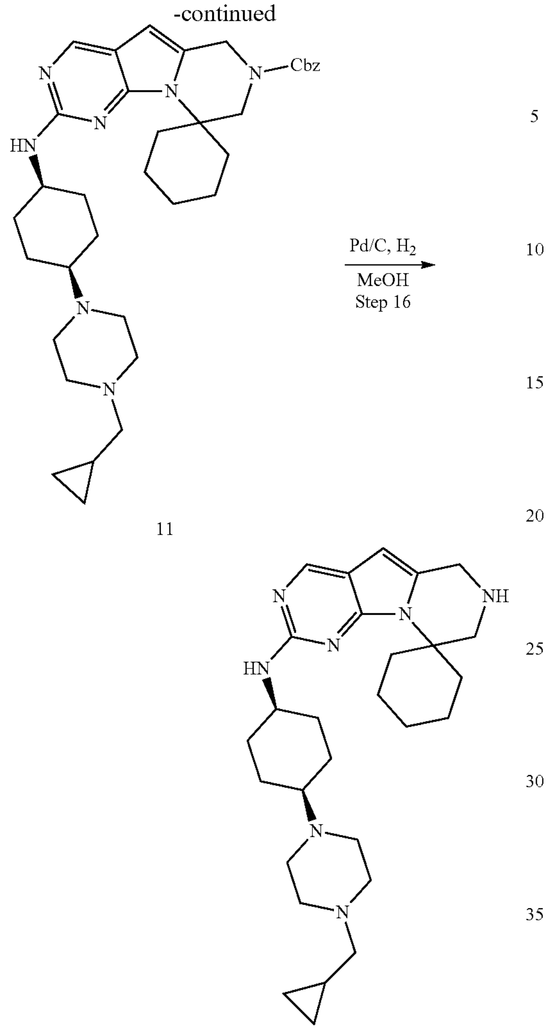

11

Step 14: 170 mg of 8 was converted to 10 using $H_2$/Pd/C/RT/overnight. After purification, 95 mg of 10 was obtained.

Step 15: 63 mg of 10 was converted to 11 using d/t-BuONa/X-phos/$Pd(OAc)_{2/60}$° C./1 h. The MS peak of the desired product was detected by LC-MS. After purification, 10 mg of 11 was obtained.

Step 16: 10 mg of 12 was converted to Compound 48 using $H_2$/Pd/C/MeOH/rt/1 h. The starting material was consumed. After purification, 2.0 mg of Compound 48 was obtained.

Scheme 19 Synthesis of 6'-hydroxy-2'-((4-((4-methylpiperazin-1-yl)sulfonyl)phenyl)amino)-6',7'-dihydro-8'H-spiro[cyclohexane-1,9'-pyrazino[1',2':1,5]pyrrolo[2,3-d]pyrimidin]-8'-one Compound 50

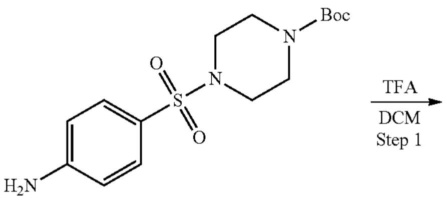

1

-continued

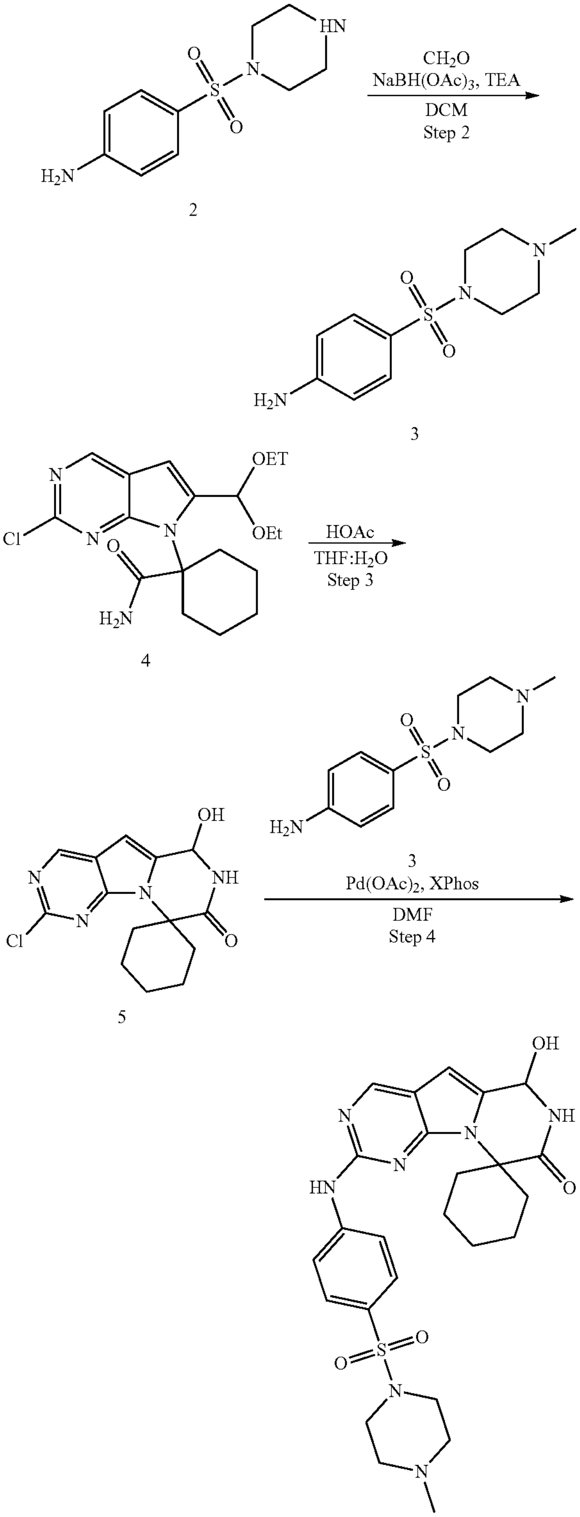

2

3

4

3

5

Step 1: 1.75 g of 1 was converted to 2 using TFA/DCM/RT/1 h. After purification, 1.14 g of 2 was obtained.

Step 2: 500 mg of 2 was converted to 3 using formaldehyde/$NaBH(OAc)_3$/TEA/DCM/RT/2 h. After purification, 520 mg of 3 was obtained.

Step 3: 2.0 g of 4 was converted to 5 using HOAc/THF/$H_2O$/50° C./3 h. After purification, 1.1 g of was obtained.

Step 4: 50 mg of 5 was converted to Compound 50 using 3/Pd(OAc)$_2$/X-phos/DMF/85° C./2 h. After purification, 6.1 mg of Compound 50 was obtained.

Scheme 20 Synthesis of 7'-((4-(4-methylpiperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 52

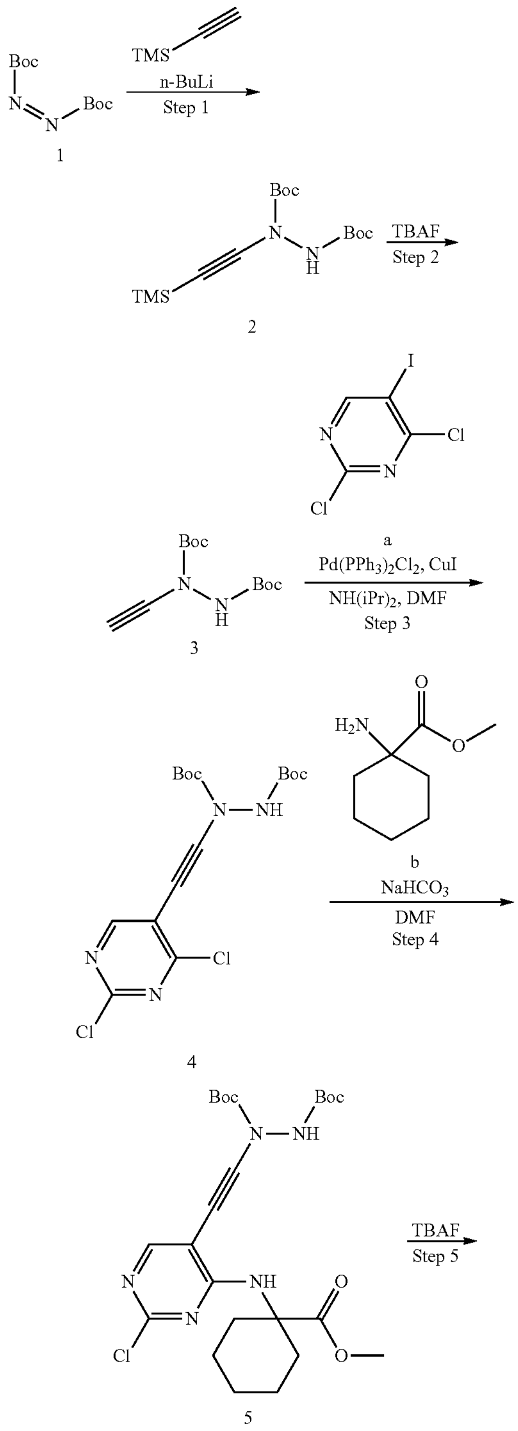

1, 2, 3, 4, 5

-continued

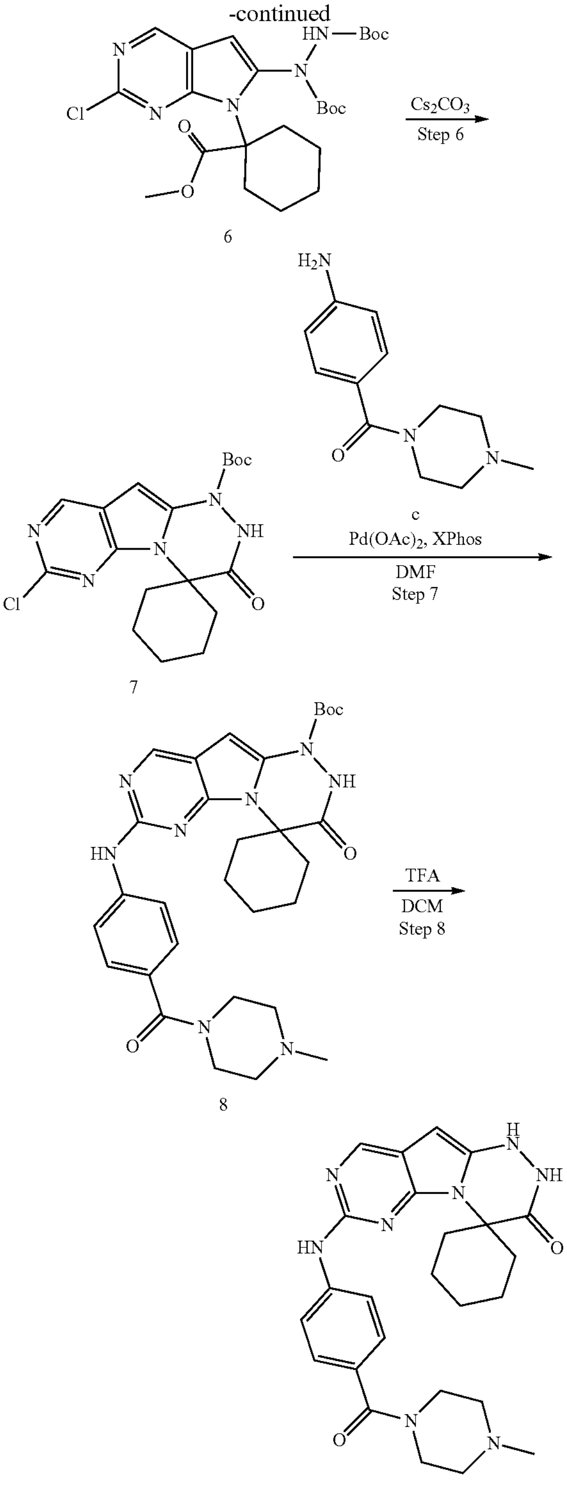

6, 7, 8

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 $[M+H]^+$.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 $[M+H]^+$.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 [M+H]+.

Step 7: 50 mg of 7 was converted to 8 using c/Pd(OAc) $_2$/X-phos/DMF/90° C./3 h. After purification, 30 mg of 8 was obtained.

Step 8: 30 mg of 8 was converted to Compound 52 using TFA/DCM/RT/2 h. The starting material was consumed. After purification, 5.6 mg of Compound 52 was obtained.

Scheme 21 Synthesis of 6'-hydroxy-2'-((4-(4-methylpiperazine-1-carbonyl)phenyl)amino)-6',7'-dihydro-8'H-spiro[cyclohexane-1,9'-pyrazino[1',2':1,5]pyrrolo[2,3-d]pyrimidin]-8'-one Compound 53

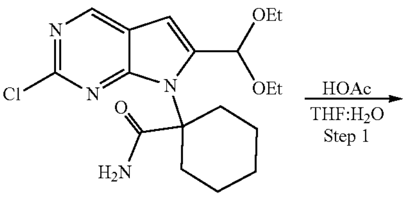

1

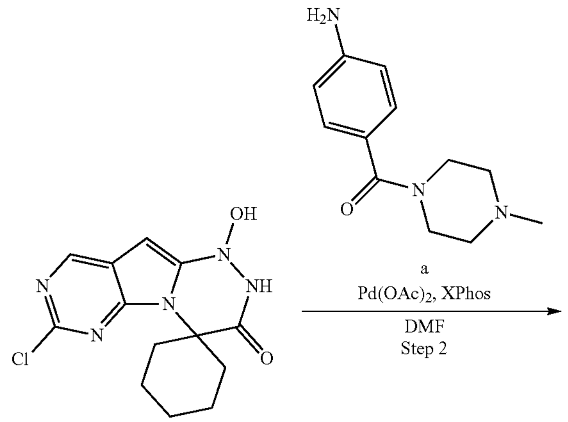

2

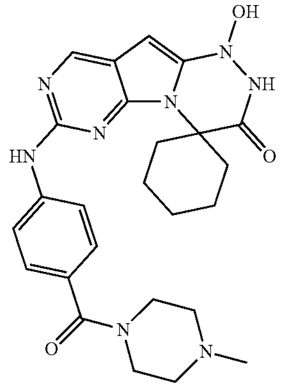

Step 1: 2.0 g of 1 was converted to 2 using HOAc/THF/$H_2O$/50° C./3 h. After purification, 1.1 g of 2 was obtained.

Step 2: 50 mg of 2 was converted to Compound 53 using a/$Pd(OAc)_2$/X-phos/DMF/85° C./2 h. After purification, 2.2 mg of Compound 53 was obtained.

Scheme 22 Synthesis of 2'-((4-(piperazine-1-carbonyl)phenyl)amino)-7',8'-dihydro-6'H-spiro[cyclohexane-1,9'-pyrazino[1',2':1,5]pyrrolo[2,3-d]pyrimidin]-6'-one Compound 55

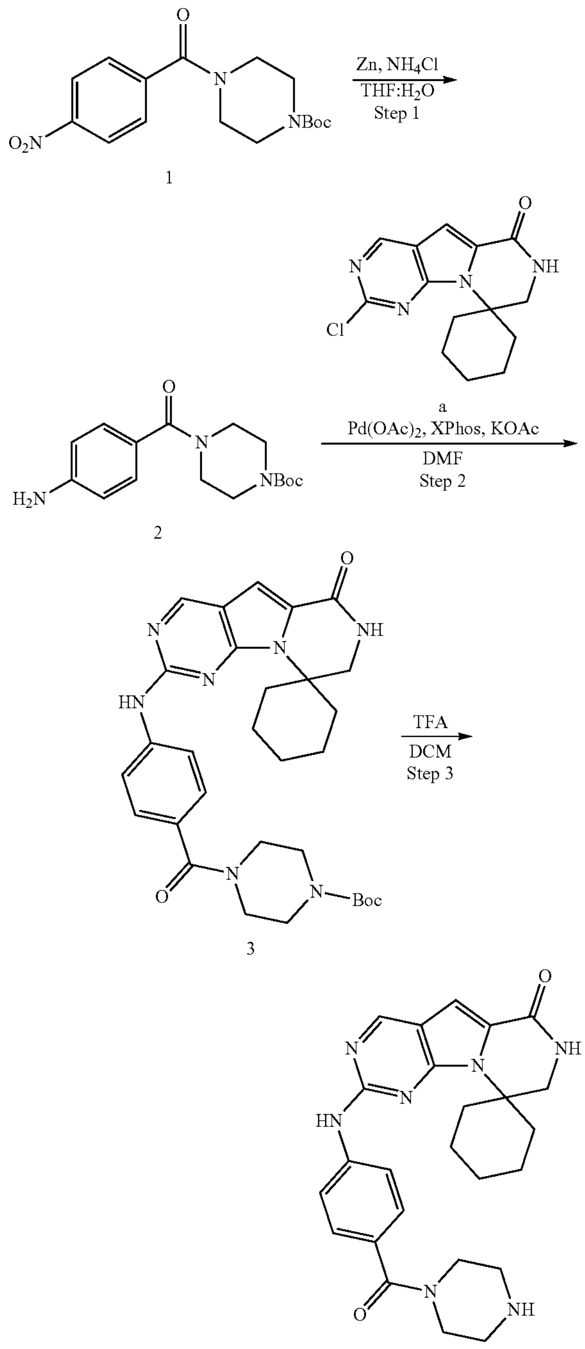

Step 1: 554 mg of 1 was converted to 2 using Zn/$NH_4Cl$/THF/$H_2O$/40° C./overnight. The starting material was consumed. After purification, 240 mg of 3 was obtained.

Step 2: 53 mg of 2 was converted to 3 using a/Pd(OAc)$_2$/X-phos/AcOK/DMF/80° C./3 h. A major new spot was observed by TLC. After purification, 40 mg of 3 was obtained.

Step 3: 15 mg of 3 was converted to Compound 55 using TFA/DCM/RT/1 h. A major new spot was observed by TLC. After purification, 10 mg of Compound 55 was obtained.

Scheme 23 Synthesis of 2'-((4-((4-methylpiperazin-1-yl)sulfonyl)phenyl)amino)-7',8'-dihydro-6'H-spiro[cyclohexane-1,9'-pyrazino[1',2':1,5]pyrrolo[2,3-d]pyrimidin]-6'-one Compound 56

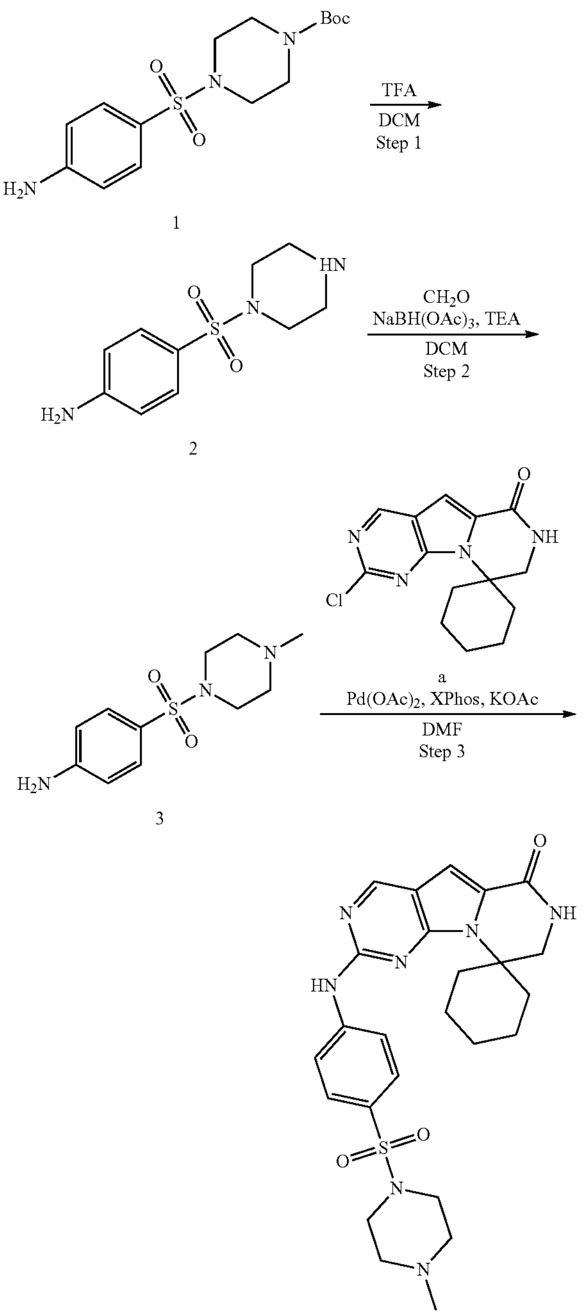

Step 1: 1.75 g of 1 was converted to 2 using TFA/DCM/RT/1 h. After purification, 1.14 g of 2 was obtained.

Step 2: 500 mg of 2 was converted to 3 using formaldehyde/$NaBH(OAc)_3$/TEA/DCM/RT/2 h. After purification, 520 mg of 3 was obtained.

Step 3: 50 mg of 3 was converted to Compound 56 using a/Pd(OAc)$_2$/X-Phos/AcOK/DMF/80° C./2 h. After purification, 3.2 mg of Compound 56 was obtained.

Scheme 24 Synthesis of 2'-((4-(piperazin-1-ylsulfonyl)phenyl)amino)-7',8'-dihydro-6'H-spiro[cyclohexane-1,9'-pyrazino[1',2':1,5]pyrrolo[2,3-d]pyrimidin]-6'-one Compound 57

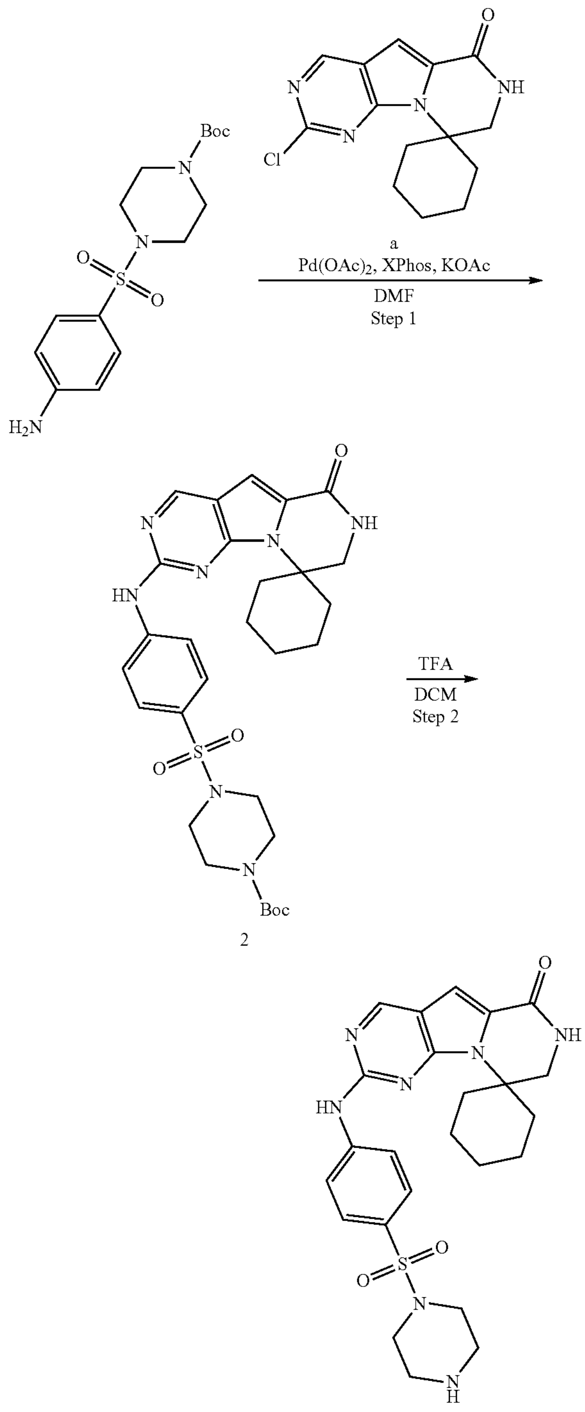

Step 1: 50 mg of 1 was converted to 2 using a/Pd(OAc)$_2$/X-phos/AcOK/DMF/80° C./3 h. A major new spot was observed by TLC. After purification, 60 mg of 2 was obtained.

Step 2: 40 mg of 2 was converted to Compound 57 using TFA/DCM/RT/2 h. After purification, 11.5 mg of Compound 57 was obtained.

Scheme 25 Synthesis of 2'-((4-(4-methylpiperazine-1-carbonyl)phenyl)amino)-7',8'-dihydro-6'H-spiro[cyclohexane-1,9'-pyrazino[1',2':1,5]pyrrolo[2,3-d]pyrimidin]-6'-one Compound 58

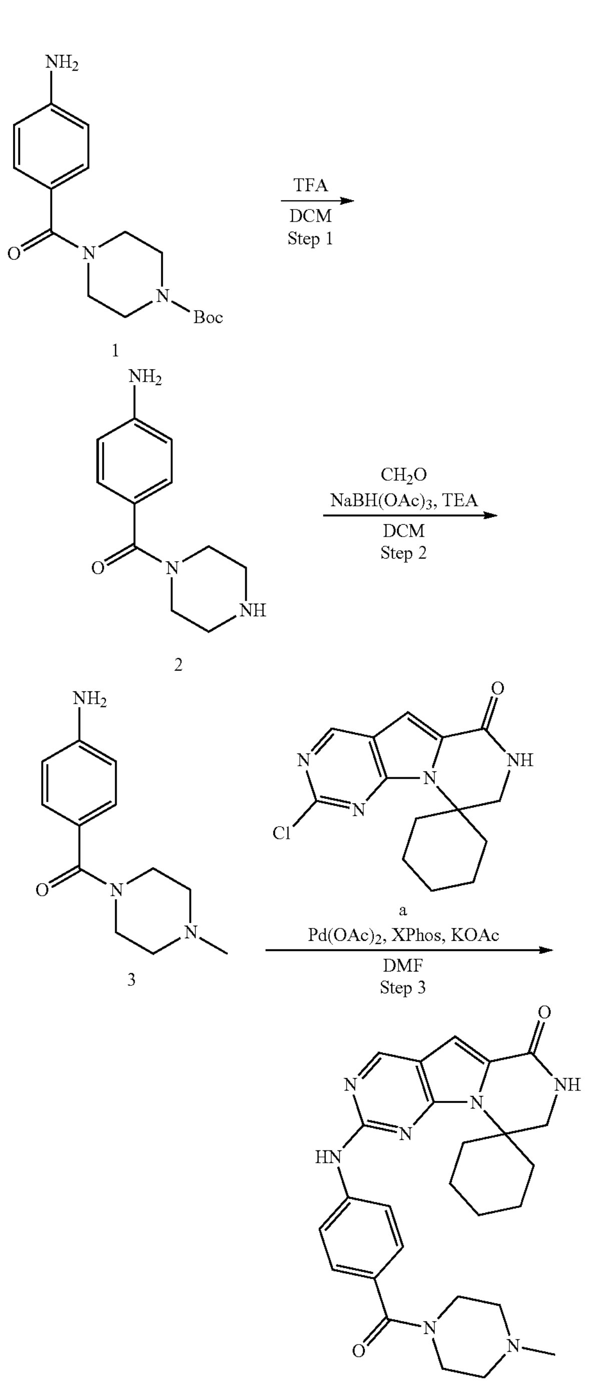

Step 1: 180 mg of 1 was converted to 2 using TFA/DCM/RT/2 h. After workup, 200 mg of crude 2 was obtained.

Step 2: 200 mg of crude 2 was converted to 3 using formaldehyde/TEA/NaBH(OAc)$_3$/DCM/RT/overnight. After purification, 100 mg of 3 was obtained.

Step 3: 50 mg of 3 was converted to Compound 58 using 3/Pd(OAc)$_2$/x-Phos/KOAc/DMF/80° C./4 h. After purification, 20 mg of Compound 58 was obtained.
Scheme 26 Synthesis of 3'-methyl-N-(4-((4-methylpiperazin-1-yl)sulfonyl)phenyl)-1'H-spiro[cyclohexane-1,4'-pyrimido[5',4':4,5]pyrrolo[2,1-c][1,2,4]triazin]-7'-amine Compound 60
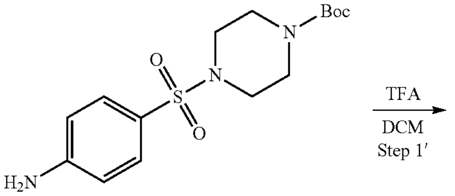
1'
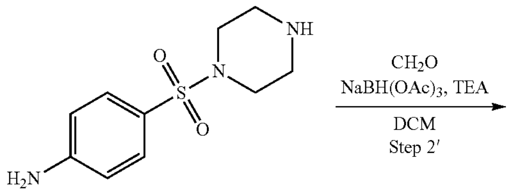
2'
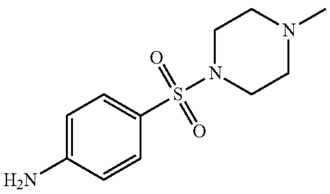
c
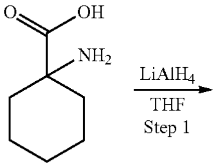
1
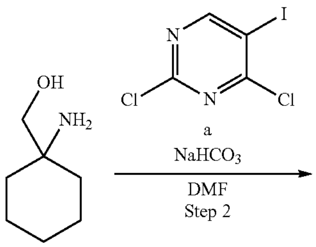
2
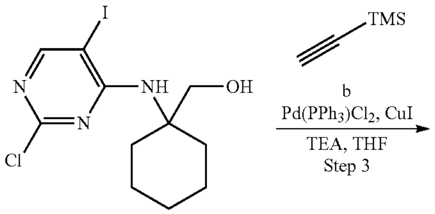
3
-continued
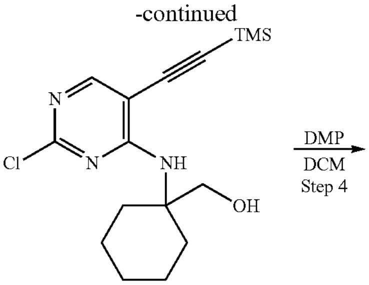
4
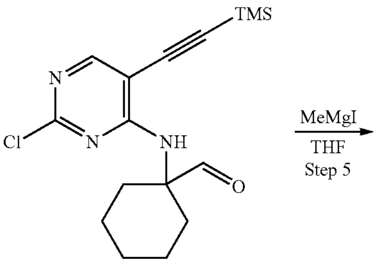
5
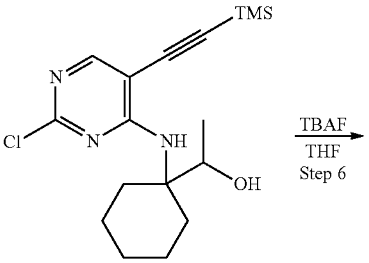
6
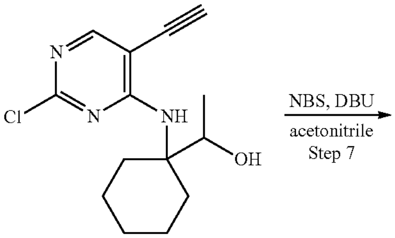
7
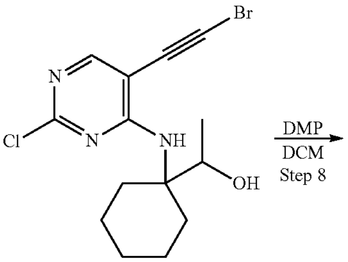
8

-continued

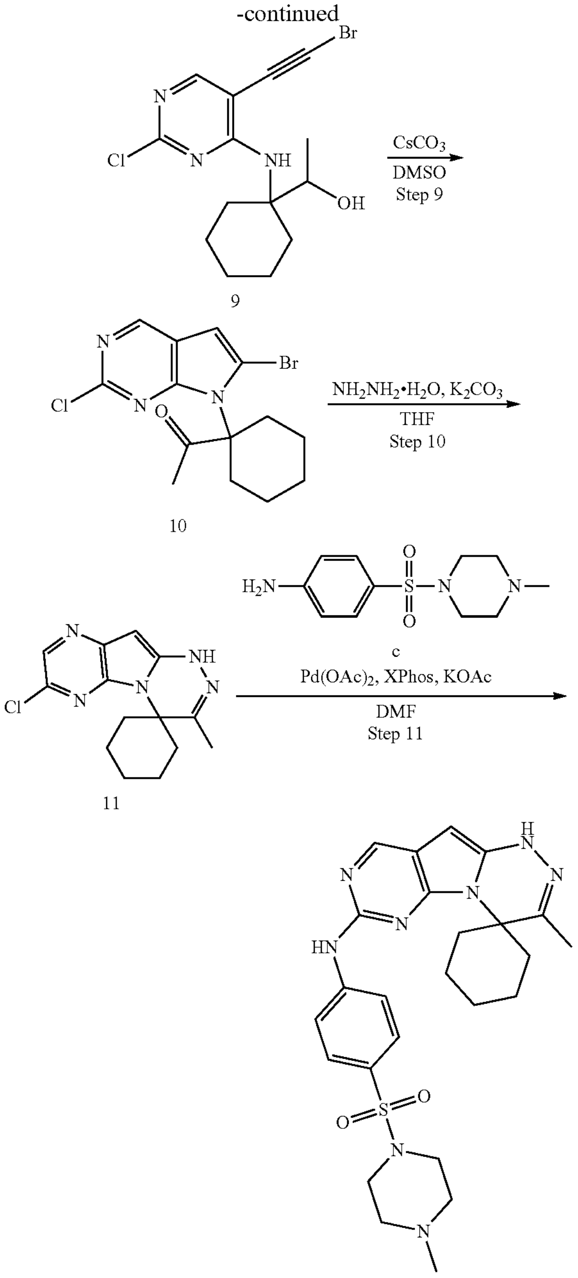

Step 1': 1.75 g of 1' was converted to 2' using TFA/DCM/RT/1 h. After purification, 1.14 g of 2' was obtained.

Step 2': 500 mg of 2' was converted to c using formaldehyde/$NaBH(OAc)_3$/TEA/DCM/RT/2 h.

After purification, 520 mg of c was obtained.

Step 1: 100.0 g of 1 was converted to 2 using $LiAlH_4$/THF/40° C.-rt/overnight. After workup, 89 g of 2 was obtained.

Step 2: 42.7 g of 2 was converted to 3 using a/$NaHCO_3$/DMAC/60° C./overnight. Purification, 76.5 g of 3 was obtained.

Step 3: 20 g of 3 was converted to 4 using b/TEA/$PdCl_2$($PPh_3$)$_2$/CuI/THF/r.t/3 h. After purification, 13 g of 4 was obtained.

Step 4: 14.39 g of 4 was converted to 5 using Dess-Martin reagent/DCM/RT/1 h. After purification, 11 g of 5 was obtained.

Step 5: 11.0 g of 5 was converted to 6 using $CH_3MgI$/THF/−75° C.-RT/2 h. After purification, 9.0 g of 6 was obtained.

Step 6: 9.0 g of 6 was converted to 7 using TBAF/THF/−20° C./20 min. After purification, 6.8 g of 7 was obtained.

Step 7: 6.8 g of 7 was converted to 8 using NBS/DBU/MeCN/RT/20 min. After purification, 8.7 g of 8 was obtained.

Step 8: 8.7 g of 8 was converted to 9 using Dess-Martin reagent/DCM/RT/1 h. After purification, 5.8 g of 9 was obtained.

Step 9: 4.2 g of 9 was converted to 10 using $Cs_2CO_3$/DMSO/RT/15 min. After purification, 1.4 g of 10 was obtained.

Step 10: 1.4 g of 10 was converted to 11 using $NH_2NH_2$·$H_2O$/THF/$K_2CO_3$/RT/overnight. After purification, 700 mg of 11 was obtained.

Step 11: 50 mg of 11 was converted to Compound 60 using c/$Pd(OAc)_2$/X-phos/AcOK/DMF/90° C./2 h. The starting material was consumed. After purification, 7.9 mg of Compound 60 was obtained.

Scheme 27 Synthesis of 4-((3'-oxo-2',3'-dihydro-1'H-spiro[cyclohexane-1,4'-pyrimido[5',4':4,5]pyrrolo[2,1-c][1,2,4]triazin]-7'-yl)amino)benzoic acid Compound 66

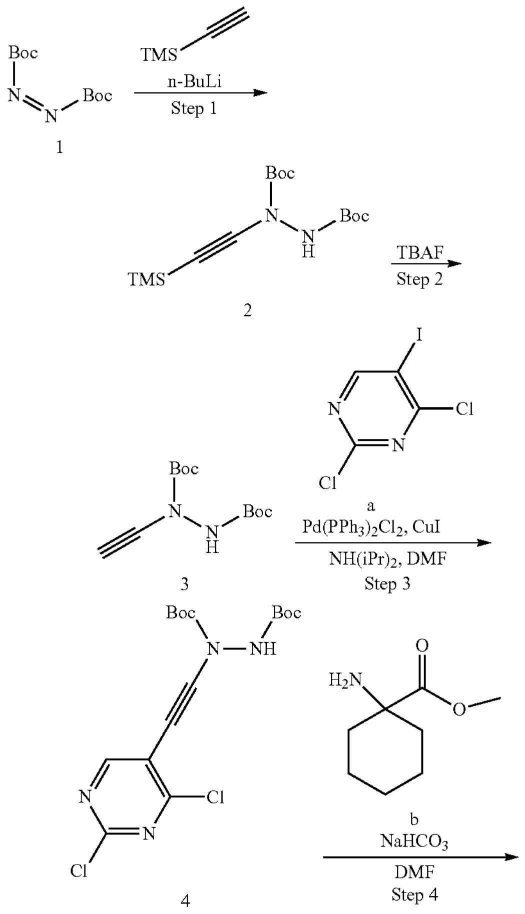

-continued

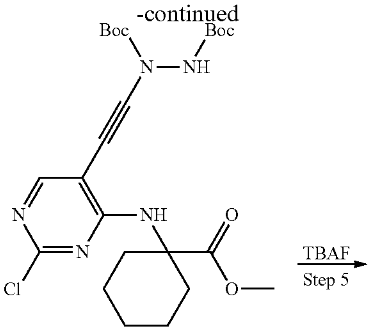

5

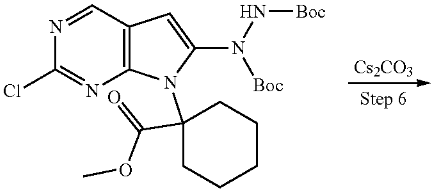

6

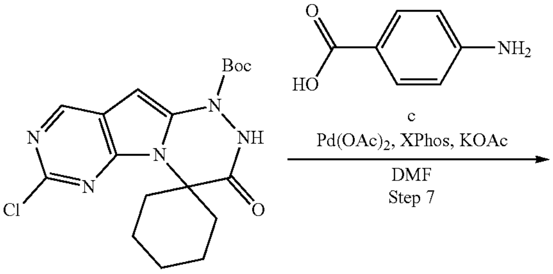

7

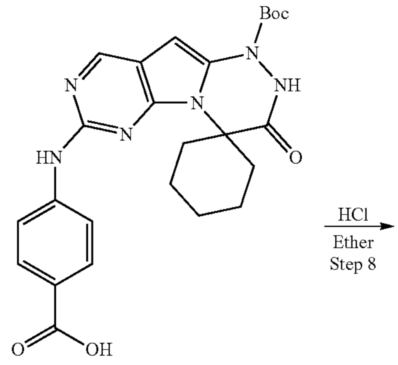

8

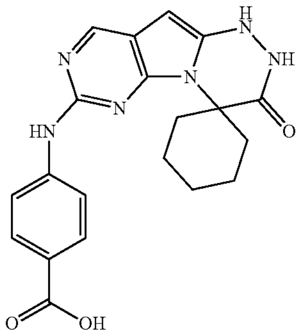

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 [M+H]+.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 [M+H]+.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 [M+H]+.

Step 7: 15 mg of 7 was converted to 8 using c/$Pd(OAc)_2$/X-Phos/KOAc/DMF/80° C./4 h. After purification, 15 mg of 8 was obtained.

Step 8: 15 mg of 8 was converted to Compound 66 using HCl/Ether/rt/1 h. After purification by preperative TLC, 5 mg of impure Compound 66 was obtained. Then the impure Compound 66 was purified by prep HPLC, 4.6 mg of Compound 66 was obtained.
Scheme 28 Synthesis of 1-(4-((3'-oxo-2',3'-dihydro-1'H-spiro[cyclohexane-1,4'-pyrimido[5',4':4,5]pyrrolo[2,1-c][1,2,4]triazin]-7'-yl)amino)phenyl)urea Compound 67
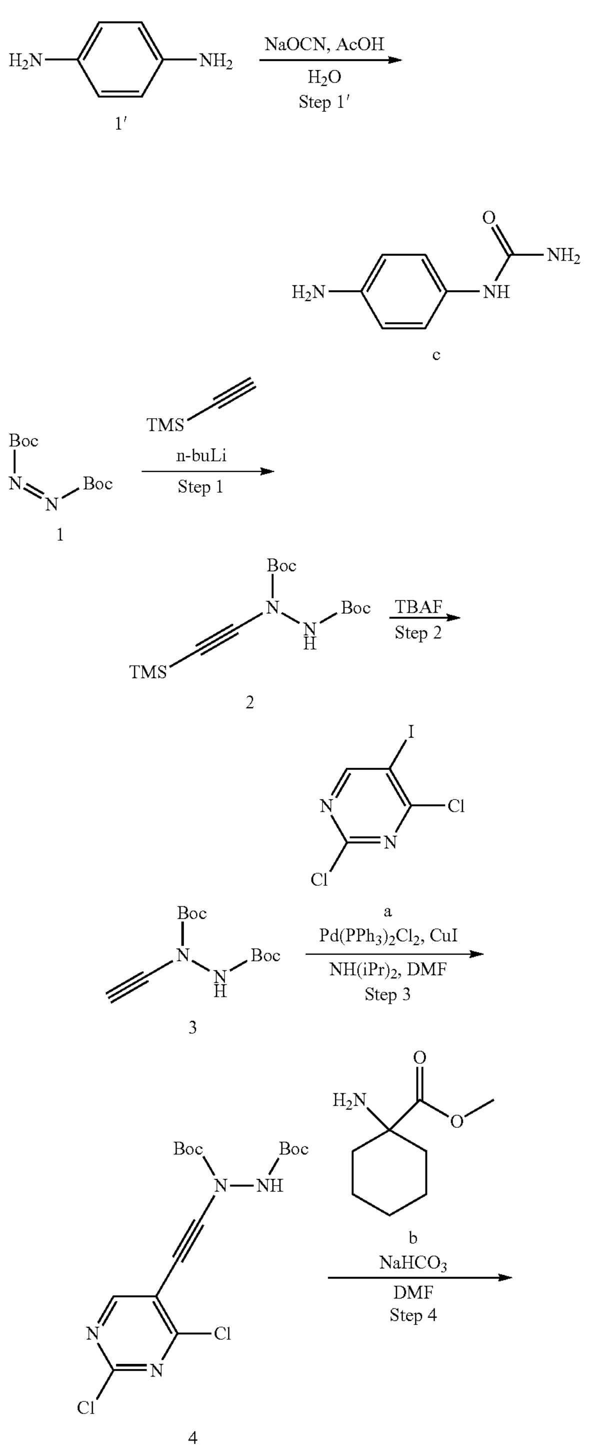
-continued
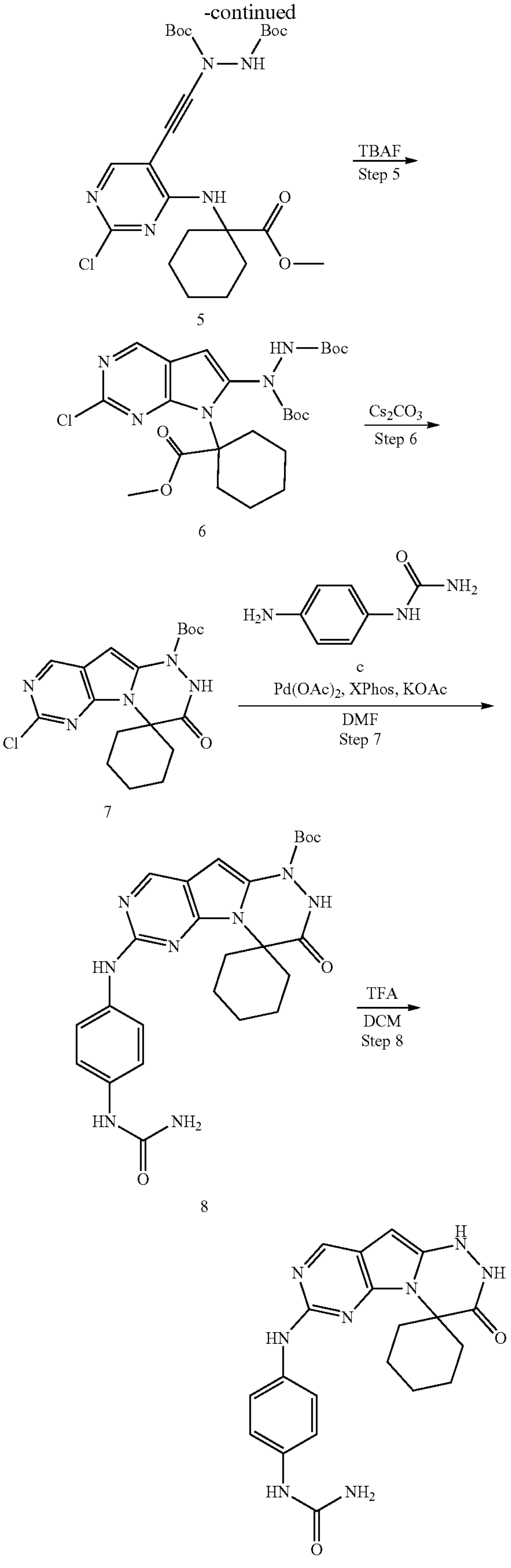

Step 1': 1 g of benzene-1,4-diamine was converted to c using sodium cyanate/HOAc/$H_2O$/50° C./2 h. The starting material was consumed. After purification, 300 mg of 3 was obtained.

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 $[M+H]^+$.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 [M+H]+.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 [M+H]+.

Step 7: 30 mg of 7 was converted to 8 using c/Pd$(OAc)_2$/X-Phos/AcOK/DMF/70° C./3 h. After the purification, 12 mg of 8 was obtained.

Step 8: 12 mg of 8 was converted to Compound 67 using TFA/DCM/RT/5 h. After purification, 2.2 mg of Compound 67 was obtained.

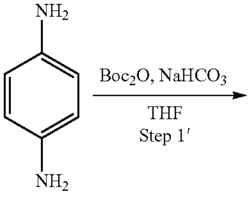

1'

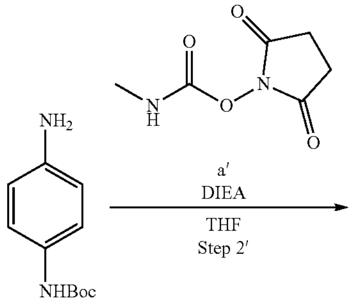

2'

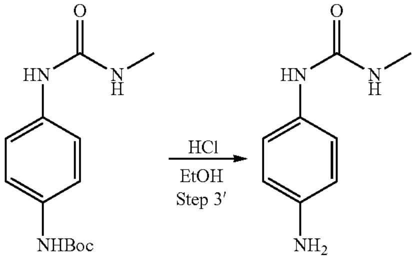

3' c

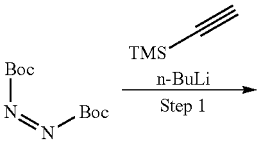

1

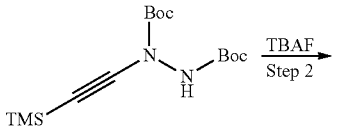

2

-continued

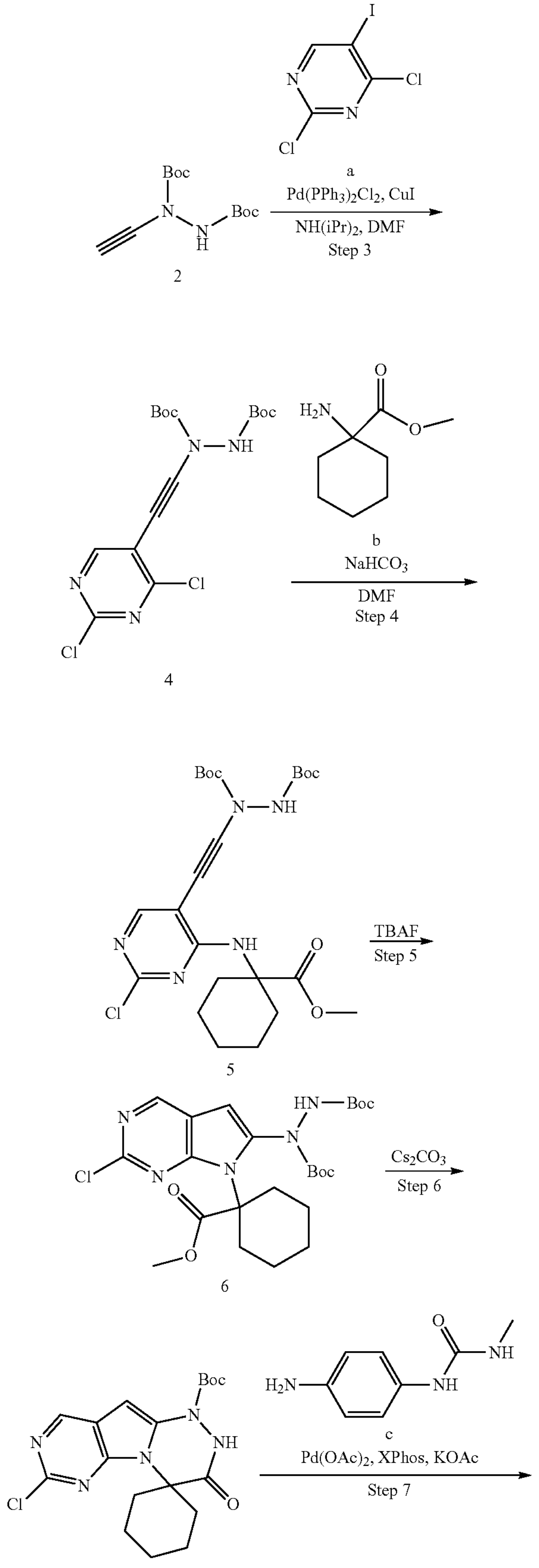

a

2 b

4

5

6 c

7

-continued

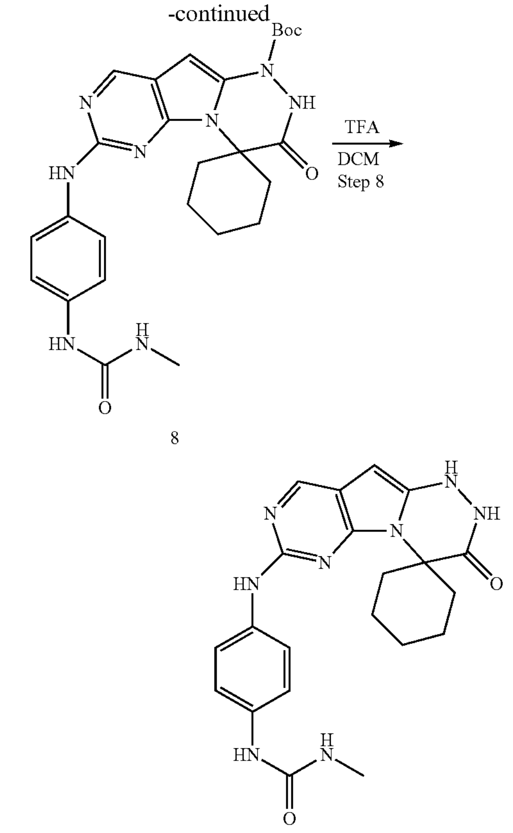

8

Step 1': 10 g of 1' was converted to 2' using $(Boc)_2O$/$NaHCO_3$/THF/RT/overnight. After purification, 13.6 g of 2' was obtained.

Step 2': 200 mg of 2' was converted to 3' using a'/DIEA/THF/reflux/6 h. After purification, 180 mg of 3' was obtained.

Step 3': 100 mg of 3' was converted to c using HCl/EtOH/RT/2 h. After purification, 50 mg of c was obtained.

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 [M+H]+.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 [M+H]+.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 [M+H]+.

Step 7: 50 mg of 7 was converted to 8 using c/Pd $(OAc)_2$/x-phos/AcOK/75° C./4 h. After purification, 14 mg of 8 was obtained.

Step 8: 14 mg of 8 was converted to Compound 68 using TFA/DCM/RT/3 h. After purification by prep TLC three times, 1.3 mg of Compound 68 was obtained.

Scheme 30 Synthesis of 8'-methyl-2'-((4-(4-methylpiperazine-1-carbonyl)phenyl)amino)-6'H-spiro[cyclohexane-1,9'-pyrrolo[1,5-a:2,3-d']dipyrimidin]-7'(8'H)-one Compound 71

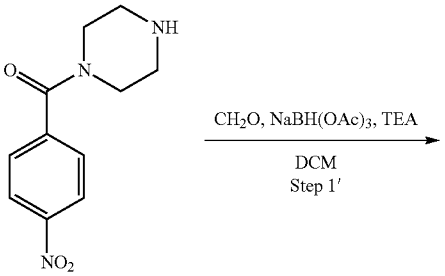

1′

-continued

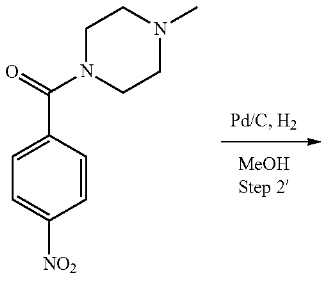

2′

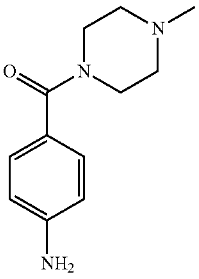

d

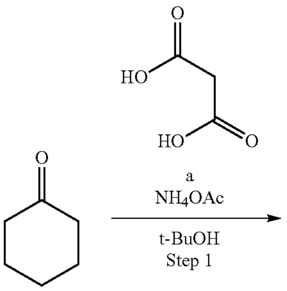

a

1

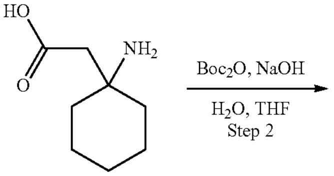

2

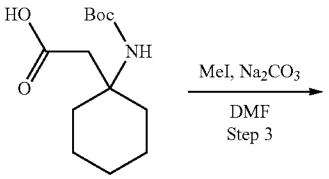

3

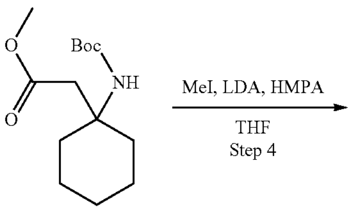

4

-continued

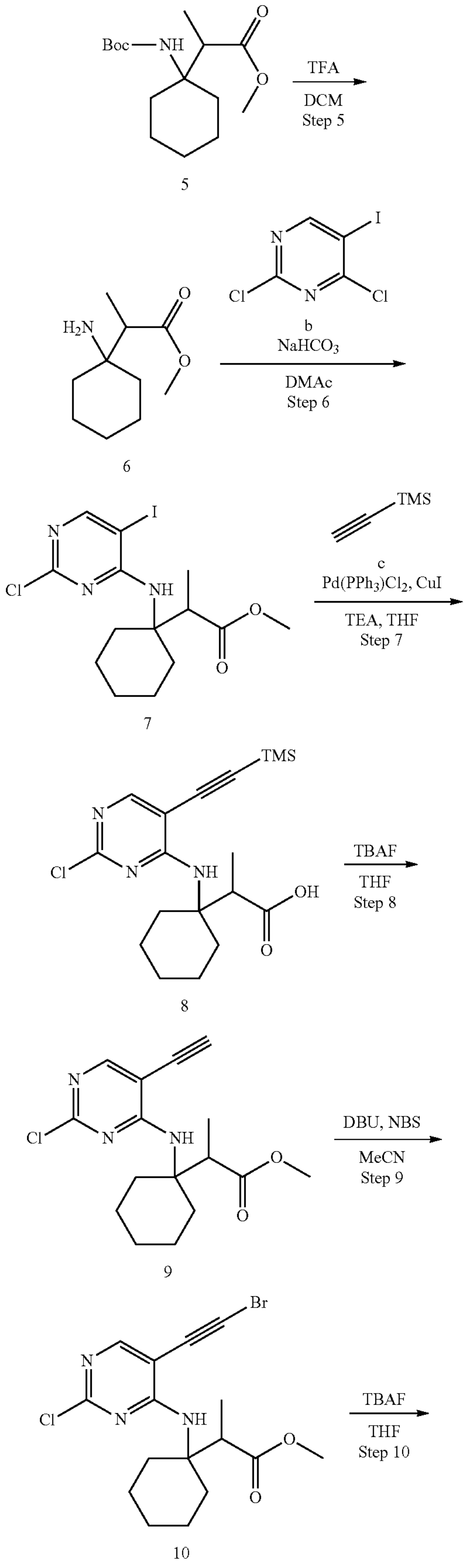

-continued

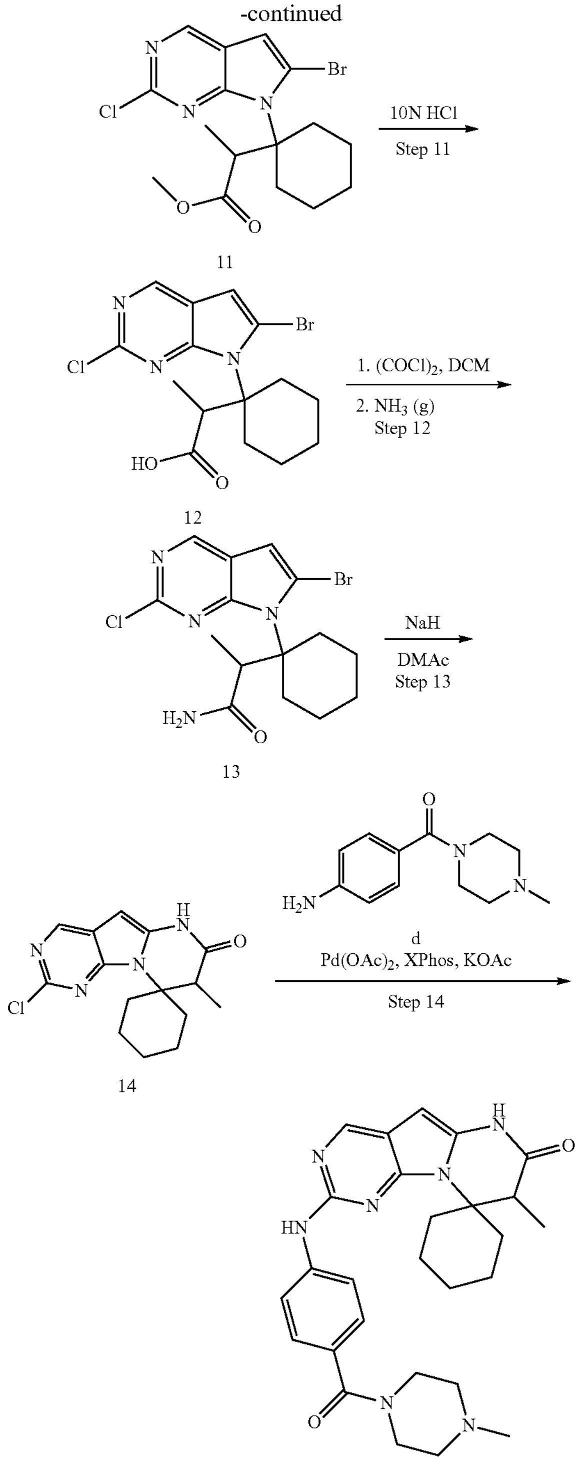

Step 1': 1 g of 1' was converted to 2' using $CH_2O/NaBH(OAc)_3$/TEA/DCM/RT/3 h. After purification, 900 mg of 2' was obtained.

Step 2': 900 mg of 2' was converted to d using $H_2$/Pd/C/MeOH/RT/3 h. After purification, 760 mg of d was obtained.

Step 1: 20 g of 1 was converted to 2 using a/$NH_4OAc$/t-BuOH/135° C./3.5 h. After purification, 19.7 g of 2 was obtained.

Step 2: 20 g of 2 was converted to 3 using $Boc_2O$/NaOH/$H_2O$/THF/RT/4 h. After purification, 21 g of 3 was obtained.

Step 3: 21 g of 3 was converted to 4 using $Na_2CO_3$/MeI/DMF/RT/2 h. After purification, 19 g of 4 was obtained.

Step 4: 14 g of 4 was converted to 5 using MeI/LDA/HMPA/THF/−78° C.-RT/3 h. After purification, 14 g of impure 5 was obtained (mixed with some of the starting material 4 and dimethyl byproduct).

Step 5: 14 g of impure 5 was converted to 6 using TFA/DCM/RT/3 h. After simple workup, 7.1 g of crude 6 was obtained.

Step 6: 7.1 g of 6 was converted to 7 using b/$NaHCO_3$/DMAc/60° C./overnight. After purification, 3.0 g of 7 was obtained.

Step 7: 2.87 g of 7 was converted to 8 using c/Pd$(PPh_3)_2Cl_2$/CuI/DIEA/THF/RT/2 h. After purification, 1.78 g of 8 was obtained.

Step 8: 1.7 g of 8 was converted to 9 using TBAF/THF/0° C./5 min. After purification, 1.4 g of 9 was obtained.

Step 9: 1.15 g of 9 was converted to 10 using DBU/NBS/acetonitrile/0° C./10 min. After workup, 1.5 g of crude 10 was obtained.

Step 10: 1.5 g of crude 10 was converted to 11 using TBAF/THF/10° C./1 h. After purification, 430 mg of pure 11 and 350 mg of impure 11 were obtained.

Step 11: 400 mg of 11 was converted to 12 using HCl (10 N)/70° C./6 h. After purification, 150 mg of 12 was obtained.

Step 12: 150 mg of 12 was converted to 13 using oxalyl chloride/DCM/RT/1 h. Then the reaction was concentrated and treated with $NH_3$ (g). After purification, 155 mg of 13 was obtained.

Step 13: 155 mg of 13 was converted to 14 using NaH/DMAc/0° C.-RT/30 min. After purification, 85 mg of 14 was obtained.

Step 14: 80 mg of 14 was converted to Compound 71 using d/$Pd(OAc)_2$/X-phos/AcOK/75° C./4 h.

After purification, 13.1 mg of Compound 71 was obtained.

-continued

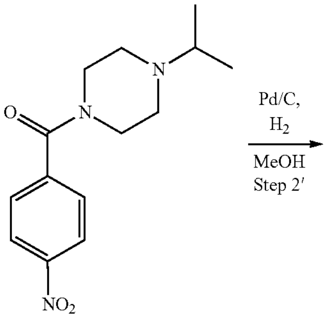

2'

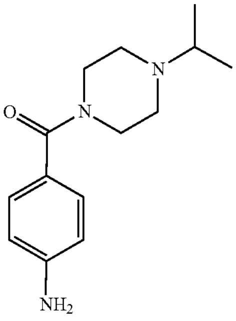

d

Scheme 31 Synthesis of 2'-((4-(4-isopropylpiperazine-1-carbonyl)phenyl)amino)-8'-methyl-6'H-spiro[cyclohexane-1,9'-pyrrolo[1,5-a:2,3-d']dipyrimidin]-7'(8'H)-one Compound 72

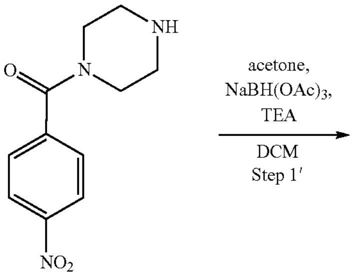

1'

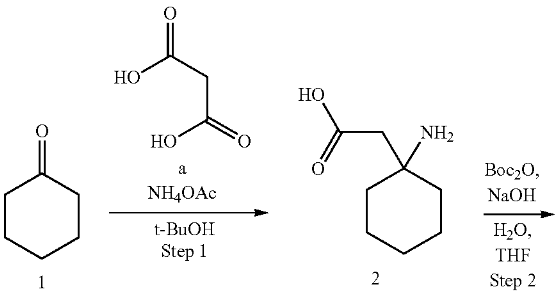

1 2

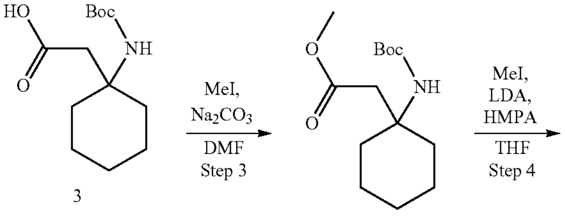

3 4

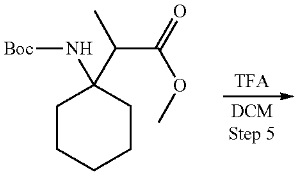

5

-continued

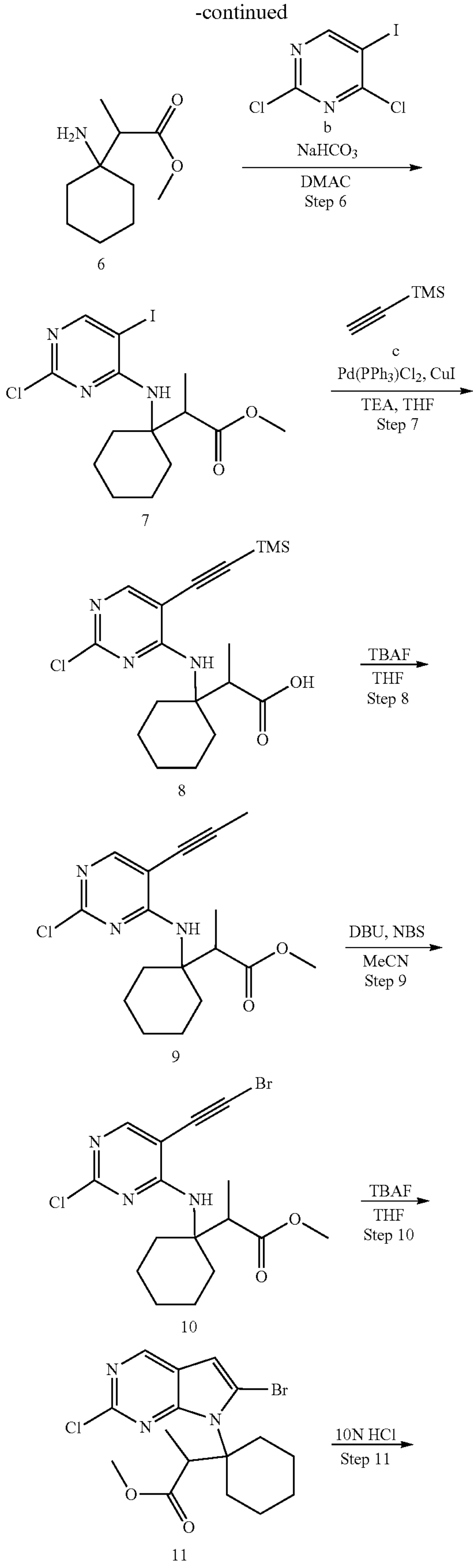

-continued

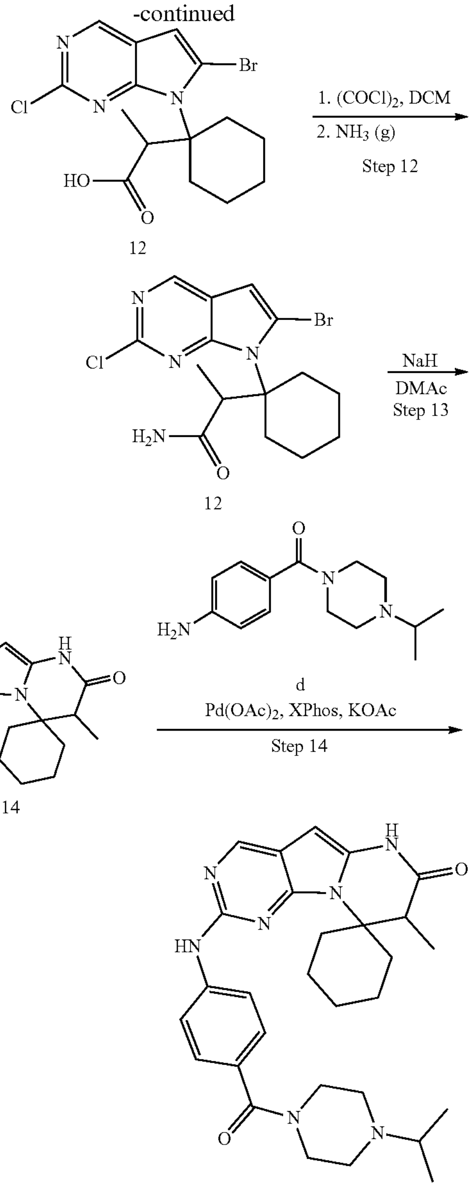

Step 1': 200 mg of 1' was converted to 2' using acetone/$NaBH(OAc)_3$/TEA/DCM/RT/overnight. After purification, 154 mg of impure 2' was obtained.

Step 2': 154 mg of 2' was converted to d using $H_2$/Pd/C/MeOH/RT/overnight. After purification, 105 mg of d was obtained.

Step 1: 30 g of 1 was converted to 2 using $NH_4OAc$/a/n-BuOH/135° C./5 h. After purification, 30 g of 2 was obtained.

Step 2: 30 g of 2 was converted to 3 using $Boc_2O$/aq.NaOH/1,4-dioxane/rt/overnight. After purification, 31 g of 3 was obtained.

Step 3: 31 g of 3 was converted to 4 using MeI/$Na_2CO_3$/DMF/RT/2 h. After purification, 26 g of 4 was obtained.

Step 4: 14 g of 4 was converted to 5 using MeI/LDA/HMPA/THF/−78° C.-RT/3 h. After purification, 14 g of impure 5 was obtained (mixed with some of the starting material 4 and dimethyl byproduct).

Step 5: 14 g of impure 5 was converted to 6 using TFA/DCM/RT/3 h. After simpe workup, 7.1 g of crude 6 was obtained.

Step 6: 7.1 g of 6 was converted to 7 using b/$NaHCO_3$/DMAc/60° C./overnight. After purification, 3.0 g of 7 was obtained.

Step 7: 2.87 g of 7 was converted to 8 using c/Pd$(PPh_3)_2Cl_2$/CuI/DIEA/THF/RT/2 h. After purification, 1.78 g of 8 was obtained.

Step 8: 1.7 g of 8 was converted to 9 using TBAF/THF/0° C./5 min. After purification, 1.4 g of 9 was obtained.

Step 9: 1.15 g of 9 was converted to 10 using DBU/NBS/acetonitrile/0° C./10 min. After workup, 1.5 g of crude 10 was obtained.

Step 10: 1.5 g of crude 10 was converted to 11 using TBAF/THF/10° C./1 h. After purification, 430 mg of pure 11 and 350 mg of impure 11 were obtained.

Step 11: 700 mg of 11 was converted to 12 using $HCl/H_2O$/90° C./5 h. After purification, 530 mg of 12 was obtained.

Step 12: 150 mg of 12 was converted to 13 using oxalyl chloride/DCM/RT/1 h. Then the reaction was concentrated and treated with $NH_3$ (g). After purification, 155 mg of 13 was obtained.

Step 13: 155 mg of 13 was converted to 14 using NaH/DMAc/0° C.-RT/30 min. After purification, 85 mg of 14 was obtained.

Step 14: 36 mg of 14 was converted to Compound 72 using d/$Pd(OAc)_2$/X-phos/AcOK/75° C./4 h. After purification, 7.2 mg of Compound 72 was obtained.

Scheme 32 Synthesis of 7'-((4-(4-(methylsulfonyl)piperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 73

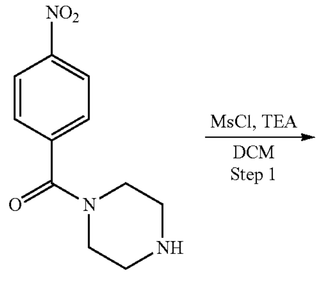

1

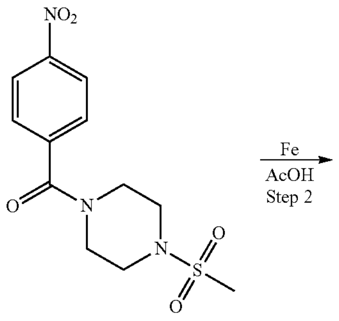

2

-continued

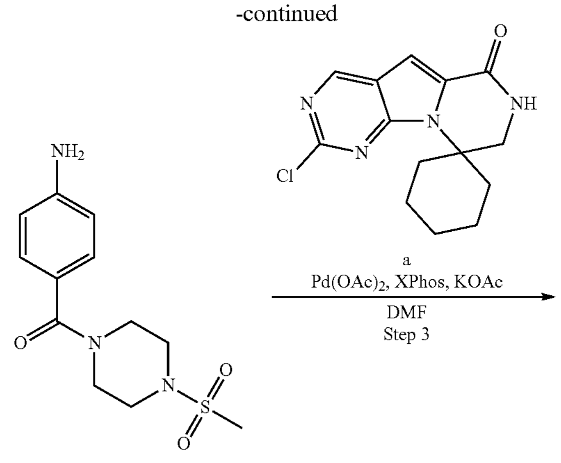

3

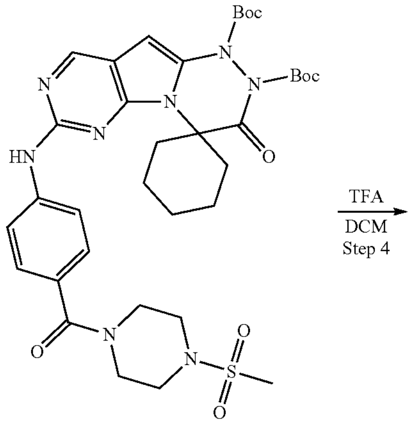

4

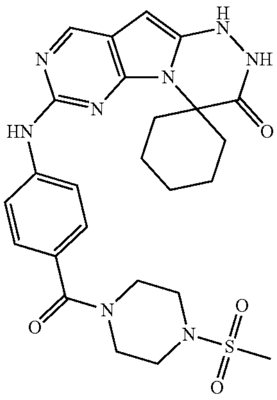

Step 1: 300 mg of 1 was converted to 2 using MsCI/TEA/DCM/RT/1 h. After purification, 146 mg of 2 was obtained.

Step 2: 146 mg of 2 was converted to 3 using Fe/HOAc/60° C./overnight. After purification, 58 mg of 3 was obtained.

Step 3: 58 mg of 3 was converted to 4 using a/Pa$(OAc)_2$/KOAc/X-phos/DMF/80° C./3 h. After purification, 130 mg of 4 was obtained.

Step 4: 130 mg of 4 was converted to Compound 73 using TFA/DCM/RT/3 h. After purification, 15.4 mg of Compound 73 was obtained.

Scheme 33 Synthesis of 7'-((4-(morpholine-4-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 74

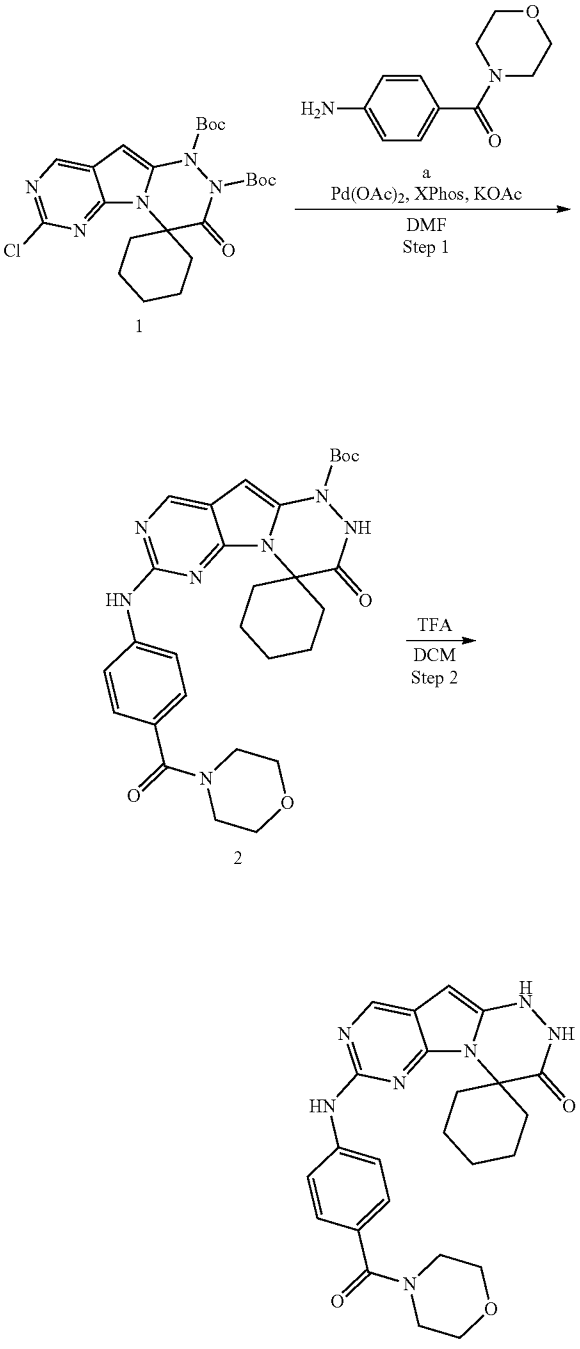

Step 1: 50 mg of 1 was converted to 2 using a/AcOK/Pd $(OAc)_2$/X-phos/DMF/85° C./3 h. After purification, 26 mg of 2 was obtained.

Step 2: 26 mg of 2 was converted to Compound 74 using TA/DCM/RT/2 h. After purification, 14.7 mg of Compound 74 was obtained.

Scheme 34 Synthesis of 7'-((4-(4-isopropylpiperidine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 75

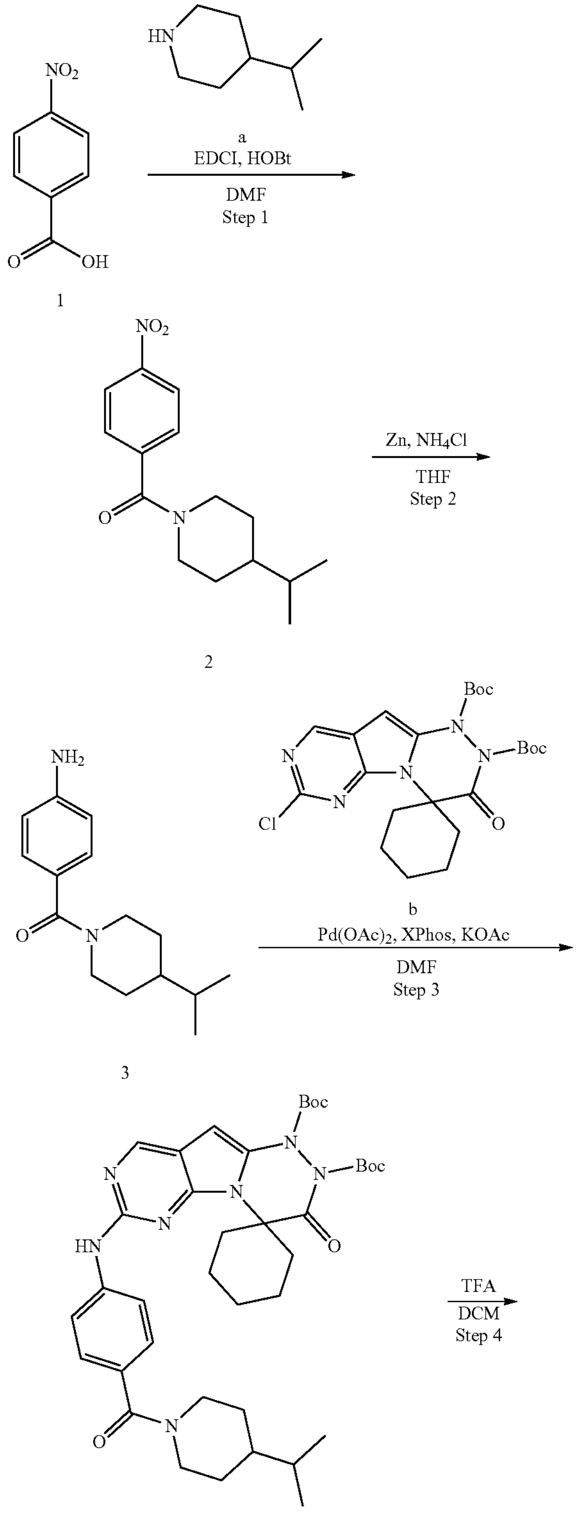

4

-continued

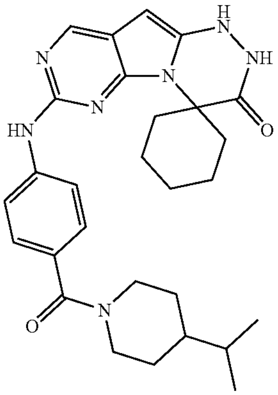

Step 1: 1 g of 1 was converted to 2 using a/EDCl/HOBt/DMF/RT/4 h. After purification, 1.9 g of 2 was obtained.

Step 2: 500 mg of 2 was converted to 3 using Zn powder/$NH_4Cl$/THF/40° C./2 h. After purification, 400 mg of 3 was obtained.

Step 3: 80 mg of 3 was converted to 4 using b/Pd $(OAc)_2$/x-Phos/KOAc/DMF/80° C./4 h. After purification, 30 mg of 4 was obtained.

Step 4: 30 mg of 4 was converted to Compound 75 using TFA/DCM/RT/1 h. After purification, 10 mg of Compound 75 was obtained.

Scheme 35 Synthesis of 7'-((4-(4-ethylpiperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 76

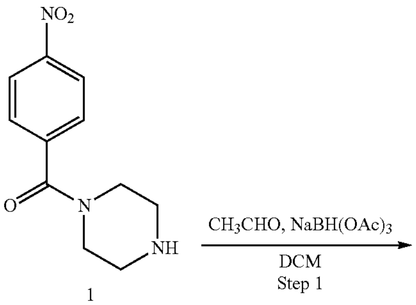

1

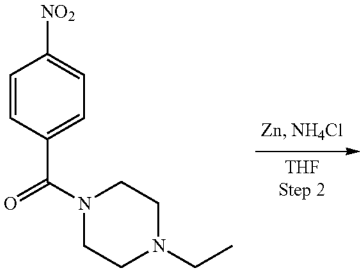

2

-continued

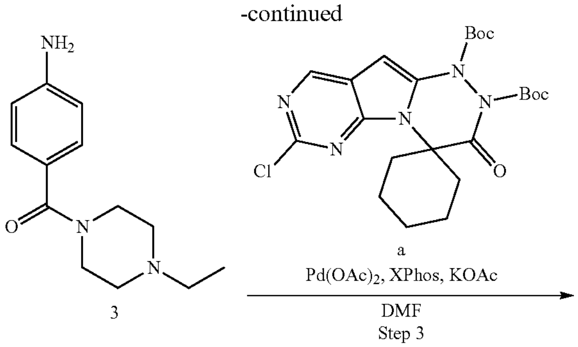

3

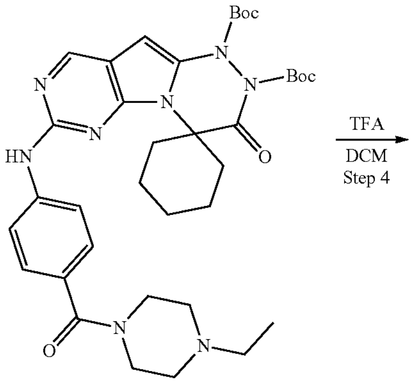

4

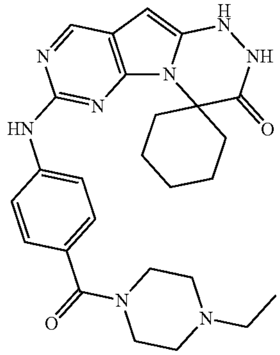

Step 1: 200 mg of 1 was converted to 2 using $CH_3CHO$/$NaHB(OAc)_3$/DCM/RT/overnight. After purification, 200 mg of 2 was obtained.

Step 2: 200 mg of 2 was converted to 3 using Zn/$NH_4Cl$/$H_2O$/THF/40° C./4 h. After purification, 150 mg of 3 was obtained.

Step 3: 40 mg of 3 was converted to 4 using a/Pd $(OAc)_2$/X-Phos/AcOK/DMF/90° C./2 h. The starting material was consumed. After purification, 15 mg of 4 was obtained.

Step 4: 15 mg of 4 was converted to Compound 76 using TFA/DCM/RT/3 h. After purification, 7.4 mg of Compound 76 was obtained.

Scheme 36 Synthesis of 7'-((4-(4-(dimethylamino) piperidine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one Compound 77

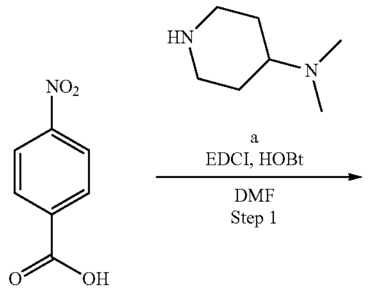

1

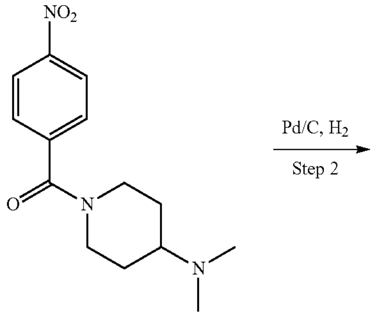

2

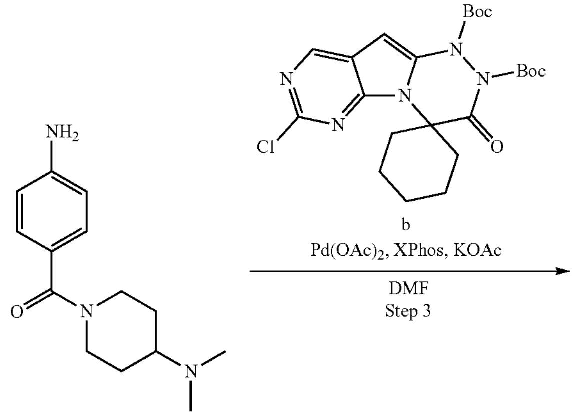

3

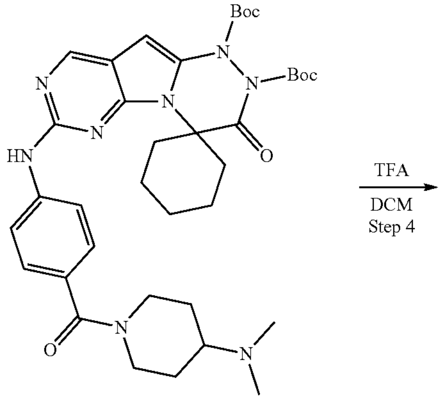

4

-continued

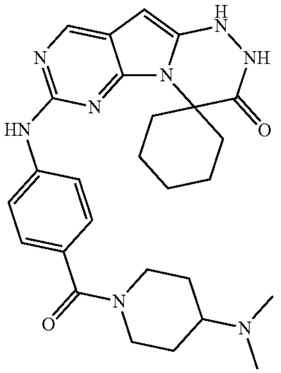 [SMILES: CN(C)C1CCN(C(=O)c2ccc(Nc3ncc4cc5n(c4n3)C3(CCCCC3)C(=O)NN5)cc2)CC1]

Step 1: 1 g of 1 was converted to 2 using a/EDCl/HOBt/DMF/RT/overnight. After purification, 2 g of impure 2 was obtained.

Step 2: 300 mg of 2 was converted to 3 using $H_2$/Pd/C/RT/overnight. After purification, 65 mg of 3 was obtained.

Step 3: 50 mg of b was converted to 4 using 3/Pd $(OAc)_2$/x-Phos/KOAc/DMF/80° C./4 h. After purification, 30 mg of 4 was obtained.

Step 4: 30 mg off 4 was converted to Compound 77 using TFA/DCM/RT/2 h. After purification, 9.5 mg of Compound 77 was obtained.

Scheme 37 Synthesis of 7'-((4-(piperidine-1-carbonyl)phenyl)amino)-1',2'-dihydro-3'H-spiro[cyclohexane-1,4'-pyrimido[5',4':4,5]pyrrolo[2,1-c][1,2,4] triazin]-3'-one Compound 78

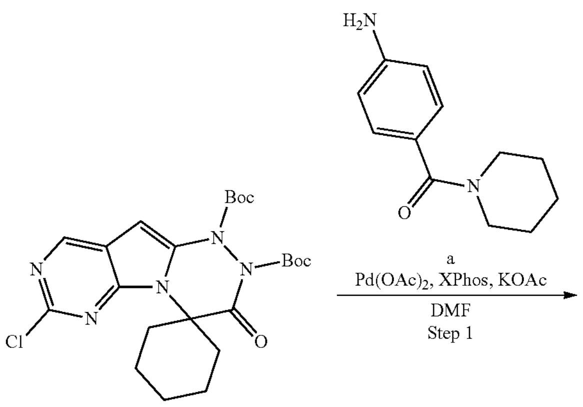

1

-continued

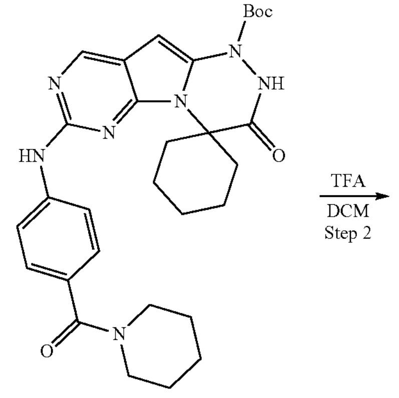

2

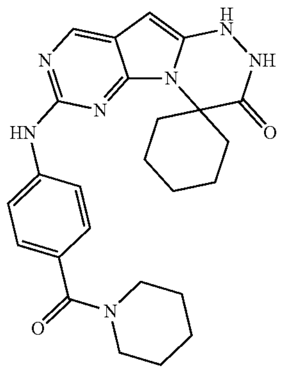

Step 1: 50 mg of 1 was converted to 2 using a/AcOK/Pd $(OAc)_2$/X-phos/DMF/85° C./2 h. After purification, 57 mg of 2 was obtained.

Step 2: 57 mg of 2 was converted to Compound 78 using TFA/DCM/RT/2 h. After purification, 8.3 mg of Compound 78 was obtained.

Scheme 38 Synthesis of 7'-((4-(S-methylsulfonimidoyl)phenyl)amino)-1',2'-dihydro-3'H-spiro[cyclohexane-1,4'-pyrimido[5',4':4,5]pyrrolo[2,1-c][1,2,4]triazin]-3'-one Compound 79

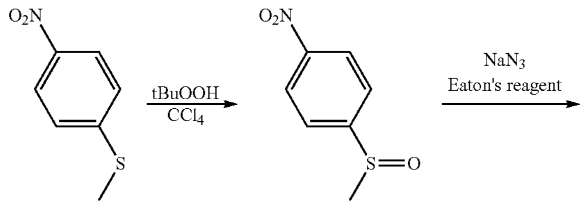

1

2

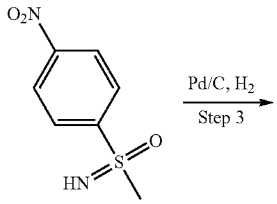

3

-continued

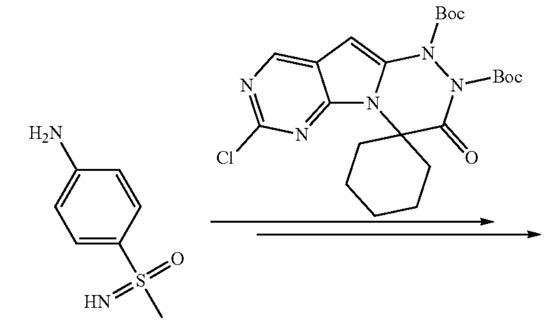

4

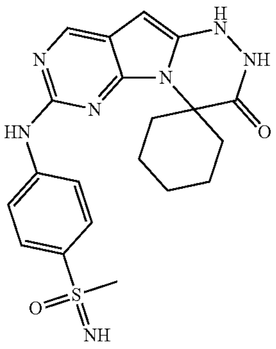

Step 1: 10 g of 1 was converted to 2 using tert-butyl hydroperoxide (10 eq)/$CCl_4$/reflux/5 h. After purification, 5.4 g of 2 was obtained.

Step 2: 1.0 g of 2 was converted to 3 using $NaN_3$/Eaton's reagent/50° C./30 min. After purification, 1.4 g of impure 3 was obtained.

Step 3: 400 mg of 3 was converted to 4 using Pd/C/$H_2$/overnight. After purification 265 mg of 4 was obtained.

Scheme 39 Synthesis of 7'-((4-((4-methylpiperazin-1-yl)sulfonyl)phenyl)amino)-1',2'-dihydro-3'H-spiro[cyclohexane-1,4'-pyrimido[5',4':4,5]pyrrolo[2,1-c][1,2,4]triazin]-3'-one Compound 49

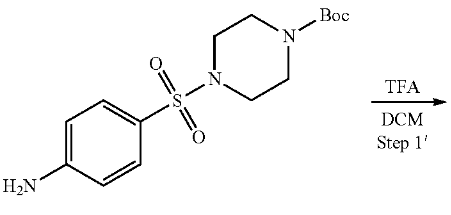

1'

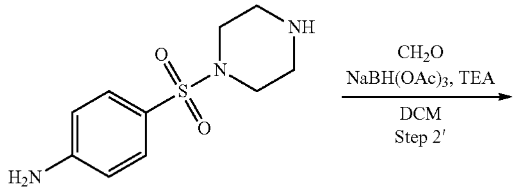

2'

-continued

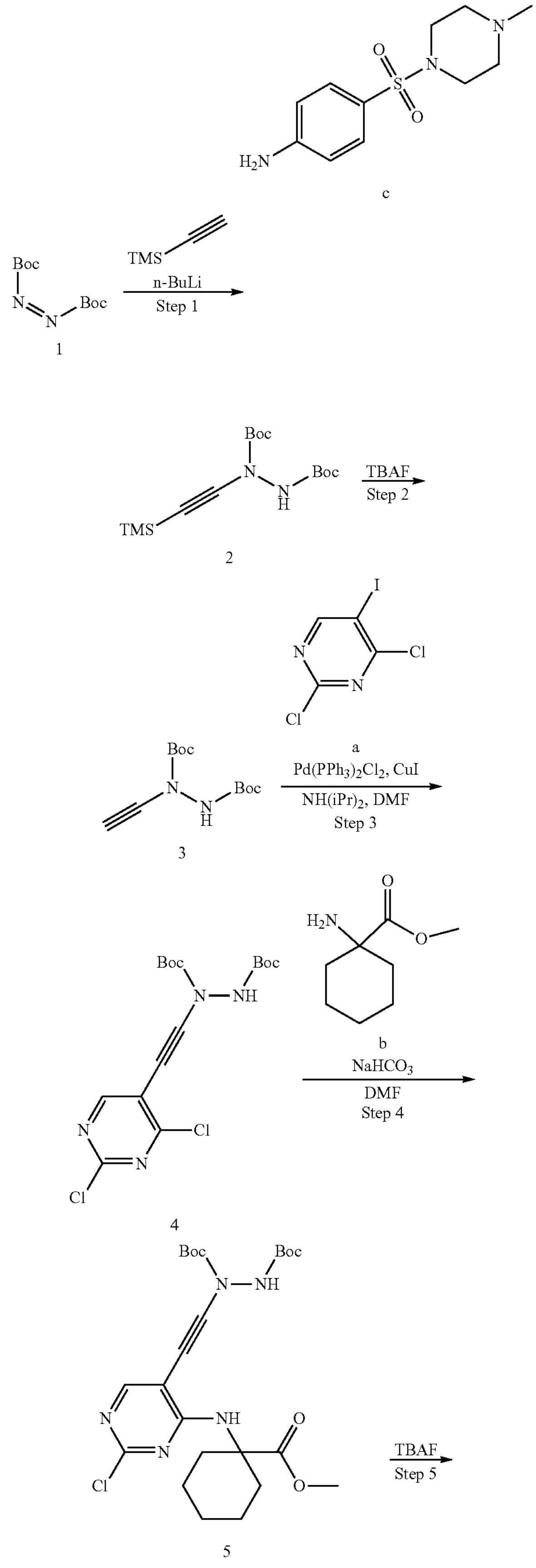

-continued

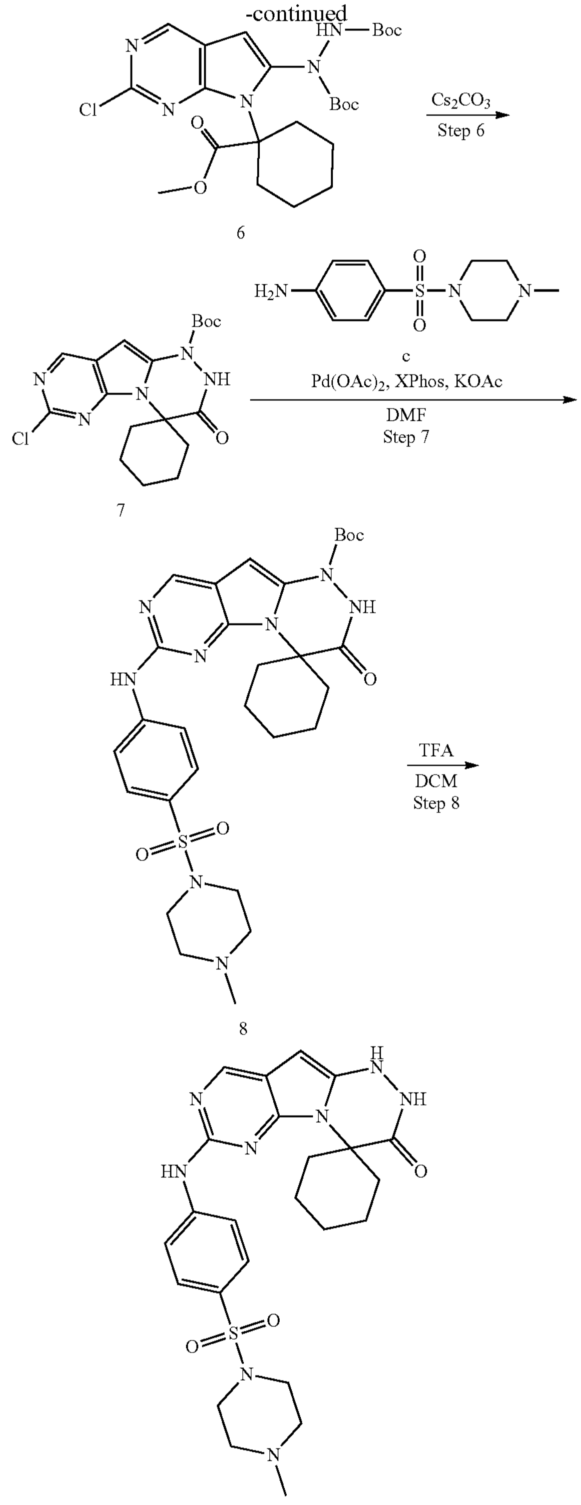

Step 1': 1.75 g of 1' was converted to 2' using TFA/DCM/RT/1 h. After purification, 1.14 g of 2' was obtained.

Step 2': 500 mg of 2' was converted to c using formaldehyde/NaBH(OAc)$_3$/TEA/DCM/RT/2 h. After purification, 520 mg of c was obtained.

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 [M+H]+.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 [M+H]+.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 $[M+H]^+$.

Step 7: 50 mg of 7 was converted to 8 using c/Pd(OAc)$_2$/X-Phos/AcOK/DMF/90° C./3 h. After purification, 20 mg of 8 was obtained.

Step 8: 20 mg of 8 was converted to Compound 49 using TFA/DCM/RT/overnight. After purification, 7.8 mg of Compound 49 was obtained.

Scheme 40 Synthesis of 4-amino-N-(6'-oxo-7',8'-dihydro-6'H-spiro[cyclohexane-1,9'-pyrazino[1',2':1,5]pyrrolo[2,3-d]pyrimidin]-2'-yl)benzenesulfonamide Compound 91

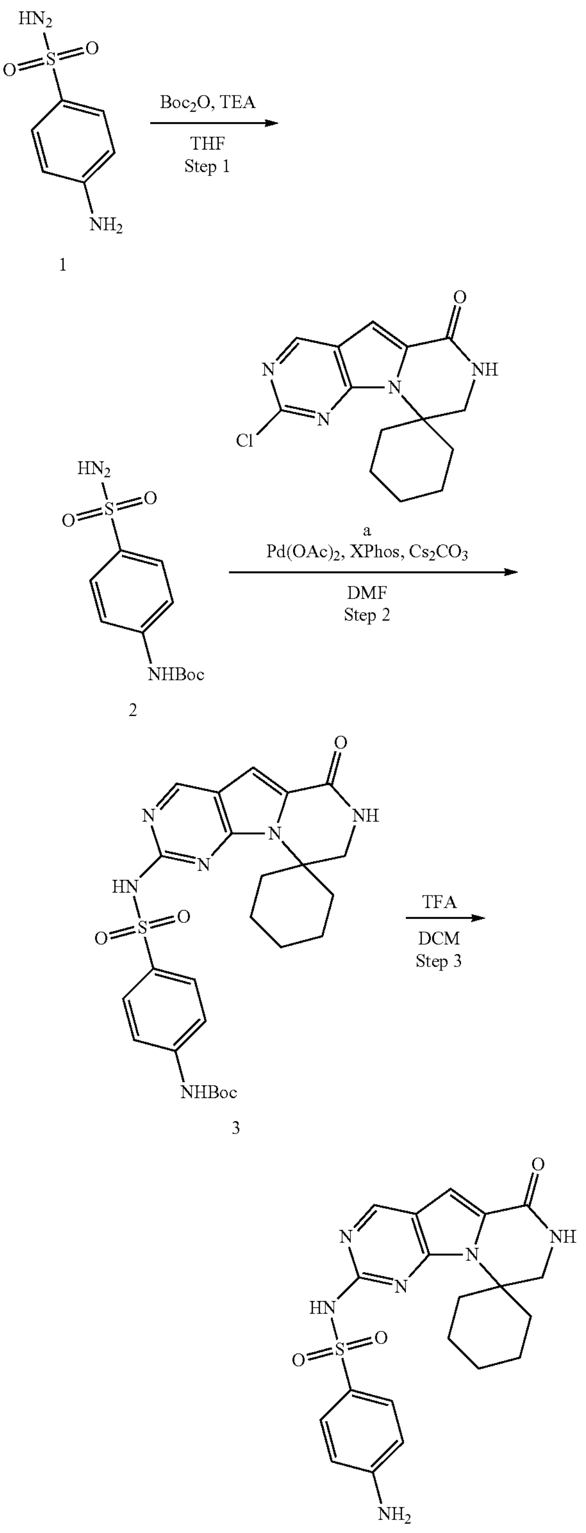

Step 1: 10 g of 1 was converted to 2 using $(Boc)_2O$/TEA/THF/40° C./overnight. After purification, 3.8 g of 2 was obtained.

Step 2: 80 mg of 2 was converted to 3 using a/$Cs_2CO_3$/$Pd(OAc)_2$/X-phos/DMF/85° C./4 h. After purification, 11 mg of 3 was obtained.

Step 3: 11 mg of 3 was converted to Compound 91 using TFA/DCM/RT/2 h. After purification, 1.5 mg of Compound 91 was obtained.

Scheme 41 Synthesis of 4-amino-N-(1'-methyl-3'-oxo-2',3'-dihydro-1'H-spiro[cyclohexane-1,4'-pyrimido[5',4':4,5]pyrrolo[2,1-c][1,2,4]triazin]-7'-yl) benzenesulfonamide Compound 92

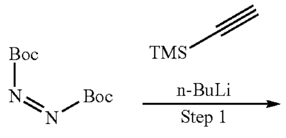

1

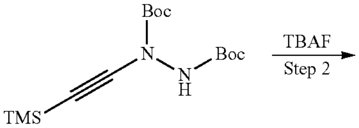

2

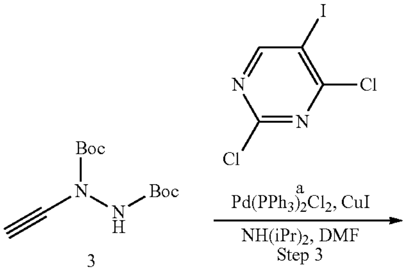

3

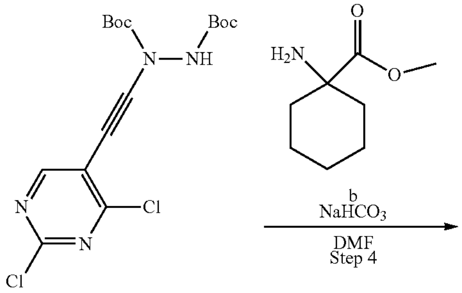

4

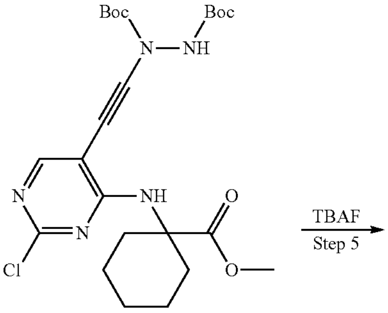

5

-continued

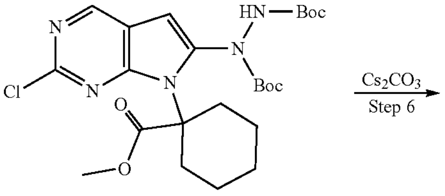

6

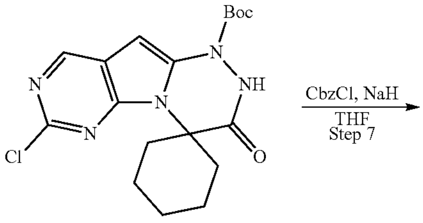

7

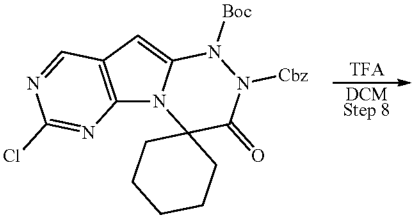

8

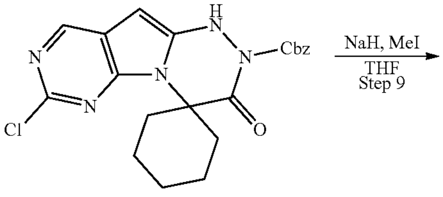

9

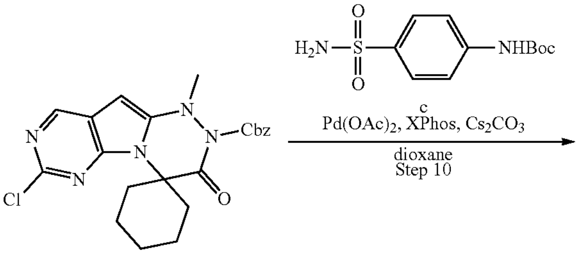

10

-continued

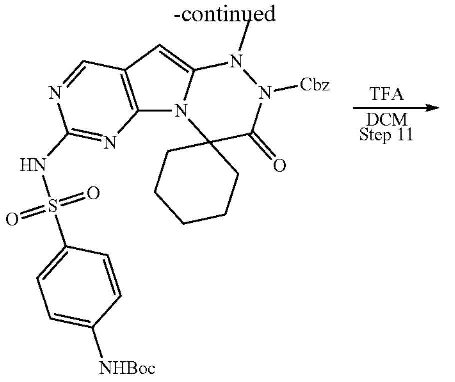

11

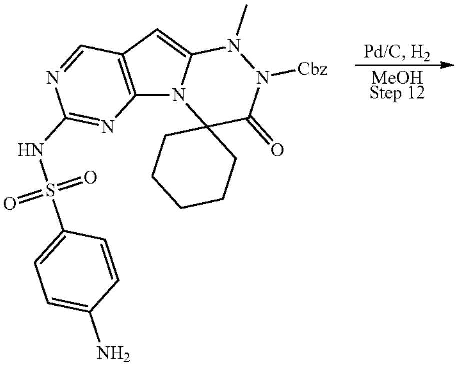

12

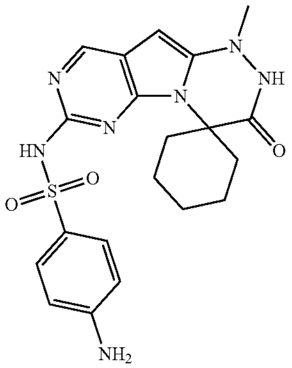 [SMILES: CN1NC(=O)C2(CCCCC2)n2c1cc1cnc(NS(=O)(=O)c3ccc(N)cc3)nc12]

Step 1: To a solution of ethynyltrimethylsilane (30 g, 305.94 mmol) in anhydrous THE (500 mL), under $N_2$ atmosphere, was added dropwise to n-BuLi (147 ml, 2.5 mol in THF, 367.5 mmol) at −78° C., over 30 min. After the addition, the reaction was stirred at −78° C. for 20 min. Then to the reaction solution was added dropwise to a solution of 1 (105 g, 456.26 mmol) in anhydrous THE (300 mL) over 60 min. After the addition, the reaction was allowed to gradually warm to −20° C. and the reaction was allowed to stir at −20° C. for 30 min. The reaction was quenched with saturated $NH_4Cl$ solution (100 mL) and water (300 mL), extracted with EA (200 mL×2). The combined organic phase was washed with brine (100 mL), dried over $Na_2SO_4$, filtered and concentrated in vacuo. The resulting residue was purified by silica column chromatography to afford 2 (60 g, 182.83 mmol) as oil.

Step 2: To a solution of 2 (60 g, 182.83 mmol) in THE (300 mL) was added a solution of TBAF trihydrate (72 g, 228.20 mmol) in THE (300 mL) at −20° C. After the addition, the reaction was stirred at −20° C. for 60 min. The reaction mixture was quenched with saturated $NH_4Cl$ solution (100 mL) and water (400 mL), extracted with EA (300 mL×2). The combined organic phase was dried over $Na_2SO_4$, filtered and concentrated in vacuo. The resulting residue was purified by silica column chromatography to afford 3 (36 g, 140.55 mmol).

Step 3: To a solution of 3, a, CuI (1.1 g, 5.79 mmol), $Pd(PPh_3)_2Cl_2$ (4.1 g, 5.86 mmol), diisopropylamine (17.6 g, 174.05 mmol) were mixed in DMF at room temperature overnight. The reaction was quenched with water (500 mL), and extracted with EA (500 mL×3). The combined organic phase was washed with water (500 mL×3), dried over $Na_2SO_4$, filtered and concentrated in vacuo. The resulting residue was purified by silica column chromatography to afford 4 (28 g, 69.64 mmol). LC-MS (ESI+): m/z 403 [M+H]+.

Step 4: To a solution of 4 (2 g, 4.97 mmol) in DMF (20 mL), under $N_2$ atmosphere, was added b (1.2 g, 7.64 mmol) and $NaHCO_3$ (1.25 g, 14.93 mmol). The reaction mixture was stirred at 60° C. overnight. Then the reaction mixture was cooled to room temperature, quenched with water (100 mL), and extracted with EA (30 mL×3). The combined organic phase was dried over $Na_2SO_4$, filtered and concentrated in vacuo. The resulting residue was purified by silica column chromatography to afford 5 (1.2 g, 2.29 mmol). LC-MS (ESI+): m/z 524 [M+H]+.

Step 5: To a solution of 5 (1.2 g, 2.29 mmol) in THE (15 mL) was added a solution of TBAF (1.2 mL, 1 mol in THF, 1.2 mmol). The reaction mixture was stirred at 60° C. for 1 hour. The reaction mixture was cooled to room temperature quenched with water (30 mL), and extracted with EA (30 mL×3). The combined organic phase was dried over $Na_2SO_4$, filtered and concentrated in vacuo. The resulting residue was purified by silica column chromatography to afford 6 (300 mg, 0.57 mmol). LC-MS (ESI+): m/z 524 [M+H]+.

Step 6: To a solution of 6 (2 g, 3.82 mmol) in DMAc (30 mL) was added $Cs_2CO_3$ (4 g, 12.28 mmol). The reaction mixture was stirred at 100° C. for 5 hours. The reaction mixture was cooled to room temperature, quenched with water (60 mL), and extracted with EA (20 mL×3). The combined organic phase was dried over $Na_2SO_4$, filtered and concentrated in vacuo. The resulting residue was purified by silica column chromatography to afford 7 (320 mg, 0.82 mmol). LC-MS (ESI+): m/z 392 [M+H]+.

Step 7: 300 mg of 7 was converted to 8 using Cbz-Cl/NaH/THF/0° C./2 h. The starting material was consumed. After purification, 380 mg of 8 was obtained.

Step 8: 380 mg of 8 was converted to 9 using TFA/DCM/RT/2 h. The starting material was consumed. After purification, 220 mg of 9 was obtained.

Step 9: 220 mg of 9 was converted to 10 using MeI/NaH/TTIF/0° C./3 h. The starting material was consumed. After purification, 200 mg of 10 was obtained.

Step 10: 100 mg of 10 was converted to 11 using c/$Pd(OAc)_2$/X-Phos/$Cs_2CO_3$/1,4-dixane/80° C./6 h. After purification, 55 mg of 11 was obtained.

Step 11: 53 mg of 11 was converted to 12 using TFA/DCM/RT/2 h. After the purification, 30 mg of 12 was obtained.

Step 12: 25 mg of 12 was converted to Compound 92 using Pd/C/$H_2$/MeOH/RT/2 h. After purification, 3.1 mg of Compound 92 was obtained.

Example 2. Representative Compounds of the Present Invention

TABLE 1A

| Entry | Compound Structure | Name |
|---|---|---|
| 1 | 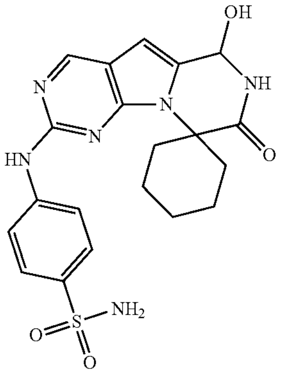 [SMILES: NS(=O)(=O)c1ccc(Nc2ncc3cc4n(c3n2)C2(CCCCC2)C(=O)NC4O)cc1] | 4-((6'-hydroxy-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 2 | 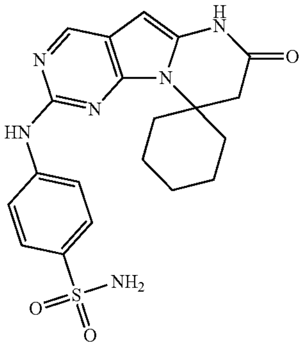 [SMILES: NS(=O)(=O)c1ccc(Nc2ncc3cc4n(c3n2)C2(CCCCC2)CC(=O)N4)cc1] | 4-((7'-oxo-7',8'-dihydro-6'H-spiro[cyclohexane-1,9'-pyrrolo[1,5-a:2,3-d']dipyrimidin]-2'-yl)amino)benzenesulfonamide |
| 3 | 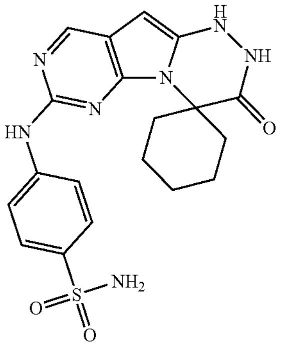 | 4-((3'-oxo-2',3'-dihydro-1'H-spiro[cyclohexane-1,4'-pyrimido[5',4':4,5]pyrrolo[2,1-c][1,2,4]triazin]-7'-yl)amino)benzenesulfonamide |
| 4 | 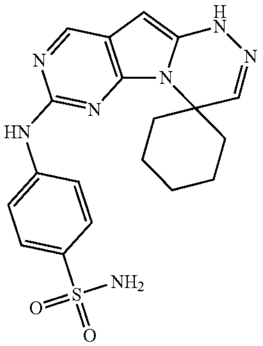 [SMILES: NS(=O)(=O)c1ccc(Nc2ncc3cc4n(c3n2)C2(C=NN4)CCCCC2)cc1] | 4-((1'H-spiro[cyclohexane-1,4'-pyrimido[5',4':4,5]pyrrolo[2,1-c][1,2,4]triazin]-7'-yl)amino)benzenesulfonamide |

TABLE 1A-continued

| Entry | Compound Structure | Name |
| --- | --- | --- |
| 5 | 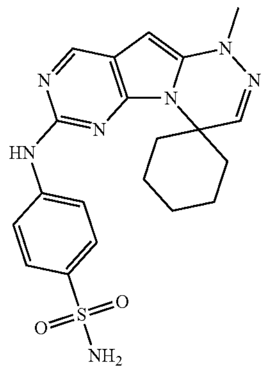 [SMILES: CN1N=CC2(CCCCC2)n2c1cc1cnc(Nc3ccc(S(N)(=O)=O)cc3)nc12] | 4-((1'-methyl-1'H-spiro[cyclohexane-1,4'-pyrimido[5',4':4,5]pyrrolo[2,1-c][1,2,4]triazin]-7'-yl)amino)benzenesulfonamide |
| 6 | 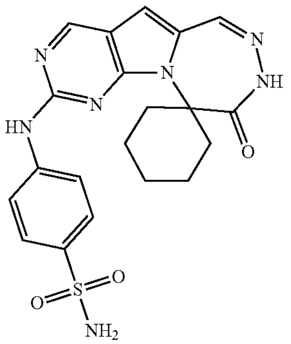 [SMILES: NS(=O)(=O)c1ccc(Nc2ncc3cc4n(c3n2)C2(CCCCC2)C(=O)NN=C4)cc1] | 4-((9'-oxo-8',9'-dihydrospiro[cyclohexane-1,10'-pyrimido[5',4':4,5]pyrrolo[2,1-d][1,2,5]triazepin]-2'-yl)amino)benzenesulfonamide |
| 7 | 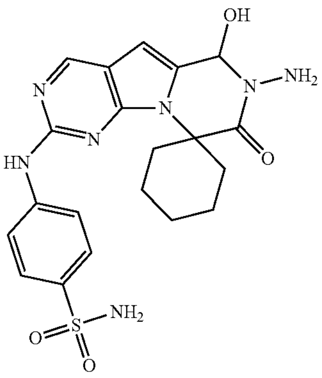 [SMILES: NN1C(=O)C2(CCCCC2)n2c(cc3cnc(Nc4ccc(S(N)(=O)=O)cc4)nc32)C1O] | 4-((7'-amino-6'-hydroxy-8'-oxo-7',8'-dihydro-6'H-spiro[cyclohexane-1,9'-pyrazino[11,2':1,5]pyrrolo[2,3-d]pyrimidin]-2'-yl)amino)benzenesulfonamide |
| 8 | 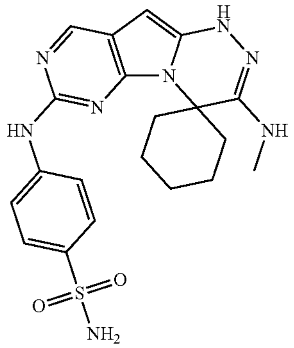 [SMILES: CNC1=NNc2cc3cnc(Nc4ccc(S(N)(=O)=O)cc4)nc3n2C12CCCCC2] | 4-((3'-(methylamino)-1'H-spiro[cyclohexane-1,4'-pyrimido[5',4':4,5]pyrrolo[2,1-c][1,2,4]triazin]-7'-yl)amino)benzenesulfonamide |

TABLE 1A-continued

| Entry | Compound Structure | Name |
| --- | --- | --- |
| 9 | 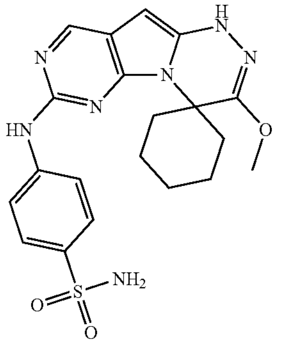 | 4-((3'-methoxy-1'H-spiro[cyclohexane-1,4'-pyrimido[5',4':4,5]pyrrolo[2,1-c][1,2,4]triazin]-7'-yl)amino)benzenesulfonamide |
| 10 | 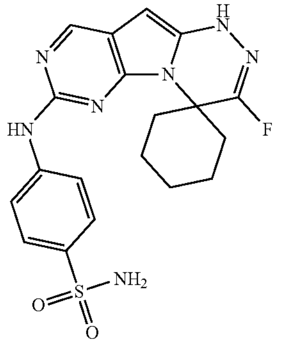 [SMILES: COC1=NNc2cc3cnc(Nc4ccc(S(N)(=O)=O)cc4)nc3n2C12CCCCC2] | 4-((3'-fluoro-1'H-spiro[cyclohexane-1,4'-pyrimido[5',4':4,5]pyrrolo[2,1-c][1,2,4]triazin]-7'-yl)amino)benzenesulfonamide |
| 11 | 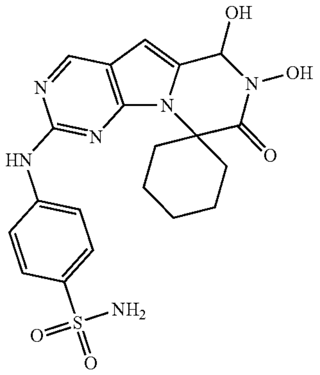 [SMILES: NS(=O)(=O)c1ccc(Nc2ncc3cc4n(c3n2)C2(CCCCC2)C(=O)N(O)C4O)cc1] | 4-((6',7'-dihydroxy-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |

TABLE 1B

| Entry | Compound Structure | Name |
| --- | --- | --- |
| 12 | 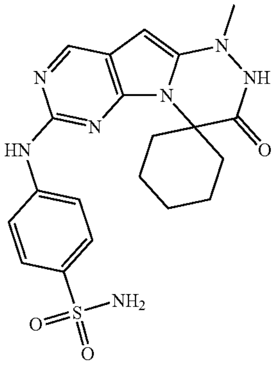 | 4-((1'-methyl-3'-oxo-2',3'-dihydro-1'H-spiro[cyclohexane-1,4'-pyrimido[5',4':4,5]pyrrolo[2,1-c][1,2,4]triazin]-7'-yl)amino)benzenesulfonamide |

TABLE 1B-continued

| Entry | Compound Structure | Name |
| --- | --- | --- |
| 13 | 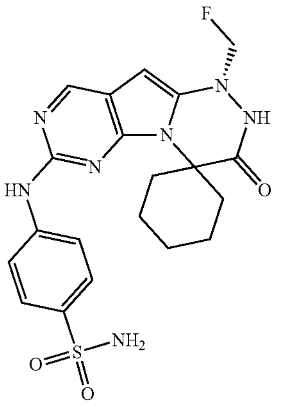 | (R)-4-((6'-(fluoromethyl)-6'H-spiro[cyclohexane-1,9'-pyrazino[1',2':1,5]pyrrolo[2,3-d]pyrimidin]-2'-yl)amino)benzenesulfonamide |
| 14 | 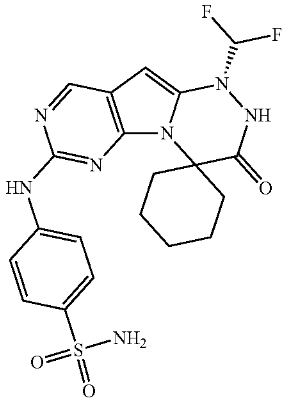 | (R)-4-((6'-(difluoromethyl)-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 15 | 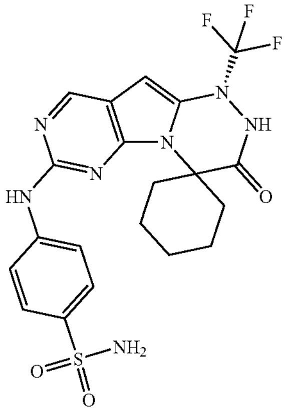 | (R)-4-((8'-oxo-6'-(trifluoromethyl)-7',8'-dihydro-6'H-spiro[cyclohexane-1,9'-pyrazino[1',2':1,5]pyrrolo[2,3-d]pyrimidin]-2'-yl)amino)benzenesulfonamide |

TABLE 1B-continued

| Entry | Compound Structure | Name |
| --- | --- | --- |
| 16 | 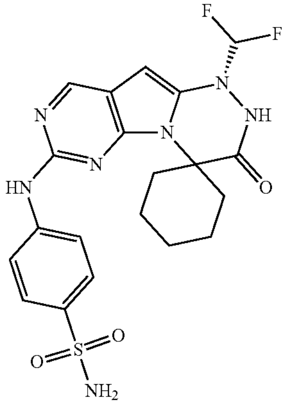 | 4-((1'-(difluoromethyl)-3'-oxo-2',3'-dihydro-1'H-spiro[cyclohexane-1,4'-pyrimido[5',4':4,5]pyrrolo[2,1-c][1,2,4]triazin]-7'-yl)amino)benzenesulfonamide |
| 17 | 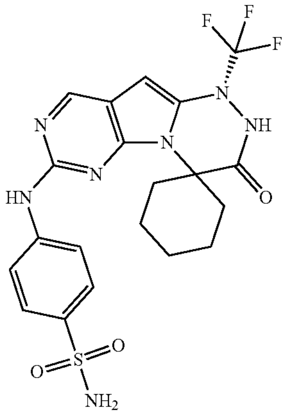 | 4-((3'-oxo-1'-(trifluoromethyl)-2',3'-dihydro-1'H-spiro[cyclohexane-1,4'-pyrimido[5',4':4,5]pyrrolo[2,1-c][1,2,4]triazin]-7'-yl)amino)benzenesulfonamide |
| 18 | 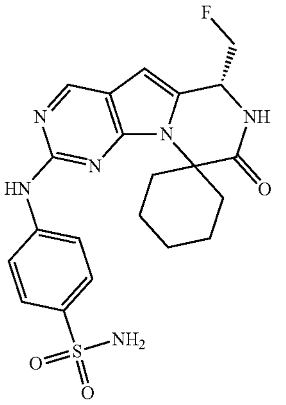 [SMILES: NS(=O)(=O)c1ccc(Nc2ncc3cc4n(c3n2)C2(CCCCC2)C(=O)N[C@H]4CF)cc1] | (R)-4-((6'-(fluoromethyl)-8'-oxo-7',8'-dihydro-6'H-spiro[cyclohexane-1,9'-pyrazino[11,2':1,5]pyrrolo[2,3-d]pyrimidin]-2'-yl)amino)benzenesulfonamide |
| 19 | 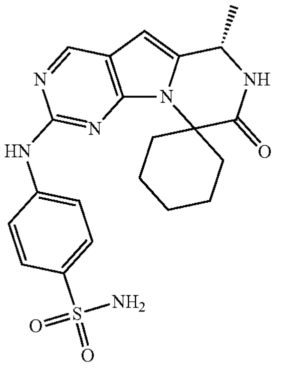 [SMILES: C[C@@H]1NC(=O)C2(CCCCC2)n2c1cc1cnc(Nc3ccc(S(N)(=O)=O)cc3)nc12] | (S)-4-((6'-methyl-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |

TABLE 1B-continued

| Entry | Compound Structure | Name |
|---|---|---|
| 20 | 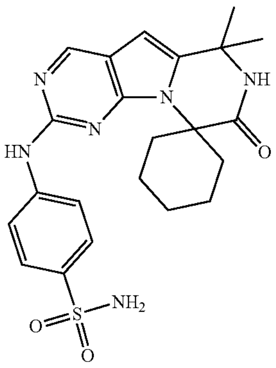 [SMILES: CC1(C)NC(=O)C2(CCCCC2)n2c1cc1cnc(Nc3ccc(S(N)(=O)=O)cc3)nc12] | 4-((6',6'-dimethyl-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 21 | 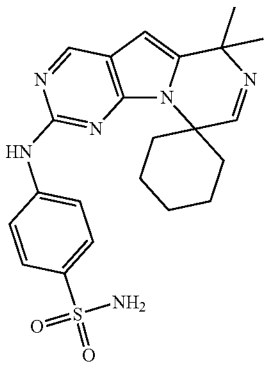 [SMILES: CC1(C)N=CC2(CCCCC2)n2c1cc1cnc(Nc3ccc(S(N)(=O)=O)cc3)nc12] | 4-((6',6'-dimethyl-6'H-spiro[cyclohexane-1,9'-pyrazino[1',2':1,5]pyrrolo[2,3-d]pyrimidin]-2'-yl)amino)benzenesulfonamide |
| 22 | 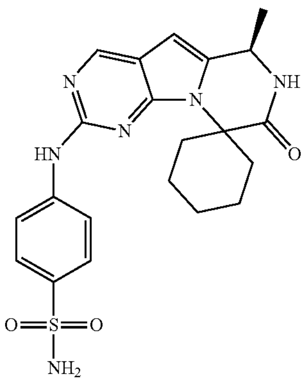 [SMILES: C[C@H]1NC(=O)C2(CCCCC2)n2c1cc1cnc(Nc3ccc(S(N)(=O)=O)cc3)nc12] | (R)-4-((6'-methyl-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 23 | 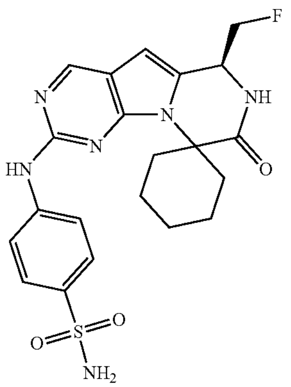 [SMILES: NS(=O)(=O)c1ccc(Nc2ncc3cc4n(c3n2)C2(CCCCC2)C(=O)N[C@@H]4CF)cc1] | (S)-4-((6'-(fluoromethyl)-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |

TABLE 1B-continued

| Entry | Compound Structure | Name |
| --- | --- | --- |
| 24 | 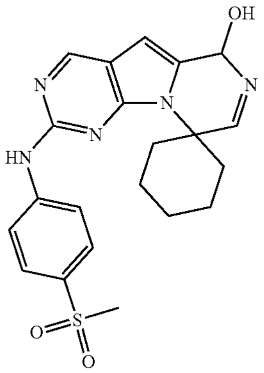 [SMILES: CS(=O)(=O)c1ccc(Nc2ncc3cc4n(c3n2)C2(C=NC4O)CCCCC2)cc1] | 2'-((4-(methylsulfonyl)phenyl)amino)-6'H-spiro[cyclohexane-1,9'-pyrazino[1',2':1,5]pyrrolo[2,3-d]pyrimidin]-6'-ol |
| 25 | 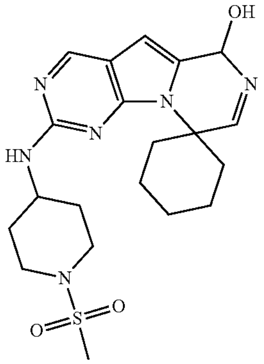 [SMILES: CS(=O)(=O)N1CCC(Nc2ncc3cc4n(c3n2)C2(C=NC4O)CCCCC2)CC1] | 2'-((1-(methylsulfonyl)piperidin-4-yl)amino)-6'H-spiro[cyclohexane-1,9'-pyrazino[1',2':1,5]pyrrolo[2,3-d]pyrimidin]-6'-ol |
| 26 | 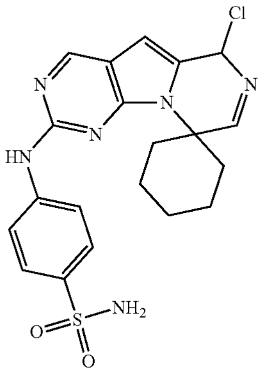 [SMILES: NS(=O)(=O)c1ccc(Nc2ncc3cc4n(c3n2)C2(C=NC4Cl)CCCCC2)cc1] | 4-((6'-chloro-6'H-spiro[cyclohexane-1,9'-pyrazino[1',2':1,5]pyrrolo[2,3-d]pyrimidin]-2'-yl)amino)benzenesulfonamide |
| 27 | 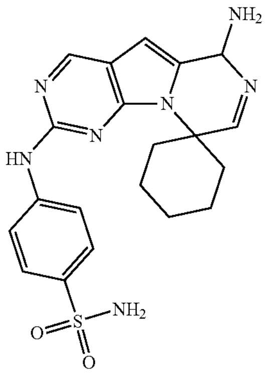 [SMILES: NC1N=CC2(CCCCC2)n2c1cc1cnc(Nc3ccc(S(N)(=O)=O)cc3)nc12] | 4-((6'-amino-6'H-spiro[cyclohexane-1,9'-pyrazino[1',2':1,5]pyrrolo[2,3-d]pyrimidin]-2'-yl)amino)benzenesulfonamide |

TABLE 1B-continued

| Entry | Compound Structure | Name |
|---|---|---|
| 28 | 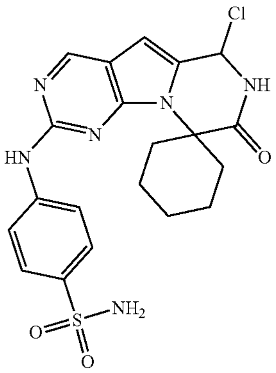 [SMILES: NS(=O)(=O)c1ccc(Nc2ncc3cc4n(c3n2)C2(CCCCC2)C(=O)NC4Cl)cc1] | 4-((6'-chloro-8'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 29 | 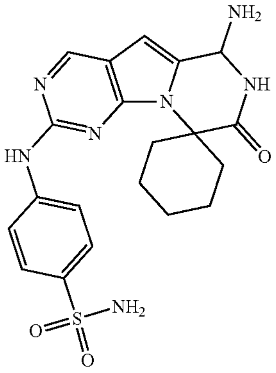 [SMILES: NC1NC(=O)C2(CCCCC2)n2c1cc1cnc(Nc3ccc(S(N)(=O)=O)cc3)nc12] | 4-((6'-amino-8'-oxo-7',8'-dihydro-6'H-spiro[cyclohexane-1,9'-pyrazino[11,2':1,5]pyrrolo[2,3-d]pyrimidin]-2'-yl)amino)benzenesulfonamide |
| 30 | 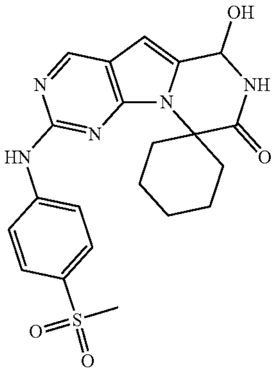 [SMILES: CS(=O)(=O)c1ccc(Nc2ncc3cc4n(c3n2)C2(CCCCC2)C(=O)NC4O)cc1] | 6'-hydroxy-2'-((4-(methylsulfonyl)phenyl)amino)-6',7'-dihydro-8'H-spiro[cyclohexane-1,9'-pyrazino[11,2':1,5]pyrrolo[2,3-d]pyrimidin]-8'-one |
| 31 | 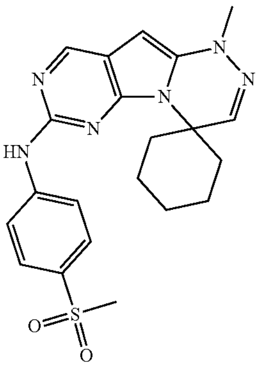 [SMILES: CN1N=CC2(CCCCC2)n2c1cc1cnc(Nc3ccc(S(C)(=O)=O)cc3)nc12] | 1'-methyl-N-(4-(methylsulfonyl)phenyl)-1'H-spiro[cyclohexane-1,4'-pyrimido[5',4':4,5]pyrrolo[2,1-c][1,2,4]triazin]-7'-amine |

TABLE 1B-continued

| Entry | Compound Structure | Name |
|---|---|---|
| 32 | 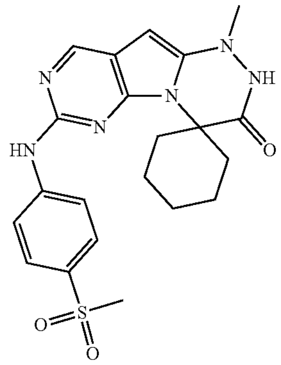 [SMILES: CN1NC(=O)C2(CCCCC2)n2c1cc1cnc(Nc3ccc(S(C)(=O)=O)cc3)nc12] | 1'-methyl-7'-((4-(methylsulfonyl)phenyl)amino)-1',2'-dihydro-3'H-spiro[cyclohexane-1,4'-pyrimido[5',4':4,5 ]pyrrolo[2,1-c][1,2,4]triazin]-3'-one |
| 33 | 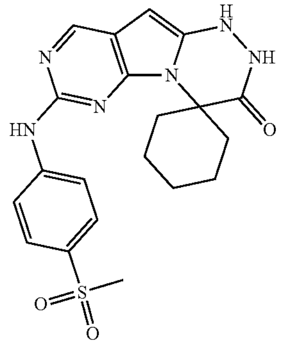 [SMILES: CS(=O)(=O)c1ccc(Nc2ncc3cc4n(c3n2)C2(CCCCC2)C(=O)NN4)cc1] | 7'-((4-(methylsulfonyl)phenyl)amino)-1',2'-dihydro-3'H-spiro[cyclohexane-1,4'-pyrimido[5',4':4,5]pyrrolo[2,1-c][1,2,4]triazin]-3'-one |
| 34 | 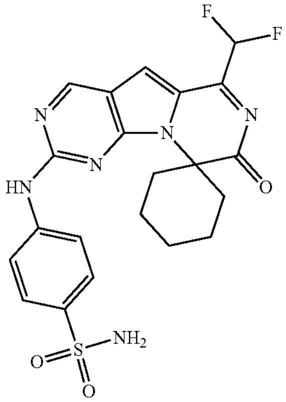 [SMILES: NS(=O)(=O)c1ccc(Nc2ncc3cc4n(c3n2)C2(CCCCC2)C(=O)N=C4C(F)F)cc1] | 4-((6'-(difluoromethyl)-8'-oxo-8'H-spiro[cyclohexane-1,9'-pyrazino[1',2':1,5]pyrrolo[2,3-d]pyrimidin]-2'-yl)amino)benzenesulfonamide |
| 35 | 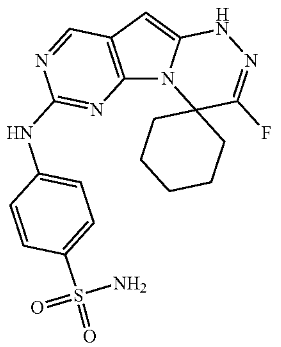 [SMILES: NS(=O)(=O)c1ccc(Nc2ncc3cc4n(c3n2)C2(CCCCC2)C(F)=NN4)cc1] | 4-((3'-fluoro-1'H-spiro[cyclohexane-1,4'-pyrimido[5',4':4,5]pyrrolo[2,1-c][1,2,4]triazin]-7'-yl)amino)benzenesulfonamide |

TABLE 1B-continued

| Entry | Compound Structure | Name |
|---|---|---|
| 36 | 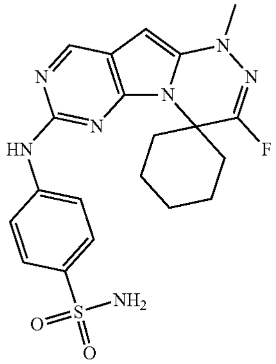 [SMILES: CN1N=C(F)C2(CCCCC2)n2c1cc1cnc(Nc3ccc(S(N)(=O)=O)cc3)nc12] | 4-((3'-fluoro-1'-methyl-1'H-spiro[cyclohexane-1,4'-pyrimido[5',4':4,5]pyrrolo[2,1-c][1,2,4]triazin]-7'-yl)amino)benzenesulfonamide |
| 37 | 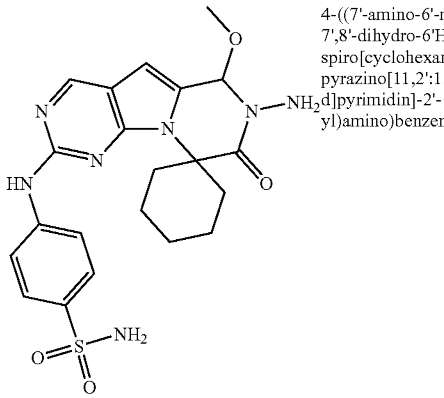 | 4-((7'-amino-6'-methoxy-8'-oxo-7',8'-dihydro-6'H-spiro[cyclohexane-1,9'-pyrazino[11,2':1,5]pyrrolo[2,3-d]pyrimidin]-2'-yl)amino)benzenesulfonamide |
| 38 | 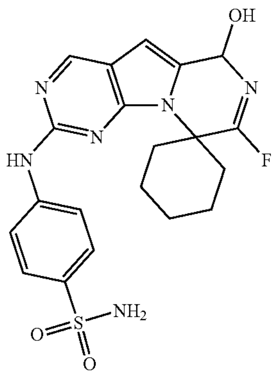 [SMILES: NS(=O)(=O)c1ccc(Nc2ncc3cc4n(c3n2)C2(CCCCC2)C(F)=NC4O)cc1] | 4-((8'-fluoro-6'-hydroxy-6'H-spiro[cyclohexane-1,9'-pyrazino[1',2':1,5]pyrrolo[2,3-d]pyrimidin]-2'-yl)amino)benzenesulfonamide |
| 39 | 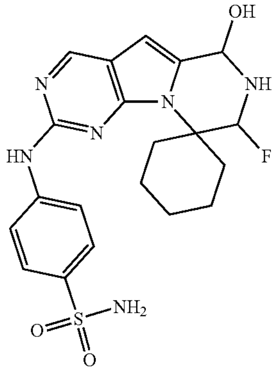 [SMILES: NS(=O)(=O)c1ccc(Nc2ncc3cc4n(c3n2)C2(CCCCC2)C(F)NC4O)cc1] | 4-((8'-fluoro-6'-hydroxy-7',8'-dihydro-6'H-spiro[cyclohexane-1,9'-pyrazino[1',2':1,5]pyrrolo[2,3-d]pyrimidin]-2'-yl)amino)benzenesulfonamide |

TABLE 1C

| Compound | Compound Structure | Name |
|---|---|---|
| 40 | 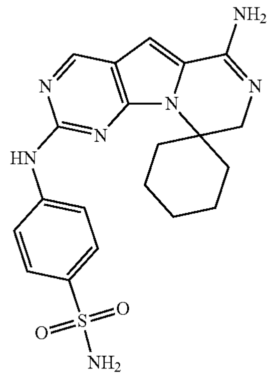 [SMILES: NC1=NCC2(CCCCC2)n2c1cc1cnc(Nc3ccc(S(N)(=O)=O)cc3)nc12] | 4-((6'-amino-8'H-spiro[cyclohexane-1,9'-pyrazino[1',2':1,5]pyrrolo[2,3-d]pyrimidin]-2'-yl)amino)benzenesulfonamide |
| 41 | 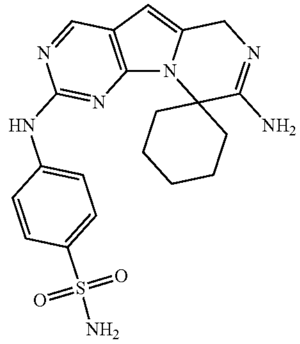 [SMILES: NC1=NCc2cc3cnc(Nc4ccc(S(N)(=O)=O)cc4)nc3n2C12CCCCC2] | 4-((8'-amino-6'H-spiro[cyclohexane-1,9'-pyrazino[1',2':1,5]pyrrolo[2,3-d]pyrimidin]-2'-yl)amino)benzenesulfonamide |
| 42 | 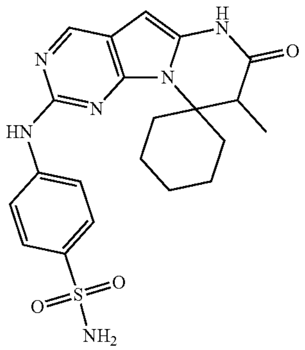 [SMILES: CC1C(=O)Nc2cc3cnc(Nc4ccc(S(N)(=O)=O)cc4)nc3n2C12CCCCC2] | 4-((8'-methyl-7'-oxo-7',8'-dihydro-6'H-spiro[cyclohexane-1,9'-pyrrolo[1,5-a:2,3-d']dipyrimidin]-2'-yl)amino)benzenesulfonamide |
| 43 | 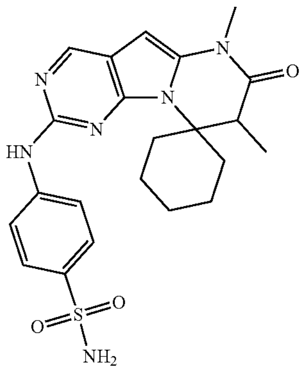 [SMILES: CC1C(=O)N(C)c2cc3cnc(Nc4ccc(S(N)(=O)=O)cc4)nc3n2C12CCCCC2] | 4-((6',8'-dimethyl-7'-oxo-7',8'-dihydro-6'H-spiro[cyclohexane-1,9'-pyrrolo[1,5-a:2,3-d']dipyrimidin]-2'-yl)amino)benzenesulfonamide |

TABLE 1C-continued

| Compound | Compound Structure | Name |
|---|---|---|
| 44 | 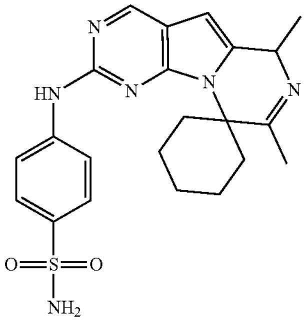 [SMILES: CC1=NC(C)c2cc3cnc(Nc4ccc(S(N)(=O)=O)cc4)nc3n2C12CCCCC2] | 4-((6',8'-dimethyl-6'H-spiro[cyclohexane-1,9'-pyrazino[1',2':1,5]pyrrolo[2,3-d]pyrimidin]-2'-yl)amino)benzenesulfonamide |
| 45 | 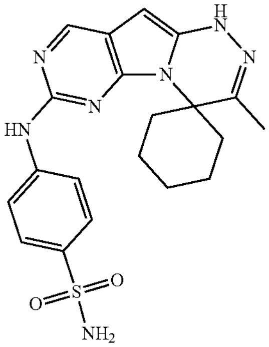 [SMILES: CC1=NNc2cc3cnc(Nc4ccc(S(N)(=O)=O)cc4)nc3n2C12CCCCC2] | 4-((3'-methyl-l'H-spiro[cyclohexane-1,4'-pyrimido[5',4':4,5]pyrrolo[2,1-c][1,2,4]triazin]-7'-yl)amino)benzenesulfonamide |
| 46 | 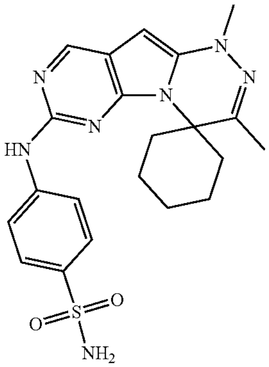 [SMILES: CC1=NN(C)c2cc3cnc(Nc4ccc(S(N)(=O)=O)cc4)nc3n2C12CCCCC2] | 4-((1',3'-dimethyl-1'H-spiro[cyclohexane-1,4'-pyrimido[5',4':4,5]pyrrolo[2,1-c][1,2,4]triazin]-7'-yl)amino)benzenesulfonamide |
| 47 | 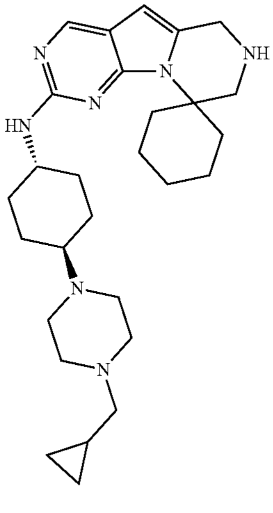 [SMILES: c1nc(N[C@H]2CC[C@H](N3CCN(CC4CC4)CC3)CC2)nc2c1cc1n2C2(CCCCC2)CNC1] | N-((1r,4r)-4-(4-(cyclopropylmethyl)piperazin-1-yl)cyclohexyl)-7',8'-dihydro-6'H-spiro[cyclohexane-1,9'-pyrazino[1',2':1,5]pyrrolo[2,3-d]pyrimidin]-2'-amine |

TABLE 1C-continued

| Compound | Compound Structure | Name |
|---|---|---|
| 48 | 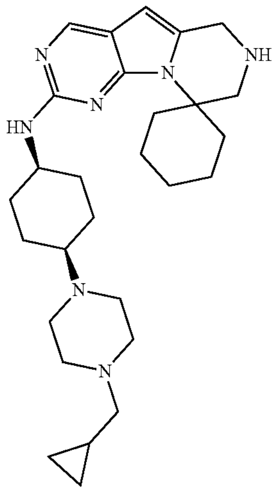 [SMILES: c1nc(N[C@H]2CC[C@@H](N3CCN(CC4CC4)CC3)CC2)nc2c1cc1n2C2(CCCCC2)CNC1] | N-((1s,4s)-4-(4-(cyclopropylmethyl)piperazin-1-yl)cyclohexyl)-7',8'-dihydro-6'H-spiro[cyclohexane-1,9'-pyrazino[11,2':1,5]pyrrolo[2,3-d]pyrimidin]-2'-amine |
| 49 | 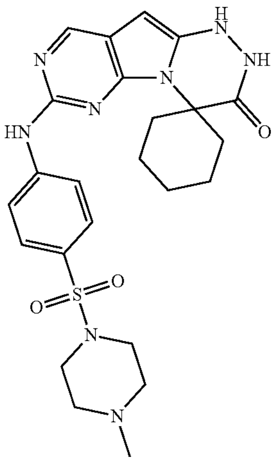 [SMILES: CN1CCN(S(=O)(=O)c2ccc(Nc3ncc4cc5n(c4n3)C3(CCCCC3)C(=O)NN5)cc2)CC1] | 7'-((4-((4-methylpiperazin-1-yl)sulfonyl)phenyl)amino)-1',2'-dihydro-3'H-spiro[cyclohexane-1,4'-pyrimido[5',4':4,5]pyrrolo[2,1-c][1,2,4]triazin]-3'-one |
| 50 | 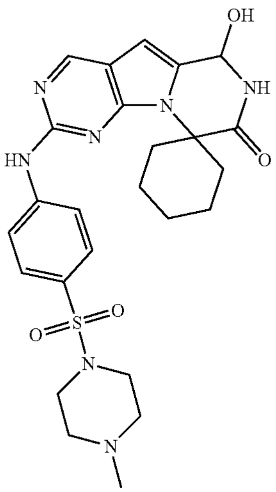 [SMILES: CN1CCN(S(=O)(=O)c2ccc(Nc3ncc4cc5n(c4n3)C3(CCCCC3)C(=O)NC5O)cc2)CC1] | 6'-hydroxy-2'-((4-((4-methylpiperazin-1-yl)sulfonyl)phenyl)amino)-6',7'-dihydro-8'H-spiro[cyclohexane-1,9'-pyrazino[1',2':1,5]pyrrolo[2,3-d]pyrimidin]-8'-one |

TABLE 1C-continued

| Compound | Compound Structure | Name |
|---|---|---|
| 51 | 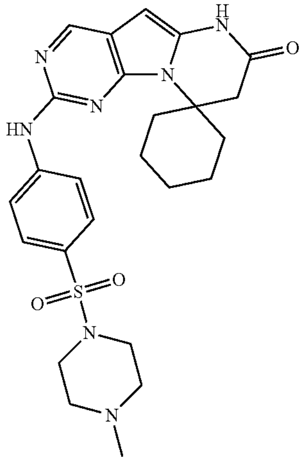 [SMILES: CN1CCN(S(=O)(=O)c2ccc(Nc3ncc4cc5n(c4n3)C3(CCCCC3)CC(=O)N5)cc2)CC1] | 2'-((4-((4-methylpiperazin-1-yl)sulfonyl)phenyl)amino)-6'H-spiro[cyclohexane-1,9'-pyrrolo[1,5-a:2,3-d']dipyrimidin]-7'(8'H)-one |
| 52 | 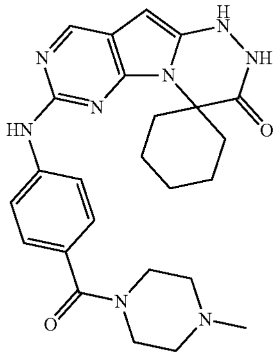 [SMILES: CN1CCN(C(=O)c2ccc(Nc3ncc4cc5n(c4n3)C3(CCCCC3)C(=O)NN5)cc2)CC1] | 7'-((4-(4-methylpiperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 53 | 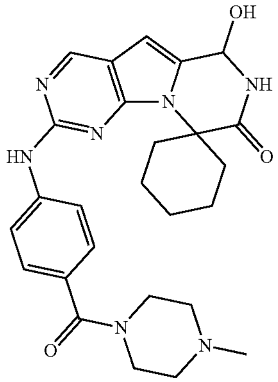 [SMILES: CN1CCN(C(=O)c2ccc(Nc3ncc4cc5n(c4n3)C3(CCCCC3)C(=O)NC5O)cc2)CC1] | 6'-hydroxy-2'-((4-(4-methylpiperazine-1-carbonyl)phenyl)amino)-6',7'-dihydro-8'H-spiro[cyclohexane-1,9'-pyrazino[1',2':1,5]pyrrolo[2,3-d]pyrimidin]-8'-one |
| 54 | 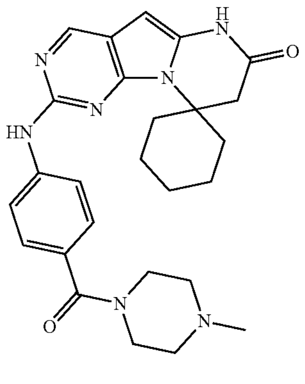 [SMILES: CN1CCN(C(=O)c2ccc(Nc3ncc4cc5n(c4n3)C3(CCCCC3)CC(=O)N5)cc2)CC1] | 2'-((4-(4-methylpiperazine-1-carbonyl)phenyl)amino)-6'H-spiro[cyclohexane-1,9'-pyrrolo[1,5-a:2,3-d']dipyrimidin]-7'(8'H)-one |

TABLE 1C-continued

| Compound | Compound Structure | Name |
|---|---|---|
| 55 | 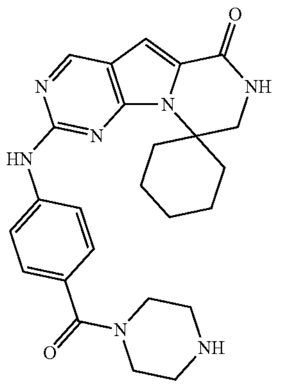 [SMILES: O=C1NCC2(CCCCC2)n2c1cc1cnc(Nc3ccc(C(=O)N4CCNCC4)cc3)nc12] | 2'-((4-(piperazine-1-carbonyl)phenyl)amino)-7',8'-dihydro-6'H-spiro[cyclohexane-1,9'-pyrazino[1',2':1,5]pyrrolo[2,3-d]pyrimidin]-6'-one |
| 56 | 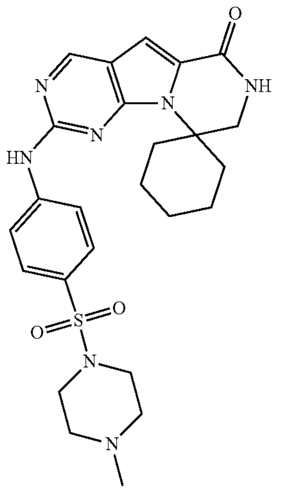 [SMILES: CN1CCN(S(=O)(=O)c2ccc(Nc3ncc4cc5n(c4n3)C3(CCCCC3)CNC5=O)cc2)CC1] | 2'-((4-((4-methylpiperazin-1-yl)sulfonyl)phenyl)amino)-7',8'-dihydro-6'H-spiro[cyclohexane-1,9'-pyrazino[1',2':1,5]pyrrolo[2,3-d]pyrimidin]-6'-one |
| 57 | 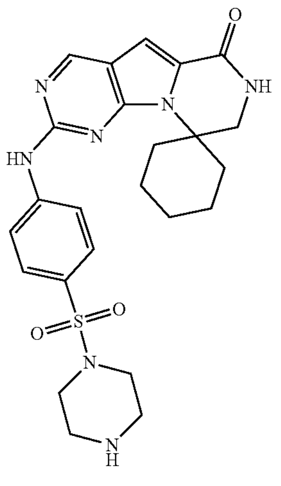 [SMILES: O=C1NCC2(CCCCC2)n2c1cc1cnc(Nc3ccc(S(=O)(=O)N4CCNCC4)cc3)nc12] | 2'-((4-(piperazin-1-ylsulfonyl)phenyl)amino)-7',8'-dihydro-6'H-spiro[cyclohexane-1,9'-pyrazino[1',2':1,5]pyrrolo[2,3-d]pyrimidin]-6'-one |

TABLE 1C-continued

| Compound | Compound Structure | Name |
|---|---|---|
| 58 | 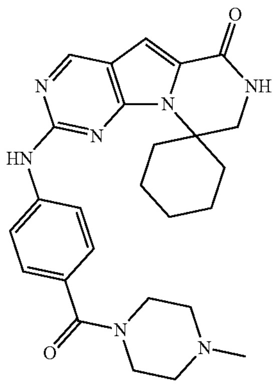 [SMILES: CN1CCN(C(=O)c2ccc(Nc3ncc4cc5n(c4n3)C3(CCCCC3)CNC5=O)cc2)CC1] | 2'-((4-(4-methylpiperazine-1-carbonyl)phenyl)amino)-7',8'-dihydro-6'H-spiro[cyclohexane-1,9'-pyrazino[1',2':1,5]pyrrolo[2,3-d]pyrimidin]-6'-one |
| 59 | 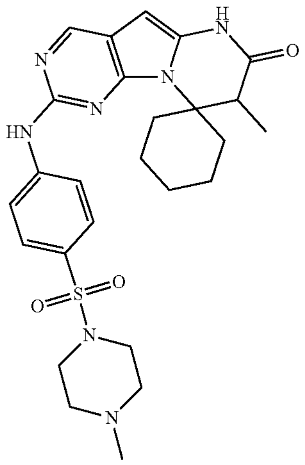 [SMILES: CC1C(=O)Nc2cc3cnc(Nc4ccc(S(=O)(=O)N5CCN(C)CC5)cc4)nc3n2C12CCCCC2] | 8'-methyl-2'-((4-((4-methylpiperazin-1-yl)sulfonyl)phenyl)amino)-6'H-spiro[cyclohexane-1,9'-pyrrolo[1,5-a:2,3-d']dipyrimidin]-7'(8'H)-one |
| 60 | 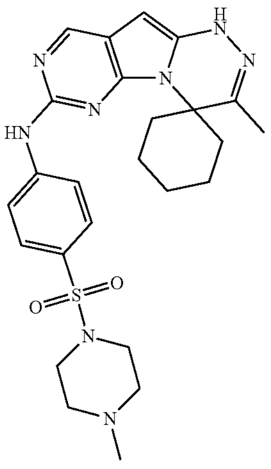 [SMILES: CC1=NNc2cc3cnc(Nc4ccc(S(=O)(=O)N5CCN(C)CC5)cc4)nc3n2C12CCCCC2] | 3'-methyl-N-(4-((4-methylpiperazin-1-yl)sulfonyl)phenyl)-1'H-spiro[cyclohexane-1,4'-pyrimido[5',4':4,5]pyrrolo[2,1-c][1,2,4]triazin]-7'-amine |

TABLE 1C-continued

| Compound | Compound Structure | Name |
| --- | --- | --- |
| 61 | 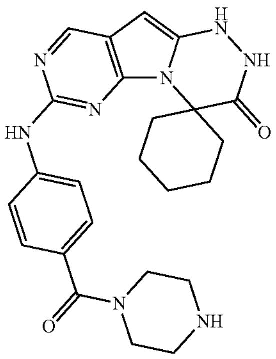 [SMILES: O=C(c1ccc(Nc2ncc3cc4n(c3n2)C2(CCCCC2)C(=O)NN4)cc1)N1CCNCC1] | 7'-((4-(piperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 62 | 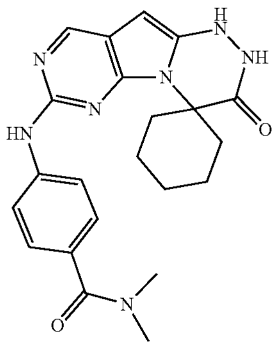 [SMILES: CN(C)C(=O)c1ccc(Nc2ncc3cc4n(c3n2)C2(CCCCC2)C(=O)NN4)cc1] | N,N-dimethyl-4-((3'-oxo-2',3'-dihydro-1'H-spiro[cyclohexane-1,4'-pyrimido[5',4':4,5]pyrrolo[2,1-c][1,2,4]triazin]-7'-yl)amino)benzamide |
| 63 | 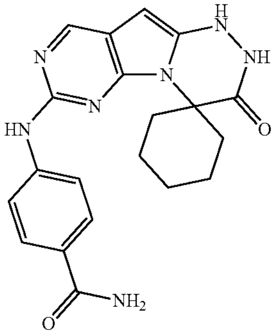 [SMILES: NC(=O)c1ccc(Nc2ncc3cc4n(c3n2)C2(CCCCC2)C(=O)NN4)cc1] | 4-((3'-oxo-2',3'-dihydro-1'H-spiro[cyclohexane-1,4'-pyrimido[5',4':4,5]pyrrolo[2,1-c][1,2,4]triazin]-7'-yl)amino)benzamide |
| 64 | 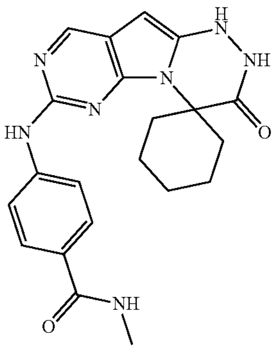 [SMILES: CNC(=O)c1ccc(Nc2ncc3cc4n(c3n2)C2(CCCCC2)C(=O)NN4)cc1] | N-methyl-4-((3'-oxo-2',3'-dihydro-l'H-spiro[cyclohexane-1,4'-pyrimido[5',4':4,5]pyrrolo[2,1-c][1,2,4]triazin]-7'-yl)amino)benzamide |

TABLE 1C-continued

| Compound | Compound Structure | Name |
|---|---|---|
| 65 | 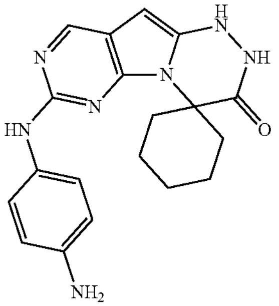 [SMILES: Nc1ccc(Nc2ncc3cc4n(c3n2)C2(CCCCC2)C(=O)NN4)cc1] | 7'-((4-aminophenyl)amino)-1',2'-dihydro-3'H-spiro[cyclohexane-1,4'-pyrimido[5',4':4,5]pyrrolo[2,1-c][1,2,4]triazin]-3'-one |
| 66 | 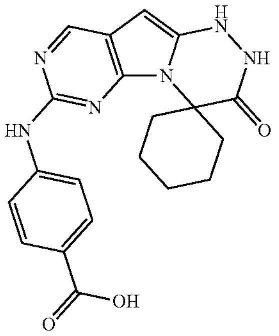 [SMILES: O=C(O)c1ccc(Nc2ncc3cc4n(c3n2)C2(CCCCC2)C(=O)NN4)cc1] | 4-((3'-oxo-2',3'-dihydro-1'H-spiro[cyclohexane-1,4'-pyrimido[5',4':4,5]pyrrolo[2,1-c][1,2,4]triazin]-7'-yl)amino)benzoic acid |
| 67 | 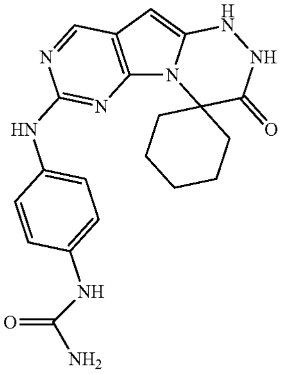 [SMILES: NC(=O)Nc1ccc(Nc2ncc3cc4n(c3n2)C2(CCCCC2)C(=O)NN4)cc1] | 1-(4-((3'-oxo-2',3'-dihydro-1'H-spiro[cyclohexane-1,4'-pyrimido[5',4':4,5]pyrrolo[2,1-c][1,2,4]triazin]-7'-yl)amino)phenyl)urea |
| 68 | 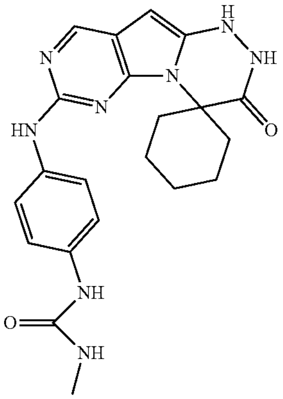 [SMILES: CNC(=O)Nc1ccc(Nc2ncc3cc4n(c3n2)C2(CCCCC2)C(=O)NN4)cc1] | 1-methyl-3-(4-((3'-oxo-2',3'-dihydro-1'H-spiro[cyclohexane-1,4'-pyrimido[5',4':4,5 ]pyrrolo[2,1-c][1,2,4]triazin]-7'-yl)amino)phenyl)urea |

TABLE 1C-continued

| Compound | Compound Structure | Name |
| --- | --- | --- |
| 69 | 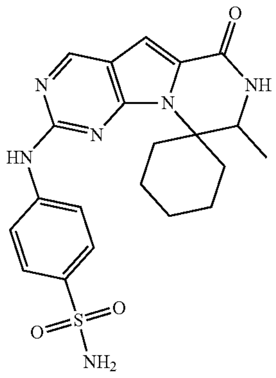 [SMILES: CC1NC(=O)c2cc3cnc(Nc4ccc(S(N)(=O)=O)cc4)nc3n2C12CCCCC2] | 4-((8'-methyl-6'-oxo-7',8'-dihydro-6'H-spiro[cyclohexane-1,9'-pyrazino[1',2':1,5]pyrrolo[2,3-d]pyrimidin]-2'-yl)amino)benzenesulfonamide |
| 70 | 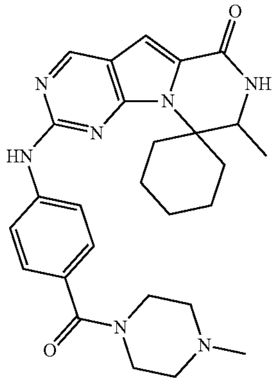 [SMILES: CC1NC(=O)c2cc3cnc(Nc4ccc(C(=O)N5CCN(C)CC5)cc4)nc3n2C12CCCCC2] | 8'-methyl-2'-((4-(4-methylpiperazine-1-carbonyl)phenyl)amino)-7',8'-dihydro-6'H-spiro[cyclohexane-1,9'-pyrazino[1',2':1,5]pyrrolo[2,3-d]pyrimidin]-6'-one |
| 71 | 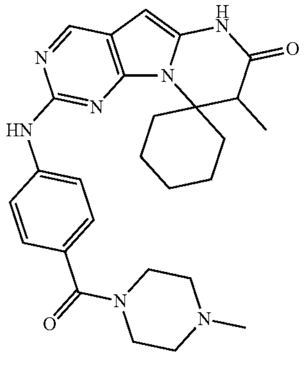 [SMILES: CC1C(=O)Nc2cc3cnc(Nc4ccc(C(=O)N5CCN(C)CC5)cc4)nc3n2C12CCCCC2] | 8'-methyl-2'-((4-(4-methylpiperazine-1-carbonyl)phenyl)amino)-6'H-spiro[cyclohexane-1,9'-pyrrolo[1,5-a:2,3-d']dipyrimidin]-7'(8'H)-one |
| 72 | 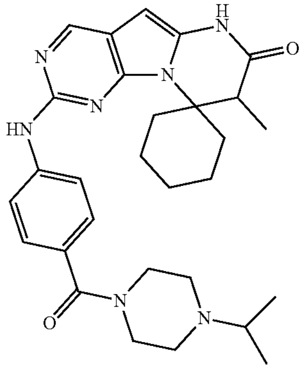 [SMILES: CC(C)N1CCN(C(=O)c2ccc(Nc3ncc4cc5n(c4n3)C3(CCCCC3)C(C)C(=O)N5)cc2)CC1] | 2'-((4-(4-isopropylpiperazine-1-carbonyl)phenyl)amino)-8'-methyl-6'H-spiro[cyclohexane-1,9'-pyrrolo[1,5-a:2,3-d']dipyrimidin]-7'(8'H)-one |

TABLE 1C-continued

| Compound | Compound Structure | Name |
| --- | --- | --- |
| 73 | 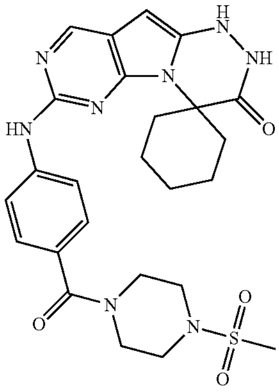 [SMILES: CS(=O)(=O)N1CCN(C(=O)c2ccc(Nc3ncc4cc5n(c4n3)C3(CCCCC3)C(=O)NN5)cc2)CC1] | 7'-((4-(4-(methylsulfonyl)piperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 74 | 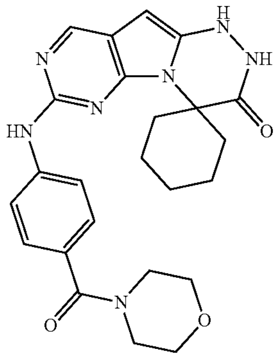 [SMILES: O=C(c1ccc(Nc2ncc3cc4n(c3n2)C2(CCCCC2)C(=O)NN4)cc1)N1CCOCC1] | 7'-((4-(morpholine-4-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 75 | 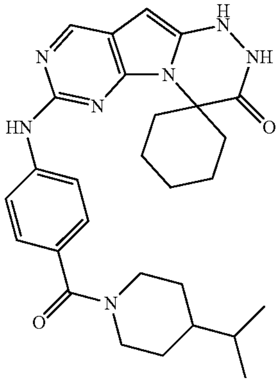 [SMILES: CC(C)C1CCN(C(=O)c2ccc(Nc3ncc4cc5n(c4n3)C3(CCCCC3)C(=O)NN5)cc2)CC1] | 7'-((4-(4-isopropylpiperidine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 76 | 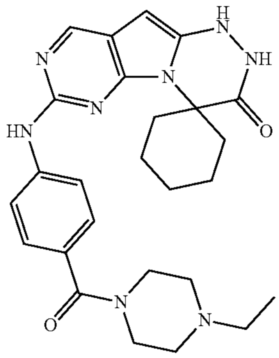 [SMILES: CCN1CCN(C(=O)c2ccc(Nc3ncc4cc5n(c4n3)C3(CCCCC3)C(=O)NN5)cc2)CC1] | 7'-((4-(4-ethylpiperazine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |

TABLE 1C-continued

| Compound | Compound Structure | Name |
|---|---|---|
| 77 | 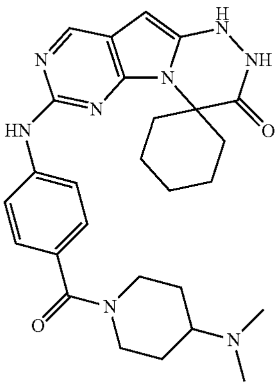 [SMILES: CN(C)C1CCN(C(=O)c2ccc(Nc3ncc4cc5n(c4n3)C3(CCCCC3)C(=O)NN5)cc2)CC1] | 7'-((4-(4-(dimethylamino)piperidine-1-carbonyl)phenyl)amino)-1',2'-dihydro-3'H-spiro[cyclohexane-1,4'-pyrimido[5',4':4,5 ]pyrrolo[2,1-c][1,2,4]triazin]-3'-one |
| 78 | 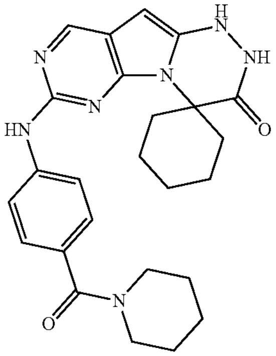 [SMILES: O=C(c1ccc(Nc2ncc3cc4n(c3n2)C2(CCCCC2)C(=O)NN4)cc1)N1CCCCC1] | 7'-((4-(piperidine-1-carbonyl)phenyl)amino)-1',2'-dihydro-3'H-spiro[cyclohexane-1,4'-pyrimido[5',4':4,5]pyrrolo[2,1-c][1,2,4]triazin]-3'-one |
| 79 | 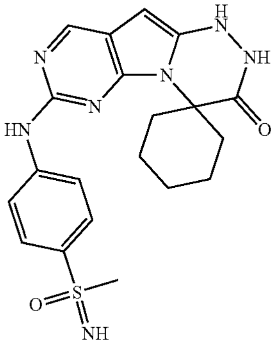 [SMILES: CS(=N)(=O)c1ccc(Nc2ncc3cc4n(c3n2)C2(CCCCC2)C(=O)NN4)cc1] | 7'-((4-(S-methylsulfonimidoyl)phenyl)amino)-1',2'-dihydro-3'H-spiro[cyclohexane-1,4'-pyrimido[5',4':4,5 ]pyrrolo[2,1-c][1,2,4]triazin]-3'-one |
| 80 | 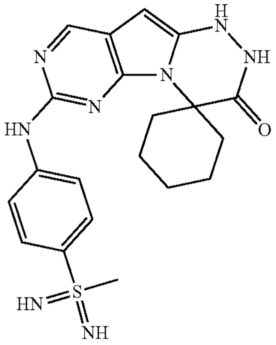 [SMILES: CS(=N)(=N)c1ccc(Nc2ncc3cc4n(c3n2)C2(CCCCC2)C(=O)NN4)cc1] | |

TABLE 1C-continued

| Compound | Compound Structure | Name |
| --- | --- | --- |
| 81 | 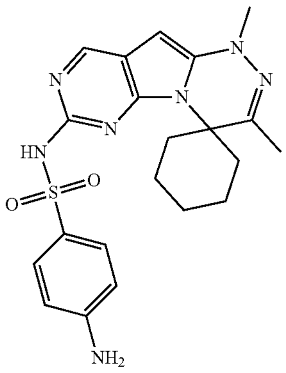 [SMILES: CC1=NN(C)c2cc3cnc(NS(=O)(=O)c4ccc(N)cc4)nc3n2C12CCCCC2] | 4-amino-N-(1',3'-dimethyl-1'H-spiro[cyclohexane-1,4'-pyrimido[5',4':4,5 ]pyrrolo[2,1-c][1,2,4]triazin]-7'-yl)benzenesulfonamide |
| 82 | 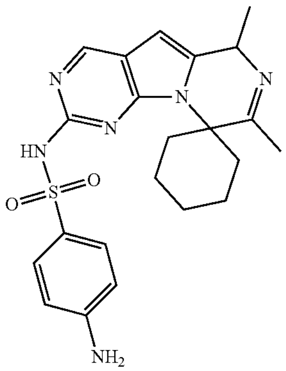 [SMILES: CC1=NC(C)c2cc3cnc(NS(=O)(=O)c4ccc(N)cc4)nc3n2C12CCCCC2] | 4-amino-N-(6',8'-dimethyl-6'H-spiro[cyclohexane-1,9'-pyrazino[1',2':1,5]pyrrolo[2,3-d]pyrimidin]-2'-yl)benzenesulfonamide |
| 83 | 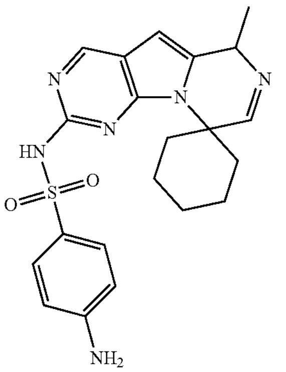 [SMILES: CC1N=CC2(CCCCC2)n2c1cc1cnc(NS(=O)(=O)c3ccc(N)cc3)nc12] | 4-amino-N-(6'-methyl-6'H-spiro[cyclohexane-1,9'-pyrazino[1',2':1,5]pyrrolo[2,3-d]pyrimidin]-2'-yl)benzenesulfonamide |
| 84 | 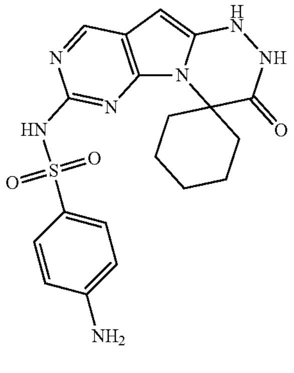 [SMILES: Nc1ccc(S(=O)(=O)Nc2ncc3cc4n(c3n2)C2(CCCCC2)C(=O)NN4)cc1] | 4-amino-N-(3'-oxo-2',3'-dihydro-1'H-spiro[cyclohexane-1,4'-pyrimido[5',4':4,5]pyrrolo[2,1-c][1,2,4]triazin]-7'-yl)benzenesulfonamide |

TABLE 1C-continued

| Compound | Compound Structure | Name |
|---|---|---|
| 85 | 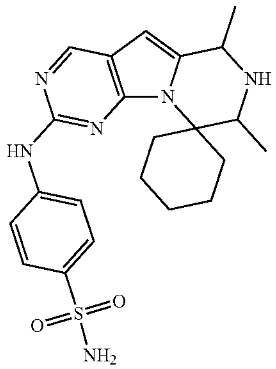 [SMILES: CC1NC(C)C2(CCCCC2)n2c1cc1cnc(Nc3ccc(S(N)(=O)=O)cc3)nc12] | 4-((6',8'-dimethyl-7',8'-dihydro-6'H-spiro[cyclohexane-1,9'-pyrazino[1',2':1,5]pyrrolo[2,3-d]pyrimidin]-2'-yl)amino)benzenesulfonamide |
| 86 | 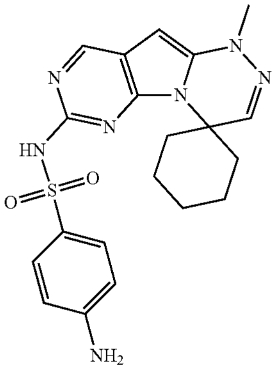 [SMILES: CN1N=CC2(CCCCC2)n2c1cc1cnc(NS(=O)(=O)c3ccc(N)cc3)nc12] | 4-amino-N-(1'-methyl-1'H-spiro[cyclohexane-1,4'-pyrimido[5',4':4,5]pyrrolo[2,1-c][1,2,4]triazin]-7'-yl)benzenesulfonamide |
| 87 | 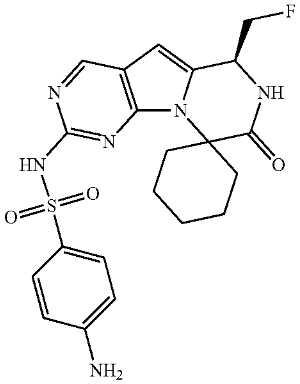 [SMILES: Nc1ccc(S(=O)(=O)Nc2ncc3cc4n(c3n2)C2(CCCCC2)C(=O)N[C@@H]4CF)cc1] | (S)-4-amino-N-(6'-(fluoromethyl)-8'-oxo-7',8'-dihydro-6'H-spiro[cyclohexane-1,9'-pyrazino[11,2':1,5]pyrrolo[2,3-d]pyrimidin]-2'-yl)benzenesulfonamide |
| 88 | 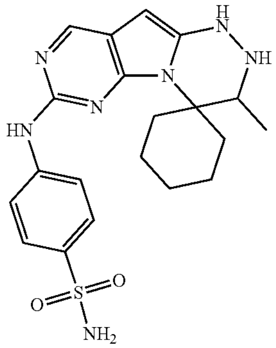 [SMILES: CC1NNc2cc3cnc(Nc4ccc(S(N)(=O)=O)cc4)nc3n2C12CCCCC2] | 4-((3'-methyl-2',3'-dihydro-1'H-spiro[cyclohexane-1,4'-pyrimido[5',4':4,5]pyrrolo[2,1-c][1,2,4]triazin]-7'-yl)amino)benzenesulfonamide |

TABLE 1C-continued

| Compound | Compound Structure | Name |
| --- | --- | --- |
| 89 | 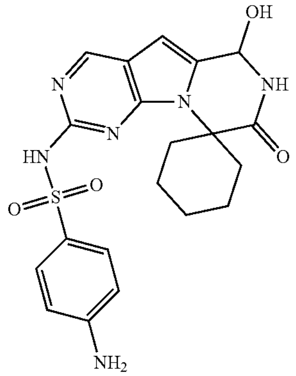 [SMILES: Nc1ccc(S(=O)(=O)Nc2ncc3cc4n(c3n2)C2(CCCCC2)C(=O)NC4O)cc1] | 4-amino-N-(6'-hydroxy-8'-oxo-7',8'-dihydro-6'H-spiro[cyclohexane-1,9'-pyrazino[1',2':1,5]pyrrolo[2,3-d]pyrimidin]-2'-yl)benzenesulfonamide |
| 90 | 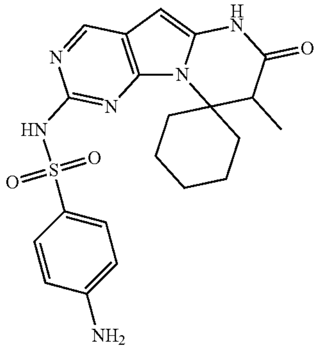 [SMILES: CC1C(=O)Nc2cc3cnc(NS(=O)(=O)c4ccc(N)cc4)nc3n2C12CCCCC2] | 4-amino-N-(8'-methyl-7'-oxo-7',8'-dihydro-6'H-spiro[cyclohexane-1,9'-pyrrolo[1,5-a:2,3-d']dipyrimidin]-2'-yl)benzenesulfonamide |
| 91 | 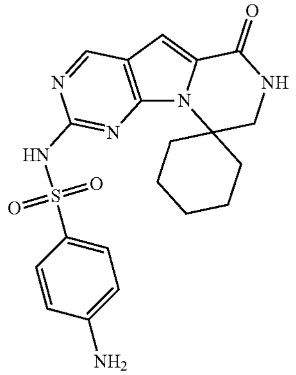 [SMILES: Nc1ccc(S(=O)(=O)Nc2ncc3cc4n(c3n2)C2(CCCCC2)CNC4=O)cc1] | 4-amino-N-(6'-oxo-7',8'-dihydro-6'H-spiro[cyclohexane-1,9'-pyrazino[1',2':1,5]pyrrolo[2,3-d]pyrimidin]-2'-yl)benzenesulfonamide |
| 92 | 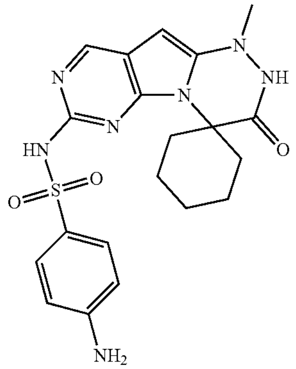 [SMILES: CN1NC(=O)C2(CCCCC2)n2c1cc1cnc(NS(=O)(=O)c3ccc(N)cc3)nc12] | 4-amino-N-(1'-methyl-3'-oxo-2',3'-dihydro-1'H-spiro[cyclohexane-1,4'-pyrimido[5',4':4,5]pyrrolo[2,1-c][1,2,4]triazin]-7'-yl)benzenesulfonamide |

Example 3: CDK Inhibition In Vitro Assays

Selected compounds disclosed herein were tested in kinase assays by Nanosyn (Santa Clara, CA) to determine their inhibitory effect on these CDKs. The assays were performed using microfluidic kinase detection technology (Caliper Assay Platform). The compounds were tested in 12-point dose-response format in singlicate at Km for ATP. Specifics of each assay are as described below:

CDK1/Cyclin $B_1$: Enzyme concentration: 0.08 nM; ATP concentration: 40 M; Incubation time: 3 hr.

CDK2/Cyclin A: Enzyme concentration: 0.1 nM; ATP concentration: 50 M; Incubation time: 3 hr.

CDK2/Cyclin E: Enzyme concentration: 0.15 nM; ATP concentration: 100 M; Incubation time: 3 hr.

CDK4/Cyclin D1: Enzyme concentration: 1 nM; ATP concentration: 200 M; Incubation time: 3 hr.

CDK6/Cyclin D3: Enzyme concentration: 2 nM; ATP concentration: 300 M; Incubation time: 3 hr.

CDK9/Cyclin T1: Enzyme concentration: 5 nM; ATP concentration: 10 M; Incubation time: 17 hr.

TABLE 2A

Biological Data

| Compound | CDK2-CYCLIN-A $IC_{50}$ (μM) | CDK2 CYCLIN-E $IC_{50}$ (μM) | CDK4-CYCLIN-D1 $IC_{50}$ (μM) | CDK6-CYCLIN-D3 $IC_{50}$ (μM) | CDK9-CYCLIN-T1 $IC_{50}$ (μM) |
|---|---|---|---|---|---|
| 1 | 0.00016 | 0.00034 | 0.0031 | 0.0075 | 0.0014 |
| 2 | 0.0004 | 0.0005 | 0.041 | 0.098 | 0.0045 |
| 3 | 0.0025 | 0.00056 | 0.130 | 0.35 | 0.062 |
| 4 | 0.001 | 0.001 | 0.053 | 0.17 | 0.011 |
| 12 | 0.0092 | 0.013 | 0.028 | 0.16 | 0.18 |
| 18 | 0.0017 | 0.0027 | 0.033 | 0.15 | 0.010 |
| 19 | 0.0043 | 0.0048 | 0.040 | 0.21 | 0.022 |

TABLE 2B

Biological Data

| Compound | CDK2-CYCLIN-A $IC_{50}$ (nM) | CDK2-CYCLIN-E $IC_{50}$ (nM) | CDK4-CYCLIN-D1 $IC_{50}$ (nM) | CDK6-CYCLIN-D3 $IC_{50}$ (nM) | CDK9-CYCLIN-T1 $IC_{50}$ (nM) |
|---|---|---|---|---|---|
| 5 | 2 | 3 | 41 | 231 | 26 |
| 23 | 1 | 1 | 19 | 45 | 11 |
| 42 | 1 | 1 | 57 | 147 | 6 |
| 43 | 4 | 4 | 69 | 186 | 21 |
| 45 | 16 | 19 | 436 | >1000 | 240 |
| 46 | 2 | 2 | 22 | 83 | 9 |
| 49 | 45 | 10 | 253 | 480 | 199 |
| 50 | 2 | 4 | 113 | 51 | 2 |
| 51 | 4 | 5 | 41 | 63 | 5 |
| 52 | 18 | 4.5 | 27 | 75 | 318 |
| 53 | 2 | 4 | 2 | 5 | 10 |
| 54 | 2 | 1 | 3 | 7 | 7 |
| 55 | 0.6 | 1 | 0.3 | 0.4 | 1 |
| 59 | 5 | 3 | 137 | 123 | 5 |
| 61 | 17 | 4 | 17 | 40 | 190 |
| 62 | 61 | 14 | 82 | 216 | 398 |
| 63 | 81 | 33 | 253 | 578 | 118 |
| 64 | 85 | 23 | 132 | 417 | 85 |
| 68 | 841 | 349 | 595 | >1000 | 284 |
| 71 | 4 | 3 | 9 | 15 | 9 |
| 74 | 29 | 8 | 60 | 137 | 653 |
| 79 | 16 | 5 | 172 | 291 | 89 |
| 84 | 571 | 207 | >1000 | >1000 | >1000 |
| 91 | 322 | 287 | 361 | 920 | 183 |

TABLE 3A

Biological Data

| Compound | CDK1 $IC_{50}$ (μM) | CDK3-CYCLIN-E $IC_{50}$ (μM) | CDK5 $IC_{50}$ (μM) | CDK5-p25 $IC_{50}$ (μM) | CDK7 $IC_{50}$ (μM) |
|---|---|---|---|---|---|
| 1 | 0.0022 | 0.00094 | 0.00068 | 0.00080 | 0.56 |
| 2 | 0.0037 | 0.0028 | 0.0014 | 0.0013 | 0.20 |
| 3 | 0.033 | 0.0099 | 0.017 | 0.014 | >1 |
| 4 | 0.089 | 0.005 | 0.006 | | 0.23 |
| 12 | 0.088 | 0.059 | 0.12 | 0.14 | >1 |
| 18 | 0.02 | 0.018 | 0.016 | 0.017 | 0.84 |
| 19 | 0.04 | 0.034 | 0.05 | 0.062 | 0.80 |

TABLE 3B

Biological Data

| Compound | CDK1 $IC_{50}$ (nM) | CDK3-CYCLIN-E IC50 (nM) | CDK5 $IC_{50}$ (nM) | CDK7 $IC_{50}$ (nM) |
|---|---|---|---|---|
| 5 | 11 | 23 | 30 | 875 |
| 23 | 20 | 6 | 12 | 682 |
| 42 | 7 | 10 | 2 | 83 |
| 43 | 33 | 29 | 15 | 250 |
| 45 | 108 | 73 | 48 | >1000 |
| 46 | 14 | 13 | 11 | 723 |
| 49 | 478 | 115 | 105 | 242 |
| 50 | 78 | 28 | 71 | 118 |
| 51 | 31 | 23 | 7 | 66 |
| 52 | 242 | 75 | 84 | >1000 |
| 53 | 27 | 10 | 4 | 615 |
| 54 | 12 | 8 | 3 | 144 |
| 55 | 5 | 6 | 1 | 27 |
| 59 | 42 | 57 | 6 | 16 |
| 61 | 133 | 58 | 72 | >1000 |
| 62 | 727 | 187 | 131 | >1000 |
| 63 | 574 | 96 | 78 | 579 |
| 64 | 505 | 105 | 65 | >1000 |
| 68 | >1000 | | | |
| 71 | 15 | | | |
| 74 | 258 | 106 | 92 | >1000 |
| 79 | 146 | | | |
| 84 | >1000 | | | |
| 91 | >1000 | | | |

All publications and patent applications cited in this specification are herein incorporated by reference as if each individual publication or patent application were specifically and individually indicated to be incorporated by reference.

The descriptions herein are described by way of illustration and example for purposes of clarity of understanding for embodiments only. It will be readily apparent to one of ordinary skill in the art in light of the teachings of this invention that certain changes and modifications may be made thereto without departing from the spirit or scope of the invention as defined in the appended claims.

I claim:

1. A pharmaceutical composition comprising a pharmaceutically acceptable excipient and a compound of Formula (III):

(III)

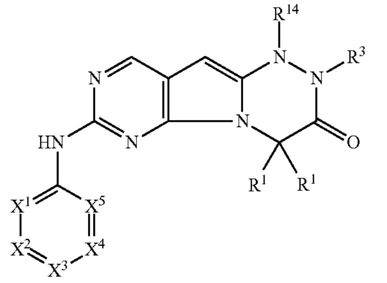

or a pharmaceutically acceptable salt thereof, wherein:

$X^1$ is CH, $CR^2$, $CR^4$, or N;
$X^2$ is CH, $CR^2$, $CR^4$, or N;
$X^3$ is CH, $CR^2$, $CR^4$, or N;
$X^4$ is CH, $CR^2$, $CR^4$, or N;
$X^5$ is CH, $CR^2$, $CR^4$, or N;

each $R^2$ is independently $C(O)R^6$, $C(S)R^6$, $NR^{14}C(O)R^6$, $NR^{14}C(S)R^6$, $NR^{14}S(O)R^6$, $NR^{14}S(O)_2R^6$, $OC(O)R^6$, $OC(S)R^6$, $OS(O)R^6$, $OS(O)_2R^6$, $S(O)R^6$, or $S(O)_2R^6$, each $R^4$ is independently hydrogen, halogen, cyano, alkyl, haloalkyl, $C(O)R^6$, $C(S)R^6$, $NR^{14}R^{15}$, $NR^{14}C(S)R^6$, $NR^{14}S(O)R^6$, $NR^{14}S(O)_2R^6$, $OR^{14}$, $OC(S)R^6$, $OS(O)R^6$, $OS(O)_2R^6$, $S(O)R^6$, $S(O)_2R^6$, cycloalkyl, heterocyclyl, aryl, or heteroaryl;

each $R^6$ is independently hydrogen, alkyl, alkenyl, alkynyl, $NR^7R^7$, $OR^7$, cycloalkyl, heterocyclyl, aryl, or heteroaryl, wherein each alkyl, alkenyl, alkynyl, cycloalkyl, heterocyclyl, aryl, and heteroaryl is optionally and independently substituted with 1, 2, 3, or 4 independently selected $R^8$ substituents;

each $R^7$ is independently hydrogen, alkyl, alkylene-aryl, alkylene-heteroaryl, alkenyl, alkynyl, cycloalkyl, heterocyclyl, aryl, or heteroaryl, wherein each alkyl, alkylene-aryl, alkylene-heteroaryl, alkenyl, alkynyl, cycloalkyl, heterocyclyl, aryl, and heteroaryl is optionally and independently substituted with 1, 2, 3, or 4 independently selected $R^8$ substituents;

each $R^8$ is independently halogen, alkyl, haloalkyl, alkylene-aryl, alkylene-heteroaryl, alkenyl, alkynyl, $NR^{12}R^{13}$, $S(O)_2$alkyl, cycloalkyl, heterocyclyl, aryl, or heteroaryl;

each $R^{12}$ is independently hydrogen, alkyl, alkylene-aryl, alkylene-heteroaryl, alkenyl, alkynyl, C(O)alkyl, C(S)alkyl, S(O)alkyl, $S(O)_2$alkyl, cycloalkyl, heterocyclyl, aryl, or heteroaryl;

each $R^{13}$ is independently hydrogen, alkyl, alkylene-aryl, alkylene-heteroaryl, alkenyl, alkynyl, C(O)alkyl, C(S)alkyl, S(O)alkyl, $S(O)_2$alkyl, cycloalkyl, heterocyclyl, aryl, or heteroaryl;

$R^1$ and $R^1$, together with the ring carbon atom to which they are attached, form a cyclohexylene, wherein the cyclohexylene is optionally substituted with 1 or 2 independently selected $R^{50}$ substituents;

each $R^{50}$ is independently halogen, cyano, alkyl, haloalkyl, $C(O)R^6$, $C(S)R^6$, $NR^{14}R^{15}$, $NR^{14}C(S)R^6$, $NR^{14}S(O)R^6$, $NR^{14}S(O)_2R^6$, $OR^{14}$, $OC(S)R^6$, $OS(O)R^6$, $OS(O)_2R^6$, $S(O)R^6$, $S(O)_2R^6$, cycloalkyl, heterocyclyl, aryl, or heteroaryl;

$R^3$ is hydrogen, alkyl, alkylene-aryl, alkylene-heteroaryl, alkenyl, alkynyl, $C(O)R^6$, C(S)alkyl, $NR^{14}R^{15}$, $OR^{14}$, $S(O)_2$alkyl, heterocyclyl, aryl, or heteroaryl;

each $R^{14}$ is independently hydrogen, alkyl, alkylene-aryl, alkylene-heteroaryl, alkenyl, alkynyl, $C(O)R^6$, C(S)alkyl, $S(O)_2$alkyl, heterocyclyl, or heteroaryl; and each $R^{15}$ is independently hydrogen, alkyl, alkylene-aryl, alkylene-heteroaryl, alkenyl, alkynyl, $C(O)R^6$, C(S)alkyl, $S(O)_2$alkyl, heterocyclyl, or heteroaryl;

with the provisos that:

(1) at least one of $X^1$, $X^2$, $X^3$, $X^4$, and $X^5$ is $CR^2$; and (2) no more than two of $X^1$, $X^2$, $X^3$, $X^4$, and $X^5$ are N.

2. The pharmaceutical composition of claim 1, wherein the compound is of the following formula:

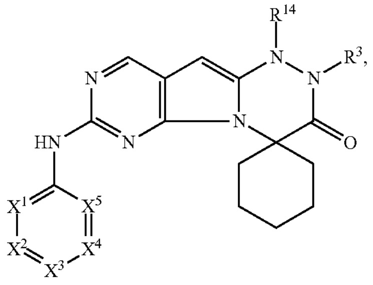

or a pharmaceutically acceptable salt thereof.

3. The pharmaceutical composition of claim 2, wherein the compound is of the following formula:

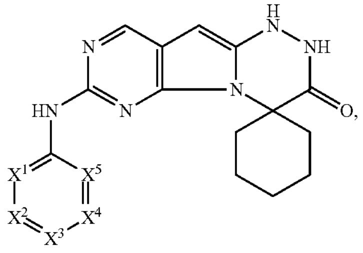

or a pharmaceutically acceptable salt thereof.

4. The pharmaceutical composition of claim 3, wherein the compound is any one of the following formulas:

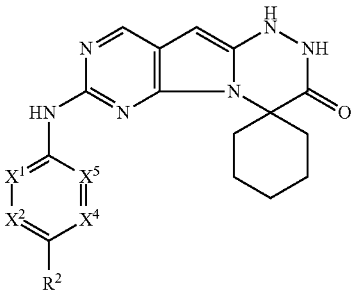

or

-continued

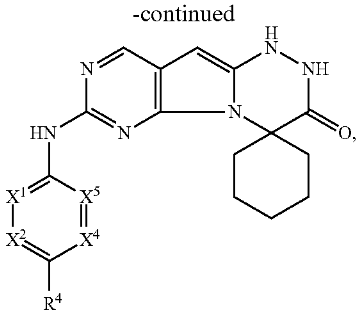

or a pharmaceutically acceptable salt thereof.

5. The pharmaceutical composition of claim 4, wherein $R^2$ is $C(O)R^6$, $C(S)R^6$, $NR^{14}C(O)R^6$, $S(O)R^6$, or $S(O)_2R^6$.

6. The pharmaceutical composition of claim 5, wherein $R^6$ is $NR^7R^7$.

7. The pharmaceutical composition of claim 6, wherein each $R^7$ is independently hydrogen.

8. The pharmaceutical composition of claim 1, wherein the compound is of the following formula:

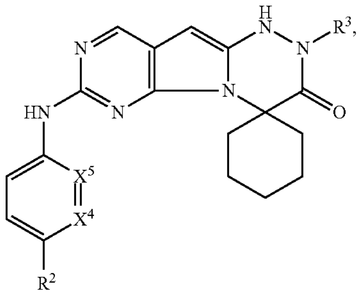

or a pharmaceutically acceptable salt thereof.

9. The pharmaceutical composition of claim 8, wherein the compound is of the following formula:

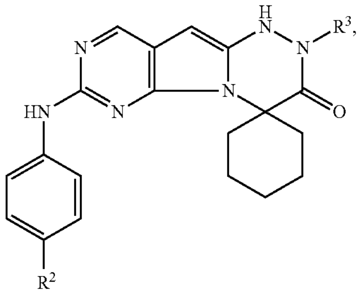

or a pharmaceutically acceptable salt thereof.

10. The pharmaceutical composition of claim 9, wherein $R^2$ is $C(O)R^6$, $C(S)R^6$, $NR^{14}C(O)R^6$, $S(O)R^6$, or $S(O)_2R^6$.

11. The pharmaceutical composition of claim 9, wherein $R^2$ is $S(O),R^6$.

12. The pharmaceutical composition of claim 11, wherein $R^6$ is $NR^7R^7$.

13. The pharmaceutical composition of claim 12, wherein each $R^7$ is independently hydrogen.

14. The pharmaceutical composition of claim 13, wherein $R^3$ is hydrogen or alkylN.

15. The pharmaceutical composition of claim 9, wherein $R^3$ is hydrogen.

16. The pharmaceutical composition of claim 1, wherein the compound is selected from the group consisting of:

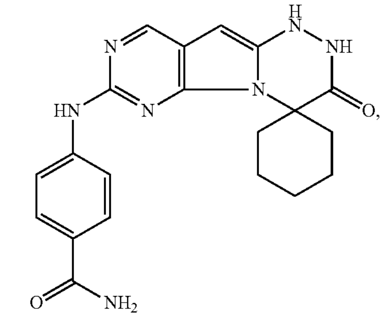

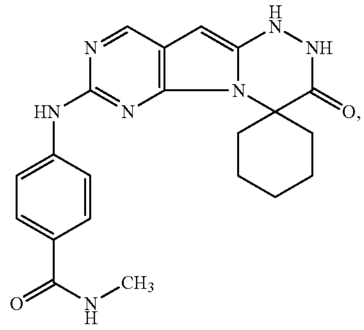

and

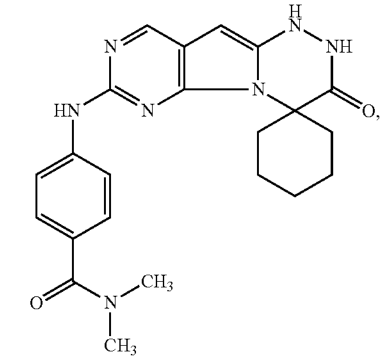

or a pharmaceutically acceptable salt thereof.

17. The pharmaceutical composition of claim 1, wherein the compound is:

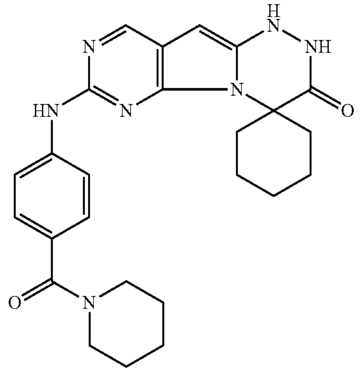

or

-continued

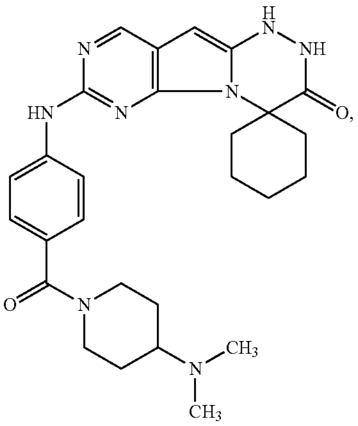

or a pharmaceutically acceptable salt thereof.

18. The pharmaceutical composition of claim 1, wherein the compound is:

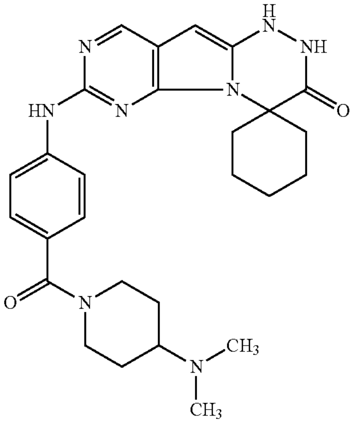

or

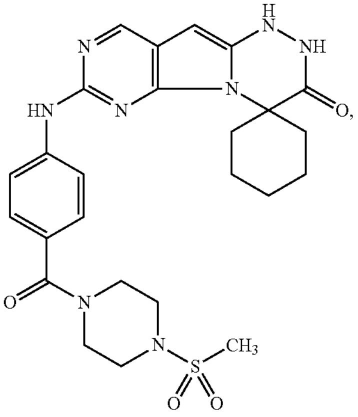

or a pharmaceutically acceptable salt thereof.

19. The pharmaceutical composition of claim 1, where the compound is:

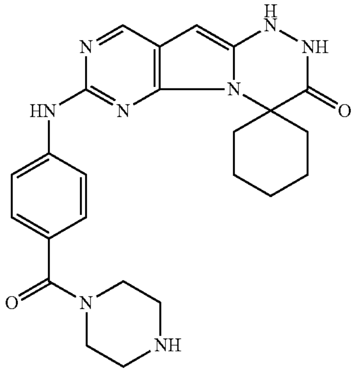

or

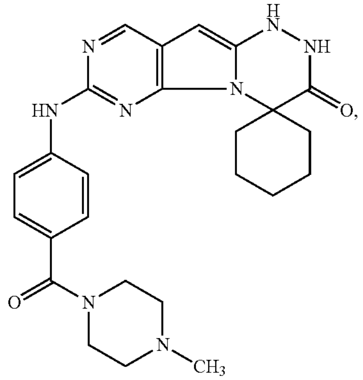

or a pharmaceutically acceptable salt thereof.

20. The pharmaceutical composition of claim 1, wherein the compound is:

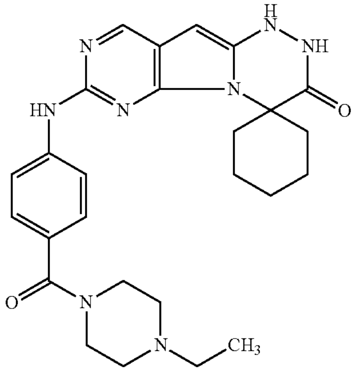

or

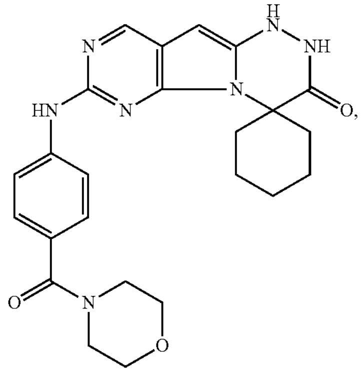

or a pharmaceutically acceptable salt thereof.

21. The pharmaceutical composition of claim 1, wherein the compound is selected from a group consisting

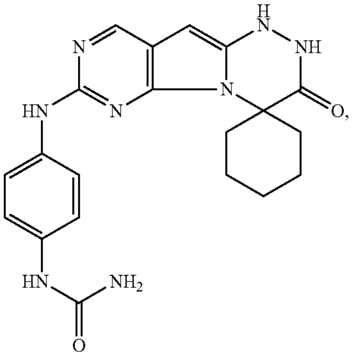

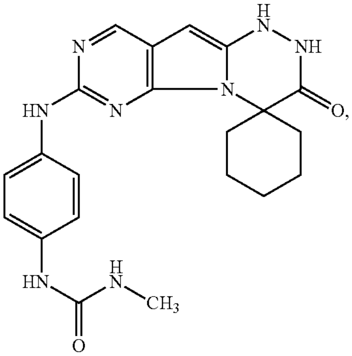

and

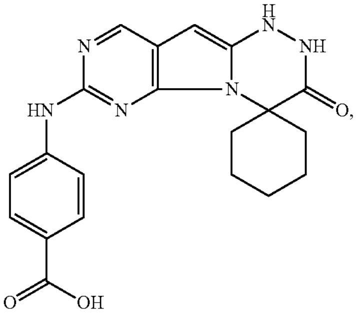

or pharmaceutically acceptable salt thereof.

22. The pharmaceutical composition of claim 1, wherein the compound is:

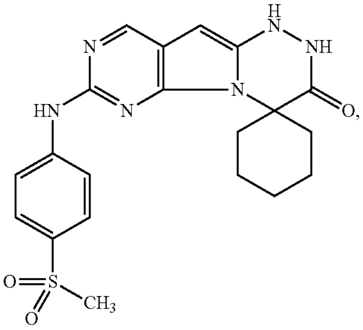 [SMILES: CS(=O)(=O)c1ccc(Nc2ncc3cc4n(c3n2)C2(CCCCC2)C(=O)NN4)cc1]

or a pharmaceutically acceptable salt thereof.

23. The pharmaceutical composition of claim 1, wherein the compound is:

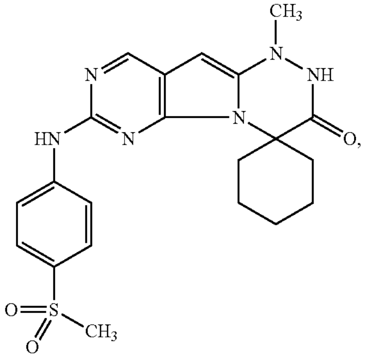 [SMILES: CN1NC(=O)C2(CCCCC2)n2c1cc1cnc(Nc3ccc(S(C)(=O)=O)cc3)nc12]

or a pharmaceutically acceptable salt thereof.

24. The pharmaceutical composition of claim 1, wherein the compound is:

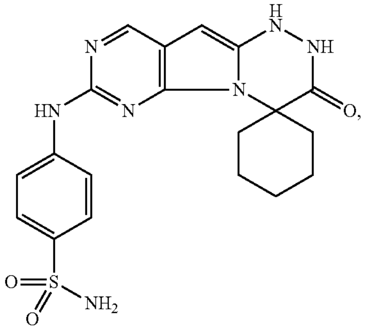 [SMILES: NS(=O)(=O)c1ccc(Nc2ncc3cc4n(c3n2)C2(CCCCC2)C(=O)NN4)cc1]

or a pharmaceutically acceptable salt thereof.

25. The pharmaceutical composition of claim 1, wherein the compound is:

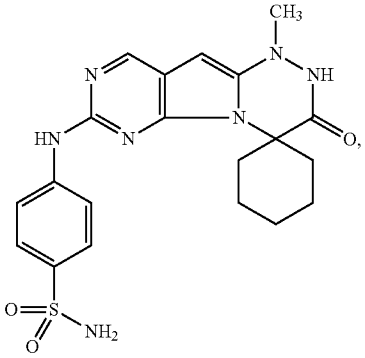 [SMILES: CN1NC(=O)C2(CCCCC2)n2c1cc1cnc(Nc3ccc(S(N)(=O)=O)cc3)nc12]

or a pharmaceutically acceptable salt thereof.

26. The pharmaceutical composition of claim 1, wherein the compound is:
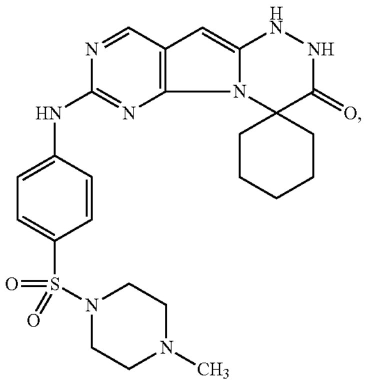 [SMILES: CN1CCN(S(=O)(=O)c2ccc(Nc3ncc4cc5n(c4n3)C3(CCCCC3)C(=O)NN5)cc2)CC1]
or pharmaceutically acceptble salt thereof.
27. A pharmaceutical composition comprising a pharmaceutically acceptable excipient and a compound of the following structure:
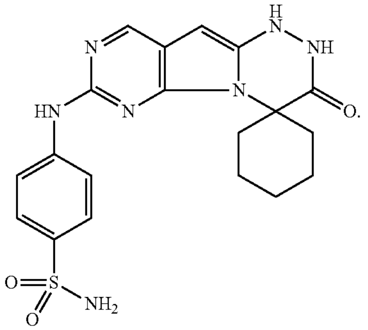 [SMILES: NS(=O)(=O)c1ccc(Nc2ncc3cc4n(c3n2)C2(CCCCC2)C(=O)NN4)cc1]
* * * * *